(12) United States Patent
Grinstaff et al.

(10) Patent No.: US 9,993,577 B2
(45) Date of Patent: Jun. 12, 2018

(54) DISSOLVABLE HYDROGEL COMPOSITIONS FOR WOUND MANAGEMENT AND METHODS OF USE

(71) Applicant: TRUSTEES OF BOSTON UNIVERSITY, Boston, MA (US)

(72) Inventors: Mark W. Grinstaff, Brookline, MA (US); Cynthia Ghobril, Reyersviller (FR); Michel Christophe Wathier, Allston, MA (US); Marlena Dagmara Konieczynska, Lawrenceville, NJ (US)

(73) Assignee: Trustees of Boston University, Boston, MA (US)

( * ) Notice: Subject to any disclaimer, the term of this patent is extended or adjusted under 35 U.S.C. 154(b) by 11 days.

(21) Appl. No.: 14/901,858

(22) PCT Filed: Jun. 30, 2014

(86) PCT No.: PCT/US2014/044908
§ 371 (c)(1),
(2) Date: Dec. 29, 2015

(87) PCT Pub. No.: WO2015/002888
PCT Pub. Date: Jan. 8, 2015

(65) Prior Publication Data
US 2016/0287745 A1 Oct. 6, 2016

Related U.S. Application Data

(60) Provisional application No. 61/841,746, filed on Jul. 1, 2013.

(51) Int. Cl.
*C12N 5/02* (2006.01)
*A61L 26/00* (2006.01)
(Continued)

(52) U.S. Cl.
CPC ............. *A61L 26/008* (2013.01); *A61L 15/44* (2013.01); *A61L 15/60* (2013.01); *A61L 15/64* (2013.01);
(Continued)

(58) Field of Classification Search
None
See application file for complete search history.

(56) References Cited

U.S. PATENT DOCUMENTS 4,060,081 A 11/1977 Yannas et al.
4,458,678 A 7/1984 Yannas et al.
(Continued)

FOREIGN PATENT DOCUMENTS

WO 2008/131325 A2 10/2008
WO 2008/133918 A1 11/2008
(Continued)

OTHER PUBLICATIONS

Solomons, G. "Organic Chemistry" 1980 (John wiley & Sons: New York) seconedition, p. 785.*

(Continued)

*Primary Examiner* — Susan M Hanley
(74) *Attorney, Agent, or Firm* — Nixon Peabody LLP

(57) ABSTRACT

The inventions provided herein relate to dissolvable hydrogel compositions and methods of uses, e.g., but not limited to, in wound management. Accordingly, methods for wound management involving the dissolvable hydrogel compositions are also provided herein. In some embodiments, the dissolvable hydrogel composition comprises an adhesive thioester hydrogel, which can facilitate adherence of the dissolvable hydrogen composition to a surface (e.g., a wound) and can be controllably dissolved later upon addition of a thiolate compound to release the dissolvable hydrogel composition from the surface (e.g., the wound).

23 Claims, 11 Drawing Sheets

(51) Int. Cl.
    *A61L 27/52*    (2006.01)
    *A61L 27/54*    (2006.01)
    *A61L 27/58*    (2006.01)
    *A61L 15/44*    (2006.01)
    *A61L 15/60*    (2006.01)
    *A61L 15/64*    (2006.01)
    *A61L 24/00*    (2006.01)

(52) U.S. Cl.
    CPC ....... *A61L 24/0015* (2013.01); *A61L 24/0031* (2013.01); *A61L 24/0042* (2013.01); *A61L 26/009* (2013.01); *A61L 26/0028* (2013.01); *A61L 26/0066* (2013.01); *A61L 27/52* (2013.01); *A61L 27/54* (2013.01); *A61L 27/58* (2013.01)

(56) References Cited

U.S. PATENT DOCUMENTS

| | | |
|---|---|---|
| 4,485,097 A | 11/1984 | Bell |
| 8,304,468 B2 | 11/2012 | Athanasius et al. |
| 2004/0116305 A1 | 6/2004 | Osada et al. |

FOREIGN PATENT DOCUMENTS

| | | |
|---|---|---|
| WO | 2012/021144 A2 | 3/2012 |
| WO | 2012/050591 A1 | 4/2012 |
| WO | 2012/065751 A1 | 5/2012 |

OTHER PUBLICATIONS

Strehin et al. Biomater. Sci (2013) 1: 603-613.*

Aboushwareb et al., "A Keratin Biomaterial Gel Hemostat Derived from Human Hair: Evaluation in a Rabbit Model of Lethal Liver Injury", Journal of Biomedical Materials Research Part B: Applied Biomaterials, 90(1):45-54 (2009).

Hattori et al., "Hemostasis for Severe Hemorrhage with Photocrosslinkable Chitosan Hydrogel and Calcium Alginate", Annals of Biomedical Engineering, 38(12):3724-3732 (2010).

Kulling et al., "Poly-N-Acetyl Glucosamine: Will It Replace Cyanoacrylate for Treatment of Gastric Varices? A Pilot Study in a Rabbit Model", Endoscopy, 30(3):S41-S42 (1998).

Luo et al., "Fabrication of self-assembling D-form peptide nanofiber scaffold d-EAK16 for rapid hemostasis", Biomaterials, 32:2013-20 (2011).

Park et al., "Hydrogels and biodegradable polymers for bioapplications", Chapter 1: Hydrogels in Bioapplications, Editor: Ottenbrite, Raphael M., ACS Symposium Series, American Chemical Society, Washington D.C, (1996).

Peppas et al., "Hydrogel in Medicine and Pharmacy Volume I: Fundamentals", Chapter 1: Preparation Methods and Structures of Hydrogels, Editor: Peppas, Nickolaos A., CRC Press, Boca Raton, Florida (1987).

Peppas, "Hydrogel in Medicine and Pharmacy Volume II: Polymers", Chapter 1: Hydrogels of Poly(Vinyl Alcohol) and It's Copolymers, Editor: Peppas, Nickolaos A., CRC Press, Boca Raton, Florida (1987).

Wichterle et al., "Hydrophilic Gels for Biological Use", Nature, 185:117-18 (1960).

Yannas et al., "Design of an artificial skin. I. Basic design principles", Journal of Biomedical Materials Research 14:65-81 (1980).

Alam et al., "Hemorrhage control in the battlefield: role of new hemostatic agents", Military Medicine, 170:63-69 (2005).

Anumolu et al., "Doxycycline hydrogels with reversible disulfide crosslinks for dermal wound healing of mustard injuries", Biomaterials, 32(4):1204-1217 (2011).

Bracher et al., "The relative rates of thiol-thioester exchange and hydrolysis for alkyl and aryl thioalkanoates in water", Orig. Life Evol. Biosph 41(5):399-412 (2011).

Dwortzan M., "Easy on, Easy off: Reversible Hydrogel Seals Wounds," BME News, Dec. 16, 2013.

Ghobril et al., "A dendritic thioester hydrogel based on thiol-thioester exchange as a dissolvable sealant system for wound closure," Angewandete Chemie, 52(52):14070-14074 (2013).

Hu et al. "Hydrogels Cross-Linked by Native Chemical Ligation," Biomacromolecules, 10(8):2194-2200 (2009).

Ruan et al., "Designed amphiphilic peptide forms stable nanoweb, slowly releases encapsulated hydrophobic drug, and accelerates animal hemostasis", PNAS, 106(13):5105-5110 (2009).

Villa et al. "A Reversible Hydrogel Dressing for Hemostasis and Wound Management," ORS 2014 Annual Meeting, Mar. 2014.

* cited by examiner

FIGs. 1A-1B
A  Chemistry of Native Chemical Ligation (NCL)
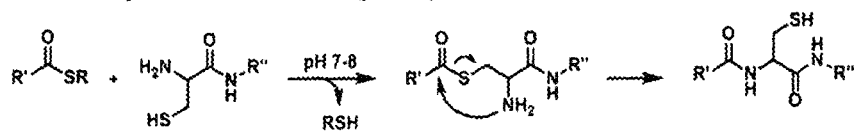
B  Dissolution of PEG-LysSH hydrogel based on NCL
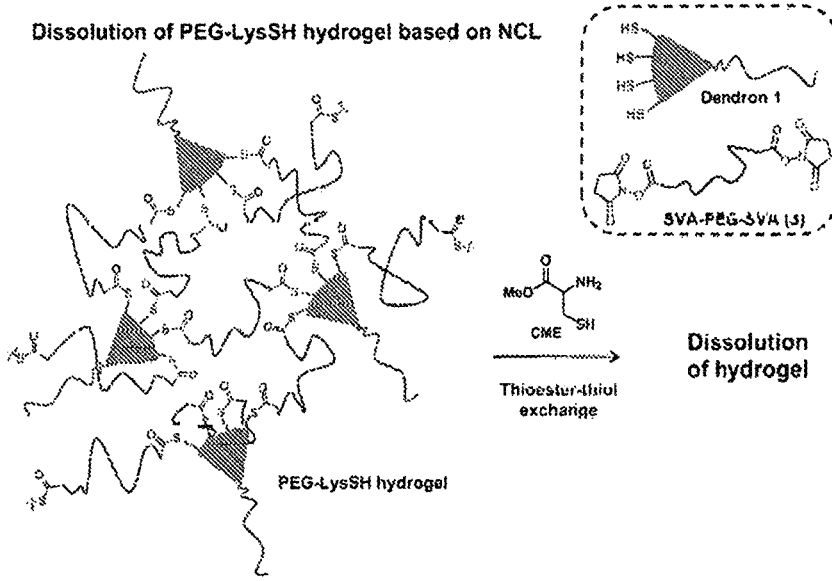
FIG. 2
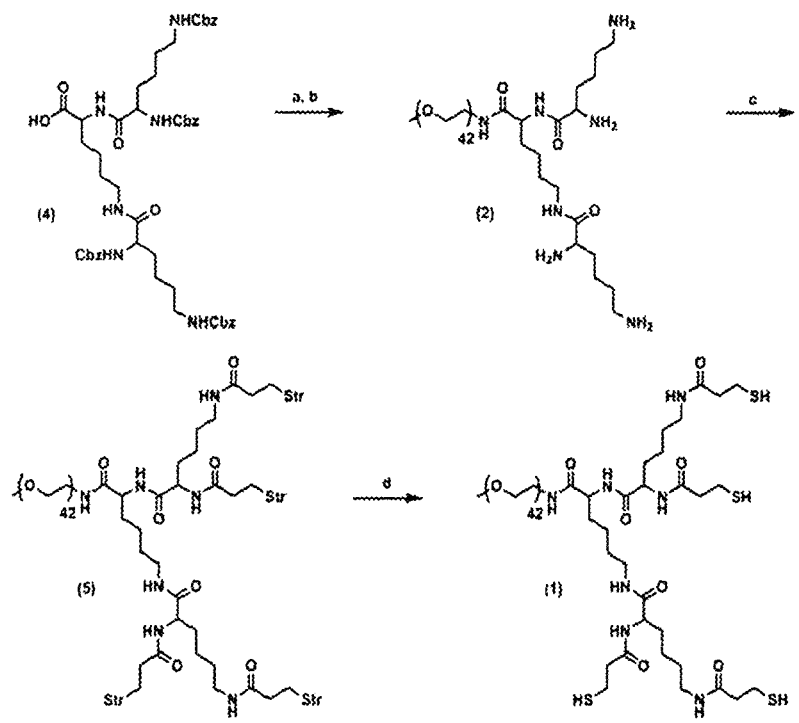

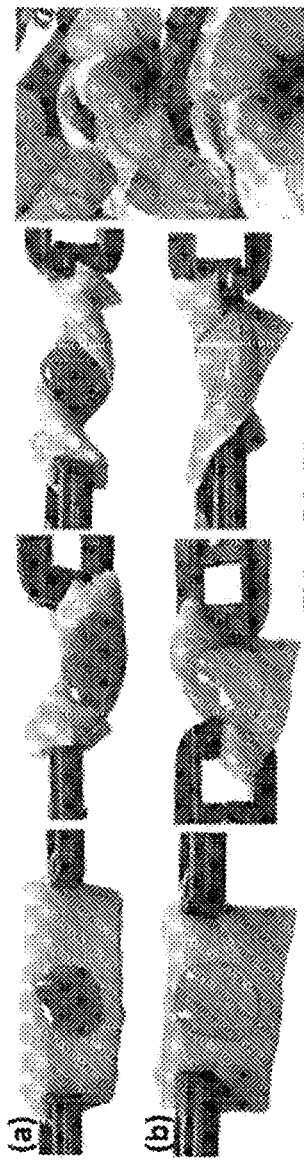
FIGs. 5A-5B
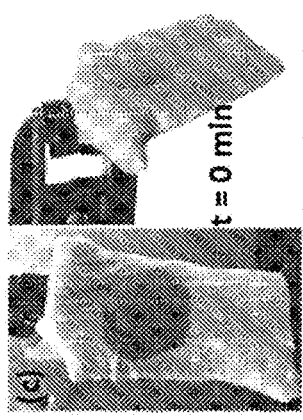
FIG. 5C

Stability of PEG-LysSH 30 wt%

Key: a) EDCI, phosphate buffer pH 6, 80%

DISSOLVABLE HYDROGEL COMPOSITIONS FOR WOUND MANAGEMENT AND METHODS OF USE

CROSS-REFERENCE TO RELATED APPLICATIONS

This Application claims benefit under 35 U.S.C. § 119(e) of the U.S. Provisional Application No. 61/841,746 filed Jul. 1, 2013, the content of which is incorporated herein by reference in its entirety.

GOVERNMENT SUPPORT

This invention was made with Government Support under Contract No. EB013721 awarded by the National Institutes of Health. The Government has certain rights in the invention.

TECHNICAL FIELD

The inventions described herein generally relate to dissolvable hydrogel compositions, kits comprising the same and methods of uses. In some embodiments, the dissolvable hydrogel compositions and kits described herein are formulated for wound management.

BACKGROUND

Skin is an organ that can be damaged by disease or injury. Skin plays a vital role of protecting the body from fluid loss and disease. Skin grafts have been prepared previously from animal skin or the patient's skin, more recently "artificial skin" formed by culturing epidermal cells. In U.S. Pat. No. 4,485,097 Bell discusses a skin-equivalent material composed of a hydrated collagen lattice with platelets and fibroblasts and cells such as keratinocytes. U.S. Pat. No. 4,060,081, to Yannas et al. discuss a multilayer membrane useful as synthetic skin formed from an insoluble non-immunogenic and a non-toxic material such as a synthetic polymer for controlling the moisture flux of the overall membrane. In U.S. Pat. No. 4,458,678, Yannas et al. discuss a process for making a skin-equivalent material wherein a fibrous lattice formed from collagen cross-linked with glycosaminoglycan is seeded with epidermal cells. However, one of the disadvantages to these artificial skins is that the matrix is formed from a "permanent" synthetic polymer. Thus, these artificial skins are not dissolvable. Additional limitations of these materials are also discussed in Yannas and Burke, J. Biomed. Mater. Res., 14, 65-81 (1980).

Classical suture technique is another method for treatment of a wound closure. However, depending on the type and/or origin of a wound as well as the location of a patient, use of tissue adhesives (e.g., glues, sealants, patches, films and the like) can be a more attractive alternative to use of sutures. In addition to an easy and fast application on a wound, other criteria for an adhesive include, but are not limited to an ability to bind to a tissue (necrosed or not, sometimes wet) with an adequate adhesion force, non-toxic material, biodegradable or resorbable material, sterilizable material, material selectively permeable to gases but impermeable to bacteria and able to control evaporative water loss, material mechanically strong enough to protect the wound and to enhance the healing process or at least not prevent it. Adhesive hemostats, based on fibrin, have been previously used and are usually constituted of fibrinogen, thrombin and factor XIII, as well as fibrinogen/photosensitizers systems. However, autologous products (which are time-consuming in emergency) or treatments of allogenic products before clinical use are needed to avoid any contamination to a patient.

Synthetic materials, e.g., polymers and hydrogels, have been developed for wound closure. For example, alkyl-cyanoacrylates ("super glues") have been previously discussed for the repair of cornea perforations. However, monomers of these "super glues," in particular those with short alkyl chains, can be toxic and polymerize too quickly, leading to difficulty in treating a wound. Once polymerized, the surface of the glue is rough and hard. This can cause discomfort to the patient and, for example, in case of cornea perforation treatment, a contact lens needs to be worn. Other materials have been commercialized such as "Biobrane II" (composite of polydimethylsiloxane on nylon fabric) and "Opsite" (polyurethane layer with vinyl ether coating on one side). A new polymeric hemostat (poly-N-acetyl glucosamine) has been assessed for biomedical applications such as treatment of gastric varices in order to replace cyanoacrylate (Kulling et al., Endoscopy, 30(3): S41-42 (1998)). Adhesives based on modified gelatin are also found to treat skin wounds. Photopolymerizable poly(ethylene glycol) substituted with lactate and acrylate groups are previously discussed for sealing air leaks in lung surgery.

Sealants and adhesives can help patients recover from surgery or trauma. There are medical sealant/adhesive products, CoSeal™, DuraSeal™, and Adherus®, currently existing in the market that are based on hydrogel formulations. These products comprise multiple components housed in separate containers. CoSeal™ Surgical Sealant (CoSeal™) is composed of two synthetic polyethylene glycols (PEGs), a dilute hydrogen chloride solution and a sodium phosphate/sodium carbonate solution. The DuraSeal™ Dural Sealant System consists of components for preparation of a synthetic, absorbable sealant and an applicator for delivery of the sealant to the target site the sealant is composed of two solutions, a polyethylene glycol (PEG) ester solution and a trilysine amine solution. Adherus® is composed of two solutions of polyethylene glycol (PEG) ester NHS derivative and polyalkyleneimine.

Fibrin glues are also sold in packaging and applicator systems that are similar to those used for CoSeal™ and DuraSeal™. One example is Baxter's Tisseel. Tisseel VH (Fibrin Sealant) consists of a two-component fibrin biomatrix that offers highly concentrated human fibrinogen to seal tissue and stop diffuse bleeding. However, all of the existing wound dressing, sealants or glues cannot be dissolved after application to the tissue site. That is, they have to be removed by mechanical debridement and/or surgical incision, if needed.

Hydrogels are one class of biomaterials currently used in medical and clinical applications, including sealing of wounds. See, e.g., Ruan, L. et al., PNAS 2009, 106, 5105-5110; Aboushwareb, T. et al. J. Biomed. Mater. Res. Part B: Appl. Biomater. 2009, 90B, 45-54; Hattori, H. et al., Annals of Biomedical Engineering, 2010, 38, 3724-3732; and Luo, Z. et al. Biomaterials, 2011, 32, 2013-2020. Hydrogels can be used as coatings (e.g. biosensors, catheters, and sutures), as "homogeneous" materials (e.g. contact lenses, burn dressings, and dentures), and as devices (e.g. artificial organs and drug delivery systems) (Peppas, N. A. Hydrogel in Medicine and Pharmacy, Vol I and II 1987. Wichterle, O.; Lim, D. Nature 1960, 185, 117-118. Ottenbrite, R. M.; Huang, S. J.; Park, K. Hydrogels and Biodegradable polymers for Bioapplications 1994; Vol. 627, pp 268).

Synthetic hydrogel based hemostats/sealants can offer a number of advantages because the chemical composition of the hydrogels can be tuned for various properties, e.g., but not limited to, water content, sensitivity to environmental conditions (e.g., but not limited to, pH, temperature, solvent, stress), softness, tissue adhesion, rubbery consistency, mechanical, degradation, and swelling properties. However, we are not aware of a hydrogel reported, e.g., for emergency care, where a hydrogel is applied to a wound and can be subsequently removed to allow for definitive surgical care at the hospital.

A desirable or useful hydrogel or sealant system, e.g., for trauma scenarios sustained in military injuries or in rural or wilderness settings, should: (1) provide consistent hemostasis for several hours; (2) adhere to the tissue; (3) be easily applied; (4) enable controlled dissolution of the sealant in the surgical theatre setting to allow for gradual wound re-exposure during definitive surgical care. Alam, H. B. et al. Military Medicine 2005, 170, 63-69. However, we are not aware of a dissolution capability present in any available wound hemostatic system as discussed above. Indeed, removal of a clotting agent or dressing from a wound is currently performed via mechanical debridement and/or surgical excision, which could potentially cause additional damage to tissue at and/or surrounding the wound. Accordingly, there is a need for an improved wound dressing or sealant composition, e.g., for use in wound management.

SUMMARY

Existing materials for use in wound dressings, sealants or clotting agents are generally not reversible or dissolvable. Thus, once a dressing material is adhered on a wound and/or tissue surrounding the wound, mechanical debridement or surgical incision is usually required if the dressing material is desired to be removed or replaced later. Yet the physical removal process can cause additional tissue damage or trauma or pain. Accordingly, there is a need for an improved material for wound management such that it can be easily or controllably removed from a wound in a minimally invasive manner if needed. Embodiments of various aspects described herein stem in part from development of thioester hydrogels that are not only mechanically strong, e.g., for use as a sealant, dessing, bandage, glue, or scaffold, but can also adhere to a surface and be controllably removed or dissolved on-demand later by contacting the hydrogels with a thiolate compound/composition. Such dissolution capability of thioester hydrogels allows for gradual re-exposure of a surface, e.g., a wound surface for further examination and/or treatment.

In a particular embodiment, a thioester hydrogel derived from multi-thiol-containing linear, branched, and/or dendritic macromolecules (e.g., but not limited to multi-thiol-containing peptide dendrimers, and/or dendrons) and activated ester-containing linear, branched, and/or dendritic macromolecules (e.g., but not limited to, activated ester-containing poly(ethylene glycol)) was developed and assessed for its mechanical properties, adhesive strength, and controlled dissolution in the presence of a thiolate composition (e.g., a thiolate solution) when it was applied on a skin tissue or as a sealant to seal a blood vessel puncture or as a bandage to treat a burn wound.

In some embodiments, a thioester hydrogel can be derived from multi-thioester-containing linear, branched, and/or dendritic macromolecules (e.g., but not limited to multi-thioester-containing peptide dendrimers, and/or dendrons), and activated ester-containing linear, branched, and/or dendritic macromolecules (e.g., but not limited to activated ester-containing poly(ethylene glycol)). In some embodiments, a thioester hydrogel can be derived from multi-amine-containing linear, branched and/or dendritic macromolecules (e.g., but not limited to multi-amine-containing peptide dendrimers, and/or dendrons) and activated ester-thioester-containing linear, branched and/or dendritic macromolecules (e.g., but not limited to, activated ester-thioester-containing poly(ethylene glycol)). In some embodiments, a thioester hydrogel can be derived from multi-amine- and thioester-containing linear, branched and/or dendritic macromolecules (e.g., but not limited to multi-amine- and thioester-containing peptide dendrimers, and/or dendrons) and activated ester containing linear, branched and/or dendritic macromolecules (e.g., but not limited to, activated ester-containing poly(ethylene glycol)). In some embodiments, a thioester hydrogel can be derived from multi-amine- and thioester-containing linear, branched and/or dendritic macromolecules (e.g., but not limited to multi-amine- and thioester-containing peptide dendrimers, and/or dendrons) and activated ester-thioester-containing linear, branched and/or dendritic macromolecules (e.g., but not limited to, activated ester-thioester-containing poly(ethylene glycol)). In some embodiments, a thioester hydrogel can be derived from multi-thiol-containing linear, branched and/or dendritic macromolecules (e.g., but not limited to multi-thiol-containing peptide dendrimers, and/or dendrons) and maleimide-thioester-containing linear, branched and/or dendritic macromolecules (e.g., but not limited to, maleimide-thioester-containing poly(ethylene glycol)).

Accordingly, embodiments of various aspects described herein relate to dissolvable hydrogel compositions, kits, and methods of uses. The dissolvable hydrogel compositions each comprises a thioester hydrogel (e.g., as a layer), which can be dissolved and/or washed away by addition of a composition comprising at least one nucleophile. In one embodiment, at least one nucleophile comprises a thiol moiety. The dissolvable hydrogel compositions can be optionally loaded with one or more biologically and/or pharmacologically active agent and/or chemically modified to contain or couple to active agent(s).

The dissolvable hydrogel compositions, kits and/or methods described herein can be used in any application where a surface or void (e.g., a physical or environmental surface/void or a biological surface/void) needs to be covered, filled, and/or sealed. In some embodiments, the dissolvable hydrogel compositions, kits, and/or methods described herein can be used in any application where a surface or void requires temporary and/or immediate treatment, covering and/or structural support, which can be removed later to expose the surface or void for additional care and/or management (e.g., but not limited to, examination, drug treatment, and/or surgical treatment). In these embodiments, a new composition, but not necessarily a new dissolvable hydrogel composition described herein, can be applied on the exposed surface, if necessary.

Accordingly, in some embodiments of various aspects described herein, the dissolvable hydrogel compositions, kits and methods of uses described herein can be used for wound management, e.g., but not limited to, sealing, treating, and/or repairing wounds, treatment of burns or other traumatized or degenerative tissue, or repair or replacement of tissues or organs. In some embodiments of various aspects described herein, the hydrogel compositions, kits and methods of uses described herein can be used for wound management with vacuum assisted closure.

In some aspects, methods for wound management are provided herein. In one aspect, the method comprises (a) contacting a wound in a subject with a hydrogel composition comprising a dissolvable hydrogel layer, wherein the dissolvable hydrogel layer comprises linear, branched, and/or dendritic crosslinkable polymers held together by thioester linkages formed between the first crosslinkable polymer and the second crosslinkable polymer; and (b) allowing the dissolvable hydrogel layer to adhere to tissue surrounding the wound. In some embodiments, the method further comprises dissolving the dissolvable hydrogel layer by adding a nucleophile, thereby releasing the hydrogel layer from the wound. In one embodiment, the nucleophile can comprise a thiolate compound or molecule. In some embodiments, the first crosslinkable polymers and the second crosslinkable polymers do not necessarily possess thioester linkage or functional group in their molecular structures. In these embodiments, thioester linkages present within a dissolvable hydrogel can result or be formed from covalent interaction between the first crosslinkable polymers and the second crosslinkable polymers. For example, the thioester linkages present within a dissolvable hydrogel can result from reacting a first crosslinkable polymer comprising at least two thiols with a second crosslinkable polymer comprising crosslinking moieties (e.g., but not limited to N-succinimidyl moiety and/or activated ester groups), wherein neither of the crosslinkable polymers has any thioester bonds in their molecular structure.

In another aspect, the method comprises (a) contacting a wound in a subject with a hydrogel composition comprising a dissolvable hydrogel layer, wherein the dissolvable hydrogel layer comprises first linear, branched, and/or dendritic crosslinkable polymers and second linear, branched, and/or dendritic crosslinkable polymers covalently held together, wherein the first crosslinkable polymers and/or the second crosslinkable polymers comprise at least one thioester linkage or functional group in their molecular structures; and (b) allowing the dissolvable hydrogel layer to adhere to tissue surrounding the wound. In some embodiments, the method further comprises dissolving the dissolvable hydrogel layer by adding a nucleophile, thereby releasing the hydrogel layer from the wound. In one embodiment, the nucleophile can comprise a thiolate compound or molecule. In these embodiments, at least some of the thioester linkages present within a dissolvable hydrogel network can be contributed from one or both of the first crosslinkable polymers and the second crosslinkable polymers that comprise a thioester linkage or functional group in their molecular structure. For example, the thioesters can be present within the crosslinkable macromolecules or polymers such that a new covalent bond is formed (e.g., amide) which results in a hydrogel containing thioester linkages. In some embodiments, the first crosslinkable polymers and/or the second crosslinkable polymers can be covalently linked together via any art-recognized chemical reactions, including, e.g., but not limited to an amine-ester reaction.

In some embodiments of various aspects described herein where vacuum assisted closure is applied, the method can further comprise removing the dissolved hydrogel from the wound with vacuum.

Without wishing to be bound by theory, a thiol-thioester exchange reaction between thioester linkages present in the dissolvable hydrogel layer and thiols of a thiolate compound or molecule leads to dissolution of the dissolvable hydrogel layer. In some embodiments, the thioester-thiol exchange can also result in formation of an amide linkage, thereby preventing re-formation of the dissolvable hydrogel.

In some embodiments of this aspect and other aspects described herein, the hydrogel composition can be present as a thin sheet or layer. In some embodiments of this aspect and other aspects described herein, the hydrogel composition can be present as a thin sheet or layer supported by a sheet support member to provide mechanical strength. In alternative embodiments of this aspect and other aspects described herein, the hydrogel composition can be a multi-layer composite comprising at least one layer of the dissolvable hydrogel layer described herein and at least one additional layer. The additional layer can be a drug-releasing layer, another material layer (e.g., another polymer layer), and/or a sheet support member.

In some embodiments of this aspect and other aspects described herein, the hydrogel composition can further comprise at least one active agent. The active agent can be incorporated into the dissolvable hydrogel layer and/or additional layer(s), if any. In some embodiments, the active agent can be a bioactive agent. Non-limiting examples of bioactive agents include pharmaceutical agents, drugs, cells, gases and gaseous precursors, synthetic organic molecules, proteins, enzymes, growth factors, vitamins, steroids, polyanions, nucleosides, nucleotides, polynucleotides, polymer nanoparticles, metal nanoparticles, diagnostic agents, genetic materials, and any combinations thereof.

The hydrogel compositions of various aspects described herein can be adapted to form any wound management devices or articles, e.g., but not limited to, a dressing, bandage, glue, sealant, coating, and/or covering. In some embodiments, the hydrogel compositions of various aspects described herein can be adapted for use with vacuum assisted closure. Accordingly, one aspect described herein relates to a dissolvable hydrogel composition or a wound management device comprising an adhesive hydrogel layer, wherein the adhesive hydrogel layer comprises a first water-soluble linear, branched, and/or dendritic crosslinkable polymer and a second water soluble linear, branched, and/or dendritic crosslinkable polymer held together by thioester linkages between the first crosslinkable polymer and the second crosslinkable polymer.

The adhesiveness and reversibility of the dissolvable hydrogel described herein provide a novel means of wound management. The dissolvable hydrogel layer or the dissolvable hydrogel composition or the wound management device can be dissolved partially or completely, whenever appropriate, after the dissolvable hydrogel layer is adhered to tissue surrounding a wound. In accordance with embodiments of various aspects described herein, the dissolvable hydrogel layer can be dissolved, partially or completely, by addition of a thiolate compound or molecule. Examples of thiolate compounds/molecules include, without limitations, linear, branched and/or dendritic multi-thiol macromolecules, poly(ethylene glycol) thiol, thiol-containing glycerol, thiol-containing glycerol polymers, thiol-containing peptides, cysteine, cystine, alkyl ester of cysteine, alkyl ester of cystine, MeSCH$_2$SH, (R)/(S)-3-methyl-3-sulfanylhexan-1-ol, Ethanethiol, 1-Propanethiol, 2-Propanethiol, Butanethiol, tert-Butyl mercaptan, Pentanethiols, Thiophenol, Dimercaptosuccinic acid, Thioacetic acid, 5-mercapto-4H-[1,2,4]triazol-3-ol, 2-mercaptoacetamide, 2-Mercaptoethanol, 1,2-Ethanedithiol, Ammonium thioglycolate, Cysteamine, Methyl thioglycolate, Thiolactic acid, 1-Mercapto-2-propanol, 2-methoxyethanethiol, 3-Mercapto-1-propanol, 2,3-Dimercapto-1-propanol, 1-Thioglycerol, Mercaptosuccinic acid, 4-ethyl-5-mercapto-4H-1,2,4-triazol-3-ol, N-Carbamoyl-L-cysteine, 2-Methyl-3-sulfanylpropanoic acid, 4-mercaptobutyric acid, N-Acetylcysteamine, 3-Methyl-1- butanethiol, 1,5-Pentanedithiol, 4-Chlorothiophenol, 4-Aminothiophenol, Benzyl mercaptan, 2-furanmethanethiol, 3-mercaptohexanol, furfuryl thiol, derivatives thereof, a disulfide complex of one or more of the aforementioned compounds, and any combinations thereof.

The thiolate compound/molecules can be formulated in any form to suit the application format, e.g., but not limited to spraying and/or injection. In some embodiments, the thiolate compound/molecules can be formulated in a form of a solution, a spray, a powder, or any combinations thereof.

Additional objects, advantages, and features will become apparent from the following description and the claims that follow, considered in conjunction with the accompanying drawings.

BRIEF DESCRIPTION OF THE DRAWINGS

FIGS. 1A-1B are schematic representations, respectively, showing chemistry of native chemical ligation (NCL) (FIG. 1A), and a cross-linked PEG-LysSH hydrogel (in accordance with one embodiment described herein) formed between Dendron 1 and N-hydroxysuccinimide-containing PEG molecule 3 (e.g., SVA-PEG-SVA) and its reversibility based on NCL (FIG. 1B).

FIG. 2 shows an exemplary scheme of a synthetic route to form PEG-peptide dendrons 1 and 2. The alphabets in the figure indicate process condition as described follows: (a) MPEG2000-NH$_2$, DIPEA, HOBT, EDCI, DMF, room temperature, 16 hrs, 90%; (b) Pd/C, H$_2$ (1 atm), MeOH, room temperature, 16 hrs, 90%; (c) PFP-3(tritylthio)propionic acid, HOBT, DMF, room temperature, 24 hrs, 76%; (d) Et$_3$SiH, TFA, DCM, room temperature, 3 hrs, 95%. Cbz=benzyloxycarbonyl, DIPEA=diisopropylethylamine, DMF=N,N-dimethylformamide, EDCI=1-(3-dimethylaminopropyl-3-ethyl-carbodiimide, HOBT=1-hydroxybenzotriazole, PFP=pentafluorophenol, Tr=trityl, TFA=trifluoroacetic acid.

FIGS. 5A-5C are photographs showing adhesion strength and dissolution of hydrogels PEG-LysSH and PEG-LysNH$_2$. FIGS. 5A-5B are photographs of hydrogels PEG-LysSH (green; upper panel) and PEG-LysNH$_2$ (pink; lower panel) adhered to human tissue skin, under torsional stress. FIG. 5C is a set of photographs showing dissolution of PEG-LysSH hydrogel in ~0.3 M CME solution in PBS at pH ~8.5, at different time intervals (0, ~10, ~20 and ~30 min). PEG-LysNH$_2$ used as control, swelled and did not dissolve. The PEG-LysSH and PEG-LysNH$_2$ hydrogel sealants were dyed with green food coloring or nile red dye, respectively.

FIG. 6A is a photograph of a beef jugular vein. FIG. 6B shows the vein linked to a syringe pump and filled with a buffered solution, e.g., PBS at pH ~7.4;

FIG. 6C shows generation of a ~2.5 mm puncture on the vein surface. FIG. 6D shows PEG-LysSH hydrogel (e.g., ~30 wt %) applied on the puncture. The hydrogel was dyed in green. FIG. 6E shows PEG-LysSH hydrogel (e.g., ~30 wt %) applied on a deep second-degree burn wound model. FIG. 6F is a set of photographs showing the dissolution of PEG-LysSH hydrogel upon exposure to cysteine methyl ester solution. The left panel shows applying a cysteine methyl ester solution on the hydrogel surface. The right panel shows complete dissolution of the hydrogel after application of the cysteine methyl ester solution.

FIG. 8A is a schematic representation showing a chemical reaction of citric acid and cysteamine to form S,S,S-tris(2-aminoethyl) 2-hydroxypropane-1,2,3-tris (carboxylothioate) hydrochloride salt (product A), which is then reacted with NHS-PEG-NHS (MW ~2400 Da) to form a thioester hydrogel in accordance with one embodiment described herein, as shown in step 1 of FIG. 8B. By addition of a cysteine solution to the thioester hydrogel, the thioester hydrogel dissolved (step 2 of FIG. 8B). FIG. 8C is a bar graph showing storage modulus G' and loss modulus G" of the thioester gel and its precursors.

FIG. 9A is a schematic representation showing the reaction of the precursors to form the hydrogel. FIG. 9B details the synthetic route of the second-water soluble crosslinkable macromolecule, MAL-thio-PEG-thio-MAL 9. FIG. 9C is a bar graph showing storage modulus G and loss modulus G" of the thioester hydrogel. FIG. 9D shows the efficacy of the hemostatic thioester hydrogel in an in vivo model of venous hemorrhage (where the hydrogel was applied on a hepatic incision of an in vivo rat model) (left panel), followed by its dissolution using methyl ester cysteine solution (right panel). FIG. 9E shows the efficacy of the hemostatic thioester hydrogel in an in vivo model of arterial hemorrhage (where the hydrogel was applied on an aortic incision of an in vivo rat model) (left panel), followed by its dissolution using methyl ester cysteine solution (right panel).

FIG. 10A is a schematic representation showing the reaction of the precursors to form the hydrogel. FIG.

Figure 3:
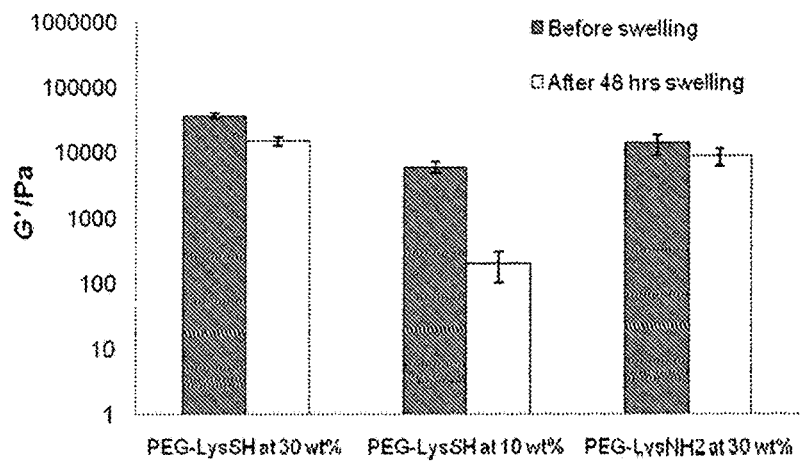
FIG. 3 is a bar graph showing the storage modulus G' of dissolvable hydrogel compositions according to one or more embodiments described herein before and after 48-hour swelling. The storage modulus G' was performed for ~10 wt % and ~30 wt % PEG-LysSH and ~30 wt % PEG-LysNH$_2$ hydrogels at ~50 Pa oscillatory stress, ~1 Hz frequency, and ~20° C.

10B details the synthetic route of the second-water soluble crosslinkable macromolecule, NHS-thio-PEG-thio-NHS 10.

DETAILED DESCRIPTION OF THE INVENTION

In military fields or rural areas, injuries or wounds may sometimes not be able to receive immediate medical treatment. Thus, temporary covering and/or treatment of a wound or an injury can help minimize its exposure to pathogen infection (e.g., bacterial infection) and/or additional tissue damage before it is attended for an appropriate medical treatment. However, existing materials for use in wound dressings, sealants or clotting agents are generally not reversible or dissolvable or easily detached from tissue after adhering thereto, thus currently requiring mechanical debridement or surgical incision for removal of the dressings, sealants, or clotting agents to re-expose a tissue surface, e.g., a wound, for example, in order to permit further examination and/or treatment as needed. Further, the removal process can cause additional tissue damage or trauma. Accordingly, there is a need for an improved material for wound management such that, after the material adheres to a wound or tissue, it can be easily or controllably removed therefrom in a minimally-invasive manner, whenever necessary.

Embodiments of various aspects described herein stem in part from development of thioester hydrogels that are not only mechanically strong, e.g., for use as a sealant or dressing, but can also adhere to a surface and be controllably removed or dissolved on-demand later by contacting the hydrogels with a thiolate composition, to allow for gradual re-exposure of a surface, e.g., for further examination and/or treatment. In one embodiment, a thioester hydrogel derived from multi-thiol-containing linear, branched, and/or dendritic macromolecules (e.g., but not limited to multi-thiol-containing peptide dendrimers, and/or dendrons) and activated ester-containing linear, branched and/or dendritic macromolecules (e.g., but not limited to activated ester-containing poly(ethylene glycol)) was developed and assessed for its mechanical properties, adhesive strength, and controlled dissolution in the presence of a thiolate composition (e.g., a thiolate solution) when it was applied on a skin tissue or as a sealant to seal a blood vessel puncture or as a bandage to treat a burn wound. In another embodiment, a thioester hydrogel derived from multi-thiol-containing linear, branched and/or dendritic macromolecules (e.g., but not limited to multi-thiol-containing peptide dendrimers, and/or dendrons) and maleimide-thioester-containing linear, branched and/or dendritic macromolecules (e.g., but not limited to maleimide-containing poly(ethylene glycol)) was also developed and assessed for its mechanical properties, adhesive strength and controlled dissolution in the presence of a thiolate composition (e.g., a thiolate solution) when it was applied as a hemostatic dressing in an aortic and/or hepatic injury model. In other embodiments, thioester hydrogels derived from linear, branched and/or dendritic crosslinkable polymers comprising the thioester linkages within their structures were developed and assessed for their mechanical properties, adhesive strength and controlled dissolution in the presence of a thiolate composition (e.g. a thiolate solution). For example, a thioester hydrogel can be derived from multi-amine-containing linear, branched and/or dendritic macromolecules (e.g., but not limited to multi-amine-containing peptide dendrimers, and/or dendrons) and activated ester-thioester-containing linear, branched and/or dendritic macromolecules (e.g., but not limited to, activated ester-thioester-containing poly(ethylene glycol)). In some embodiments, a thioester hydrogel can be derived from multi-amine- and thioester-containing linear, branched and/or dendritic macromolecules (e.g., but not limited to multi-amine- and thioester-containing peptide dendrimers, and/or dendrons) and activated ester-containing linear, branched and/or dendritic macromolecules (e.g., but not limited to, activated ester-containing poly(ethylene glycol)). In some embodiments, a thioester hydrogel can be derived from multi-amine- and thioester-containing linear, branched and/or dendritic macromolecules (e.g., but not limited to multi-amine-containing peptide dendrimers, and/or dendrons) and activated ester-thioester-containing linear, branched and/or dendritic macromolecules (e.g., but not limited to, activated ester-thioester-containing poly(ethylene glycol)).

Accordingly, embodiments of various aspects described herein relate to dissolvable hydrogel compositions, kits, and methods of uses. The dissolvable hydrogel compositions each comprise a thioester hydrogel (e.g., as a layer), which can be dissolved and/or washed away by addition of a composition comprising at least one nucleophile. In one embodiment, at least one nucleophile comprises a thiol moiety. The dissolvable hydrogel compositions can be optionally loaded with one or more biologically and/or pharmacologically active agent and/or chemically modified to contain or couple to the active agent(s).

The dissolvable hydrogel compositions, kits and/or methods described herein can be used in any application where a surface or void (e.g., a physical or environmental surface/void or a biological surface/void) needs to covered, filled, and/or sealed. In some embodiments, the dissolvable hydrogel compositions, kits, and/or methods described herein can be used in any application where a surface or void requires temporary and/or immediate treatment, covering and/or structural support, which can be removed later to expose the surface or void for additional care and/or management (e.g., but not limited to, examination, drug treatment, and/or surgical treatment). In these embodiments, a new composition, but not necessarily a new dissolvable hydrogel composition described herein, can be applied on the exposed surface, if necessary.

Accordingly, in some embodiments, the dissolvable hydrogel compositions, kits and methods of uses described herein can be used for clinical treatments, e.g., but not limited to, sealing, treating, and/or repairing wounds, treatment of burns or other traumatized or degenerative tissue, or repair or replacement of tissues or organs. In some embodiments, the dissolvable hydrogel compositions, kits and/or methods described herein can be used at a void, wound or injury site, e.g., but not limited to, ophthalmological, orthopedic, cardiovascular, pulmonary, skin, burn, or urinary wounds and/or injuries, including those created during surgery as well as drug delivery and tumor removal. In some embodiments, the dissolvable hydrogel compositions, kits and/or methods described herein can be used as a sealant, glue, dressing, and/or coating for surgical procedures where the site of the wound is not easily accessible and/or when sutureless surgery is desirable.

While the dissolvable hydrogel compositions described herein can exist in any form or part of a wound management device, in some embodiments, the dissolvable hydrogel compositions can be formulated for uses as bandages, sealants, dressing, glues, coatings, coverings, and/or scaffolds, which, if needed, can be subsequently dissolved by adding an aqueous solution of a thiol or other nucleophile revealing the originally-covered site. The dissolvable hydrogel compositions can be applied to a target tissue site in any formulation, e.g., but not limited to, a spray, liquid, foam, and/or preformed structure.

In some embodiments, the dissolvable hydrogel compositions, kits, and/or methods described herein can be used to form a three-dimensional scaffold, gel, matrix or template (e.g., of any shapes and/or sizes) for cell growth.

Dissolvable Hydrogels or Dissolvable Hydrogel Layers Described Herein

In one aspect, provided herein relates to compositions comprising a dissolvable thioester hydrogel. As used herein, the term "hydrogel" generally refers to a hydrophilic gel regardless of the state of hydration, and therefore includes, for example, hydrogels that are in a dehydrated or anhydrous state or in a state of partial hydration. Hydrogels are generally polymers characterized by their hydrophilicity (e.g., capacity to absorb large amounts of fluid such as water or wound exudate) and insolubility in water. Thus, they are capable of swelling in water while generally preserving their shape. Stated another way, in some embodiments, a hydrogel is a polymeric material, which exhibits the ability to swell in water and to retain a fraction of water within the structure without dissolving.

Without wishing to be limited, the hydrophilicity of hydrogels is generally due to groups such as hydroxyl, carboxyl, carboxamide, amines, sulphonate and esters, among others. On contact with water, the hydrogel assumes a swollen hydrated state that results from a balance between the dispersing forces acting on hydrated chains and cohesive forces that do not prevent the penetration of water into the polymer network. The cohesive forces are most often the result of crosslinking, but may result from electrostatic, hydrophobic or dipole-dipole interactions.

Additional information about hydrogels are described in Hydrogels, Kirk-Othmer Encyclopedia of Chemical Technology, 4th Edition, vol. 7, pp. 783-807, John Wiley and Sons, New York, the contents of which are incorporated herein by reference.

As used herein, the term "thioester hydrogel" refers to a hydrogel comprising thioester linkages/bonds throughout the hydrogel. A thioester hydrogel can be a hydrogel comprising crosslinkable macromolecules or polymers held together by thioester linkages connecting between the crosslinkable macromolecules or polymers, or a hydrogel possessing thioester linkages which are not formed from a crosslinking reaction between the crosslinkable macromolecules or polymers, but are conferred by the thioester groups inherently present in at least some of the crosslinkable macromolecules or polymers.

A thioester hydrogel is a polymeric network comprising at least about two or more thioester linkages, including, e.g., at least about two, at least about five, at least about 10, at least about 20, at least about 30, at least about 40, at least about 50, at least about 60, at least about 70, at least about 80, at least about 90, at least about 100, at least about 500, at least about 1000 or more thioester linkages. The number of the thioester linkages in a thioester hydrogel can vary with the number of reactive functional groups present in the crosslinkable macromolecules or polymers, or the number of thioester present in the macromolecules or polymers to be crosslinked.

In some embodiments, the thioester linkages within a thioester hydrogel can be contributed from or conferred by at least some of the crosslinkable macromolecules or polymers comprising the thioester linkages. For example, a thioester hydrogel can be derived from multi-amine-containing linear, branched and/or dendritic macromolecules (e.g., but not limited to multi-amine-containing peptide dendrimers, and/or dendrons) and activated ester-thioester-containing linear, branched and/or dendritic macromolecules (e.g., but not limited to activated ester-thioester-containing poly(ethylene glycol)). Alternatively, a thioester hydrogel can be derived from multi-amine- and thioester-containing linear, branched and/or dendritic macromolecules (e.g., but not limited to multi-amine- and thioester-containing peptide dendrimers, and/or dendrons) and activated ester containing linear, branched and/or dendritic macromolecules (e.g., but not limited to activated ester-containing poly(ethylene glycol)). In another embodiment, a thioester hydrogel can be derived from multi-amine- and thioester-containing linear, branched and/or dendritic macromolecules (e.g., but not limited to multi-amine- and thioester-containing peptide dendrimers, and/or dendrons) and activated ester-thioester-containing linear, branched and/or dendritic macromolecules (e.g., but not limited to, activated ester-thioester-containing poly(ethylene glycol)).

In some embodiments, thioester hydrogels are "thioester-crosslinked hydrogels." The term "thioester-crosslinked hydrogel" refers to a hydrogel comprising crosslinkable macromolecules or polymers held together by thioester linkages connecting between the crosslinkable macromolecules or polymers. In these embodiments, the thioester linkages within the thioester-crosslinked hydrogels are resulted from covalent interaction between the crosslinkable macromolecules or polymers. For example, the thioester linkages within a thioester-crosslinked hydrogel can result from reacting a first crosslinkable macromolecule or polymer comprising at least two thiols with a second crosslinkable macromolecule or polymer comprising crosslinking moieties (e.g., but not limited to N-succinimidyl moiety and/or activated ester groups) such that a crosslinking reaction between the first and second crosslinkable macromolecules or polymers forms thioester linkages. In some embodiments, the first and/or second crosslinkable macromolecules or polymers do not inherently possess any thioester groups/bonds.

In accordance with embodiments of various aspects described herein, the thioester hydrogels are dissolvable. As used herein, the term "dissolvable" refers to the capability of a hydrogel to partially or completely transform into a flowable state. For example, in some embodiments, the dissolvable thioester hydrogels can be transformed into a solution upon contact with a nucleophile as described herein. In some embodiments, the dissolution process is reversible, i.e., a hydrogel dissolved into a solution can reform from the solution. In other embodiments, the dissolution process is not reversible.

In accordance with embodiments of various aspects described herein, at least a portion of the thioester linkages within a thioester hydrogel network can react with a nucleophile that is selected to cause dissociation of the polymeric network and thus dissolution of at least a portion of the thioester hydrogel. The term "nucleophile" is recognized in the art, and as used herein generally means a chemical moiety having a reactive pair of electrons. Any molecule or ion with electrons available for donation to another molecule, e.g., a free pair of electrons or at least one pi bond, can be considered as a nucleophile. Examples of nucleophiles include, without limitations, uncharged molecules or moieties such as water, amines, thiols, mercaptans and alcohols, and charged moieties such as alkoxides, thiolates, carbanions, and a variety of organic and inorganic anions.

In one embodiment, the nucleophile selected for use in dissolution of a dissolvable thioester hydrogel described herein includes a thiol moiety. Examples of molecules comprising at least one thiol moiety include, but are not limited to, linear, branched and/or dendritic multi-thiol macromolecules, poly(ethylene glycol) thiol, thiol-containing glycerol, thiol-containing polyglycerol, thiol-containing peptides, cysteine, cystine, alkyl ester of cysteine, alkyl ester of cystine, MeSCH$_2$SH, (R) (S)-3-methyl-3-sulfanylhexan-1-ol, Ethanethiol, 1-Propanethiol, 2-Propanethiol, Butanethiol, tert-Butyl mercaptan, Pentanethiols, Thiophenol, Dimercaptosuccinic acid, Thioacetic acid, 5-mercapto-4H-[1,2,4]triazol-3-ol, 2-mercaptoacetamide, 2-Mercaptoethanol, 1,2-Ethanedithiol, Ammonium thioglycolate, Cysteamine, Methyl thioglycolate, Thiolactic acid, 1-Mercapto-2-propanol, 2-methoxyethanethiol, 3-Mercapto-1-propanol, 2,3-Dimercapto-1-propanol, 1-Thioglycerol, Mercaptosuccinic acid, 4-ethyl-5-mercapto-4H-1,2,4-triazol-3-ol, N-Carbamoyl-L-cysteine, 2-Methyl-3-sulfanylpropanoic acid, 4-mercaptobutyric acid, N-Acetylcysteamine, 3-Methyl-1-butanethiol, 1,5-Pentanedithiol, 4-Chlorothiophenol, 4-Aminothiophenol, Benzyl mercaptan, 2-furanmethanethiol, 3-mercaptohexanol, furfuryl thiol, a disulfide complex of one or more of the aforementioned thiol-containing molecules, derivatives of the aforementioned thiol-containing molecules, and any combinations thereof. Without wishing to be bound by theory, the thiol moiety can react with thioester moieties within the hydrogel based on thioester-thiol exchange, resulting in dissolution of at least a portion of the thioester hydrogel and optionally formation of amide linkages to prevent hydrogel re-formation.

Figure 7:
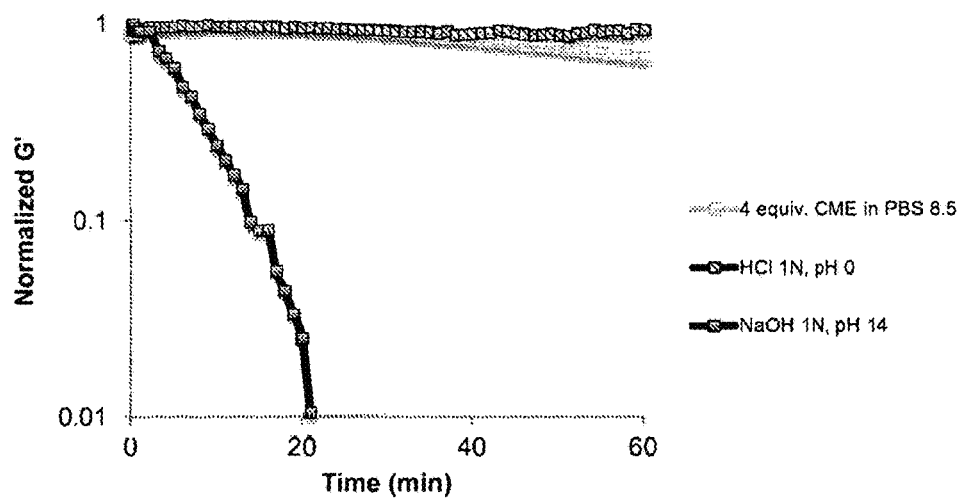
FIG. 7 is a data graph showing the stability of PEG-LysSH hydrogel (e.g., ~30 wt %) subjected to different conditions, as indicated by normalized storage moduli G' values. For example, reducing the equivalent number of thiols present in a thiolate solution (e.g., with a pH ~8.5) to four based on the number of thioester linkages resulted in almost no change in mechanical properties after at least about 60 minutes with the thiol-thioester exchange reaction occurring slowly. In addition, the PEG-LysSH hydrogel substantially maintained its mechanical property after exposure to pH 0 for at least about 60 minutes. However, the mechanical property of the PEG-LysSH hydrogel decreased over time as it was exposed to pH~14, indicating a gradual dissolution of the hydrogel.

In some embodiments, thioester hydrogels can be hydrolytically stable across a range of various pH values. In some embodiments, thioester hydrogels can be hydrolytically stable at pH in a range of about 0 to about 14, in a range of about 0 to about 12, in a range of about 0 to about 9, or in a range of about 0 to about 7. Hydrolysis of small-molecule thioesters has been previously reported in the context of the origins of life that small molecule thioesters such as CH$_3$C(O)SCH$_3$ (with a molecule weight of about 90 Da or 90 g/mol) hydrolyze ~10,000 times faster at high pH (e.g., above pH~7) and low pH (e.g., below pH~3) and are relatively stable at pH ~3 to ~7. That is, small molecule thioesters (e.g., with a molecular weight of no more than 500 Da) are hydrolytically unstable at a pH below 3 or above 7. Surprisingly, in accordance with various embodiments described herein, a thioester hydrogel, which generally has high water content, is hydrolytically stable at pH from 0 to at least about 9 (FIG. 7). Without wishing to be bound by theory, this significant increase in stability of a thioester hydrogel can be, at least in part, a result of the polymer chain backbone stabilizing the thioester bond, since hydrolysis of a thioester hydrogel would require the polymer chain to change conformation or rearrange in space. As the chains are generally confined to an area via a hydrogel, a conformational change or rearrangement of polymer chains can become less favorable.

In some embodiments, thioester hydrogels are adhesive. For example, the thioester hydrogel can adhere to a tissue, e.g., even in the presence of wound exudate and/or blood. In these embodiments, the thioester hydrogel can adhere to a tissue, e.g., tissue at or surrounding a wound, and be subsequently dissolved by adding a thiolate compound, e.g., for wound management.

In some embodiments, a thioester hydrogel can be a hydrogel comprising a network of crosslinkable macromolecules or polymers covalently held together by linkages comprising a thioester moiety. For example, in some embodiments, a thioester hydrogel can be derived or formed from a first water-soluble macromolecule or polymer comprising at least two thiol moieties and a second water-soluble macromolecule or polymer comprising at least two crosslinking moieties that can react with the thiol moieties of the first water-soluble macromolecule or polymer, to form at least two thioester crosslinks. In some embodiments, a thioester hydrogel can be derived or formed from a first water-soluble macromolecule or polymer comprising at least two thioester moieties and a second water-soluble macromolecule or polymer comprising at least two crosslinking moieties that can crosslink with the first water-soluble macromolecule. In some embodiments, a thioester hydrogel can be derived or formed from a first water-soluble macromolecule or polymer comprising at least two nucleophilic moieties that can crosslink with at least two crosslinking moieties of a second water-soluble macromolecule or polymer comprising at least two thioester moieties. In some embodiments, a thioester hydrogel can be derived or formed from a first water-soluble macromolecule or polymer comprising at least two nucleophilic moieties that can crosslink with at least two crosslinking moieties of a second water-soluble macromolecule or polymer such that the resulting hydrogel contains thioester moieties.

As used herein, the term "crosslinkable" in the context of crosslinkable macromolecules or polymers refers to the ability of macromolecules or polymers to form at least one or more covalent bonds (crosslinks) with one another to form a polymeric network (hydrogel) under a certain condition.

As used herein, the term "water-soluble" refers to the ability of crosslinkable macromolecules or polymers described herein (prior to a crosslinking reaction to form a hydrogel) to dissolve in a water-based solution under a certain condition (e.g., temperature, pH, and/or pressure). In some embodiments, the water-based solution is water, a buffered solution (e.g., phosphate buffered saline (PBS)), saline, or salt solution of pH in the range from 4 to 10.

As used interchangeably herein, the terms "macromolecule" and "polymer" refer to a natural and/or synthetic molecule with a molecular weight of at least about 200 Da, at least about 500 Da, at least about 1 kDa or more, e.g., at least about 2 kDa, at least about 3 kDa, at least about 4 kDa, at least about 5 kDa, at least about 10 kDa, at least about 20 kDa, at least about 30 kDa, at least about 40 kDa, at least about 50 kDa or more. In some embodiments, the macromolecule (or polymer) can comprise repeating structural units.

The first water-soluble macromolecule and/or the second water-soluble macromolecule can independently have a backbone in any structure, e.g., but not limited to, linear, branched, comb-like, dendritic-like including, e.g., dendrimers, dendrons and hyperbranched polymers, or any combinations thereof.

In some embodiments, the first and the second water-soluble macromolecules can both have substantially the same or similiar type of structure. For example, both the first and the second water-soluble macromolecules can have substantially linear structures, or both can have substantially dendritic-like structures, or both can have structures comprising a combination of linear and dendritic-like structures. In some embodiments, the first and the second water-soluble macromolecules can have different type of structures, e.g., one can have a linear structure, while another can have a dendritic-like structure. In some embodiments, the first water-soluble macromolecule or the second water-soluble macromolecule can comprise a substantially linear structure. In some embodiments, the first water-soluble macromolecule or the second water-soluble macromolecule can comprise a dendritic-like structure. In some embodiments, the first water-soluble macromolecule or the second water-soluble macromolecule can have a structure comprising a combination of both linear and dendritic-like structures.

In some embodiments, the first water-soluble macromolecule and/or the second water-soluble macromolecular can comprise polyesters, polyethers, polyether-esters, polyester-amines, polythioesters, polyamino acids, polyurethanes, polycarbonates, polyamino alcohols, thiols, thioesters, thioester-containing polymers (e.g., thioester-containing polymers described herein), crosslinking moieties (as described in detail below) such as N-hydroxysuccinimide moiety, maleimide (MAL) moiety, or any combinations thereof.

In some embodiments, one of the first water-soluble macromolecule and the second water-soluble macromolecule can comprise poly(ethylene glycol) in its backbone structure. In some embodiments, both of the first water-soluble macromolecule and the second water-soluble macromolecule can comprise poly(ethylene glycol) in its backbone structure. In some embodiments, neither of the first nor the second water-soluble macromolecule comprises poly(ethylene glycol) in its backbone structure.

As used herein, the term "linear" refers to a macromolecule having a backbone that is substantially free of branching. The term "substantially free of branching" as used herein means that the macromolecule backbone is either not substituted with branches or is substituted with no more than 3 branches per 1000 carbon atoms. The term "substantially free of branching" can also mean that the macromolecule backbone has no more than 2, no more than 1, no more than 0.1, or no more than 0.01 branches per 1000 carbon atoms.

The terms "branching" and "branches" as used herein refers to a side chain comprising at least one or more carbon atoms, including, e.g., at least two, at least three, at least four, at least five, at least six, at least seven, at least eight, at least nine, at least 10, at least 15, at least 20, at least 25, at least 50, at least 75, at least 100, or more carbon atoms. The side chain can be linear, branched, comb-like, and dendritic-like as defined herein. The side chain can comprise one or more (e.g., one, two, three, four or more) functional groups selected from the group consisting of hydrogen, straight or branched alkyl, cycloalkyl, aryl, olefin or alkene, alkyne, silyl, alkylsilyl, arylsilyl, alkylaryl or arylalkyl chain of 1-50 carbons, fluorocarbon, and any combinations thereof, wherein each alkyl, cycloalkyl, aryl, olefin, silyl, alkylsilyl, arylsilyl, alkylaryl, fluorocarbon, or arylalkyl chain can be optionally substituted internally or terminally by one or more hydroxyl, hydroxyether, carboxyl, carboxyester, carboxyamide, amino, mono- or di-substituted amino, thiol, thioester, sulfate, sulfonate, phosphate, phosphonate, halogen substituents, and any combinations thereof. The terms "branching" and "branches" do not include hydroxyl and acetate groups.

As used herein, the term "branched" refers to a macromolecule having a backbone with one or more substituent side chains or branches. A branched macromolecule can encompass a comb-like macromolecule and a dendritic-like macromolecule.

As used herein, the term "comb-like" refers to a macromolecule having a backbone with multiple trifunctional branchpoints from each of which a linear side chain or branch emanates. The linear side chain can be of any length, e.g., comprising at least one or more carbon atoms, including, e.g., at least two, at least three, at least four, at least five, at least six, at least seven, at least eight, at least nine, at least 10, at least 15, at least 20, at least 25, at least 50, at least 75, at least 100, or more carbon atoms.

As used herein, the term "dendritic-like" refers to a macromolecule that is highly branched and is generally defined by three components: a central core or a focal point, an interior dendritic structure (the branches), and an exterior surface with functional surface groups. The number of branch points increases upon moving from the central core or focal point to its surface and defines the generation of a dendritic-like macromolecule. The dendritic-like macromolecule can have Generation 1, Generation 2, Generation 3, Generation 4, Generation 5 or more. The dendritic-like molecules can encompass dendrimers, dendrons, hyperbranched polymers, and any combinations thereof.

In some embodiments, the dendritic-like macromolecules can comprise "dendrimers," which are generally globular monodispersed macromolecules having repeated branching units radially emanating from a central core. See, e.g., U.S. Pat. No. 5,714,166; U.S. Pat. No. 4,289,872; U.S. Pat. No. 4,435,548; U.S. Pat. No. 5,041,516; U.S. Pat. No. 5,362,843; U.S. Pat. No. 5,154,853; U.S. Ser. No. 05/739,256; U.S. Pat. No. 5,602,226; U.S. Pat. No. 5,514,764; Bosman, A. W.; Janssen, H. M.; Meijer, E. W. Chem. Rev. 1999, 99, 1665-1688. Fischer, M.; Vogtle, F. Angew. Chem. Int. Ed. 1999, 38, 884-905. Zeng, F.; Zimmerman, S. C. Chem. Rev. 1997, 97, 1681-1712. Tomalia, D. A.; Naylor, A. M.; Goddard, W. A. Angew. Chem. Int. Ed. Engl. 1990, 29, 138. These macromolecules can be synthesized using either a divergent (from core to surface) (Buhleier, W.; Wehner, F. V.; Vogtle, F. Synthesis 1987, 155-158. Tomalia, D. A.; Baker, H.; Dewald, J.; Hall, M.; Kallos, G.; Martin, S.; Roeck, J.; Ryder, J.; Smith, P. Polymer Journal 1985, 17, 117-132. Tomalia, D. A.; Baker, H.; Dewald, J.; Hall, M.; Kallos, G.; Martin, S.; Roeck, J.; Ryder, J.; Smith, P. Macromolecules 1986, 19, 2466. Newkome, G. R.; Yao, Z.; Baker, G. R.; Gupta, V. K. J. Org. Chem. 1985, 50, 2003.) or a convergent (from surface to core) (Hawker, C. J.; Frechet, J. M. J. J. Am. Chem. Soc. 1990, 112, 7638-7647) approach. Compared to linear polymers, dendrimers are highly ordered, possess high surface area to volume ratios, and exhibit numerous end groups for functionalization. Thus, dendrimers display several favorable physical properties for both industrial and biomedical applications including: small polydispersity indexes (PDI), low viscosities, high solubility and miscibility, and adhesive properties. In some embodiments, dendrimers can include derivatives of aromatic polyether or aliphatic amides, which may not be ideal for in vivo uses. (Service, R. F. Science 1995, 267, 458-459. Lindhorst, T. K.; Kieburg, C. Angew. Chem. Int. Ed. 1996, 35, 1953-1956. Ashton, P. R.; Boyd, S. E.; Brown, C. L.; Yayaraman, N.; Stoddart, J. F. Angew. Chem. Int. Ed. 1997, 1997, 732-735. Wiener, E. C.; Brechbeil, M. W.; Brothers, H.; Magin, R. L.; Gansow, O. A.; Tomalia, D. A.; Lauterbur, P. C. Magn. Reson. Med. 1994, 31, 1-8. Wiener, E. C.; Auteri, F. P.; Chen, J. W.; Brechbeil, M. W.; Gansow, O. A.; Schneider, D. S.; Beldford, R. L.; Clarkson, R. B.; Lauterbur, P. C. J. Am. Chem. Soc. 1996, 118, 7774-7782. Toth, E.; Pubanz, D.; Vauthey, S.; Helm, L.; Merbach, A. E. Chem. Eur. J. 1996, 2, 1607-1615. Adam, G. A.; Neuerburg, J.; Spuntrup, E.; Muhler, A.; Scherer, K.; Gunther, R. W. J. Magn. Reson. Imag. 1994, 4, 462-466. Bourne, M. W.; Margerun, L.; Hylton, N.; Campion, B.; Lai, J. J.; Dereugin, N.; Higgins, C. B. J. Magn. Reson. Imag. 1996, 6, 305-310. Miller, A. D. Angew. Chem. Int. Ed. 1998, 37, 1768-1785. Kukowska-Latallo, J. F.; Bielinska, A. U.; Johnson, J.; Spinder, R.; Tomalia, D. A.; Baker, J. R. Proc. Natl. Acad. Sci. 1996, 93, 4897-4902. Hawthorne, M. F. Angew. Chem. Int. Ed. 1993, 32, 950-984. Qualmann, B.; Kessels M. M.; Musiol H.; Sierralta W. D.; Jungblut P. W.; L., M. Angew. Chem. Int. Ed. 1996, 35, 909-911). Biodendrimers are a class of dendritic macromolecules having substantially all of the building blocks known to be biocompatible or degradable to natural metabolites in vivo, for example, but not limited to glycerol, lactic acid, glycolic acid, succinic acid, ribose, adipic acid, malic acid, glucose, citric acid, and any combinations thereof.

In some embodiments, the dendritic-like crosslinkable polymers described herein can comprise polyesters, polyethers, polyether-esters, and polyamino acids, copolymers thereof, or any combinations thereof. For example, poly (glycolic acid), poly(lactic acid), and their copolymers are synthetic polyesters that have been approved by the FDA for certain uses, and have been used successfully as sutures, drug delivery carriers, and tissue engineering scaffold for organ failure or tissue loss (Gilding and Reed, Polymer, 20:1459 (1979); Mooney et al., Cell Transpl., 2:203 (1994); and Lewis, D. H. in Biodegradable Polymers as Drug Delivery Systems, Chasin, M., and Langer, R., Eds., Marcel Dekker, New York, 1990). Some of their advantages include their degradability in the physiological environment to yield naturally occurring metabolic products and the ability to control their rate of degradation by varying the ratio of lactic acid. In the dendritic structures the degradation can be controlled by both the type of monomer used and the generation number.

In some embodiments, the dendritic-like macromolecules can comprise "dendrons." Dendrons are generally wedge-shaped dendrimer sections with multiple terminal groups and a single reactive function at the focal point. Dendrons can undergo orthogonal reactions utilizing the focal point and surface groups. For example, dendrons can be conjugated to another dendron or to another macromolecule. Examples of a dendron are shown in FIG. 1B (dendron 1); and in FIG. 2 (dendron 1 and dendron 2).

In some embodiments, the dendritic-like macromolecules can comprise "hyperbranched polymers." Typically, hyperbranched polymers are polydisperse dendritic macromolecules that possess dendrimer-like properties but are usually imperfectly branched and have an average number of terminal functional groups, rather than a precise number of terminal functional groups. These hyperbranched polymers can be prepared in single synthetic polymerization step.

In some embodiments, the crosslinkable polymers can be modified to suit the need of an application, such as tissue engineering applications, wound management, contrast agent(s) vehicles, and drug delivery vehicles. For example, in some embodiments, the crosslinkable polymers can comprise a biological recognition unit for cell recognition, e.g., but not limited to a peptide sequence and/or a growth factor. By way of example only, a biological recognition unit for cell recognition can be attached to the end groups or within the crosslinkable polymers. An example of a biological recognition unit for cell recognition includes a tripeptide arginine-glycine-aspartic (RGD), which can be added to the crosslinkable polymers, e.g., to improve interaction of the polymers with cells, tissues, and/or bones. Barrera et al. described the synthesis of a poly(lactic acid) (pLAL) containing a low concentration of N-epsilon-carbobenzoxy-(L)-lysine units. The polymers were chemically modified through reaction of the lysine units to introduce arginine-glycine-aspartic acid peptide sequences or other growth factors to improve polymer-cell interactions (Barrera et al., J. Am. Chem. Soc., 115:11010 (1993); U.S. Pat. No. 5,399,665 to Bartera et al.). In some embodiments, the crosslinkable polymers can be introduced with at least one or more functionalities, for example, without limitations, polyamino acids, peptides, carbohydrates, etc. in order to improve the biocompatibility and other material properties of the polymers.

First Water-Soluble Crosslinkable Macromolecule or Polymer:

The first water-soluble macromolecule or polymer comprises at least two or more nucleophilic moieties, including, at least about three, at least about four, at least about five or more nucleophilic moieties. In some embodiments, the nucleophilic moieties are selected to react with a second-water soluble macromolecule to from a thioester hydrogel. As used herein, the term "nucleophilic moiety" refers to an atom, a molecule or a functional group having at least one reactive pair of electrons. Any atom, molecule or functional group with electrons available for donation to another atom, molecule or functional group, e.g., a free pair of electrons or at least one pi bond, can be considered as a nucleophilic moiety. Examples of nucleophilic moieties include, without limitations, amines, thiols, alcohols, and any combinations thereof.

The nucleophilic moieties can be part of the side group or side chain of the first water-soluble macromolecule, the terminal group of the first water-soluble macromolecule, or a combination thereof. In one embodiment, the first water-soluble macromolecule comprises at least four thiol moieties (as nucleophilic moieties). Alternatively, in another embodiment, the first water-soluble macromolecule comprises at least three amine moieties (as nucleophilic moieties). In some embodiments, the water-soluble macromolecule can also comprise at least one or more thioester linkages that form part of the backbone structure of the macromolecule. For example, in one embodiment, the first water-soluble macromolecule comprises at least three amine moieties (as nucleophilic moieties), wherein the macromolecule further comprises thioester linkages forming part of the backnone structure of the macromolecule.

The first water-soluble macromolecule or polymer comprises at least two or more thiol moieties, including, at least about three, at least about four, at least about five or more thiol moieties. The thiol moieties can be part of the side group or side chain of the first water-soluble macromolecule, the terminal group of the first water-soluble macromolecule, or a combination thereof. In one embodiment, the first water-soluble macromolecule comprises at least four thiol moieties.

In some embodiments, the first water-soluble macromolecule can have a chemical structure of formula (I) selected from the group consisting of chemical structure (i)

(i)

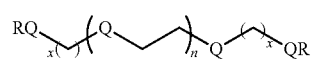

(ii)
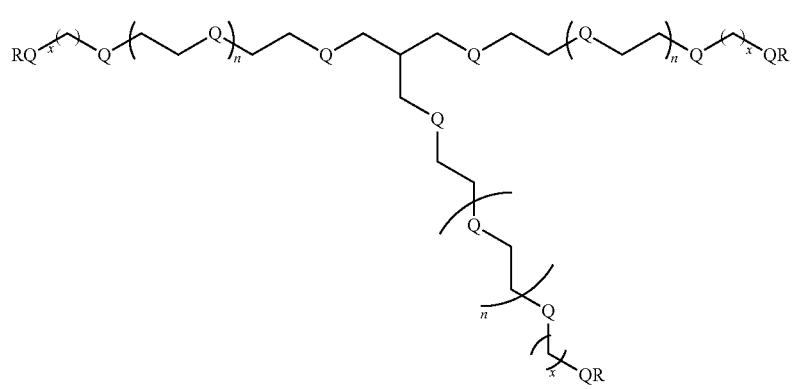
(iii)
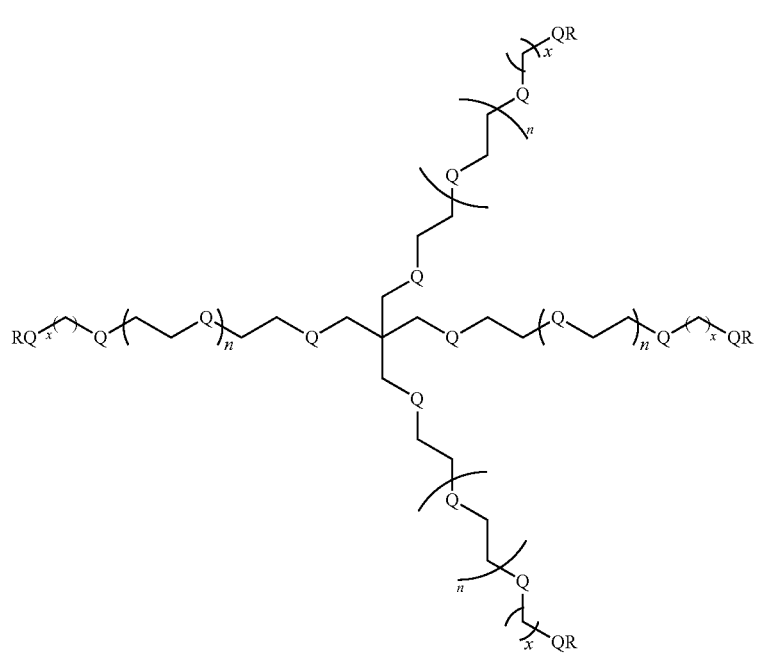
(iv)
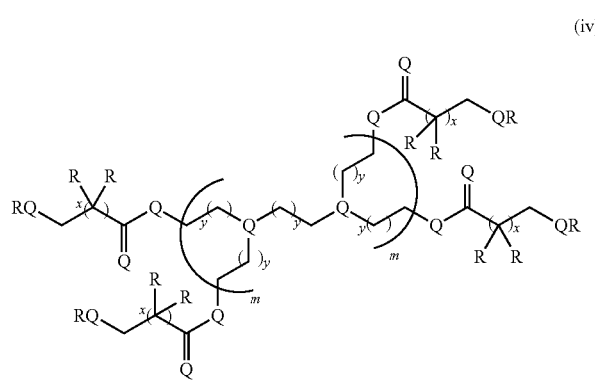
(v)
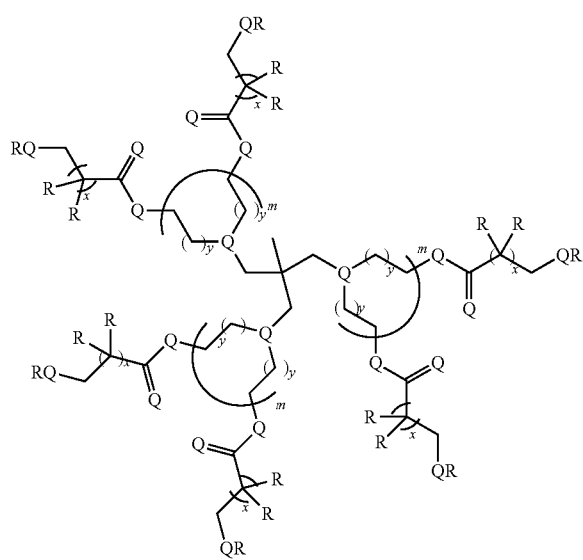

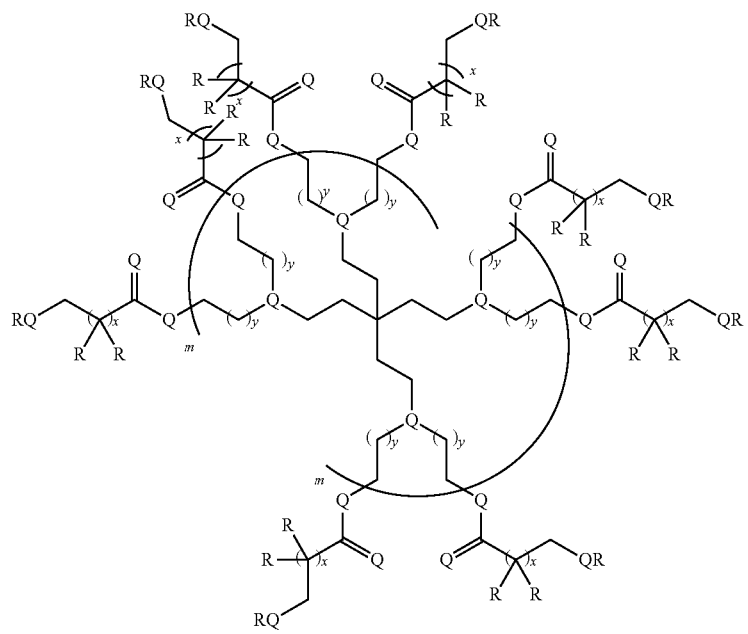
(vi)
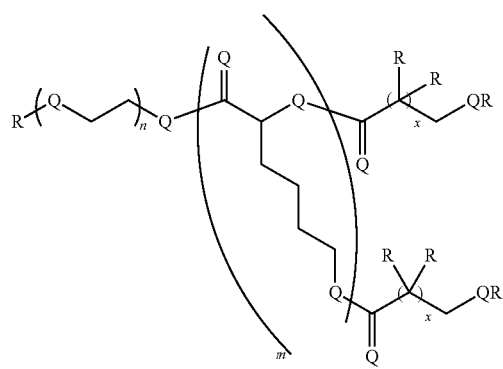
(vii)
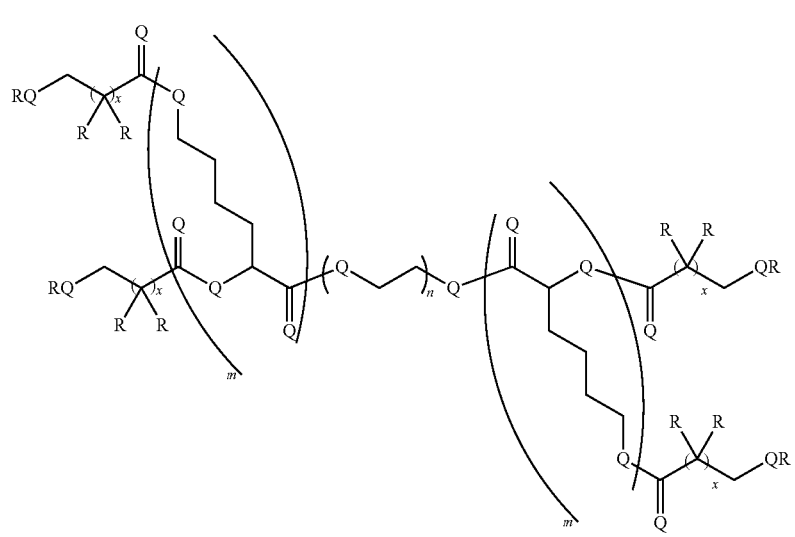
(viii)

(ix)

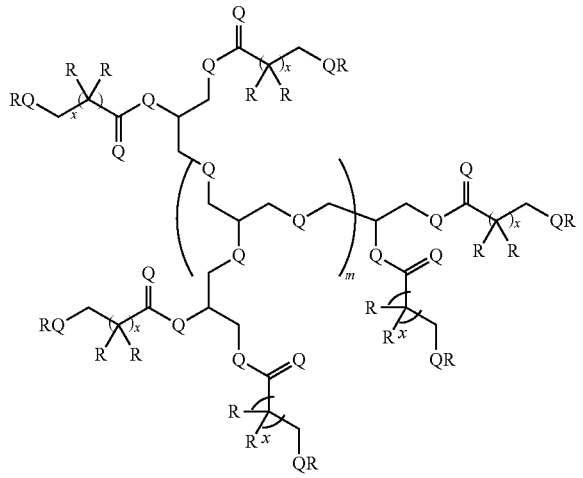

(x)

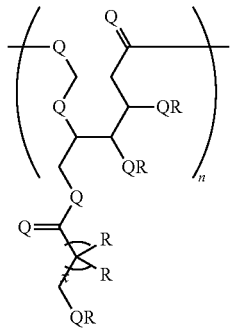

(xi)

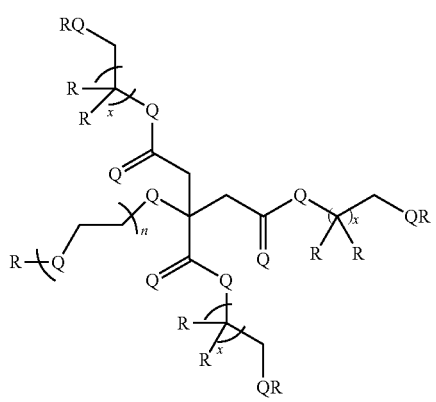

(xii)

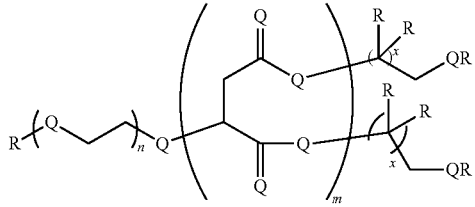

and any combinations thereof.

Q can be any atom or a group of atoms (e.g., at least two atoms or more) provided that it can form a bond (e.g., a single bond, a double bond, or a triple bond) with its neighboring atoms or groups of atoms. In some embodiments, Q can be independently selected from the group consisting of O, S, Se, NH, $CH_2$, and any combination thereof. In some embodiments, the first water-soluble macromolecule can comprise at least two Q atoms or groups, wherein the Q atoms or groups can be the same or different from at least one of the others.

R can be any atom or a group of atoms (e.g., at least two atoms or more) provided that it can form a bond (e.g., a single bond, a double bond, or a triple bond) with its adjacent atom. R can be linear, branched, aromatic, cyclic, comb-like, or dendritic-like as defined herein. In some embodiments, the first water-soluble macromolecule can comprise at least two R groups, wherein the R groups can be the same or different from at least one of the others. In some embodiments where at least two R groups are in substantially the same structure, at least one R group can be different from another R group.

In some embodiments, R can be independently selected from the group consisting of a hydrogen, straight or branched alkyl, cycloalkyl, aryl, olefin or alkene, alkyne, silyl, alkylsilyl, arylsilyl, alkylaryl or arylalkyl chain of 1-50 carbons, fluorocarbon, and any combinations thereof, wherein each alkyl, cycloalkyl, aryl, olefin, silyl, alkylsilyl, arylsilyl, alkylaryl, fluorocarbon, or arylalkyl chain can be optionally substituted internally or terminally by one or more hydroxyl, hydroxyether, carboxyl, carboxyester, carboxyamide, amino, mono- or di-substituted amino, thiol, thioester, sulfate, phosphate, phosphonate, halogen substituents, and any combinations thereof.

In some embodiments, R can comprise an oligomer or polymer of a biocompatible material, e.g., but not limited to, poly(ethylene glycol) and/or poly(ethylene oxide); poly(hydroxy acid); a carbohydrate; a protein; a polypeptide; an amino acid; a nucleic acid; a nucleotide; a polynucleotide; a DNA segment; a RNA segment; a lipid; a polysaccharide; an antibody; a pharmaceutical agent, an epitope for a biological receptor; or any combinations thereof. In some embodiments, R does not include poly(ethylene glycol).

In some embodiments, R can comprise an oligomer or polymer of a biocompatible material. As used herein, the term "biocompatible" refers to a material exhibiting essentially no cytotoxicity or immunogenicity while in contact with body fluids or tissues. The biocompatible material can be biodegradable or non-biodegradable. As used herein, the term "biodegradable" refers to the ability of a polymeric material to erode or degrade in vivo to form smaller chemical fragments. Degradation may occur, for example, by enzymatic, chemical or physical processes. Non-limiting examples of biodegradable polymeric materials can include polyesters, polyamides, polyethers, polycarbonates, polyanhydrides, polyorthoesters, polycaprolactone, polyesteramides, polycyanoacrylate, polyetherester, poly(phosphates), poly(phosphonates), poly(phosphites), polyhydric alcohol esters, blends and copolymers thereof. As used herein, the term "non-biodegradable" refers to the ability of a polymeric material to resist erosion or degradation in vivo.

In one embodiment, the first water-soluble macromolecule has a chemical structure of formula (II), wherein the formula (II) is represented as follows:

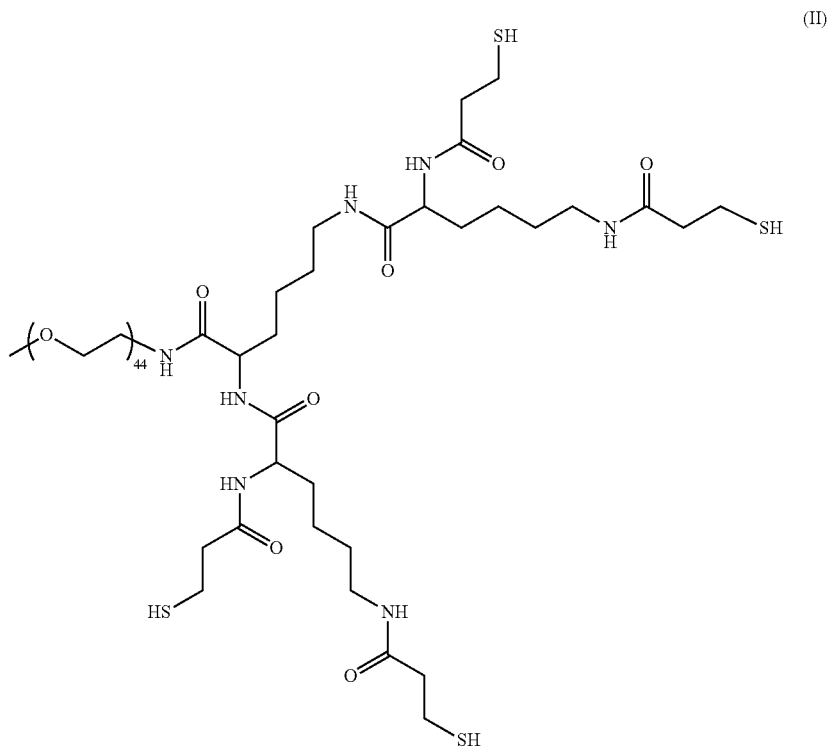

Thus, a non-biodegradable material can stay in vivo for a significantly long amount of time, or even permanently. Non-limiting examples of degradation-resistant polymeric materials can include polyethylene, polypropylene, polytetrafluoroethylene, polyurethanes, silicon, polyacrylates, ethylene-vinyl acetates (and other acyl-substituted cellulose acetates), polystyrenes, polyvinyl oxides, polyvinyl fluorides, poly(vinyl imidazoles), chlorosulphonated polyolefins, polyethylene oxides, polyvinyl alcohols (PVA), any art-recognized degradation-resistant polymers, or any combinations thereof.

In one embodiment, R can comprise poly(ethylene glycol) and/or poly(ethylene oxide);

m, n, x, and y can each independently be any integer of zero or greater (e.g., at least one or more) provided that the first water-soluble macromolecule has a molecular weight of at least about 200 Da or more (e.g., at least about 1 kDa, at least about 2 kDa or more) and can react with the second water-soluble macromolecule to form a gel. For example, m, n, x, and y can each independently be an integer of 0 or greater, including, e.g., at least one, at least two, at least three, at least four, at least five, at least six, at least seven, at least eight, at least nine, at least 10, at least 20, at least 25, at least 50, at least 75, at least 100, at least 250, at least 500, at least 750, at least 1000, at least 1500 or more. In some embodiments, m, n, x, and y can each be independently selected from an integer of 1-1000, or from an integer of 10-1000.

In some embodiments, the first water-soluble macromolecule can be a dendritic-like macromolecule as defined herein. In one embodiment, the first water-soluble macromolecule can be a dendron.

Additionally or alternatively, the first water-soluble macromolecule can comprise at least two thioester linkages or more, including, at least about three, at least about four, at least about five or more thioester linkages. In one embodiment, the first water-soluble macromolecule comprises at least three or more thioester moieties. The thioester linkages can form part of the backbone structure of the first water-soluble macromolecule. For example, the first water-soluble macromolecule can have a chemical structure of formula (III), wherein the formula (III) is represented as follows:

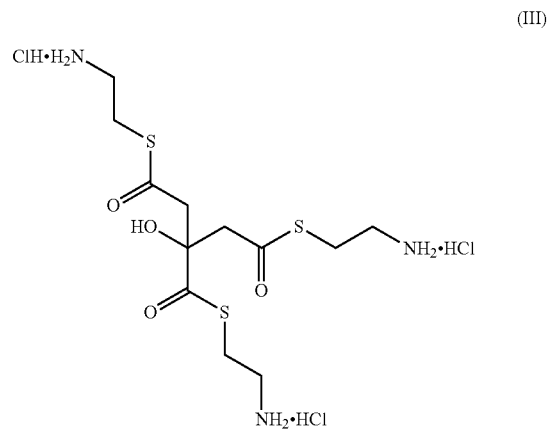

Synthesis of the first water-soluble macromolecule of formula (III) from citric acid is described in Example 6.

In some embodiments, the first water-soluble macromolecule comprises at least two or more nucleophilic moieties (e.g., but not limited to thiol, amine, alcohol), including at least about three, at least about four, at least about five or more nucleophilic moieties, that can react with a second-water soluble macromolecule that contains at least two or more thioester linkages to from a thioester hydrogel. For example, the first and the second-water soluble macromolecules can have chemical structures of formula (IV) and (V), respectively, wherein the formula (IV) and (V) are represented as follows:

of atoms (e.g., a group of at least two or more atoms) that can react with the nucleophilic moieties (e.g., but not limited to thiol (—SH), alcohol (—OH), amine (—NH$_2$) of the first water-soluble macromolecule. The second water-soluble macromolecule can comprise any art-recognized crosslinking moieties, e.g., but not limited to, I-Ethyl-3-[3-dimethylaminopropyl]carbodiimide hydrochloride (EDC or EDAC), hydroxybenzotriazole (HOBT), N-Hydroxysuccinimide (NHS), N-Hydroxysuccinimide ester (NHS ester), imidoester, maleimide, haloacetyl (e.g., iodoacetyl or bromoacetyl), hydrazide, alkoxyamine, photoreactive cross-

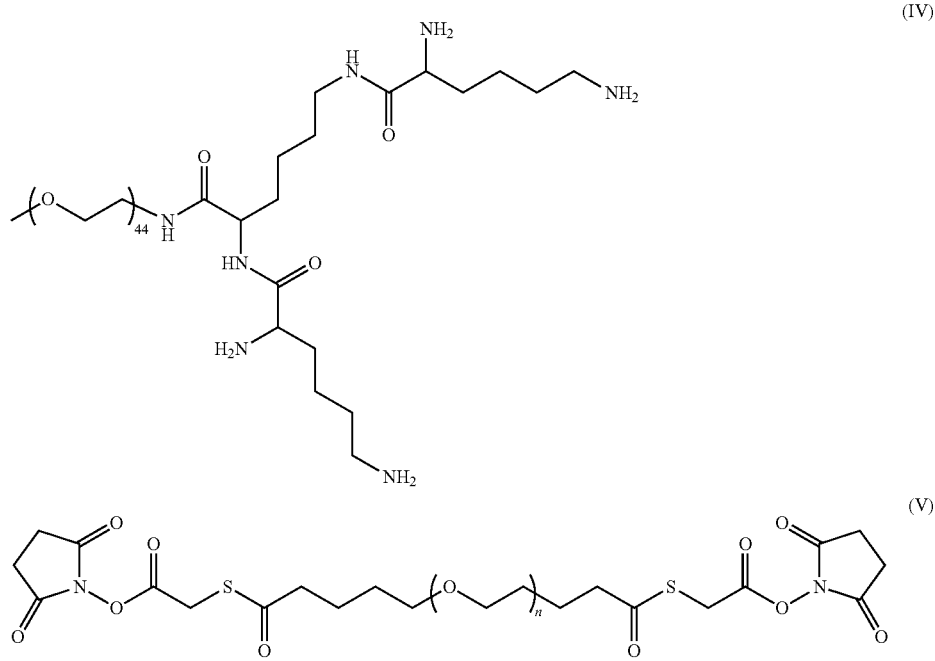

Syntheses of the first and second water-soluble macromolecules of formula (IV) and (V) are described in Examples 1 and 8, respectively.

Second Water-Soluble Macromolecule Comprising at Least Two Crosslinking Moieties:

In some embodiments, the second water-soluble macromolecule comprises at least two crosslinking moieties that can form a linkage with the nucleophilic moieties of the first water-soluble macromolecule to enable formation of a thioester hydrogel comprising at least two thioester bonds (—S—C═O—). In some embodiments, the second water-soluble macromolecule comprises at least two crosslinking moieties that can react with the thiol moieties (—SH) of the first water-soluble macromolecule to enable formation of a thioester hydrogel comprising at least two thioester bonds (—S—C═O—). For example, the second water-soluble macromolecule can comprise at least two or more crosslinking moieties, including, at least about three, at least about four, at least about five or more crosslinking moieties. The crosslinking moieties can be part of the side group or side chain of the second water-soluble macromolecule, the terminal group of the second water-soluble macromolecule, or a combination thereof. In one embodiment, the second water-soluble macromolecule comprises at least two crosslinking moieties.

As used herein, the term "crosslinking moiety" or "crosslinking moieties" refers to an organic reactive atom or group linking moieties (e.g., but not limited to phenyl azide, and diazirine), 2-(1H-7-Azabenzotriazol-1-yl)-1,1,3,3-tetramethyl uronium hexafluorophosphate methanaminium (HATU), silanization, alkyl halide, aldehyde, amino, bromo or iodoacetyl, carboxyl, hydroxyl, epoxy, ester, silane, and any combinations thereof.

In some embodiments, at least one of the crosslinking moieties of the second water-soluble macromolecule can comprise a N-Hydroxysuccinimide (NHS) moiety. In some embodiments, the second water-soluble macromolecule can further comprise at least two thioester linkages within the backbone structure of the macromolecule.

In some embodiments, at least one of the crosslinking moieties of the second water-soluble macromolecule can comprise a maleimide (MAL) moiety. In some embodiments, the second water-soluble macromolecule can further comprise at least two thioester linkages within the backbone structure of the macromolecule.

In some embodiments, at least one of the crosslinking moieties of the second water-soluble macromolecule can comprise N-Hydroxysuccinimide (NHS) and/or maleimide (MAL) moieties. In some embodiments, the second water-soluble macromolecule can further comprise at least two thioester linkages within the backbone structure of the macromolecule.

In some embodiments, at least one of the crosslinking moieties of the second water-soluble macromolecule can comprise a NHS ester, e.g., but not limited to succinimidyl valerate (SVA), succinimidyl carbonate (SC), succinimidyl glutarate (SG), succinimidyl succinate (SS), succinimidyl carboxymethyl (SCM), succinimidyl propionate (SPA), and any combinations thereof. In one embodiment, at least one of the crosslinking moieties of the second water-soluble macromolecule comprises a succinimidyl valerate.

In some embodiments, the second water-soluble macromolecule can have a chemical structure of formula (VI) selected from the group consisting of chemical structures (xiii)-(xI).

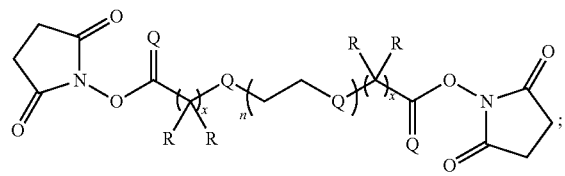
(xiii)

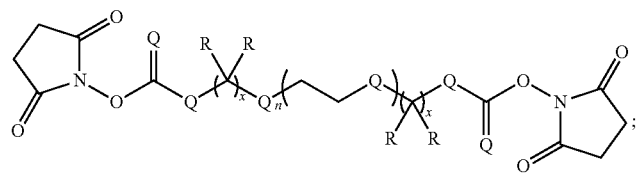
(xiv)

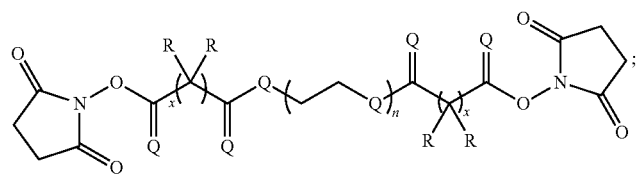
(xv)

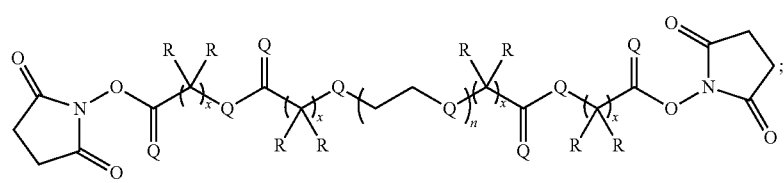
(xvi)

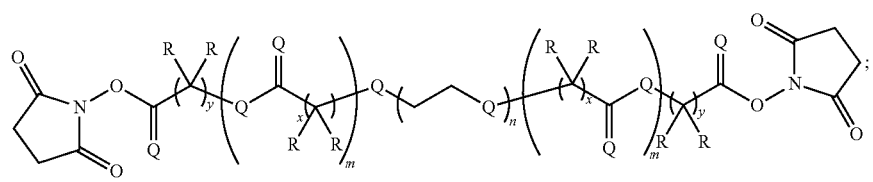
(xvii)

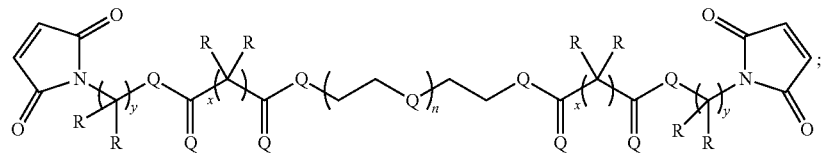
(xviii)

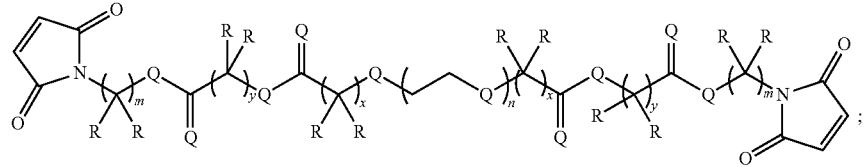
(xix)

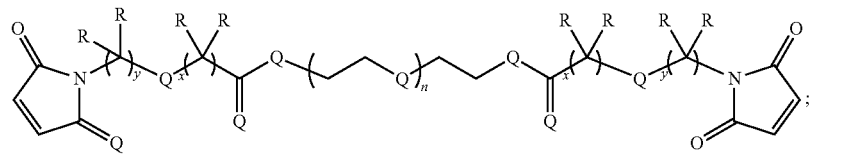
(xx)

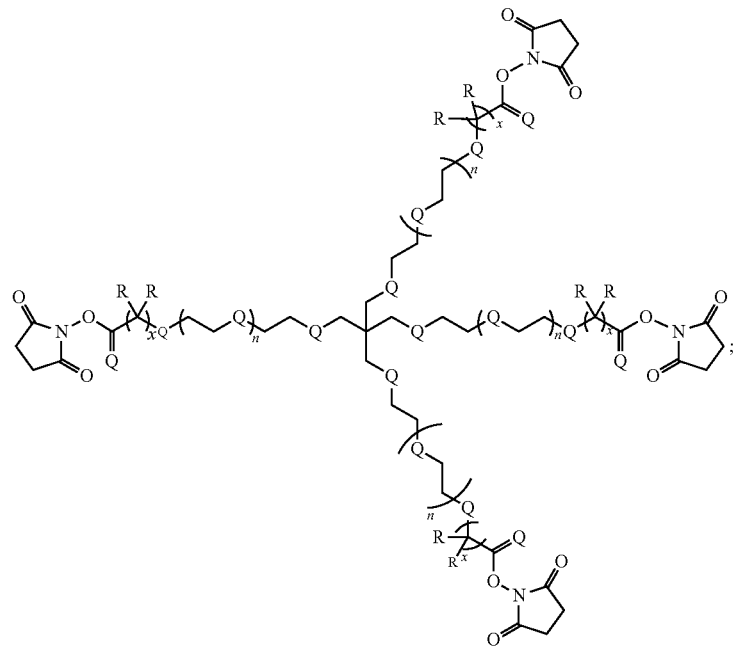
(xxi)
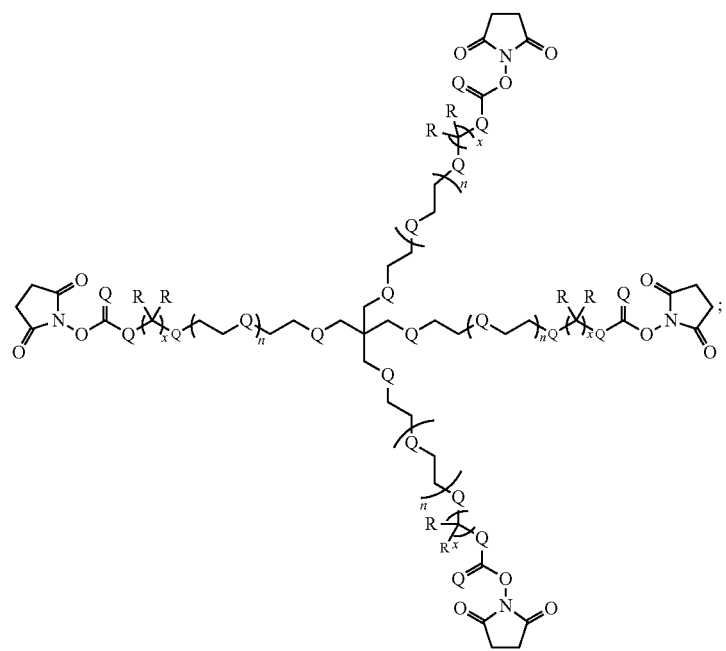
(xxii)

-continued
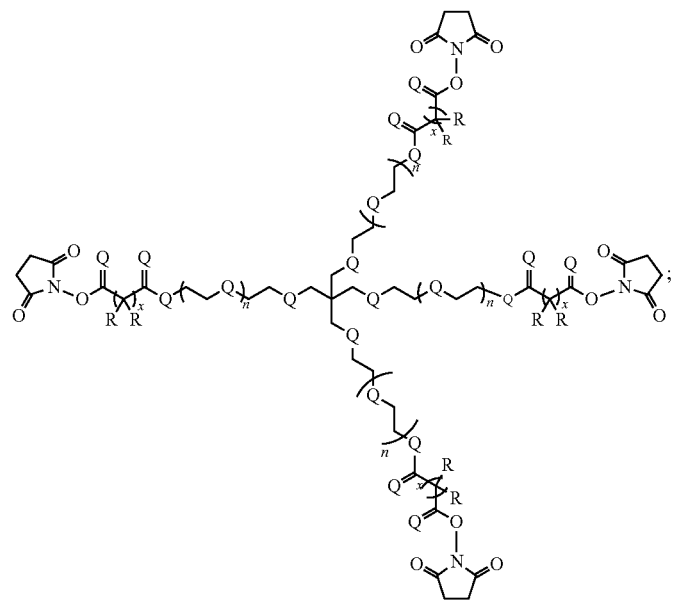
(xxiii)
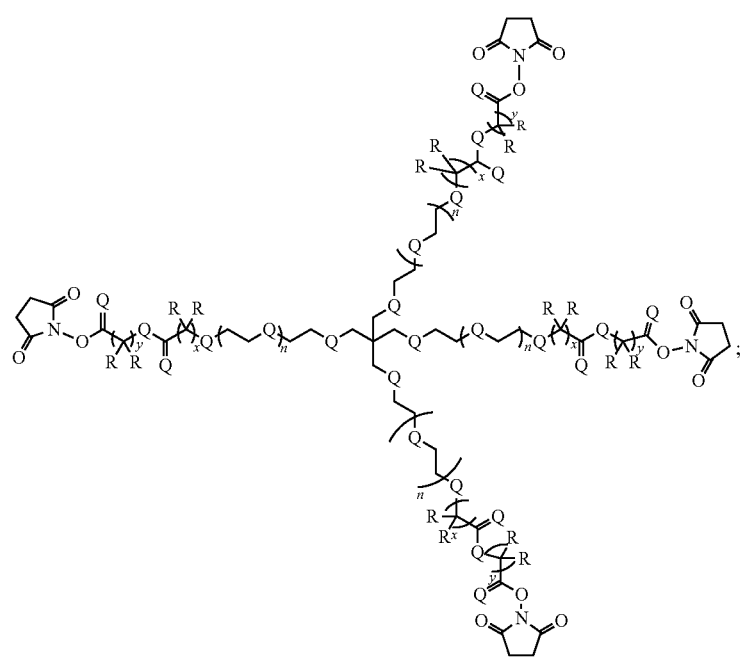
(xxiv)

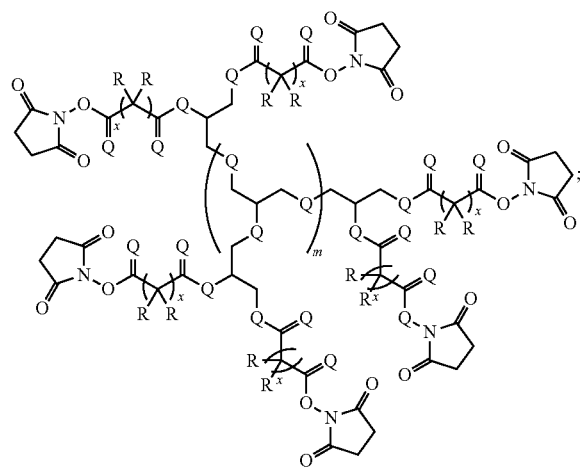
(xxv)
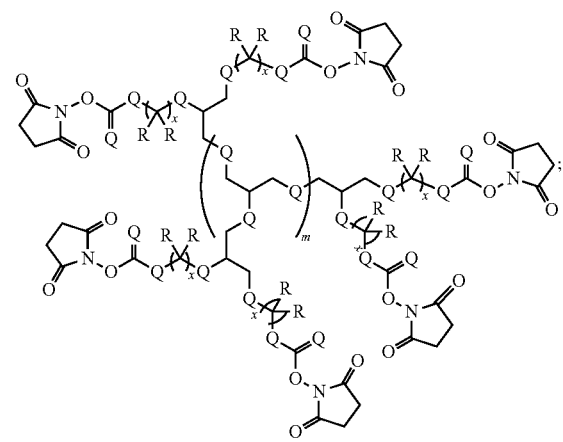
(xxvi)
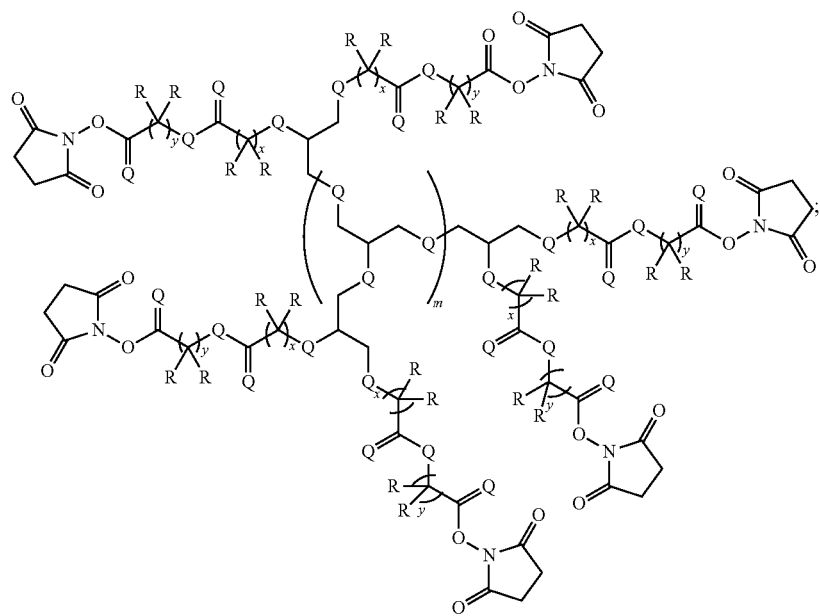
(xxvii)

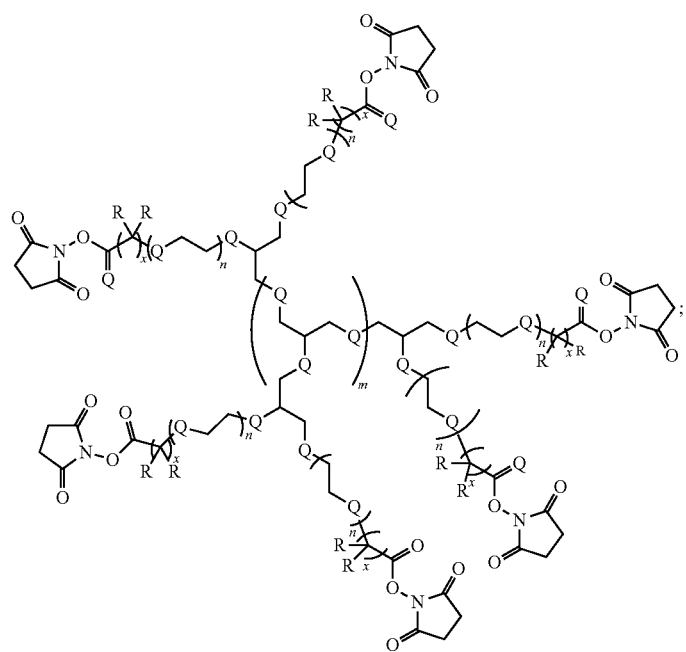
(xxviii)
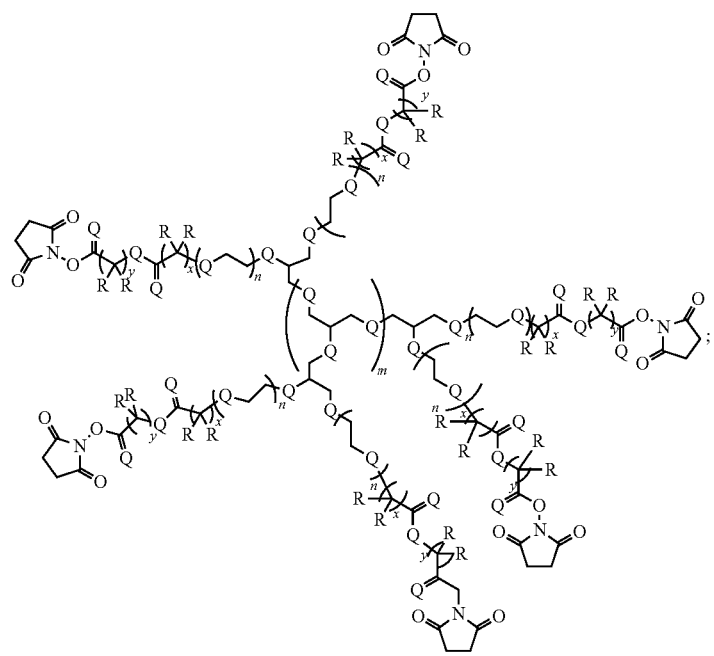
(xxix)

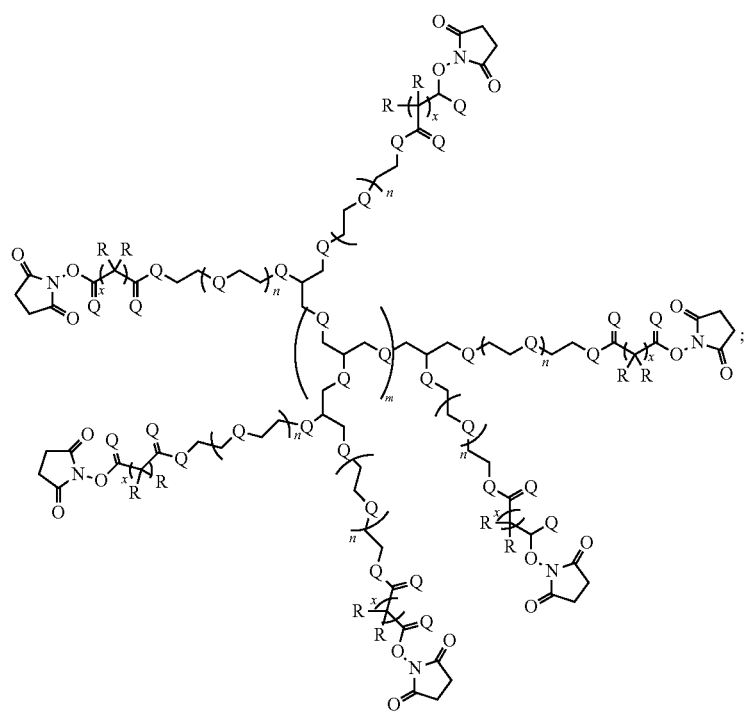
(xxx)
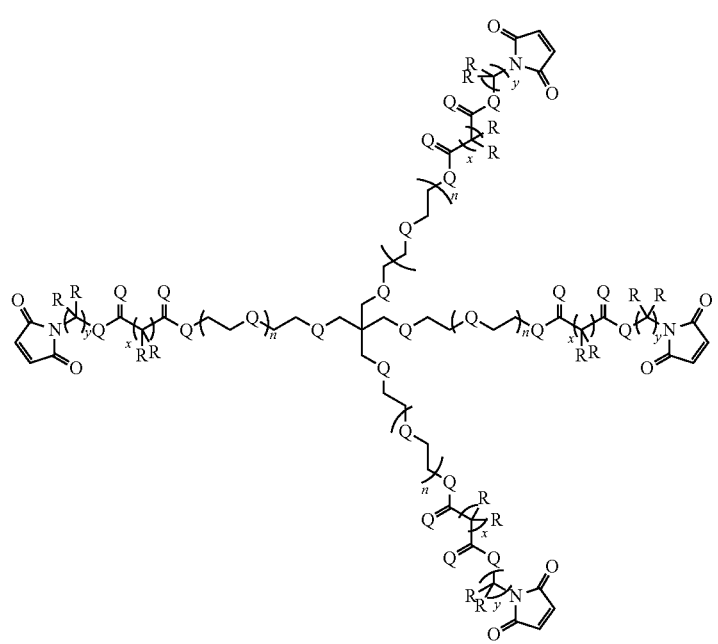
(xxxi)

-continued
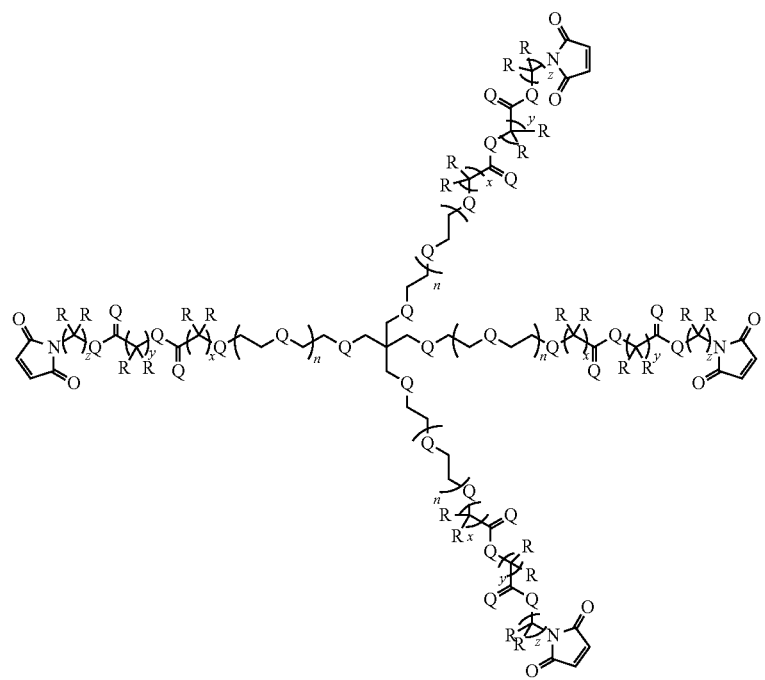
(xxxii)
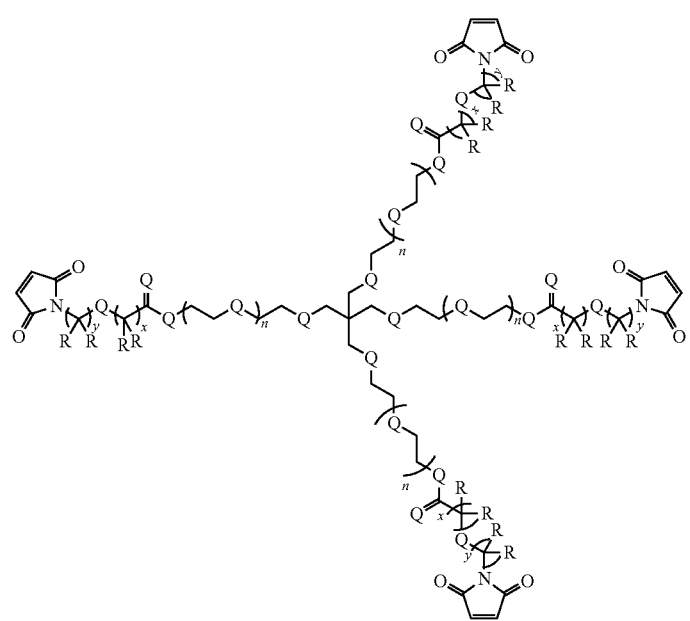
(xxxiii)

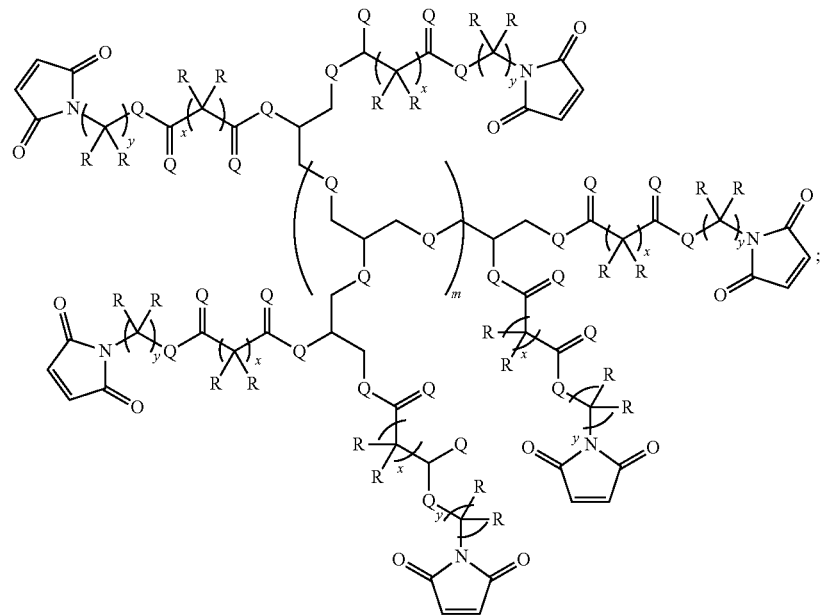
(xxxiv)
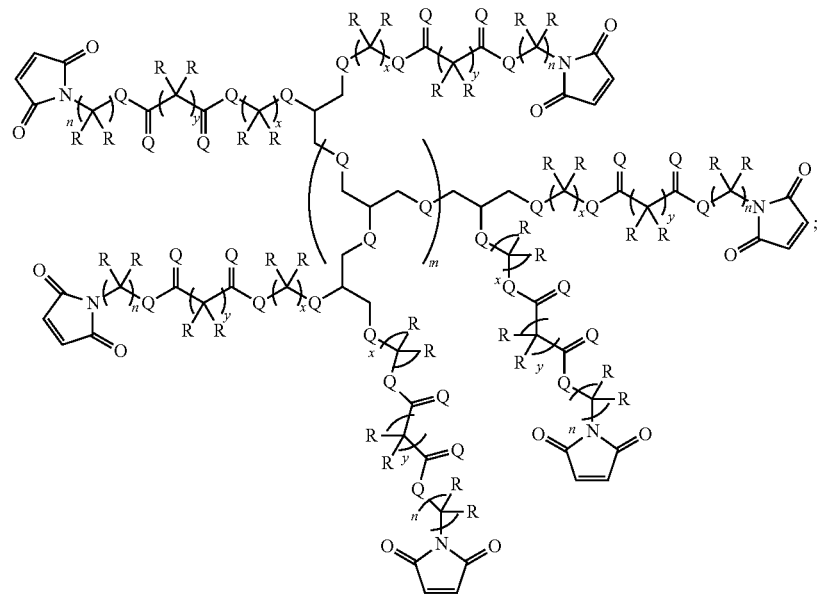
(xxxv)

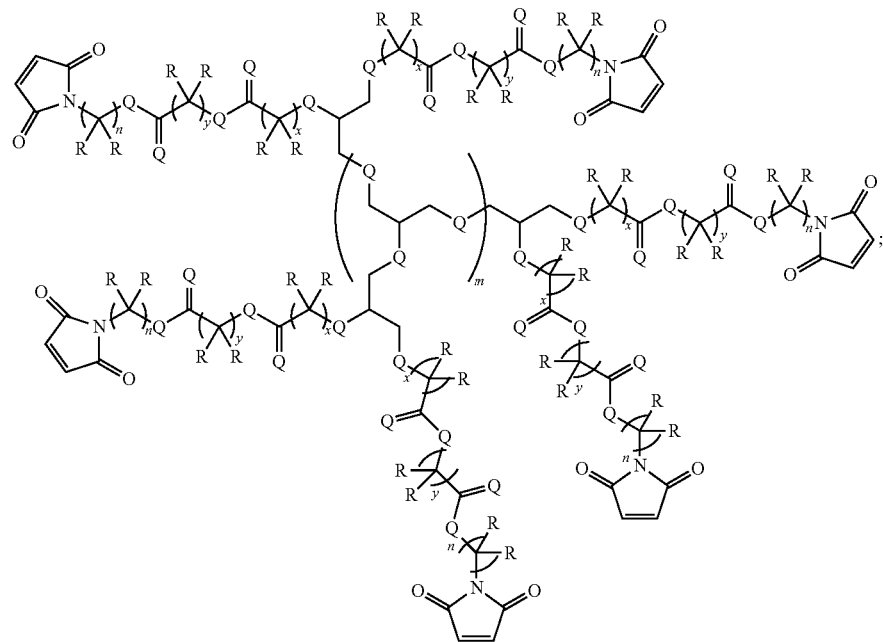
(xxxvi)
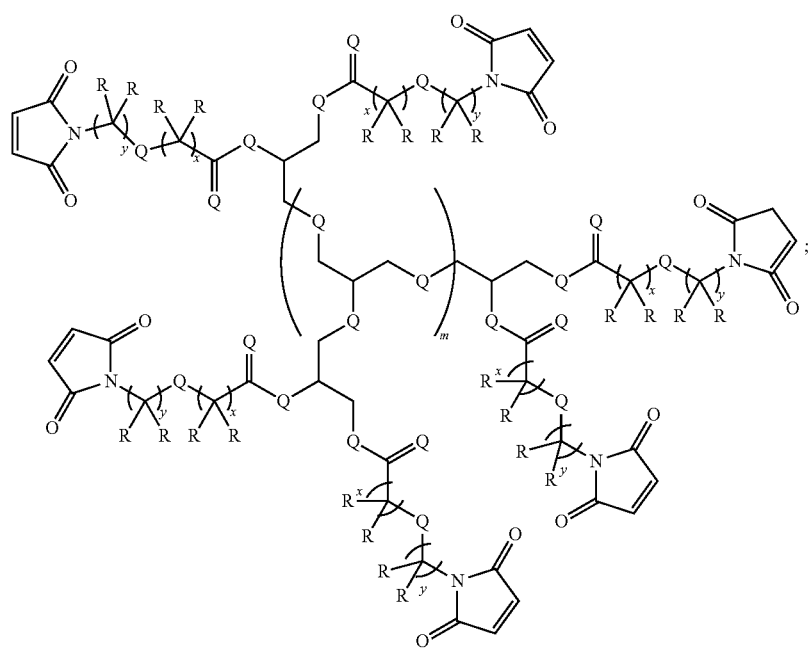
(xxxvii)

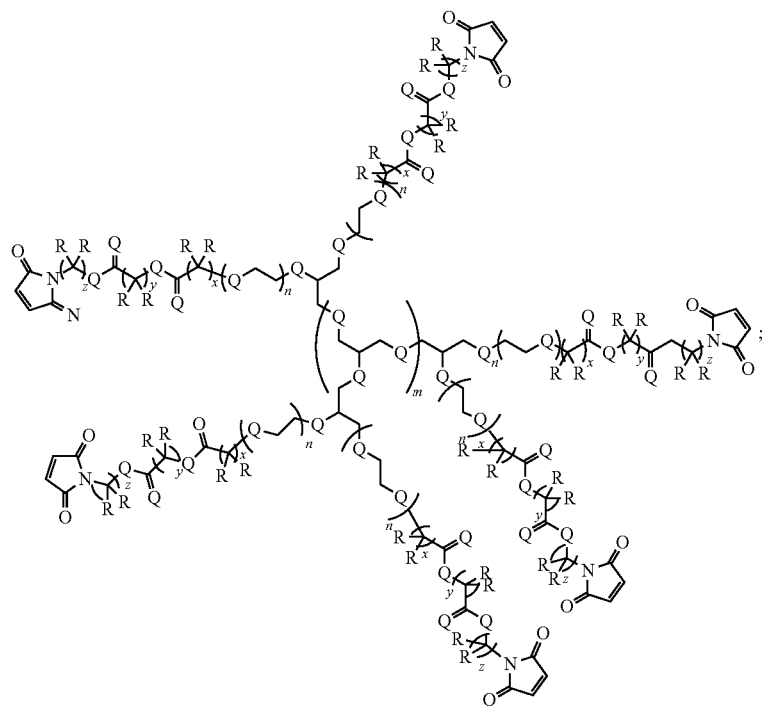
(xxxviii)
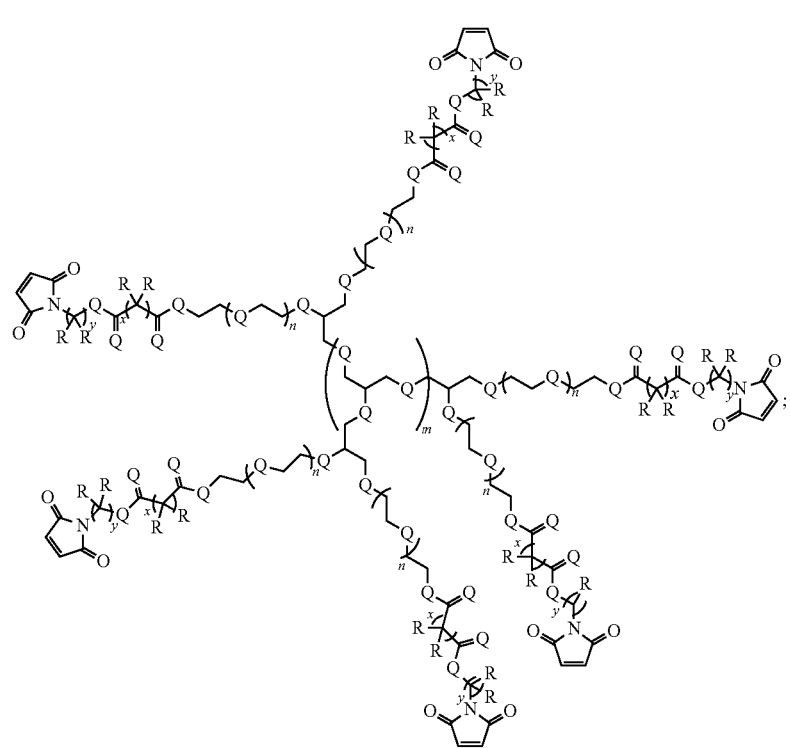
(xxxix)

(xl)

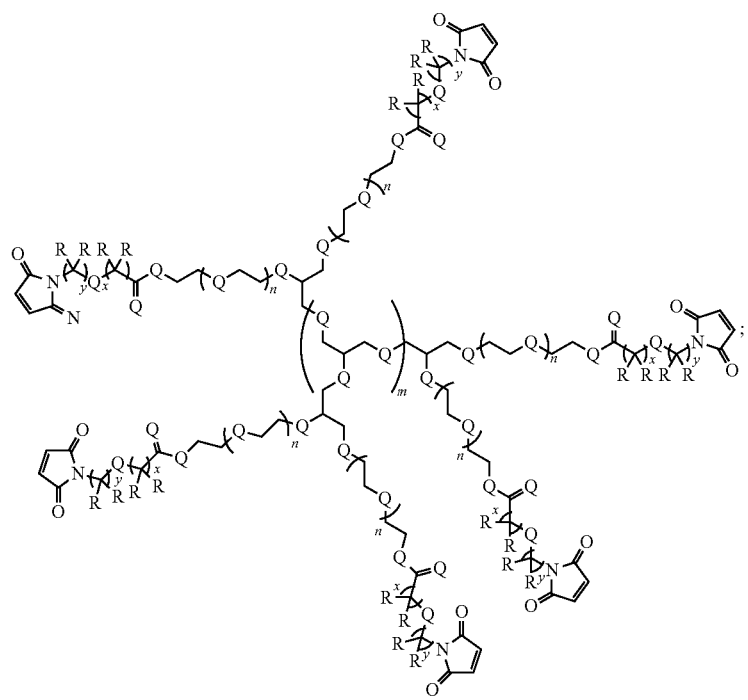

and any combinations thereof.

Q can be any atom or a group of atoms (e.g., at least two atoms or more) provided that it can form a bond (e.g., a single bond, a double bond, or a triple bond) with its neighboring atoms or groups of atoms. In some embodiments, Q can be independently selected from the group consisting of O, S, Se, NH, $CH_2$, and any combination thereof. In some embodiments, the second water-soluble macromolecule can comprise at least two Q atoms or groups, wherein the Q atoms or groups can be the same or different from at least one of the others.

R can be any atom or a group of atoms (e.g., at least two atoms or more) provided that it can form a bond (e.g., a single bond, a double bond, or a triple bond) with its adjacent atom. R can be linear, branched, aromatic, cyclic, comb-like, or dendritic-like as defined herein. In some embodiments, the second water-soluble macromolecule can comprise at least two R groups, wherein the R groups can be the same or different from at least one of the others. In some embodiments where at least two R groups are in substantially the same structure, at least one R group can be different from another R group.

In some embodiments, R can be independently selected from the group consisting of a hydrogen, straight or branched alkyl, cycloalkyl, aryl, olefin or alkene, alkyne, silyl, alkylsilyl, arylsilyl, alkylaryl or arylalkyl chain of 1-50 carbons, fluorocarbon, and any combinations thereof, wherein each alkyl, cycloalkyl, aryl, olefin, silyl, alkylsilyl, arylsilyl, alkylaryl, fluorocarbon, or arylalkyl chain can be optionally substituted internally or terminally by one or more hydroxyl, hydroxyether, carboxyl, carboxyester, carboxyamide, amino, mono- or di-substituted amino, thiol, thioester, sulfate, phosphate, phosphonate, halogen substituents; and any combinations thereof.

In some embodiments, R can comprise an oligomer or polymer of a biocompatible material, e.g., but not limited to, poly(ethylene glycol) and/or poly(ethylene oxide); poly(hydroxy acid); a carbohydrate; a protein; a polypeptide; an amino acid; a nucleic acid; a nucleotide; a polynucleotide; a DNA segment; a RNA segment; a lipid; a polysaccharide; an antibody; a pharmaceutical agent, an epitope for a biological receptor; or any combinations thereof.

m, n, x, y, and z can each independently be any integer of 0 or greater (e.g., at least 1 or greater) provided that the first water-soluble macromolecule has a molecular weight of at least about 200 Da or more (e.g., at least about 1 kDa, at least about 2 kDa or more) and can react with the first water-soluble macromolecule to form a gel. For example, m, n, x, y, and z can each independently be an integer of zero or greater, including, e.g., at least one, at least two, at least three, at least four, at least five, at least six, at least seven, at least eight, at least nine, at least 10, at least 20, at least 25, at least 50, at least 75, at least 100, at least 250, at least 500, at least 750, at least 1000, at least 1500 or more. In some embodiments, m, n, x, y, and z can each be independently selected from an integer of 1-1000, or from an integer of 10-1000.

In some embodiments, the second water-soluble macromolecule can be a linear macromolecule as defined herein. For example, in some embodiments, the second water-soluble macromolecule can have the following chemical structure (xiii), wherein R is hydrogen:

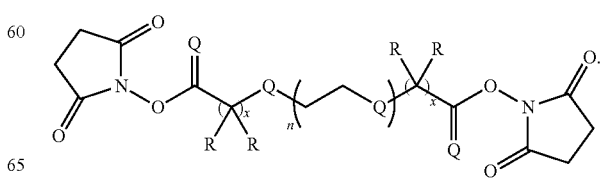

In these embodiments, Q can be oxygen. In these embodiments, x can be an integer of four. In one embodiment, the second water-soluble macromolecule is poly(ethylene glycol) disuccinimidyl valerate, e.g., with a molecular weight of about 3400 Da. The molecular weight of the poly(ethylene glycol) disuccinimidyl valerate can vary with the chain length of the poly(ethylene glycol).

In some embodiments, the second water-soluble macromolecule can have a chemical structure of formula (V) shown as follows:

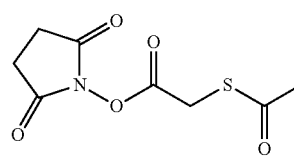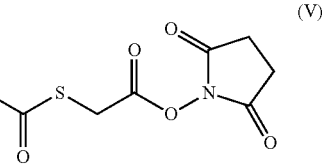

(V)

In some embodiments, the second water-soluble macromolecule can have a chemical structure of formula (VII) shown as follows:

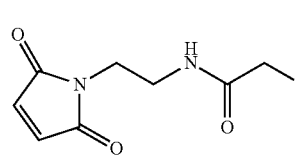

(VII)

In some embodiments, the thioester hydrogel described herein can be entirely or partially flexible. As used herein, the term "flexible" generally refers to a material being capable of bending or flexing such that it is pliant and yieldable in response to a change in surrounding condition (e.g., an external force or pressure), without causing any macroscopic breaking. A flexible material can generally alter geometric shape and/or volume to accommodate a change in surrounding condition and/or to conform to the shape of an object brought in contact with it without losing its integrity. Thus, the term "flexible" when used in reference to the thioester hydrogel described herein refers to a hydrogel being capable of swelling without losing its integrity when it is exposed to an aqueous condition and/or being conformal to the shape of a surface or void to which the thioester hydrogel is applied.

In some embodiments, the thioester hydrogel described herein can be capable of withstanding a fluid pressure of at least about 2 mmHg, including, e.g., at least about 5 mmHg, at least about 10 mmHg, at least about 20 mmHg, at least about 30 mmHg, at least about 40 mmHg, at least about 50 mmHg, at least about 60 mmHg, at least about 70 mmHg, at least about 80 mmHg, including, e.g., at least about 90 mmHg, at least about 100 mmHg, at least about 150 mmHg, at least about 200 mmHg, at least about 250 mmHg, at least about 300 mmHg, at least about 350 mmHg or more. In some embodiments, the thioester hydrogel when used as a sealant in a blood vessel can withstand an arterial pressure of at least about 80 mmHg, at least about 100 mmHg, at least about 120 mmHg, at least about 150 mmHg, at least about 200 mmHg. Thioester hydrogels can be adapted for various mechanical strengths to provide appropriate treatment of different types of wounds.

In some embodiments, the thioester hydrogel described herein can be transparent. The term "transparent" as used herein refers to a hydrogel material which can transmit an average of greater than 30% or more (including, e.g., greater than 40%, greater than 50%, greater than 60%, greater than 70%, greater than 80%, greater than 90%, greater than 95% or more) of incident visible light across the visible light spectrum.

In some embodiments, the thioester hydrogels described herein are hydrophilic. As used herein, the term "hydrophilic" in reference to a hydrogel means that the hydrogel can interact with water molecules by electrostatic interaction and/or hydrogen bonds. For example, a hydrophilic hydrogel can attract and absorb water from a surrounding environment and swell to a larger volume. A hydrophilic hydrogel can be water-soluble or water-insoluble. In accordance with embodiments of various aspects described herein, the thioester hydrogel can be dissolved in an aqueous solution comprising a thiolate compound, but remain hydrolytically stable in water or a salt solution at a pH value in a range from about 3 to at least about 9. Hydrophilicity of the hydrogel can, in part, depend on the hydrophilicity of the crosslinkable polymers that form the hydrogel. In some embodiments, a hydrophilic thioester hydrogel is a hydrogel comprising hydrophilic crosslinkable polymers, e.g., crosslinkable polymers comprising polar and/or charged functional groups, rending them to soluble in water. Examples of hydrophilic crosslinkable polymers can include, but are not limited to, poly(ethylene glycol), poly(ethylene oxide), poly(glycerol), poly(vinyl acetate), poly(vinyl pyrrolidone), poly(propylene glycol), poly(vinyl alcohol), polysiloxane, maleic anhydride copolymers, polyethers, copolymers thereof, and any combinations thereof.

In some embodiments, the thioester hydrogel described herein can be elastic. As used herein, the term "elastic" refers to a hydrogel having low Young's modulus and high yield strain compared with other types of polymeric materials.

In some embodiments, the thioester hydrogel described herein can be viscoelastic. As used herein, the term "viscoelastic" refers to a hydrogel exhibiting both elastic and viscous characteristics. For example, a viscoelastic hydrogel can at least partially return to its original form when an applied stress is released, and the response is time-dependent. In dynamic mechanical characterization, the level of viscoelasticity is proportional to the damping coefficient measured by the tan (delta) of the material. The tan (delta) is generally the ratio of the viscous dissipative loss modulus to the elastic storage modulus. High tan (delta) values can indicate a high viscous component in the material behavior and hence a strong damping to any perturbation will be observed. The measurement of these moduli is described in An Introduction to Rheology, by Barnes, H. A., Hutton, J. F., and Walters, K.; Elsevier, Amsterdam (1997).

In some embodiments, the thioester hydrogels described herein are at least 50% or more mechanically stronger than a disulfide-crosslinked hydrogel (e.g., 8-arm-PEG-SH (20 kDa)) described in Sinko, P. J. et al. Biomaterials, 2011, 32, 1204-1217) of the same weight percent. For example, in one embodiment, the ~10 wt % thioester hydrogel described herein has a storage modulus of about 6000 Pa, while a ~10 wt % disulfide-crosslinked hydrogel has a storage modulus of about 3000 Pa. In some embodiments, the thioester hydrogel described herein can have a storage modulus of at least about 3000 Pa or higher, including, e.g., at least about 4000 Pa, at least about 5000 Pa, at least about 6000 Pa, at least about 7000 Pa, at least about 8000 Pa, at least about 9000 Pa, at least about 10000 Pa, at least about 20000 Pa, at least about 30000 Pa, at least about 40000 Pa or higher.

The thioester hydrogel can form any shape, e.g., a film, a sheet, a coating, or a three-dimensional construct, e.g., a hollow and/or solid structure. In some embodiments, the thioester hydrogel can form a film, a sheet, a coating, or a layer and termed as "dissolvable hydrogel layer" herein.

In some embodiments, the thioester hydrogel can further comprise at least one or more bioactive agents described herein. In some embodiments, the thioester hydrogel can further comprise at least two or more, including, e.g., 2, 3, 4, 5, 6 or more bioactive agents described herein.

Definitions of some chemical functional groups used herein are defined as follows. As used herein, the term "alkyl" refers to an aliphatic hydrocarbon group which can be straight or branched having one to about 60 carbon atoms in the chain, and which preferably have about six to about 50 carbons in the chain. "Lower alkyl" refers to an alkyl group having one to about nine carbon atoms. "Higher alkyl" refers to an alkyl group having about 10 to about 20 carbon atoms. The alkyl group can be optionally substituted with one or more alkyl group substituents which can be the same or different, where "alkyl group substituent" includes halo, amino, aryl, hydroxy, alkoxy, aryloxy, alkyloxy, alkylthio, arylthio, aralkyloxy, aralkylthio, carboxy, alkoxycarbonyl, oxo and cycloalkyl. There can be optionally inserted along the alkyl chain one or more oxygen, silicon, sulfur, or substituted or unsubstituted nitrogen atoms, wherein the nitrogen substituent is lower alkyl. "Branched" when used in reference to an alkyl group means an alkyl group in which a lower alkyl group, such as methyl, ethyl or propyl, is attached to a linear alkyl chain. Exemplary alkyl groups include methyl, ethyl, i-propyl, n-butyl, t-butyl, n-pentyl, heptyl, octyl, decyl, dodecyl, tridecyl, tetradecyl, pentadecyl and hexadecyl. Useful alkyl groups include branched or straight chain alkyl groups of six to 50 carbon, and also include the lower alkyl groups of one to about four carbons and the higher alkyl groups of about 12 to about 16 carbons.

As used herein, the term "alkenyl" or "alkene" refers to an alkyl group containing at least one carbon-carbon double bond. The alkenyl group can be optionally substituted with one or more "alkyl group substituents." Exemplary alkenyl groups include vinyl, allyl, n-pentenyl, decenyl, dodecenyl, tetradecadienyl, heptadec-8-en-1-yl and heptadec-8,11-dien-1-yl.

As used herein, the term "alkynyl" or "alkyne" refers to an alkyl group containing a carbon-carbon triple bond. The alkyne group can be optionally substituted with one or more "alkyl group substituents." Exemplary alkynyl groups include ethynyl, propargyl, n-pentynyl, decynyl and dodecynyl. Useful alkynyl groups include the lower alkynyl groups.

As used herein, the term "cycloalkyl" refers to a non-aromatic mono- or multicyclic ring system of about four to about 10 carbon atoms. The cycloalkyl group can be optionally partially unsaturated. The cycloalkyl group can be also optionally substituted with an aryl group substituent, oxo and/or alkylene. Representative monocyclic cycloalkyl rings include cyclopentyl, cyclohexyl and cycloheptyl. Useful multicyclic cycloalkyl rings include adamantyl, octahydronaphthyl, decalin, camphor, camphane, and noradamantyl.

As used herein, the term "aryl" refers to an aromatic carbocyclic radical containing about 6 to about 10 carbon atoms. The aryl group can be optionally substituted with one or more aryl group substituents, which can be the same or different, where "aryl group substituent" includes alkyl, alkenyl, alkynyl, aryl, aralkyl, hydroxy, alkoxy, aryloxy, aralkoxy, carboxy, aroyl, halo, nitro, trihalomethyl, cyano, alkoxycarbonyl, aryloxycarbonyl, aralkoxycarbonyl, acyloxy, acylamino, aroylamino, carbamoyl, alkylcarbamoyl, dialkylcarbamoyl, rylthio, alkylthio, alkylene and —NRR', where R and R' are each independently hydrogen, alkyl, aryl and aralkyl. Exemplary aryl groups include substituted or unsubstituted phenyl and substituted or unsubstituted naphthyl.

As used herein, the term "acyl" refers to an alkyl-CO— group, wherein alkyl is as previously described. Exemplary acyl groups comprise alkyl of 1 to about 30 carbon atoms. Exemplary acyl groups also include acetyl, propanoyl, 2-methylpropanoyl, butanoyl and palmitoyl.

As used herein, the term "aroyl" means an aryl-CO— group, wherein aryl is as previously described. Exemplary aroyl groups include benzoyl and 1- and 2-naphthoyl.

As used herein, the term "alkoxy" refers to an alkyl-O— group, wherein alkyl is as previously described. Exemplary alkoxy groups include methoxy, ethoxy, n-propoxy, i-propoxy, n-butoxy, and heptoxy.

As used herein, the term "aryloxy" refers to an aryl-O— group, wherein the aryl group is as previously described. Exemplary aryloxy groups include phenoxy and naphthoxy.

As used herein, the term "alkylthio" refers to an alkyl-S— group, wherein alkyl is as previously described. Exemplary alkylthio groups include methylthio, ethylthio, i-propylthio and heptylthio.

As used herein, the term "arylthio" refers to an aryl-S— group, wherein the aryl group is as previously described. Exemplary arylthio groups include phenylthio and naphthylthio.

As used herein, the term "aralkyl" refers to an aryl-alkyl-group, wherein aryl and alkyl are as previously described. Exemplary aralkyl groups include benzyl, phenylethyl and naphthylmethyl.

As used herein, the term "aralkyloxy" refers to an aralkyl-O— group, wherein the aralkyl group is as previously described. An exemplary aralkyloxy group is benzyloxy.

As used herein, the term "aralkylthio" refers to an aralkyl-S— group, wherein the aralkyl group is as previously described. An exemplary aralkylthio group is benzylthio.

As used herein, the term "dialkylamino" refers to an —NR'R" group, wherein each of R' and R" is independently an alkyl group as previously described. Exemplary alkylamino groups include ethylmethylamino, dimethylamino, and diethylamino.

As used herein, the term "alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

As used herein, the term "aryloxycarbonyl" refers to an aryl-O—CO— group. Exemplary aryloxycarbonyl groups include phenoxy- and naphthoxy-carbonyl.

As used herein, the term "aralkoxycarbonyl" refers to an aralkyl-O—CO— group. An exemplary aralkoxycarbonyl group is benzyloxycarbonyl.

As used herein, the term "carbamoyl" refers to an $H_2N$—CO— group.

As used herein, the term "alkylcarbamoyl" refers to a R'R"N—CO— group, wherein one of R" and R' is hydrogen and the other of R" and R' is alkyl as previously described.

As used herein, the term "dialkylcarbamoyl" refers to R'R"N—CO— group, wherein each of R" and R' is independently alkyl as previously described.

As used herein, the term "acyloxy" refers to an acyl-O— group, wherein acyl is as previously described.

As used herein, the term "acylamino" refers to an acyl-NH— group, wherein acyl is as previously described.

As used herein, the term "aroylamino" refers to an aroyl-NH— group, wherein aroyl is as previously described.

As used herein, the term "alkylene" refers to a straight or branched bivalent aliphatic hydrocarbon group having from one to about 30 carbon atoms. The alkylene group can be straight, branched, or cyclic. The alkylene group can be also optionally unsaturated and/or substituted with one or more "alkyl group substituents." There can be optionally inserted along the alkylene group one or more oxygen, sulphur, or substituted or unsubstituted nitrogen atoms, wherein the nitrogen substituent is alkyl as previously described. Exemplary alkylene groups include methylene (—$CH_2$-), ethylene (—$CH_2$-$CH_2$-), propylene (—$(CH_2)_3$-), cyclohexylene (—$C_6H_{10}$-), —CH═CH—CH═CH—, —CH═CH—$CH_2$-, —$(CF_2)_n(CH_2)_m$-, wherein n is an integer from about 1 to about 50 and m is an integer from zero to about 50, —$(CH_2)_n$-N(R)—$(CH_2)_m$-, wherein each of m and n is independently an integer from zero to about 50 and R is hydrogen or alkyl, methylenedioxy $CH_2$—O—) and ethylenedioxy (—O—$(CH_2)_2$-O—). An alkylene group can have about two to about three carbon atoms and can further have 6-50 carbons.

As used herein, the term "halo" or "halide" refers to fluoride, chloride, bromide, or iodide.

As used herein, the term "fluorocarbon" includes fluoroalkyl, fluorocycloalkyl, and fluoroether groups.

As used herein, the term "silyl" refers to hydrocarbyl derivatives of the silyl group: $R'_3Si$, wherein R' can be hydrogen, alkyl, aryl, or any combinations thereof.

Dissolvable Hydrogel Compositions Comprising a Dissolvable Hydrogel Layer Described Herein In another aspect, provided herein relates to a dissolvable hydrogel composition comprising at least one layer of the dissolvable hydrogel described herein. In some embodiments, the dissolvable hydrogel layer can function as an adhesive layer, allowing the dissolvable hydrogel composition to adhere to a surface (e.g., a tissue surrounding a wound) and be controllably removed from the tissue surface, when needed at a later time, by addition of a thiolate compound. In some embodiments, the dissolvable hydrogel layer can further comprise a bioactive agent described herein that can be released from the hydrogel layer to the adhered tissue. Examples of bioactive agents can include, but are not limited to, pharmaceutical agents, drugs, cells, gases and gaseous precursors, synthetic organic molecules, proteins, enzymes, growth factors, vitamins, steroids, polyanions, nucleosides, nucleotides, polynucleotides, nanoparticles, diagnostic agents, genetic materials, and any combinations thereof. Additional information about bioactive agents is described below in section "Bioactive agents."

In some embodiments, the dissolvable hydrogel composition can be present as a thin sheet or layer. In some embodiments, the dissolvable hydrogel composition can be present as a thin sheet or layer supported by a sheet support member to provide mechanical strength. The sheet support member for the hydrogel can, for example, be a thin scrim or net structure, for example formed of a synthetic and/or natural polymer such as polyethylene or polypropylene. The sheet support member for the dissolvable hydrogel can be disposed on the surface of the dissolvable hydrogel composition that is directed away from a surface (e.g., a wound or lesion) in use. Alternatively or additionally, the sheet support member can be embedded within the hydrogel polymer. The sheet support member can, if desired, extend beyond the margins of the hydrogel composition, and can be provided with a skin-adhesive portion to further secure the dissolvable hydrogel composition to the skin. The skin-adhesive portion can be hydrogel in nature (for example a plasticized tacky hydrogel, which can be the same as or different from the hydrogel provided on the support member), or may be another type of skin adhesive selected from the many skin adhesives known in the wound dressings art. The support member can be or can comprise a sheet member as defined in WO 2007/113452, the content of which is incorporated herein by reference. In some embodiments, the support member can comprise or be a "fibrous absorbent sheet member" as defined in WO 2007/113452 and/or can comprise one or more other sheet members defined as "other absorbent sheet members" in WO 2007/113452.

In some embodiments, the dissolvable hydrogel composition can be a multi-layer composite comprising at least one layer of the dissolvable hydrogel described herein and at least one additional layer such as additional hydrogel layer (s), and/or other polymer(s), and/or other sheet support members. By way of example only, in some embodiments, a multi-layer hydrogel composition can comprise at least one layer of the dissolvable hydrogel described herein overlaid by at least one or more drug-releasing layers and/or a breathable (air and/or moisture permeable) polymeric film (e.g., but not limited to, polyurethane film) as the top layer. The drug-releasing layer(s) can comprise a pharmaceutically active agent described herein entrapped in a hydrogel and/or polymeric matrix. The pharmaceutically active agent can be physically entrapped in the hydrogel and/or polymeric matrix, and/or conjugated to matrix-forming monomers that form the hydrogel and/or polymeric matrix.

In some embodiments, the dissolvable hydrogel composition can be provided with a protectant layer (e.g. of non-stick paper or plastic, such as siliconised paper or plastic) to protect one or both surfaces of the hydrogel composition prior to use.

While not necessary, in some embodiments, the dissolvable hydrogel composition can further comprise a degradable or non-degradable mesh to be used in combination with the dissolvable hydrogel to provide additional adhesion to a tissue site. Further, the combination of the mesh and the dissolvable hydrogel layer can provide for improved strength, which can be desirable when the area of tissue repair is large, such as a tissue plane or a hernie repair.

Meshes to be used in combination with the dissolvable hydrogel layer include, but are not limited to, commercially available products. Examples of films and meshes include INTERCEED (Johnson & Johnson, Inc.), PRECLUDE (W. L. Gore), and POLYACTIVE (poly(ether ester) multiblock copolymers (Osteotech, Inc., Shrewsbury, N.J.), based on poly(ethylene glycol) and poly(butylene terephthalate), and SURGICAL absorbable hemostat gauze-like sheet from Johnson & Johnson. Another mesh is a prosthetic polypropylene mesh with a bioresorbable coating called SEPRAMESH Biosurgical Composite (Genzyme Corporation, Cambridge, Mass.). One side of the mesh is coated with a bioresorbable layer of sodium hyaluronate and carboxymethylcellulose, providing a temporary physical barrier that separates the underlying tissue and organ surfaces from the mesh. The other side of the mesh is uncoated, allowing for complete tissue ingrowth similar to bare polypropylene mesh. In one embodiment, the fibrosis-inducing agent may be applied only to the uncoated side of SEPRAMESH and not to the sodium hyaluronate/carboxymethylcellulose coated side. Other films and meshes include: (a) BARD MARLEX mesh (C. R. Bard, Inc.), which is a very dense knitted fabric structure with low porosity; (b) monofilament polypropylene mesh such as PROLENE available from Ethicon, Inc. Somerville, N.J. (see, e.g., U.S. Pat. Nos. 5,634,931 and 5,824,082)); (c) SURGISIS GOLD and SURGISIS IHM soft tissue graft (both from Cook Surgical, Inc.) which are devices specifically configured for use to reinforce soft tissue in repair of inguinal hernias in open and laparoscopic procedures; (d) thin walled polypropylene surgical meshes such as are available from Atrium Medical Corporation (Hudson, N.H.) under the trade names PROLITE, PROLITE ULTRA, and LITEMESH; (e) COMPOSIX hernia mesh (C. R. Bard, Murray Hill, N.J.), which incorporates a mesh patch (the patch includes two layers of an inert synthetic mesh, generally made of polypropylene, and is described in U.S. Pat. No. 6,280,453) that includes a filament to stiffen and maintain the device in a flat configuration; (f) VISILEX mesh (from C. R. Bard, Inc.), which is a polypropylene mesh that is constructed with monofilament polypropylene; (g) other meshes available from C. R. Bard, Inc. which include PERFIX Plug, KUGEL Hernia Patch, 3D MAX mesh, LHI mesh, DULEX mesh, and the VENTRALEX Hernia Patch; and (h) other types of polypropylene monofilament hernia mesh and plug products include HERTRA mesh 1, 2, and 2A, HERMESH 3, 4 & 5 and HERNIAMESH plugs T1, T2, and T3 from Herniamesh USA, Inc. (Great Neck, N.Y.).

In some embodiments, the dissolvable hydrogel composition can constitute a dressing, bandage, glue, sealant, coating, and/or covering for a wound, tissue void or lesion. The dissolvable hydrogel composition can, after removal of any protectant layer as appropriate, be applied to the wound directly so that the dissolvable hydrogel layer can adhere to tissue surrounding the wound, thus contacting and/or protecting the wound and surrounding tissues. While not necessary, in some embodiments, additional conventional bandages, cloths or other protective fabrics or materials can be subsequently applied to further encase the dissolvable hydrogel composition.

In some embodiments, these compositions can be formulated to treat, seal, and/or adhere various tissues, for example, but not limited to, dura mater, cardiovascular tissue, ducts, bladders, lung tissue, liver, other parenchymal organs, bones, skeletal muscles, skin, as well as soft tissues. In some embodiments, these compositions can be formulated to treat patients suffering from a variety of internal or topical conditions, including, but not limited to, lacerations, tears, wounds, ulcers, astamoses, and surgical procedures. In some embodiments, the compositions can be formulated for use in any indication or application where a suture or staple is being used. In some embodiments, the dissolvable hydrogel composition can be formulated to form a sealant and/or glue for use where the site of the wound is not easily accessible or where sutureless surgery is desired, including, e.g., but not limited to urinary tract surgery (e.g., nephrotomy closure, urethral repair, hypospadia repair), pulmonary surgery (e.g., sealing parenchymal & bronchial leaks, bronchopleural fistula repair, persistent air leak repairs), gastrointestinal tract and stomach surgery (e.g., parotid cutaneous fistula, tracheo-oesophageal fistula, peptic ulcer repair), joint surgery (e.g., cartilage repair, meniscal repair), heart surgery (e.g., cardiac ventricular rupture repair), brain surgery (e.g., dural defect repairs), ear surgery (e.g., ear drum perforation), and post-surgical drainage reduction (e.g., mastectomy, axillary dissection). The ease of application, as well as the ability to quickly form a gel to seal a wet or dry wound, and the ability to dissolve upon addition of a thiolate compound, if needed, to release the hydrogel composition at a later time point from the wound can provide better management of a wound (e.g., delicate tissue) without any further unnecessary tissue damage and can thus promote wound healing.

In some embodiments, the dissolvable hydrogel composition can be formulated to form a cell construct or scaffold or matrix or gel, e.g., for organ/tissue repair or replacement. In these embodiments, the dissolvable hydrogel composition can further comprise cells. The cells can be incorporated into the dissolvable hydrogel layer and/or additional layers such as additional hydrogel layer(s) and/or polymer matrices, if any.

By way of example only, islets of Langerhans (the insulin producing cells of the pancreas) can be embedded in the dissolvable hydrogel and/or the dissolvable hydrogel composition, which can then be transplanted into a subject to regulate blood sugar level in a diabetic subject. Accordingly, microencapsulation of tissue-specific cells into the dissolvable hydrogel and/or the dissolvable hydrogel composition can be used to treat a number of disease states, e.g., due to cell dysfunction, including, but not limited to, Parkinson's disease (e.g., L-dopamine cells), liver disease (e.g., hepatocyte cells), and diabetes (e.g., islets of Langerhans).

Additional examples of cells that can be incorporated in the dissolvable hydrogel composition include but are not limited to hepatocytes and bile duct cells, islet cells of the pancreas, parathyroid cells, thyroid cells, cells of the adrenal-hypothalmic-pituitary axis including hormone-producing gonadal cells, epithelial cells, nerve cells, heart muscle cells, blood vessel cells, lymphatic vessel cells, kidney cells, and intestinal cells, cells forming bone and cartilage, smooth and skeletal muscle. Besides these types of cells, stem cells and/or derived stem cells (e.g., induced pluripotent stem cells) can also be used in the dissolvable hydrogel composition. For example, stem cells and/or derived stem cells can be incorporated in the dissolvable hydrogel composition and be subsequently converted to a desired specific cell type according to methods known in the art. The cells can be obtained from a patient's body (autologous cells), from a donor (allogeneic cells) and/or from established cell lines.

In some embodiments, the dissolvable hydrogel composition can be formulated to form temporary scaffolding, e.g., for cellular growth (e.g., in vitro, in vivo, and in situ) and implantation. The dissolvable hydrogel composition or the dissolvable hydrogel can be formed prior to implantation or in situ by crosslinking the crosslinkable polymers. The dissolvable hydrogel composition or the dissolvable hydrogel can adhere to the tissue after implantation, thus preventing the dissolvable hydrogel composition or the dissolvable hydrogel from moving away from the implanted site over time and allowing cells to adhere to the hydrogel for cellular growth and/or tissue regeneration. The dissolvable hydrogel or the dissolvable hydrogel composition as a temporary scaffolding can then be dissolved by addition of a thiolate compound at an appropriate time, e.g., after there is sufficient cellular growth within the hydrogel and/or tissue integration with the dissolvable hydrogel composition or the dissolvable hydrogel. In some embodiments, the dissolvable hydrogel composition can further comprise a bioactive agent described herein, e.g., but not limited to angiogenesis-inducing factors (e.g., vascular endothelial growth factors) and/or differentiation factors, to enhance vascularization and/or differentiation of the growing cell mass following implantation.

In some embodiments, the crosslinkable polymers used to form the dissolvable hydrogel described herein can have pendent heteroatom and/or functional groups (e.g., but not limited to amine, carboxylic acid) that allow control of physical properties, derivatization of the polymers with at least one bioactive agent, e.g., but not limited to a drug, and/or alteration of the biodegradability of the polymers. In some embodiments, a dissolvable hydrogel composition can form a long or a short-term implantable medical device. In some embodiments, the composition can further comprise a biologically and/or pharmaceutically active agent described herein (e.g., but not limited to, drugs, peptides, nucleic acids, and small molecules) sufficient for effective site-specific or systemic drug delivery (Gutowska et al., J. Biomater. Res., 29, 811-21 (1995) and Hoffman, J. Controlled Release, 6, 297-305 (1987)). The biologically and/or pharmaceutically active agents can be physically mixed, embedded in, dispersed in, covalently attached, or adhered to the hydrogel matrix and/or the crosslinkable polymers that form the hydrogel matrix by covalent interaction (e.g., but not limited to, hydrogen bonds) or non-covalent interaction (e.g., van der Waals interaction, electrostatic interaction, physical adsorption, and/or physical entrapment). When biologically and/or pharmaceutically active agent(s) described herein is attached to the hydrogel matrix and/or the crosslinkable polymers that form the hydrogel matrix by covalent bonds, sustained release of the active agent can be provided by means of hydrolysis of the covalent bond between the active agent and the polymer backbone as well as by the site of the active agent in the hydrogel structure (e.g., interior vs. exterior). In some embodiments, the pendent groups on the hydrogel structure can be pH sensitive such as carboxylic acid groups which further controls the pH dependent dissolution rate.

In some embodiments of various aspects described herein, the dissolvable hydrogels (or the dissolvable hydrogel layers) as described herein can be used with vacuum assisted closure. Vacuum assisted closure (also known as vacuum therapy, vacuum sealing or negative pressure wound therapy) generally employs vacuum assisted drainage to remove blood and/or serous fluid from a wound, burn area or operation site. This technique can promote healing in acute or chronic wound and/or burns. See, e.g., Xie et al. "The clinical effectiveness of negative pressure would therapy: a systematic review," Journal of Wound Care (2010) Vol. 19 (11): 490-495.

Accordingly, in some embodiments, the dissolvable hydrogel compositions described herein can further comprise a film for covering the dissolvable hydrogel or dissolvable hydrogel layer described herein, and a drainage tube connected to an opening of the film such that blood or fluid exudate from a wound can be removed via the drainage tube in the presence of vacuum or sub-atmospheric pressure. The film can provide a sealing to tissue surrounding a wound and thus allow sub-atmospheric pressure to be applied to a local wound environment.

The vacuum or sub-atmospheric pressure can be applied to a wound, burn area, or operation site continuously or intermittently, depending on the type of wound or burn being treated. The vacuum or sub-atmospheric pressure can be created using any art-recognized device or apparatus, including, e.g., wall suction apparatus, surgical vacuum bottles, and/or any commercial systems designed for vacuum assisted closure. In some embodiments, such device or apparatus can provide controlled levels of continuous or intermittent sub-atmospheric pressure ranging from about 25 mmHg to about 400 mmHg or from about 25 mmHg to 200 mmHg.

In some embodiments, the vacuum device or apparatus can comprise a vacuum generator and optionally a container to collect blood or fluid exudate from a wound. The vacuum device or apparatus can be designed to suit the needs of different situations (e.g., but not limited to hospital setting, home use, and/or during transportation in an ambulance).

Applications of the Dissolvable Hydrogels and/or Dissolvable Hydrogel Compositions Described Herein and Methods of Uses The dissolvable hydrogels, dissolvable hydrogel compositions, and/or kits described herein can be used in any biomedical applications where adherence of the hydrogels to a surface (e.g., a tissue surface, a wound surface, and/or a non-biological surface) followed by a subsequent release of the hydrogel from the surface is desirable. Where the surface is a delicate surface, e.g., a tissue surface or a wound surface, release or removal of an adhesive hydrogel from the surface by a physical force, e.g., mechanical debridement and/or surgical incision can be undesirable, as it can potentially create undesirable damage and/or trauma to the surface. In accordance with embodiments of various aspects described herein, the dissolvable hydrogel described herein, while adhesive to a tissue surface, can be dissolved by addition of a thiolate compound, thus releasing the dissolvable hydrogel off the surface and allowing the surface to be re-exposed. Exemplary applications that can be benefited from the reversibility of the dissolvable hydrogel or dissolvable hydrogel composition include, but are not limited to, wound management, tissue and/or organ repair/regeneration, temporary cell scaffolding, drug delivery, and/or any combinations thereof.

As used herein, the phrase "reversibility of the dissolvable hydrogel" refers to ability of converting the dissolvable hydrogel described herein to a solution or any flowable state by addition of a nucleophile, e.g., a thiolate compound. Without wishing to be bound by theory, conversion of the dissolvable hydrogel described herein to a flowable state or a solution is based on thioester-thiol exchange reaction. However, the flowable state or the solution does not necessarily need to be able to re-form a hydrogel. For example, the thioester-thiol exchange reaction can prevent hydrogel re-formation after dissolving the hydrogel to solution.

In some embodiments, the dissolvable hydrogels, dissolvable hydrogel compositions, and/or kits described herein can be used to improve wound management where existing dressings and/or sealants applied on a wound are removed by physical force such as mechanical debridement and/or surgical incision. Accordingly, methods for wound management in a subject are also provided herein. In one aspect, the method comprises (a) contacting a wound in a subject with a hydrogel composition comprising a dissolvable hydrogel layer, wherein the dissolvable hydrogel layer comprises first linear, branched, and/or dendritic crosslinkable polymers and second linear, branched, and/or dendritic crosslinkable polymers covalently held together, wherein the first crosslinkable polymers and/or the second crosslinkable polymers comprise at least one thioester linkage or functional group in their molecular structures; and (b) allowing the dissolvable hydrogel layer to adhere to tissue surrounding the wound. In some embodiments, the method further comprises dissolving the dissolvable hydrogel layer by adding a nucleophile, thereby releasing the hydrogel layer from the wound. In one embodiment, the nucleophile can comprise a thiolate compound or molecule. In these embodiments, at least some of the thioester linkages present within a dissolvable hydrogel network can be contributed from one or both of the first crosslinkable polymers and the second crosslinkable polymers that comprise a thioester linkage or functional group in their molecular structure. In these embodiments, the first crosslinkable polymers and/or the second crosslinkable polymers can be covalently linked together via any art-recognized chemical reactions, including, e.g., but not limited to an amine-ester reaction.

In another aspect, the method comprises (a) contacting a wound in a subject with a hydrogel composition comprising a dissolvable hydrogel layer, wherein the dissolvable hydrogel layer comprises linear, branched, and/or dendritic crosslinkable polymers held together by thioester linkages formed between the first crosslinkable polymer and the second crosslinkable polymer; and (b) allowing the dissolvable hydrogel layer to adhere to tissue surrounding the wound. In some embodiments, the method further comprises dissolving the dissolvable hydrogel layer by adding a nucleophile, thereby releasing the hydrogel layer from the wound. In one embodiment, the nucleophile can comprise a thiolate compound or molecule. In some embodiments, the first crosslinkable polymers and the second crosslinkable polymers do not necessarily possess thioester linkage or functional group in their molecular structures. In these embodiments, thioester linkages present within a dissolvable hydrogel can result or be formed from covalent interaction between the first crosslinkable polymers and the second crosslinkable polymers. For example, the thioester linkages present within a dissolvable hydrogel can result from reacting a first crosslinkable polymer comprising at least two thiols with a second crosslinkable polymer comprising crosslinking moieties (e.g., but not limited to N-succinimidyl moiety and/or activated ester groups), wherein neither of the crosslinkable polymers has any thioester bonds in their molecular structure.

Without wishing to be bound by theory, a thioester-thiol exchange between thioester linkages in the dissolvable hydrogel layer and thiols in the thiolate compound leads to dissolution of the dissolvable hydrogel layer. In some embodiments, the thiol-thioester exchange can also result in formation of an amide linkage, thereby preventing re-formation of the first dissolvable hydrogel.

In some embodiments, the hydrogel composition comprising the dissolvable hydrogel layer can be pre-formed prior to contacting the wound. Upon the contact, the dissolvable hydrogel layer can adhere to the tissue surrounding the wound.

In alternative embodiments, the dissolvable hydrogel layer can form in situ between other components (e.g., a sheet support member, a protectant layer, a mesh) of a hydrogel composition described herein and the wound, and adhere to the tissue surrounding the wound, thus attaching the other components of the hydrogel composition to the wound. In these embodiments, the method can further comprise forming a dissolvable hydrogel layer between other components of a hydrogel composition described herein and the wound by contacting the wound and the other components of the hydrogel composition with a solution or a spray comprising a first water-soluble crosslinkable polymer and a second water-soluble crosslinkable polymer, wherein the first and the second crosslinkable polymers become covalently held together to form a thioester hydrogel.

In some embodiments, the first crosslinkable polymers and/or the second crosslinkable polymers can comprise at least one thioester linkage or functional group in their molecular structures.

In some embodiments, the first crosslinkable polymers and the second crosslinkable polymers become held together by thioester linkages formed between the first crosslinkable polymer and the second crosslinkable polymer. In these embodiments, the first crosslinkable polymers and the second crosslinkable polymers do not necessarily possess thioester linkage or functional group in their molecular structures. In these embodiments, thioester linkages present within a dissolvable hydrogel can result or be formed from covalent interaction between the nucleophilic moieties of the first crosslinkable polymers and the crosslinking moieties of the second crosslinkable polymers. For example, the thioester linkages present within a dissolvable hydrogel can result from reacting a first crosslinkable polymer comprising at least two thiols with a second crosslinkable polymer comprising crosslinking moieties (e.g., but not limited to N-succinimidyl moiety and/or activated ester groups).

In various aspects described herein, the dissolvable hydrogel layer described herein can form and adhere to the tissue surrounding the wound within seconds to minutes, e.g., within about one second to 60 minutes, within about one second to about 30 minutes, within about one second to about 15 minutes, within about one second to about 10 minutes, or within about one second to about five minutes.

While not necessary, in some embodiments, the hydrogel composition can further comprise a degradable or non-degradable mesh, as discussed earlier, to be used in combination with the dissolvable hydrogel to provide additional adhesion to a tissue site. Further, the combination of the mesh and the dissolvable hydrogel layer can provide for improved strength, which can be desirable when the area of tissue repair is large, such as a tissue plane or a hernie repair.

In some embodiments, the dissolvable hydrogel and/or the hydrogel composition comprising a dissolvable hydrogel layer described herein can be used, for example as a sealant, along with suture or staples to further close or secure a wound. When used in this manner, the sealant can provide a leak tight barrier for liquids or air.

The dissolvable hydrogel layer of the hydrogel composition can be dissolved at any appropriate time (e.g., determined by a skilled practitioner such as a physician or surgeon) after it is adhered to the tissue surrounding the wound. By way of example only, in some embodiments, the wound can be contacted with the hydrogel composition, e.g., to stop the bleeding, and/or provide temporary treatment of the wound, where immediate medical attention is not easily accessible such as in a military field, in the wild, in a rural area, at home, and/or during transportation. In these embodiments, the dissolvable hydrogel layer can be remained on the wound until the subject gains access to more definitive medical care and/or treatment, e.g., in a clinic or hospital. Then, the medical practitioner can dissolve the dissolvable hydrogel layer by addition of a thiolate compound, thereby releasing the hydrogel composition from the wound, for example, for examination and/or treatment. Accordingly, in some embodiments, the method can further comprise subjecting the re-exposed wound, upon release of the hydrogel composition from the wound, to a treatment and/or examination.

In another example where the hydrogel composition comprises a bioactive agent for treatment of a wound, the dissolvable hydrogel layer can be dissolved whenever replenishment of the bioactive agent in the hydrogel composition or administration of a different bioactive agent is required. Accordingly, in some embodiments, the method can further comprise contacting the exposed wound, upon release or removal of the prior hydrogel composition from the wound, to another hydrogel composition comprising the same bioactive agent or a different bioactive agent.

In other embodiments, the dissolvable hydrogel layer can be remained on the wound until the wound stops bleeding and/or is completely healed before the dissolvable hydrogel layer is dissolved.

Accordingly, the time duration between the step of contacting the wound with a hydrogel composition and the step of dissolving the dissolvable hydrogel layer to release the hydrogel composition from the wound can vary, for example, from about 30 minutes to about weeks or months. In some embodiments, the time duration can vary from about one hour to about one month, from about three hours to about two weeks, from about six hours to about one week, from about 12 hours to about four days, or from about 24 hours to about three days As used herein, the term "dissolving" refers to converting the dissolvable hydrogel layer to a liquid state, a solution or any flowable state. The term "flowable state" as used herein refers to a state of a material having a consistency or viscosity that permits the material to flow, e.g., with the aid of a gentle wash or rinse. In some embodiments, the dissolvable hydrogel layer is dissolved by addition of a thiolate compound to form a solution.

In some embodiments of various aspects described herein, the dissolvable hydrogels (or the dissolvable hydrogel layers) as described herein can be used with vacuum assisted closure as described earlier. For example, a dissolvable hydrogel (or dissolvable hydrogel layer) described herein can be applied to a wound, where the dissolvable hydrogel (or dissolvable hydrogel layer) can then be covered with a film to which a vacuum hose is connected. Accordingly, in some embodiments of various aspects described herein, the method can further comprise applying vacuum or providing a sub-atmospheric pressure to the wound, after the dissolvable hydrogel layer has adhered to the tissue surrounding the wound. In some embodiments, the method can further comprise, prior to application of vacuum to the wound, covering the dissolvable hydrogel (or dissolvable hydrogel layer) with a film or a thin material, to which a drainage tube is connected. The film can provide a sealing to tissue surrounding a wound and thus allow sub-atmospheric pressure to be applied to a local wound environment.

The vacuum or sub-atmospheric pressure can be applied to a wound, burn area, or operation site continuously or intermittently, depending on the type of wound or burn being treated. The vacuum or sub-atmospheric pressure can be created using any art-recognized device or apparatus, including, e.g., wall suction apparatus, surgical vacuum bottles, and/or any commercial systems designed for vacuum assisted closure. In some embodiments, such device or apparatus can provide controlled levels of continuous or intermittent sub-atmospheric pressure ranging from about 25 mmHg to about 400 mmHg or from about 25 mmHg to 200 mmHg.

When it is desired to remove the dissolvable hydrogel composition from the wound (e.g., when it is time to change the wound dressing or bandage, or for examination and/or treatment), the vacuum or sub-atmospheric pressure applied to the wound can be turned off. A nucleophile described herein (e.g., a thiolate compound or molecule) can be applied to the dissolvable hydrogel (e.g., by injection) to dissolve the hydrogel, which can then be removed from the wound using vacuum. The film or thin material, if present, can be also removed. Alternatively, the film or thin material can be removed prior to adding a nucleophile (e.g., a thiolate compound or molecule) to the dissolvable hydrogel adhered to the wound and subsequent removal of the dissolved hydrogel with a vacuum. Accordingly, in some embodiments of various aspects described herein, the method can further comprise, upon dissolving the dissolvable hydrogel or hydrogel layer, removing at least the dissolved hydrogel from the wound with vacuum. In some embodiments, blood, fluid exudate, and/or particulates present on the wound surface can also be removed by vacuum during removal of the dissolved hydrogel. In some embodiments, the vacuum assisted closure can be repeated.

A Thiolate Compound or Molecule:

A thiolate compound or molecule for use to dissolve the dissolvable hydrogel layer can be a compound or molecule comprising a thiol group (—SH). In some embodiments, the thiolate compound is a small molecule, e.g., less than 1 kDa, less than 500 Da, less than 400 Da, less than 300 Da, less than 200 Da, less than 100 Da or lower. In some embodiments, a thiolate compound is a water-soluble macromolecule greater than 500 Da. Examples of thiolate compounds include, without limitations, linear, branched and/or dendritic multi-thiol macromolecules, poly(ethyleneglycol) thiol, thiol-containing glycerol, thiol-containing polyglycerol, thiol-containing polypeptides, cysteine, cystine, alkyl ester of cysteine, alkyl ester of cystine, MeSCH2SH, (R)/(S)-3-methyl-3-sulfanylhexan-1-ol, Ethanethiol, 1-Propanethiol, 2-Propanethiol, Butanethiol, tert-Butyl mercaptan, Pentanethiols, Thiophenol, Dimercaptosuccinic acid, Thioacetic acid, 5-mercapto-4H-[1,2,4]triazol-3-ol, 2-mercaptoacetamide, 2-Mercaptoethanol, 1,2-Ethanedithiol, Ammonium thioglycolate, Cysteamine, Methyl thioglycolate, Thiolactic acid, 1-Mercapto-2-propanol, 2-methoxyethanethiol, 3-Mercapto-1-propanol, 2,3-Dimercapto-1-propanol, 1-Thioglycerol, Mercaptosuccinic acid, 4-ethyl-5-mercapto-4H-1,2,4-triazol-3-ol, N-Carbamoyl-L-cysteine, 2-Methyl-3-sulfanylpropanoic acid, 4-mercaptobutyric acid, N-Acetylcysteamine, 3-Methyl-1-butanethiol, 1,5-Pentanedithiol, 4-Chlorothiophenol, 4-Aminothiophenol, Benzyl mercaptan, 2-furanmethanethiol, 3-mercaptohexanol, furfuryl thiol, derivatives thereof, a disulfide complex of one or more of the aforementioned compounds, and any combinations thereof. In some embodiments, the thiolate compound is selected such that it is inert and does not react with the tissue, or cause any adverse or undesirable effect to the tissue. In some embodiments, the thiolate compound also encompasses a mixture of thiolate compounds described herein.

The thiolate compound can be formulated in any form to suit the application format, e.g., but not limited to spraying and/or injection and/or bath. In some embodiments, the thiolate compound can be formulated as a solution, a spray, powder, or any combinations thereof. In one embodiment, the thiolate compound is provided in an aqueous buffered solution. When the thiolate compound is applied to the dissolvable hydrogel layer adhered to a biological tissue, the pH of the aqueous buffered solution is desired to be maintained at a physiological pH, e.g., between pH ~6 and pH~8.

Figure 4:
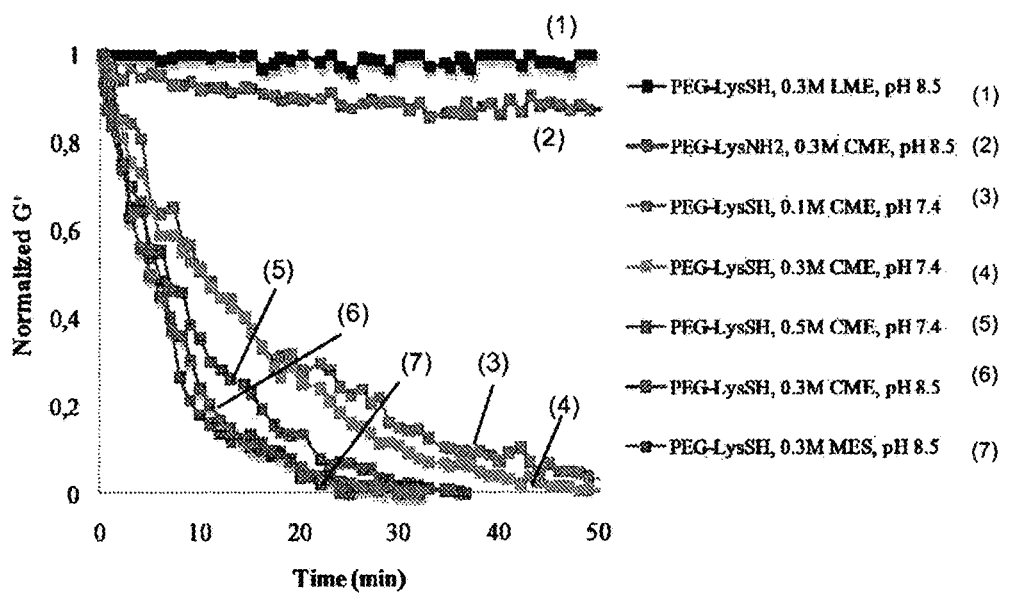
FIG. 4 is a line graph showing the reversibility of PEG-LysSH and PEG-LysNH$_2$ hydrogels at ~30 wt % upon exposure to different concentrations of (L)-cysteine methyl ester (CME) in a buffered solution, e.g., PBS, at different pHs, e.g., pH ~7.4 and pH ~8.5, or to ~0.3 M (L)-lysine methyl ester (LME) in PBS at pH ~8.5, or to ~0.3 M 2-mercaptoethanesulfonate (MES) in PBS at pH ~8.5. Storage moduli G' values were normalized to the highest G' value for each experiment.

Without wishing to be bound by theory, addition of the thiolate compound to the dissolvable hydrogel layer results in a thioester-thiol exchange (or used interchangeably herein with the term "thiol-thioester exchange"). Thiol-thioester exchange in water, where a thiol replaces a thiol in a thioester, is known to occur readily in solution with small molecules. For example, adding an equivalent number of free thiols to a solution of thioester small molecules (e.g., thiol:thioester stoichiometric ratio is about 1:1) is sufficient to lead to thiol-thioester exchange. However, thiol-thioester exchange in macromolecule assemblies, e.g., hydrogel systems, has not been explored. Surprisingly, thioester crosslinked hydrogels (also termed "dissolvable hydrogels" described herein" are shown to be unexpectedly stable. As shown in FIG. 7, when the equivalent number of thiols added to a thioester hydrogel was four (based on the number thioester linkages), there was almost no change in mechanical properties over a period of at least about 60 minutes. Thiol-thioester exchange reactions appeared to occur very slowly or insignificantly. That is, adding an equivalent number of free thiols to a thioester crosslinked hydrogel is not sufficient to allow significant thiol-thioester exchange to occur. Instead, the thioester crosslinked hydrogel is dissolved upon addition of an excess of free thiols (e.g., as shown in FIG. 4). These combined data indicate that the thioester exchange reaction in a thioester crosslinked hydrogel is generally slow and unfavorable unless an excess of free thiols is used. Without wishing to be bound by theory, as the polymer chains are generally confined to an area via the crosslinked hydrogel, a conformational change or rearrangement of polymer chains can become less favorable.

Further, as shown in FIG. 4, the rate of hydrogel dissolution can increase with concentration of the thiolate compound and/or the pH of the media in which the thiolate compound is dispersed.

Accordingly, the concentration of the thiolate compound added can, in part, depend on the number of thioester linkages present in the dissolvable hydrogel layer, pH of the media in which the thiolate compound is dispersed, and/or a desirable rate of hydrogel dissolution. To provide excess thiols relative to available thioester linkages, the stoichiometric ratio (e.g., mole ratio) of the total thiol groups added to the total thioester linkages present in the dissolvable hydrogel described herein should be greater than 1:1, greater than 2:1; greater than 3:1, greater than 4:1, greater than 5:1, greater than 10:1, greater than 20:1, greater than 25:1, greater than 50:1 or higher. In some embodiments, the thiolate compound is provided as a saturated solution. The term "saturated solution" as used herein refers to a solution of the thiolate compound present in an amount that reaches the point at which no more of the thiolate compound can be dissolved in the solution and any additional amounts will appear as a separate phase. The method need not be limited to a fully saturated thiolate solution but can include a substantially saturated or near saturated thiolate solution or concentrated thiolate solution.

As used herein, the term "wound" refers to physical disruption of the continuity or integrity of tissue structure caused by a physical (e.g., mechanical) force, a biological (e.g., thermic or actinic force), or a chemical means. In one embodiment, the term "wound" encompasses wounds of the skin. The term "wound" also encompasses contused wounds, as well as incised, stab, lacerated, open, penetrating, puncture, abrasions, grazes, burns, frostbites, corrosions, wounds caused by ripping, scratching, pressure, burns, and biting, and other types of wounds. In some embodiments, the term "wound" encompasses ulcerations (e.g., ulcers), or ulcers of the skin. In some embodiments, the term "wound" also includes surgical wounds.

The wound can be acute or chronic. As used herein, the term "chronic wound" refers to a wound that does not fully heal even after a prolonged period of time (e.g., two to three months or longer). Chronic wounds, including pressure sores, venous leg ulcers and diabetic foot ulcers, can simply be described as wounds that fail to heal. Whilst the exact molecular pathogenesis of chronic wounds is not fully understood, it is acknowledged to be multi-factorial. As the normal responses of resident and migratory cells during acute injury become impaired, these wounds are characterized by a prolonged inflammatory response, defective wound extracellular matrix (ECM) remodeling and a failure of re-epithelialization.

The wound can be an internal wound, e.g. where the external structural integrity of the skin is maintained, such as in bruising or internal ulceration, or external wounds, particularly cutaneous wounds, and consequently the tissue can be any internal or external bodily tissue. In some embodiment the tissue is skin (such as human skin), i.e. the wound is a cutaneous wound, such as a dermal or epidermal wound.

Wounds can be classified in one of two general categories, partial thickness wounds or full thickness wounds. A partial thickness wound is limited to the epidermis and superficial dermis with no damage to the dermal blood vessels. A full thickness wound involves disruption of the dermis and extends to deeper tissue layers, involving disruption of the dermal blood vessels. The healing of the partial thickness wound occurs by simple regeneration of epithelial tissue. Wound healing in full thickness wounds is more complex.

In some embodiments, the wound is selected from the group consisting of cuts and lacerations, surgical incisions or wounds, punctures, grazes, scratches, compression wounds, abrasions, friction wounds (e.g. nappy rash, friction blisters), decubitus ulcers (e.g. pressure or bed sores), thermal effect wounds (burns from cold and heat sources, either directly or through conduction, convection, or radiation, and electrical sources), chemical wounds (e.g. acid or alkali burns) or pathogenic infections (e.g. viral, bacterial or fungal) including open or intact boils, skin eruptions, blemishes and acne, ulcers, chronic wounds, (including diabetic-associated wounds such as lower leg and foot ulcers, venous leg ulcers and pressure sores), skin graft/transplant donor and recipient sites, immune response conditions, e.g. psoriasis and eczema, stomach or intestinal ulcers, oral wounds, including a ulcers of the mouth, damaged cartilage or bone, amputation wounds, corneal lesions, and any combinations thereof.

Adhesion formation is a major post-surgical complication. The incidence of clinically significant adhesion is about 5 to 10 percent with some cases as high as 100 percent. Among the most common complications of adhesion formation are obstruction, infertility, and pain. Occasionally, adhesion formation requires a second operative procedure to remove adhesion, further complicating the treatment. Given the wide-spread occurrence of post-surgical adhesions, a number of approaches have been attempted for preventing adhesions (Stangel et al., "Formation and Prevention of Postoperative Abdominal Adhesions", The Journal of Reproductive Medicine, Vol. 29, No. 3, March 1984 (pp. 143-156), and diZerega, "The Cause and Prevention of Postsurgical Adhesions", published by Pregnancy Research Branch, National Institute of Child Health and Human Development, National Institutes of Health, Building 18, Room 101, Bethesda, Md. 20205.)

Exemplary approaches for prevention of post-surgical adhesion include 1) systemic administration of ibuprofen (e.g., see Singer, U.S. Pat. No. 4,346,108), 2) parenteral administration of antihistamines, corticosteroids, and antibiotics, 3) intraperitoneal administration of dextran solution and of polyvinylpyrrolidone solution, 4) systemic administration of oxyphenbutazone, a non-steroidal anti-inflammatory drug that acts by inhibiting prostaglandin production, and 5) administration of linear synthetic and natural polymers (Hubell 6060582; Fertil. Steril., 49:1066; Steinleitner et al. (1991) "Poloxamer 407 as an Intraperitoneal Barrier Material for the Prevention of Postsurgical Adhesion Formation and Reformation in Rodent Models for Reproductive Surgery," Obstetrics and Gynecology, 77(1):48 and Leach et al. (1990) "Reduction of postoperative adhesions in the rat uterine horn model with poloxamer 407", Am. J. Obstet. Gynecol., 162(5):1317. Linsky et al., 1987 "Adhesion reduction in a rabbit uterine horn model using TC-7," J. Reprod. Med., 32:17, Diamond et al., 1987 "Pathogenesis of adhesions formation/reformation: applications to reproductive surgery," Microsurgery, 8:103).

For example, formation of post-surgical adhesions involving organs of the peritoneal cavity and the peritoneal wall is undesirable result of abdominal surgery. This occurs frequently and arises from surgical trauma. During the operation, serosanguinous (proteinaceous) exudate is released which tends to collect in the pelvic cavity (Holtz, G., 1984). If the exudate is not absorbed or lysed within a short period of time, it becomes ingrown with fibroblasts, with subsequent collagen deposition occurs leading to adhesions.

In some embodiments, the method described herein can be used to prevent formation of adhesions between injured tissues by introducing a barrier comprising the dissolvable hydrogel and/or the hydrogel composition comprising a dissolvable hydrogel layer described herein between the injured tissues. This polymeric barrier can as a sheet or coating on the exposed injured tissue to prevent surgical adhesions (Urry et al., Mat. Res. Soc. Symp. Proc., 292, 253-64 (1993)). This polymeric barrier can be controllably dissolved over a time course by addition of an appropriate amount of a thiolate compound that allows for normal healing to occur without formation of adhesions/scars etc.

In some embodiments, the wound to be contacted and/or treated by the hydrogel composition comprising a dissolvable hydrogel layer described herein can include skin lacerations. Skin lacerations are tears in the skin produced by accidents, trauma, or as a result of a surgical procedure. Lacerations often require treatment in order to close the hole in the skin, stop bleeding, and/or prevent infection. Depending on degree of lacerations, different formats of the dissolvable hydrogel compositions (e.g., bandage, glue, sealant, and/or coating) can be used to treat skin lacerations. For example, minor lacerations in the skin can be treated using an adhesive hydrogel bandage to cover the wound. However, larger lacerations may require a dissolvable hydrogel glue to help seal the wound. For example, a dissolvable hydrogel composition in a form of glue can be used to treat lacerations deeper than 0.25 inches having a jagged edge or loose flap of tissue. The location of the laceration can also affect the form of treatment. For example, it can be more desirable to treat a skin laceration on a joint using glue because adhesive bandage can tend to limit mobility of the joint. The use of glues to treat skin lacerations can also reduce the chance of scar formation.

In some embodiments, the wound to be contacted and/or treated by the hydrogel composition comprising a dissolvable hydrogel layer described herein can include liver lacerations. Lacerations of the liver can occur from trauma or as a result of a surgical procedure. The liver is a highly vascularized organ and bleeds profusely when lacerated or traumatized. Liver lacerations are generally difficult to repair owing to the nature of liver tissue. Liver tissue has very weak cohesive strength, and, consequently, sutures and staples are not satisfactory because they may pull through the liver tissue. The lack of satisfactory wound treatment methods for liver lacerations combined with the fact that it is difficult to reach the veins that feed the liver renders liver lacerations particularly serious. In fact, severe lacerations of the liver often result in the patient's death due to bleeding.

In some embodiments, the hydrogel composition (e.g., in a form of a sealant) comprising a dissolvable hydrogel described herein can be used in lung surgery to decrease or eliminate some of the problematic aspects of lung surgery, such as treatment of pneumothorax and pulmonary leaks. Types of lung surgery include, without limitations, lobectomy, lung biopsy, lung-tissue removal, pneumonectomy, thoracoscopy, and thoracotomy. Risks associated with lung surgery include wound infection, post-surgical internal bleeding, air leaks through the lung wall, pain or numbness at the incision site, and inflammation of the lungs (pneumonia). Further, air leakage is frequently observed after thoracic procedures, such as pulmonary resection and decortication. The dissolvable hydrogel can be used as a sealant to create an air-tight seal so as to prevent or reduce severe complications, such as bronchopleural fistulas and/or infection resulting from extended chest tube drainage, extended recovery time, and/or postoperative morbidity related to pulmonary surgery.

In some embodiments, the dissolvable hydrogel and/or the hydrogel composition comprising a dissolvable hydrogel described herein can be used for sealing cornea perforation. Corneal perforations afflict a fraction of the population and are produced by a variety of medical conditions (e.g., but not limited to, infection, inflammation, xerosis, neurotrophication, and/or degeneration) and/or traumas (e.g., but not limited to, chemical, thermal, surgical, and penetrating). Unfortunately, corneal perforations often lead to loss of vision and a decrease in an individual's quality of life. Depending on the type and the origin of the perforation, different treatments are currently available from suturing the wound to a cornea graft. However, this is a difficult surgical procedure given the delicate composition of the cornea and the severity of the wound, which increase the likelihood for leakage and severe astigmatism after surgery. In some embodiments where perforations cannot be treated by standard suture procedures, the dissolvable hydrogels described herein (e.g., in a form of tissue adhesive and/or glue) can be used to repair the wound. This type of treatment can be simple, quick and safe, and correspond to the requirement of a quick restoration of the integrity of the globe to avoid further complications.

Besides an easy and fast application on the wound, the criteria for an adhesive are to 1) bind to the tissue (necrosed or not, very often wet) with an adequate adhesion force, 2) be non-toxic, 3) be biodegradable or resorbable, 4) be sterilizable and 5) not interfere with the healing process. Various alkyl-cyanoacrylates are available for the repair of small perforations. However, the monomers of these "super glues", in particular those with short alkyl chains, can be toxic. They also polymerize too quickly leading to applications that might be difficult and, once polymerized, the surface of the glue is rough and hard which can result in patient discomfort and a need to wear contact lens. Even though cyanoacrylate is tolerated as a corneal sealant, a number of complications have been reported including cataract formation, corneal infiltration, glaucoma, giant papillary conjunctivitis, and symblepharon formation. Furthermore, in more than 60% of the patients, additional surgical intervention was needed.

Other glues have also been developed, for example, adhesive hemostats, based on fibrin, being usually constituted of fibrinogen, thrombin and factor XIII, as well as systems with fibrinogen and photosensitizers activated with light. However, autologous products (time consuming in an emergency) or severe treatments of the non-autologous products before clinical use are needed to avoid any contamination to the patient. An ideal sealant for corneal perforations should 1) not impair normal vision, 2) quickly restore the intraocular pressure, IOP, 3) maintain the structural integrity of the eye, 4) promote healing, 5) adhere to moist tissue surfaces, 6) possess solute diffusion properties which are molecular weight dependent and favorable for normal cornea function, 7) possess rheological properties that allow for controlled placement of the polymer on the wound, and 8) polymerize under mild conditions.

In some embodiments, the dissolvable hydrogel and/or the hydrogel composition comprising a dissolvable hydrogel described herein can be used for sealing a retinal hole. Existing techniques used for the treatment of retinal holes such as cryotherapy, diathermy and photocoagulation are unsuccessful in the case of complicated retinal detachment, partly because of the delay in the application and/or the weak strength of the chorioretinal adhesion. Cyanoacrylate retinopexy is previously discussed for use in special cases and shown that the chorioretinal adhesion can be stronger and last longer than the earlier techniques. As noted previously with regard to corneal perforation treatment, the extremely rapid polymerization of cyanoacrylate glues (for example, risk of adhesion of the injector to the retina), the difficulty to use them in aqueous conditions and the toxicity are some of the inconvenience and/or risks associated with the method of using cyanoacrylate glues. While the polymerization can be slowed down by adding iophendylate to the monomers, the reaction still occurs in two to three seconds. Risks of retinal tear at the edge of the treated hole can also be observed because of the hardness of cyanoacrylate once polymerized.

In some embodiments, the dissolvable hydrogel and/or the hydrogel composition comprising a dissolvable hydrogel described herein can be used for sealing a corneal transplant. In a corneal transplant the surgeon usually makes approximately 16 sutures around the transplant to secure the new cornea in place. A sutureless procedure by using the dissolvable hydrogel and/or the hydrogel composition comprising a dissolvable hydrogel described herein can be desirable, as 1) sutures can provide a site for infection, 2) the sutured cornea can take three months to heal before the sutures need to be removed, and/or 3) the strain applied to the new cornea tissue from the sutures can distort the cornea.

In some embodiments, the dissolvable hydrogel and/or the hydrogel composition comprising a dissolvable hydrogel described herein can be used in oculoplastics or oculoplastic surgery. For example, blepharoplasty incisions blepharoplasty is an operation to remove excess skin, fat and muscle from around the eyes to correct droopy eyelids and bagginess under the eyes. It can be performed on the upper lids and lower lids, at the same time or separately. The operation may be done using either conventional or laser techniques. For surgery on the upper eyelids, cuts are made into the natural lines and creases in the lid, and into the laughter lines at the corner of the eye. For surgery on the lower eyelids, a cut is usually made just below the eyelashes. This means the scars run along the eye's natural folds, concealing them as much as possible. Excess fat, muscle and loose skin are removed, and the cut is currently closed using sutures. If only fat is being removed, sometimes the cut is made on the inside of the lower eyelid, leaving no visible scar. A dissolvable hydrogel described herein formulated as a tissue adhesive can provide a means to secure the cuts made during surgery.

In some embodiments, the dissolvable hydrogel and/or the hydrogel composition comprising a dissolvable hydrogel described herein can be used as sealants using the methods described herein in gastrointestinal anastomosis procedures. Gastrointestinal anastomosis is the technique of joining two pieces of bowel together. There are many techniques for gastro-intestinal anastomosis, including both mechanical stapled techniques and hand-sutured procedures. The technique may involve a simple end-end anastomosis of two pieces of jejunum, a more complex colo-anal anastomosis, or a biliary enteric join. One of the problems with techniques employing sutures or staples is that leakage may occur around the sutures or staples. See, for example, Bruce et al. Br. J. Surg. 88:1157-1168 (2001) reporting leakage rates of 5-8%. Accordingly, the dissolvable hydrogel as sealants and methods of use described herein can be used to supplement the sutures or staples used in intestinal anastomoses, providing a better seal that can reduce leakage. The consequences of a failed anastomosis are severe and frequently life-threatening. Although failures can be caused by myriad factors, including poor surgical technique (e.g., sutures that were not inserted correctly, knots that were tied too tightly rendering the ends ischaemic, and/or incorrect use of a staple gun), in some embodiments, use of the dissolvable hydrogel as sealants and/or methods of use described herein can decrease or eliminate some of the causes of failed gastrointestinal anastomosis procedures.

In some embodiments, the dissolvable hydrogel and/or the hydrogel composition comprising a dissolvable hydrogel described herein can be used as sealants using the methods described herein in prostatectomy urethral-bladder anastomosis procedures. Prostatectomy urethral-bladder anastomosis is the technique of joining together a patient's ureter and bladder after surgical removal of his prostate gland. Failures can be caused by myriad factors, including poor surgical technique (e.g., sutures that were not inserted correctly; and/or knots that were tied too tightly rendering the ends ischaemic). In some embodiments, use of the dissolvable hydrogel as sealants and/or methods of use described herein can decrease or eliminate some of the causes of failed prostatectomy urethral-bladder anastomosis procedures.

In some embodiments, the dissolvable hydrogel and/or the hydrogel composition comprising a dissolvable hydrogel described herein can be used as sealants and/or tissue scaffold in the methods described herein to repair cartilage, meniscus and/or disk. Cartilaginous tissues play important roles in contributing to load support and energy dissipation in the joints of the musculoskeletal system. These tissues include articular cartilage, which is predominantly an avascular, and alymphatic tissue with very low cell-density. As a result, articular cartilage has limited capacity for self-repair following injury or aging. Degeneration of cartilage in the meniscus, intervertebral disks, or joints can lead to severe and debilitating pain in patients. Injuries to these tissues are often retained for many years and may eventually lead to more severe secondary damage. See Moskowitz, R. W., Osteoarthritis: diagnosis and medical/surgical management. 2nd ed.; W.B. Saunders Company: 1984. Today, more than one million knee, hip, and shoulder joint surgical procedures are performed annually in the United States as a consequence of trauma or a lifetime of wear and tear. See Praemer, A.; Furner, S.; Rice, D. P. Musculoskeletal Conditions in the United States, American Academy of Orthopaedic Surgeons: Rosemont, Ill., 1999. Despite the large number of patients suffering from cartilage degeneration, the only existing treatment options for cartilage degeneration include chronic administration of anti-inflammatory agents, total joint replacement, osteotomy, and/or allograft transplantation, each of which leads to mixed long-term results.

In some embodiments, the dissolvable hydrogel and/or the hydrogel composition comprising a dissolvable hydrogel described herein can be used as sealants and/or glues using the methods described herein in tissue plane applications. For example, the dissolvable hydrogel and/or the hydrogel composition comprising a dissolvable hydrogel described herein can be applied between two planes of tissue to seal them together. Over time the dissolvable hydrogel can be controllably dissolved by addition of a thiolate compound as new tissue grows into the area. Example applications include, but are not limited to, a number of cosmetic and tissue restoration surgeries. In some embodiments, the dissolvable hydrogel and/or the hydrogel composition comprising a dissolvable hydrogel described herein can be used when the procedures involve significant tissue plane separation that may result in formation of seroma with associated complications, such as infection, e.g., general surgery procedures, such as mastectomies and lumpectomies, and/or plastic surgery procedures, such as abdominoplastys, rhytidectomy or rhinoplastys, mammaplasty and reconstruction, forehead lifts and buttocks lifts, as well as skin grafts, biopsy closure, cleft-palate reconstruction, hernia repair, lymph node resection, groin repair, Caesarean section, laparoscopic trocar repair, vaginal tear repair, and hand surgery.

Adhesion formation is a major post-surgical complication. The incidence of clinically significant adhesion is about 5 to 10 percent with some cases as high as 100 percent. Among the most common complications of adhesion formation are obstruction, infertility, and pain. Occasionally, adhesion formation requires a second operative procedure to remove adhesion, further complicating the treatment. Given the wide-spread occurrence of post-surgical adhesions, a number of approaches have been attempted for preventing adhesions (Stangel et al., "Formation and Prevention of Postoperative Abdominal Adhesions", The Journal of Reproductive Medicine, Vol. 29, No. 3, March 1984 (pp. 143-156), and diZerega, "The Cause and Prevention of Postsurgical Adhesions", published by Pregnancy Research Branch, National Institute of Child Health and Human Development, National Institutes of Health, Building 18, Room 101, Bethesda, Md. 20205.)

Exemplary approaches for prevention of post-surgical adhesion include 1) systemic administration of ibuprofen (e.g., see Singer, U.S. Pat. No. 4,346,108), 2) parenteral administration of antihistamines, corticosteroids, and antibiotics, 3) intraperitoneal administration of dextran solution and of polyvinylpyrrolidone solution, 4) systemic administration of oxyphenbutazone, a non-steroidal anti-inflammatory drug that acts by inhibiting prostaglandin production, and 5) administration of linear synthetic and natural polymers (Hubell 6060582; Fertil. Steril., 49:1066; Steinleitner et al. (1991) "Poloxamer 407 as an Intraperitoneal Barrier Material for the Prevention of Postsurgical Adhesion Formation and Reformation in Rodent Models for Reproductive Surgery," Obstetrics and Gynecology, 77(1):48 and Leach et al. (1990) "Reduction of postoperative adhesions in the rat uterine horn model with poloxamer 407", Am. J. Obstet. Gynecol., 162(5):1317. Linsky et al., 1987 "Adhesion reduction in a rabbit uterine horn model using TC-7," J. Reprod. Med., 32:17, Diamond et al., 1987 "Pathogenesis of adhesions formation/reformation: applications to reproductive surgery," Microsurgery, 8:103).

For example, formation of post-surgical adhesions involving organs of the peritoneal cavity and the peritoneal wall is undesirable result of abdominal surgery. This occurs frequently and arises from surgical trauma. During the operation, serosanguinous (proteinaceous) exudate is released which tends to collect in the pelvic cavity (Holtz, G., 1984). If the exudate is not absorbed or lysed within a short period of time, it becomes ingrown with fibroblasts, with subsequent collagen deposition occurs leading to adhesions.

In some embodiments, the method described herein can be used to prevent formation of adhesions between injured tissues by introducing a barrier comprising the dissolvable hydrogel and/or the hydrogel composition comprising a dissolvable hydrogel layer described herein between the injured tissues. This polymeric barrier can as a sheet or coating on the exposed injured tissue to prevent surgical adhesions, and can be controllably dissolved over a time course by gradual addition of an appropriate amount of a thiolate compound that allows for normal healing to occur without formation of adhesions/scars etc.

In some embodiments, the dissolvable hydrogel and/or the hydrogel composition comprising a dissolvable hydrogel described herein can be used as sealants and/or glues using the methods described herein to repair, close and/or secure vascular and/or cardiovascular tissue. Representative procedures include, for example, coronary artery bypass grafts, coronary angioplasty, diagnostic cardia catheterization, carotid endarterectomy, and valve repair. An additional use of the dissolvable hydrogel and/or the hydrogel composition comprising a dissolvable hydrogel described herein as sealants can include repair of cardiac tissue after a myocardial infarction. The dissolvable hydrogel and/or the hydrogel composition comprising the dissolvable hydrogel described herein can be applied to the infarcted tissue to provide structural support to the weakened tissue. For example, the dissolvable hydrogel described herein can act as a sleeve for the cardiac tissue.

In some embodiments, the dissolvable hydrogel and/or the hydrogel composition comprising a dissolvable hydrogel described herein can be used as adhesive, coating, sealants and/or glues using the methods described herein to repair a dura tissue. Dura tissue is a fibrous membrane covering the brain and the spinal cord and lining the inner surface of the skull. Existing methods of dural repair involve the application of interrupted sutures and the use of dural replacement materials (duraplasty), which is a meticulous surgery and suffers from the limitation that pinholes produced by surgical needles can cause leakage. Moreover, intraoperative dehydration can shrink the dura creating a difficult closure since it is difficult to approximate the edges with sutures. In older patients, the dura can be often more susceptible to tearing when stretched and/or sutured because the dura can be thin and fragile. Adhesives such as fibrin have been used for repair of dura tissue, but have had limited success. See "Glue in the Repair of Dural Defects in Craniofacial Resections," J. Latyngology and Otology 106: 356-57 (1992); Kjaergard et al., "Autologous Fibrin Glue Preparation and Clinical Use in Thoracic Surgery," Eur. J. Cardio-Thorc. Surg. 6: 52-54 (1992); Thompson et al., "Fibrin Glue: A Review of Its Preparation, Efficacy, and Adverse Effects as a Topical Hemostat," Drug Intelligence and Clinical Pharmacy 22: 946-52 (1988); and Brennan, "Fibrin Glue," Blood Reviews 5: 240-44 (1991). The dissolvable hydrogels as sealants and methods of use described herein can be used to repair the dura after a craniotomy or laminectomy and/or prevent postoperative leakage of cerebrospinal fluid. See Preul et al. Neurosurgery 53:1189-1199 (2003) and Balance, Calif. in Some Points in the Surgery of the Brain and Its Membranes. London, Macmillan & Co. Injection Site Wound.

In some embodiments, the dissolvable hydrogel and/or the hydrogel composition comprising a dissolvable hydrogel described herein can be used in the methods described herein to deliver a bioactive agent such as growth factor. For example, the dissolvable hydrogel and/or the hydrogel composition comprising a dissolvable hydrogel described herein can comprise a bioactive agent described herein and be used as a patch to cover an infracted tissue in a myocardial infarction to help reduce loss of tissue function. In some embodiments, the dissolvable hydrogel and/or the hydrogel composition comprising a dissolvable hydrogel described herein can be used for vascular applications where the dissolvable hydrogel and/or the hydrogel composition described herein can be loaded with site-specific angiogenesis factor(s), e.g., but not limited to, vascular endothelial growth factor, platelet derived growth factor, and/or other angiogenesis factors. The dissolvable hydrogel and/or the hydrogel composition used as a vascular graft/patch can be used to bypass, replace, and/or repair a part of the diseased/dysfunctional blood vessel. In some embodiments, the dissolvable hydrogel and/or the hydrogel composition comprising a dissolvable hydrogel described herein can form an implant comprising an angiogenesis antagonist, e.g., for inhibiting undesired angiogenesis in a specific site, such as tumor, cancer, retinopathy, or the like.

Vascular endothelial growth factor is a secreted angiogenic mitogen whose target cell specificity appears to be restricted to vascular endothelial cells. The resulting angiogenesis properties may also be induced using platelet derived growth factor, tissue treatment factor, and the like. The phrase "vascular endothelial growth factor" refers broadly to all members of the vascular endothelial growth factor family, which may comprise polynucleotides, polypeptides encoded by such polynucleotides that facilitate angiogenesis, and the like. U.S. Pat. No. 6,040,157 to Hu et al. (hereby incorporated by reference) discusses general characteristics and specific properties of vascular endothelial growth factor and is incorporated herein by reference. Notably, VEGF has at least four different forms of 121, 165, 189 and 206 amino acids due to alternative splicing, which are designated as VEGF121, VEGF165, VEGF189, and VEGF206, respectively. In some embodiments, the growth factor can be added to the dissolvable hydrogel described herein at the time of implantation. In some embodiments, the growth factors can be introduced into the tissue site, e.g., vascular graft, followed by treatment with the dissolvable hydrogel and/or composition described herein.

The dissolvable hydrogel and/or the hydrogel composition comprising a dissolvable hydrogel described herein can be utilized to diagnose disease, promote healing and/or prevent disease or disorder by targeting or concentrating a bioactive agent such as a drug to local and regional areas.

In some embodiments, the dissolvable hydrogel and/or the hydrogel composition comprising a dissolvable hydrogel described herein can also be used for a variety of applications including, but not limited to, production of micro- and nanoparticles. Such materials can be used to repair an injured tissue, organ, bone, or genetic defect. Other uses of the dissolvable hydrogel and/or composition described herein provided herein include treatment of early, late or previously treated malignancies, pre-treatment of malignancies or other condition as a sensitizer to augment therapy of another agent such as with radiation sensitizers, avoidance of locoregional lymph node metastasis, augmentation of local wound healing and decrease in infection, manipulation of structure and abnormal scar formation, delivery of drugs, cytokines or steroids-into, for example, joint capsules-insulin, glucagon, or genetically missing enzymes and for the treatment of post-operative pain. In one embodiment, the dissolvable hydrogel and/or the hydrogel composition comprising a dissolvable hydrogel described herein can be used to treat cancer. For example, the dissolvable hydrogel and/or the hydrogel composition comprising a dissolvable hydrogel described herein can be used to treat various malignancies, e.g., but not limited to, lung, colon, prostate, pancreas, ovarian, sarcoma, mesothelioma, or breast cancer at all stages.

The dissolvable hydrogel and/or the hydrogel composition comprising a dissolvable hydrogel described herein can be used to deliver any agent at a specific site. The agent can be in any pharmaceutically acceptable form of an agent, including pharmaceutically acceptable salts. A large number of pharmaceutically active agents are known in the art and are amenable for use in the pharmaceutical compositions of the dissolvable hydrogel described herein. Pharmaceutically active agent include, but are not limited to, chemotherapeutic agents, such as radiosensitizers, receptor inhibitors and agonists or other anti-neoplastic agents; immune modulators, anti-inflammatory agents, and bioactive agents, such as cytokines, growth factors, or steroids with or without the co-incorporation of tumor or pathogen antigens to increase the anti-neoplastic response as a means of vaccine development; local anesthetic agents; antibiotics; or nucleic acids as a means of local gene therapy.

Accordingly, methods for site-specific or systemic delivery of a bioactive agent are provided herein. For example, the method comprises: a) implanting at a target site in the body of a patient in need thereof a dissolvable hydrogel and/or a hydrogel composition comprising a dissolvable hydrogel layer described herein, wherein a therapeutically effective amount of a biologically or pharmaceutically active agent is incorporated into the dissolvable hydrogel and/or the hydrogel composition; b) allowing the dissolvable hydrogel layer to adhere to the target site; and c) dissolving the dissolvable hydrogel layer by addition of a thiolate compound, thereby releasing the hydrogel composition from the target site. In some embodiments, the thiolate compound can be added by injection, e.g., via a syringe and/or catheter, and/or by spraying, e.g., on a skin surface.

The dissolvable hydrogel and/or the hydrogel composition comprising a dissolvable hydrogel described herein can also be used in cosmetic applications using the methods described herein. In some embodiments, the dissolvable hydrogel and/or compositions (e.g., adhesives) can be used alone or in combination with a void filler, where the cross-linkable polymers can be injected under the skin to form the dissolvable hydrogel in situ. Alternatively, the dissolvable hydrogel and/or the hydrogel composition comprising a dissolvable hydrogel described herein (e.g., adhesives) can be applied as a topical cosmetic or therapeutic composition, used, e.g., in connection with creams, shampoos, soaps, sun screen, lotions to moisturize the tissue, and oils, for dermatological purposes, cleansing, and the like. The dissolvable hydrogel and/or the hydrogel composition comprising a dissolvable hydrogel described herein (e.g., adhesives) can also be used with agents such as rapamycin or analogs e.g., everolimus or biolimus, which can help minimize scaring after plastic surgery performed on the face, body, or other external skin area.

In some embodiments, the dissolvable hydrogel and/or the hydrogel composition comprising a dissolvable hydrogel layer described herein can be injected or placed in vivo as a void filling composition or used as a sealant/adhesive alone or in combination with natural polymers, e.g., but not limited to, collagen, hyaluronic acid, gelatin, heparin, fibrin and/or heparin sulfate. Voids that can be filled using the dissolvable hydrogel and/or composition described herein include, without limitations, a nasal airway, or an organ of the gastro-intestinal track, for example, in order to arrest localized bleeding and/or promote healing following trauma, injury, or surgery.

In some embodiments, the dissolvable hydrogel and/or the hydrogel composition comprising a dissolvable hydrogel layer described herein can be used where the site of the wound is not easily accessible or when sutureless surgery is desired, e.g., but not limited to, in cardiovascular surgery, urinary tract surgery (e.g., nephrotomy closure, urethral repair, hypospadia repair), pulmonary surgery (e.g., sealing parenchymal & bronchial leaks, bronchopleural fistula repair, persistent air leak repairs), gastrointestinal tract and stomach surgery (e.g., parotid cutaneous fistula, tracheo-oesophageal fistula, peptic ulcer repair), joint surgery (e.g., cartilage repair, meniscal repair), heart surgery (e.g., cardiac ventricular rupture repair), brain surgery (e.g., dural defect repairs), ear surgery (e.g., ear drum perforation), and post-surgical drainage reduction (e.g., mastectomy, axillary dissection) and alveolar osteitis ("dry socket") and related post-surgical oral indications, and post-surgical drainage reduction (mastectomy, axillary dissection).

In cardiovascular surgery, the dissolvable hydrogel and/or the hydrogel composition comprising a dissolvable hydrogel layer described herein can be used as sealants, for example, for needle holes, suture lines, diffuse and nonspecific bleeding, anastomotic bleeding, friable tissue bleeding, aortic dissections, ventricular ruptures, and fistulas.

Kits

Kits, e.g., for use in the methods described herein or in any applications described herein are also provided. In one aspect, a kit comprises a) at least one or a plurality of (e.g., two or more) pre-formed dissolvable hydrogel composition(s) described herein and b) a thiolate compound. Thus, a user can directly apply the pre-formed dissolvable hydrogel composition to a target site (e.g., a wound).

In another aspect, a kit comprises a) at least two components of the crosslinkable polymers to be applied to a target site (e.g., a wound) to form a dissolvable hydrogel described herein in situ at the target site, wherein the crosslinkable polymers are each at least about 200 Da or higher (e.g., at least about 500 Da, at least about one kDa or higher), and b) a thiolate compound. In some embodiments, at least two components of the crosslinkable polymers can include a) a first water-soluble linear, branched, and/or dendritic crosslinkable polymer comprising at least two thiol moieties, and b) a second water-soluble linear, branched, and/or dendritic crosslinkable polymer that can react with the first crosslinkable polymer to form a dissolvable and adhesive hydrogel, wherein the second crosslinkable polymer comprises at least two crosslinking moieties that are capable of reacting with the thiol moieties of the first crosslinkable polymer to form thioester linkages between the first and the second crosslinkable polymers. In other embodiments, at least two components of the crosslinkable polymers can include a) a first water-soluble linear, branched, and/or dendritic crosslinkable polymer comprising at least two thioester moieties, and b) a second water-soluble linear, branched, and/or dendritic crosslinkable polymer that can react with the first crosslinkable polymer to form a dissolvable and adhesive thioester hydrogel, wherein the second crosslinkable polymer comprises at least two crosslinking moieties for crosslinking with the first crosslinkable polymer. In other embodiments, at least two components of the crosslinkable polymers can include a) a first water-soluble linear, branched and/or dendritic crosslinkable polymer that can react with the second crosslinkable polymer to form a dissolvable and adhesive thioester hydrogel, wherein the first crosslinkable polymer comprises at least two nucleophilic moieties (e.g., but not limited to, thiol, alcohol, amine) for crosslinking with the second crosslinkable polymer, and b) a second water-soluble linear, branched and/or dendritic crosslinkable polymer comprises at least two thioester moieties. In some embodiments, the first crosslinkable polymer can comprise thioester moieties.

The first crosslinkable polymer and the second crosslinkable polymer can each be independently formulated in a form selected from the group consisting of a spray, a foam, a gel, a solution, a powder, and any combinations thereof.

In some embodiments, the kit can further comprise at least one reagent. For example, a reagent can include a reconstitution buffer if the components of the crosslinkable polymers are provided as a powder. Additionally or alternatively, a reagent can include an antiseptic agent, e.g., for cleaning a wound before treatment.

In some embodiments, the at least two components of the crosslinkable polymers can be provided in a dual-barrel syringe. In these embodiments, the at least two components of the crosslinkable polymers can be mixed together by passing through a mixing tip, which can be releasably attached to the outlet of the dual-barrel syringe.

In some embodiments of the kits described herein, the kit can further comprise a bioactive agent described herein. In some embodiments, the bioactive agent can be incorporated into the pre-formed dissolvable hydrogel described herein or in at least one component of the crosslinkable polymers. In other embodiments, the bioactive agent can be provided in a separate container.

In some embodiments of the kits described herein, the thiolate compound can be formulated in a form selected from the group consisting of a spray, a foam, a solution, a gel, a powder, and any combinations thereof. Non-limiting examples of the thiolate compound can include linear, branched and/or dendritic multi-thiol macromolecules, poly(ethylene glycol) thiol, thiol-containing glycerol, thiol-containing peptides, cysteine, cystine, alkyl ester of cysteine, alkyl ester of cystine, MeSCH2SH, (R)/(S)-3-methyl-3-sulfanylhexan-1-ol, Ethanethiol, 1-Propanethiol, 2-Propanethiol, Butanethiol, tert-Butyl mercaptan, Pentanethiols, Thiophenol, Dimercaptosuccinic acid, Thioacetic acid, 5-mercapto-4H-[1,2,4]triazol-3-ol, 2-mercaptoacetamide, 2-Mercaptoethanol, 1,2-Ethanedithiol, Ammonium thioglycolate, Cysteamine, Methyl thioglycolate, Thiolactic acid, 1-Mercapto-2-propanol, 2-methoxyethanethiol, 3-Mercapto-1-propanol, 2,3-Dimercapto-1-propanol, 1-Thioglycerol, Mercaptosuccinic acid, 4-ethyl-5-mercapto-4H-1,2,4- triazol-3-ol, N-Carbamoyl-L-cysteine, 2-Methyl-3-sulfanylpropanoic acid, 4-mercaptobutyric acid, N-Acetylcysteamine, 3-Methyl-1-butanethiol, 1,5-Pentanedithiol, 4-Chlorothiophenol, 4-Aminothiophenol, Benzyl mercaptan, 2-Furanmethanethiol, 3-Mercaptohexanol, Furfuryl thiol, derivatives thereof, a disulfide complex of one or more thereof, and any combinations thereof.

In some embodiments of various aspects described herein, the kits can further comprise component(s) for performing vacuum assisted closure. Exemplary components can include, but are not limited to a film or thin material (e.g., to seal the wound and create a sub-atmospheric pressure at the local wound environment), a drainage tube that can be connected to a vacuum source or generator, a vacuum device or apparatus, a container (e.g., to collect dissolved hydrogel, blood, fluid exudate and/or any other particulates/materials present on the wound surface), and any combinations thereof.

In addition to the above-mentioned components, the kit can include informational material. The informational material can be descriptive, instructional, marketing or other material that relates to the methods described herein and/or the use/storage of the dissolvable hydrogel composition and/or components of the crosslinkable polymers. For example, the informational material describes methods to form a dissolvable hydrogel using the components of the crosslinkable polymers provided in the kit; and/or methods to dissolve the dissolvable hydrogel. The kit can also include a delivery device.

In some embodiments, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is a link or contact information, e.g., a physical address, email address, hyperlink, website, or telephone number, where a user of the kit can obtain substantive information about the formulation and/or its use in the methods described herein. In some embodiments, the informational material can also be provided in any combination of formats.

In some embodiments, the kit contains separate containers, dividers or compartments for the pre-formed dissolvable hydrogel or components of the crosslinkable polymers and informational material. For example, the pre-formed dissolvable hydrogel or components of the crosslinkable polymers can be contained in at least one bottle, vial, or syringe, and the informational material can be contained in a plastic sleeve or packet. In other embodiments, the separate elements of the kit are contained within a single, undivided container. For example, the pre-formed dissolvable hydrogel or components of the crosslinkable polymers is contained in at least one bottle, vial or syringe that has attached thereto the informational material in the form of a label.

In some embodiments, the kit includes a plurality, e.g., a pack, of individual containers, each containing one or more units of the pre-formed dissolvable hydrogel or components of the crosslinkable polymers. For example, the kit includes a plurality of syringes, ampules, foil packets, or blister packs, each containing a single-use unit of the pre-formed dissolvable hydrogel or components of the crosslinkable polymers. The containers of the kits can be air tight and/or waterproof.

Exemplary Synthesis of Dissolvable Hydrogels Described Herein

To prepare a dissolvable hydrogel described herein, linear, branched, and/or dendritic-like crosslinkable polymers are crosslinked (e.g., by a covalent bond). For example, the linear, branched and/or dendritic polymers can be made crosslinkable by chemical modification to have two or more functional groups that are capable of reacting with functional groups present on other linear, branched and/or dendritic crosslinkable polymers—in one embodiment, thiol (—SH) groups on a first crosslinkable polymer and an N-hydroxysuccinimide (NHS) or other activated ester on a second crosslinkable polymer. Each functional group on a multifunctionally linear, branched and/or dendritic crosslinkable polymer is capable of covalently binding with another crosslinkable polymer, thereby effecting crosslinking between the polymers and formation of the dissolvable hydrogel described herein.

Examples of covalently crosslinked dissolvable hydrogels can be formed by reacting a crosslinkable polymer comprising activated esters (such as an N-hydroxysuccinimide) with another crosslinkable polymer comprising thiols. Alternatively, covalently crosslinked dissolvable thioester hydrogels can be formed by reacting a crosslinkable polymer comprising maleimide (MAL) moieties with thioester linkages within its structure, with another crosslinkable polymer comprising thiols. Another example of covalently crosslinked dissolvable thioester hydrogels can be formed by reacting a crosslinkable polymer comprising activated esters (such as an N-hydroxysuccinimide) with another crosslinkable polymer comprising nucleophilic moieties with thioester linkages within its structure. Another example of covalently crosslinked dissolvable thioester hydrogels can be formed by reacting a crosslinkable polymer comprising activated esters (such as an N-hydroxysuccinimide) with thioester linkages within its structure with another crosslinkable polymer comprising nucleophilic moieties (e.g., but not limited to, alcohol, amine).

Bioactive Agents, Biologically and/or Pharmaceutically Active Agents that can be Used in the Dissolvable Hydrogel and/or Compositions Described Herein In some embodiments, the dissolvable hydrogel and/or the composition comprising the dissolvable hydrogel (e.g., as a layer) can comprise at least one bioactive agent, including, e.g., at least two, at least three, at least four or more bioactive agents. In some embodiments, the bioactive(s) can be incorporated into the dissolvable hydrogel described herein, and/or other additional layers, if any, present in the composition. The bioactive agent(s) can be covalently conjugated to the polymeric structure of the hydrogel and/or physically entrapped within the hydrogel.

In some embodiments, the bioactive agent(s) can be incorporated into the dissolvable hydrogel described herein, and/or other additional layers, if any, present in the composition in an amount between about 0.01% and about 80% by weight, or between about 1% and about 30%. One of skill in the art can determine an appropriate loading amount of active agent according to various applications and purposes.

A "bioactive agent" refers to an agent that is capable of exerting a biological effect in vitro and/or in vivo. The biological effect can be therapeutic in nature. As used herein, "bioactive agent" refers also to a substance that is used in connection with an application that is diagnostic in nature, such as in methods for diagnosing the presence or absence of a disease in a patient. The bioactive agents can be neutral or positively or negatively charged. Examples of suitable bioactive agents include pharmaceuticals and drugs, cells, gases and gaseous precursors (e.g., $O_2$), synthetic organic molecules, proteins, enzymes, growth factors, vitamins, steroids, polyanions, nucleosides, nucleotides, polynucleotides, nanoparticles, and diagnostic agents, such as contrast agents for use in connection with magnetic resonance imaging, ultrasound, positron emission tomography (PET), X-ray computed tomography or other imaging modalities.

"Genetic material" refers generally to nucleotides and polynucleotides, including, but not limited to, deoxyribonucleic acid (DNA), any types of ribonucleic acid (RNA) molecules (e.g., but not limited to, siRNA, mRNA, modified RNA, or any combinations thereof), peptide nucleic acid (PNA), and any combinations thereof. The genetic material can be made by synthetic chemical methodology known to one of ordinary skill in the art, or by the use of recombinant technology, or by a combination of the two. The DNA and RNA can optionally comprise unnatural or synthetic nucleotides or analogs and can be single or double stranded. "Genetic material" refers also to sense and anti-sense DNA and RNA, that is, a nucleotide sequence that is complementary to a specific sequence of nucleotides in DNA and/or RNA.

Examples of bioactive agents for use in the dissolvable hydrogel and/or compositions described herein include, without limitations, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment. In some embodiments, bioactive agent(s) include, but are not limited to, growth factors, such as members of the transforming growth factor (TGF) gene family (e.g., TGF-β1, TGF-β2, and TGF-β3), fibroblast growth factors (FGFs), platelet derived growth factors (PDGFs), epidermal growth factors (EGFs), connective tissue activated peptides (CTAPs), osteogenic factors, bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (IGF)); Inhibins (for example, Inhibin A, Inhibin B); growth differentiating factors (for example, GDF-1); and Activins (for example, Activin A, Activin B, Activin AB), vascular endothelium growth factor (VEGF); hormones, e.g., but not limited to, insulin, glucagon, and estrogen; therapeutic agents or drugs, e.g., but not limited to wound-healing agents, anti-inflammatory steroids, and chemotherapeutics; antimicrobial agents; an anesthetic; and biologically active analogs, fragments, and derivatives of such growth factors; and any combinations thereof.

In some embodiments, the bioactive agent(s) can be pharmaceutically active agent(s). Non-limiting examples of the pharmaceutically active agent(s) can include (1) non-steroidal anti-inflammatory drugs (NSAIDs) analgesics, including but not limited to diclofenac, ibuprofen, ketoprofen, and naproxen; (2) opiate agonist analgesics, including but not limited to codeine, vancomycin, ceftazidime, fentanyl, hydromorphone, and morphine; (3) salicylate analgesics, including but not limited to aspirin (ASA) (or enteric coated ASA); (4) H1-blocker antihistamines, including but not limited to clemastine and terfenadine; (5) H2-blocker antihistamines, including but not limited to cimetidine, famotidine, nizadine, and ranitidine; (6) anti-infective agents, including but not limited to mupirocin; (7) antianaerobic anti-infectives, including but not limited to chloramphenicol metronidazole and clindamycin; (8) antifungal antibiotic anti-infectives, including but not limited to amphotericin B, clotrimazole, fluconazole, and ketoconazole; (9) macrolide antibiotic anti-infectives, including but not limited to azithromycin and erythromycin; (10) miscellaneous beta-lactam antibiotic anti-infectives, including but not limited to aztreonam and imipenem; (11) penicillin antibiotic anti-infectives, including but not limited to nafcillin, oxacillin, penicillin G, and penicillin V; (12) quinolone antibiotic anti-infectives, including but not limited to ciprofloxacin and norfloxacin; (13) tetracycline antibiotic anti-infectives, including but not limited to doxycycline, minocycline, and tetracycline; (14) antituberculosis antimycobacterial anti-infectives including but not limited to isoniazid (INH), and rifampin; (15) antiprotozoal anti-infectives, including but not limited to atovaquone and dapsone; (16) antimalarial antiprotozoal anti-infectives, including but not limited to chloroquine and pyrimethamine; (17) antiretroviral anti-infectives, including but not limited to ritonavir and zidovudine; (18) antiviral anti-infective agents, including but not limited to acyclovir, ganciclovir, interferon alpha, and rimantadine; (19) alkylating antineoplastic agents, including but not limited to carboplatin and cisplatin; (20) nitrosourea alkylating antineoplastic agents, including but not limited to carmustine (BCNU); (21) antimetabolite antineoplastic agents, including but not limited to methotrexate; (22) pyrimidine analog antimetabolite antineoplastic agents, including but not limited to fluorouracil (5-FU), gemcitabine, or ceftazidine, aminoglycodi meroperium, or ticarcillin and tobramycin; (23) hormonal antineoplastics, including but not limited to goserelin, leuprolide, and tamoxifen; (24) natural antineoplastics, including but not limited to aldesleukin, interleukin-2, docetaxel, etoposide (VP-16), interferon alpha, paclitaxel, and tretinoin (ATRA); (25) antibiotic natural antineoplastics, including but not limited to bleomycin, actinomycin, daunorubicin, doxorubicin, and mitomycin; (26) *vinca* alkaloid natural antineoplastics, including but not limited to vinblastine and vincristine; (27) autonomic agents, including but not limited to nicotine; (28) anticholinergic autonomic agents, including but not limited to benztropine and trihexyphenidyl; (29) antimuscarinic anticholinergic autonomic agents, including but not limited to atropine and oxybutynin; (30) ergot alkaloid autonomic agents, including but not limited to bromocriptine; (31) cholinergic agonist parasympathomimetics, including but not limited to pilocarpine; (32) cholinesterase inhibitor parasympathomimetics, including but not limited to pyridostigmine; (33) alpha-blocker sympatholytics, including but not limited to prazosin; (34) beta-blocker sympatholytics, including but not limited to atenolol; (35) adrenergic agonist sympathomimetics, including but not limited to albuterol and dobutamine; (36) cardiovascular agents, including but not limited to aspirin (ASA), plavix (Clopidogrel bisulfate) etc; (37) beta-blocker antianginals, including but not limited to atenolol and propranolol; (38) calcium-channel blocker antianginals, including but not limited to nifedipine and verapamil; (39) nitrate antianginals, including but not limited to isosorbide dinitrate (ISDN); (40) cardiac glycoside antiarrhythmics, including but not limited to digoxin; (41) class I anti-arrhythmics, including but not limited to lidocaine, mexiletine, phenytoin, procainamide, and quinidine; (42) class II antiarrhythmics, including but not limited to atenolol, metoprolol, propranolol, and timolol; (43) class III antiarrhythmics, including but not limited to amiodarone; (44) class IV antiarrhythmics, including but not limited to diltiazem and verapamil; (45) alpha-blocker antihypertensives, including but not limited to prazosin; (46) angiotensin-converting enzyme inhibitor (ACE inhibitor) antihypertensives, including but not limited to captopril and enalapril; (47) beta blocker antihypertensives, including but not limited to atenolol, metoprolol, nadolol, and propanolol; (48) calcium-channel blocker antihypertensive agents, including but not limited to diltiazem and nifedipine; (49) central-acting adrenergic antihypertensives, including but not limited to clonidine and methyldopa; (50) diurectic antihypertensive agents, including but not limited to amiloride, furosemide, hydrochlorothiazide (HCTZ), and spironolactone; (51) peripheral vasodilator antihypertensives, including but not limited to hydralazine and minoxidil; (52) antilipemics, including but not limited to gemfibrozil and probucol; (53) bile acid sequestrant antilipemics, including but not limited to cholestyramine; (54) HMG-CoA reductase inhibitor antilipemics, including but not limited to lovastatin and pravastatin; (55) inotropes, including but not limited to amrinone, dobutamine, and dopamine; (56) cardiac glycoside inotropes, including but not limited to digoxin; (57) thrombolytic agents or enzymes, including but not limited to alteplase (TPA), anistreplase, streptokinase, and urokinase; (58) dermatological agents, including but not limited to colchicine, isotretinoin, methotrexate, minoxidil, tretinoin (ATRA); (59) dermatological corticosteroid anti-inflammatory agents, including but not limited to betamethasone and dexamethasone; (60) antifungal topical antiinfectives, including but not limited to amphotericin B, clotrimazole, miconazole, and nystatin; (61) antiviral topical anti-infectives, including but not limited to acyclovir; (62) topical antineoplastics, including but not limited to fluorouracil (5-FU); (63) electrolytic and renal agents, including but not limited to lactulose; (64) loop diuretics, including but not limited to furosemide; (65) potassium-sparing diuretics, including but not limited to triamterene; (66) thiazide diuretics, including but not limited to hydrochlorothiazide (HCTZ); (67) uricosuric agents, including but not limited to probenecid; (68) enzymes including but not limited to RNase and DNase; (69) immunosuppressive agents, including but not limited to cyclosporine, steroids, methotrexate, tacrolimus, sirolimus, rapamycin; (70) antiemetics, including but not limited to prochlorperazine; (71) salicylate gastrointestinal anti-inflammatory agents, including but not limited to sulfasalazine; (72) gastric acid-pump inhibitor anti-ulcer agents, including but not limited to omeprazole; (73) H2-blocker anti-ulcer agents, including but not limited to cimetidine, famotidine, nizatidine, and ranitidine; (74) digestants, including but not limited to pancrelipase; (75) prokinetic agents, including but not limited to erythromycin; (76) opiate agonist intravenous anesthetics including but not limited to fentanyl; (77) hematopoietic antianemia agents, including but not limited to erythropoietin, filgrastim (G-CSF), and sargramostim (GM-CSF); (78) coagulation agents, including but not limited to antihemophilic factors 1-10 (AHF 1-10); (79) anticoagulants, including but not limited to warfarin, heparin (important for heparin bound polymers and cardiopulmonary bypass pump circuits), argatroban—each works by a different mechanism and is metabolized differently; (80) growth receptor inhibitors, including but not limited to erlotinib and gefetinib; (82) abortifacients, including but not limited to methotrexate; (83) antidiabetic agents, including but not limited to insulin; (84) oral contraceptives, including but not limited to estrogen and progestin; (85) progestin contraceptives, including but not limited to levonorgestrel and norgestrel; (86) estrogens including but not limited to conjugated estrogens, diethylstilbestrol (DES), estrogen (estradiol, estrone, and estropipate); (87) fertility agents, including but not limited to clomiphene, human chorionic gonadatropin (HCG), and menotropins; (88) parathyroid agents including but not limited to calcitonin; (89) pituitary hormones, including but not limited to desmopressin, goserelin, oxytocin, and vasopressin (ADH); (90) progestins, including but not limited to medroxyprogesterone, norethindrone, and progesterone; (91) thyroid hormones, including but not limited to levothyroxine; (92) immunobiologic agents, including but not limited to interferon beta-1b and interferon gamma-1b; (93) immunoglobulins, including but not limited to immune globulin IM, IMIG, IGIM and immune globulin IV, IVIG, IGIV; (94) amide local anesthetics, including but not limited to lidocaine; (95) ester local anesthetics, including but not limited to benzocaine and procaine; (96) musculoskeletal corticosteroid anti-inflammatory agents, including but not limited to beclomethasone, betamethasone, cortisone, dexamethasone, hydrocortisone, and prednisone; (97) musculoskeletal anti-inflammatory immunosuppressives, including but not limited to azathioprine, cyclophosphamide, and methotrexate; (98) musculoskeletal nonsteroidal anti-inflammatory drugs (NSAIDs), including but not limited to diclofenac, ibuprofen, ketoprofen, ketorlac, and naproxen; (99) skeletal muscle relaxants, including but not limited to baclofen, cyclobenzaprine, and diazepam; (100) reverse neuromuscular blocker skeletal muscle relaxants, including but not limited to pyridostigmine; (101) neurological agents, including but not limited to nimodipine, riluzole, tacrine and ticlopidine; (102) anticonvulsants, including but not limited to carbamazepine, gabapentin, lamotrigine, phenytoin, and valproic acid; (103) barbiturate anticonvulsants, including but not limited to phenobarbital and primidone; (104) benzodiazepine anticonvulsants, including but not limited to clonazepam, diazepam, and lorazepam; (105) anti-parkisonian agents, including but not limited to bromocriptine, levodopa, carbidopa, and pergolide; (106) anti-vertigo agents, including but not limited to meclizine; (107) opiate agonists, including but not limited to codeine, fentanyl, hydromorphone, methadone, and morphine; (108) opiate antagonists, including but not limited to naloxone; (109) beta-blocker anti-glaucoma agents, including but not limited to timolol; (110) miotic anti-glaucoma agents, including but not limited to pilocarpine; (111) ophthalmic aminoglycoside antiinfectives, including but not limited to gentamicin, neomycin, and tobramycin; (112) ophthalmic quinolone anti-infectives, including but not limited to ciprofloxacin, norfloxacin, and ofloxacin; (113) ophthalmic corticosteroid anti-inflammatory agents, including but not limited to dexamethasone and prednisolone; (114) ophthalmic nonsteroidal anti-inflammatory drugs (NSAIDs), including but not limited to diclofenac; (115) antipsychotics, including but not limited to clozapine, haloperidol, and risperidone; (116) benzodiazepine anxiolytics, sedatives and hypnotics, including but not limited to clonazepam, diazepam, lorazepam, oxazepam, and prazepam; (117) psychostimulants, including but not limited to methylphenidate and pemoline; (118) antitussives, including but not limited to codeine; (119) bronchodilators, including but not limited to theophylline; (120) adrenergic agonist bronchodilators, including but not limited to albuterol; (121) respiratory corticosteroid anti-inflammatory agents, including but not limited to dexamethasone; (122) antidotes, including but not limited to flumazenil and naloxone; (123) heavy metal antagonists/chelating agents, including but not limited to penicillamine; (124) deterrent substance abuse agents, including but not limited to disulfiram, naltrexone, and nicotine; (125) withdrawal substance abuse agents, including but not limited to bromocriptine; (126) minerals, including but not limited to iron, calcium, and magnesium; (127) vitamin B compounds, including but not limited to cyanocobalamin (vitamin B12) and niacin (vitamin B3); (128) vitamin C compounds, including but not limited to ascorbic acid; (129) vitamin D compounds, including but not limited to calcitriol; (130) antiparasitic compounds including but not limited to metronidazole; (131) bronchodilators, including but not limited to salmeterol, and beta agonists; (132) leukotriene blockers/modifiers including montelukast or zileuton; (133) inhaled steroids including but not limited to fluticasone, beclomethasone, or budesonide. Anti-bleeding (hemostatic) agents including but not limited to protamine and antihelminth, radiation sensitizers, and other drugs including but not limited to racin and cyclosporine are also included. Additional anticancer drugs including but not limited to pycnidione as well as anti-Myc inhibitors. Nanoparticles can comprise silver or silver salts for antibacterial activity.

In addition to the foregoing, the following pharmaceutically active agents can also be used in the dissolvable hydrogels and/or compositions described herein, which include, but are not limited to, chlorhexidine; estradiol cypionate in oil; estradiol valerate in oil; flurbiprofen; flurbiprofen sodium; ivermectin; levodopa; nafarelin; and somatropin. Further, the following drugs can also be used: pycnidione, cyclosporine, recombinant beta-glucan; bovine immunoglobulin concentrate; bovine superoxide dismutase; the formulation comprising fluorouracil, epinephrine, and bovine collagen; recombinant hirudin (r-Hir), HIV-1 immunogen; human anti-TAC antibody; recombinant human growth hormone (r-hGH); recombinant human hemoglobin (r-Hb); recombinant human mecasermin (r-IGF-1); recombinant interferon beta-1a; lenograstim (G-CSF); olanzapine; recombinant thyroid stimulating hormone (r-TSH); and topotecan. Further still, the following intravenous products can be used: acyclovir sodium; aldesleukin; atenolol; bleomycin sulfate, human calcitonin; salmon calcitonin; carboplatin; carmustine; dactinomycin, daunorubicin HCl; docetaxel; doxorubicin HCl; epoetin alfa; etoposide (VP-16); fluorouracil (5-FU); ganciclovir sodium; gentamicin sulfate; interferon alpha; leuprolide acetate; meperidine HCl; methadone HCl; methotrexate sodium; paclitaxel; ranitidine HCl; vinblastin sulfate; and zidovudine (AZT).

Further examples of pharmaceutically active agents from the above categories include: (a) anti-neoplastics including but not limited to androgen inhibitors, antimetabolites, cytotoxic agents, receptor inhibitors, and immunomodulators; (b) anti-tussives including but not limited to dextromethorphan, dextromethorphan hydrobromide, noscapine, carbetapentane citrate, and chlorphedianol hydrochloride; (c) antihistamines including but not limited to chlorpheniramine maleate, phenindamine tartrate, pyrilamine maleate, doxylamine succinate, and phenyltoloxamine citrate; (d) decongestants including but not limited to phenylephrine hydrochloride, phenylpropanolamine hydrochloride, pseudoephedrine hydrochloride, and ephedrine; (e) various alkaloids including but not limited to codeine phosphate, codeine sulfate and morphine; (f) mineral supplements including but not limited to potassium chloride, zinc chloride, calcium carbonates, magnesium oxide, and other alkali metal and alkaline earth metal salts; (g) ion exchange resins including but not limited to cholestryramine; (h) anti-arrhythmics including but not limited to N-acetylprocainamide; (i) antipyretics and analgesics including but not limited to acetaminophen, aspirin and ibuprofen; (j) appetite suppressants including but not limited to phenyl-propanolamine hydrochloride or caffeine; (k) expectorants including but not limited to guaifenesin; (l) antacids including but not limited to aluminum hydroxide and magnesium hydroxide; (m) biologicals including but not limited to peptides, polypeptides, proteins and amino acids, hormones, interferons or cytokines, and other bioactive peptidic compounds, including but not limited to interleukins 1-18 including mutants and analogues, RNase, DNase, luteinizing hormone releasing hormone (LHRH) and analogues, gonadotropin releasing hormone (GnRH), transforming growth factor-beta. (TGF-beta), fibroblast growth factor (FGF), tumor necrosis factor-alpha & beta (TNF-alpha & beta), nerve growth factor (NGF), growth hormone releasing factor (GHRF), epidermal growth factor (EGF), fibroblast growth factor homologous factor (FGFHF), hepatocyte growth factor (HGF), insulin growth factor (IGF), invasion inhibiting factor-2 (IIF-2), bone morphogenetic proteins 1-7 (BMP 1-7), somatostatin, thymosin-alpha-1, gamma-globulin, superoxide dismutase (SOD), complement factors, hGH, tPA, calcitonin, ANF, EPO and insulin; and (n) anti-infective agents including but not limited to antifungals, anti-bacterials (including, e.g., silver nanoparticles), anti-viral s, antihelminths, antiseptics and antibiotics. Additional agents include hemoglobin, oxygen, nitric oxide, silver or other noble metals or ions thereof (e.g., silver nanoparticles, rods, crystals and other structures or silver salts). Additional agents include drugs that have renal toxicity and cardio toxicity, wherein the delivery with the particles assists in reducing the renal or cardiotoxicity by delivering the drugs in a targeted manner to a tissue site other than kidneys or the heart.

Examples of specific drugs that can be used include, but are not limited to asparaginase; bleomycin; busulfan; capecitabine; carboplatin; carmustine; chlorambucil; cisplatin; cyclophosphamide; cytarabine; dacarbizine; dactinomycin; daunorubicin; dexrazoxane; docetaxel; doxorubicin; erlotinibil/gefetinib; etoposide; floxuridine; fludarabine; fluoruracil; gemcitabine; 10-hydrocamptothecin; hydroxyurea; idarubicin; ifosfamide; irinotecan; lomustine; mechlorethamine; melphalan; mercaptopurine; methotrexate; mitomycin; mitotane; mitoxantrone; paclitaxel; pentostatin; plicamycin; pemextred procarbazine; rituximabe; streptozocin; teniposid; thioguanine; thiotepa; vinplastine; vinchristine; and vinorelbineor derivates of these molecules.

Examples of anticancer, antineoplastic agents are camptothecins. These drugs are antineoplastic by virtue of their ability to inhibit topoisomerase I. Camptothecin is a plant alkaloid isolated from trees indigenous to China and analogs thereof including but not limited to 9-aminocamptothecin, 9-nitrocamptothecin, 10-hydroxycamptothecin, 10,11-methylenedioxycamptothecin, 9-nitro 10,11,methylenehydroxycamptothecin, 9-chloro-10,11-methylenehydroxycamptothecin, 9-amino-10,11-methylenehydroxycamptothecin, 7-ethyl-10-hydroxycamptothecin (SN-38), topotecan, DX-8951, Lurtotecan (GII147221C), and other analogs (collectively referred to herein as camptothecin drugs) are presently under study worldwide in research laboratories for treatment of colon, breast, and other cancers.

Additionally, the pharmaceutically active agent can be a radiosensitizer, including but not limited to metoclopramide, sensamide or neusensamide (manufactured by Oxigene); profiromycin (made by Vion); RSR13 (made by Allos); THYMITAQ® (made by Agouron), etanidazole or lobenguane (manufactured by Nycomed); gadolinium texaphrin (made by Pharmacyclics); BuDR/Broxine (made by NeoPharm); IPdR (made by Sparta); CR2412 (made by Cell Therapeutic); LIX (made by *Terrapin*); agents that minimize hypoxia, and the like. The biologically active substance can be selected from the group consisting of peptides, polypeptides, proteins, amino acids, polysaccharides, growth factors, hormones, anti-angiogenesis factors, interferons or cytokines, elements, and pro-drugs. In one embodiment, the biologically active substance is a therapeutic drug or pro-drug, most preferably a drug selected from the group consisting of chemotherapeutic agents and other antineoplastics including but not limited to paclitaxel, carboplatin and cisplatin; nitrosourea alkylating antineoplastic agents, including but not limited to carmustine (BCNU); fluorouracil (5-FU) and gemcitabine; hormonal antineoplastics, including but not limited to goserelin, leuprolide, and tamoxifen; receptor inhibitors including but not limited to erlotinib, gefetinib, Sunitinib, Imatinib, or anti-ckit inhibitors (registered name is Gleevec); natural antineoplastics, including but not limited to aldesleukin, interleukin-2, docetaxel, etoposide (VP-16), interferon alpha, paclitaxel, and tretinoin (ATRA)carboplatin and cisplatin; nitrosourea alkylating antineoplastic agents, including but not limited to carmustine (BCNU); fluorouracil (5-FU) and gemcitabine; hormonal antineoplastics, including but not limited to goserelin, leuprolide, and tamoxifen; receptor inhibitors including but not limited to erlotinib, gefetinib, Sunitinib, Imatinib, or anti-ckit inhibitors (registered name is Gleevec); natural antineoplastics, including but not limited to aldesleukin, interleukin-2, docetaxel, etoposide (VP-16), interferon alpha, paclitaxel, and tretinoin (ATRA), antibiotics, antivirals, antifungals, anesthetics, antihelminths, anti-inflammatories, and anticoagulants.

In some embodiments, the bioactive agent(s) to be delivered is dissolved in an aqueous solution or in an aqueous solution containing another compound to increase the agent's solubility including but not limited to cremaphor E/L for paclitaxel.

Non-limiting examples of additional pharmaceutically active agents include the following therapeutic categories: anabolic agents, anesthetic agents, antacids, anti-asthmatic agents, anti cholesterolemic and anti-lipid agents, anti-coagulants, anti-convulsants, anti-diarrheals, antiemetics, anti-infective agents, anti-inflammatory agents, anti-manic agents, anti-nauseants, antineoplastic agents, anti-obesity agents, anti-pyretic and analgesic agents, anti-spasmodic agents, anti-thrombotic agents, anti-uricemic agents, antianginal agents, antihistamines, anti-tussives, appetite suppressants, biologicals, cerebral dilators, coronary dilators, decongestants, diuretics, diagnostic agents, erythropoietic agents, expectorants, gastrointestinal sedatives, hyperglycemic agents, hypnotics, hypoglycemic agents, ion exchange resins, laxatives, mineral supplements, mucolytic agents, neuromuscular drugs, peripheral vasodilators, psychotropics, sedatives, small molecule inhibitors, receptor enzymes, stimulants, thyroid and anti-thyroid agents, uterine relaxants, vitamins, and prodrugs.

More specifically, non-limiting examples of pharmaceutically active agents include the following therapeutic categories: analgesics, including but not limited to nonsteroidal anti-inflammatory drugs, opiate agonists and salicylates; antihistamines, including but not limited to H1-blockers and H2-blockers; anti-infective agents, including but not limited to anthelmintics, antianaerobics, antibiotics, aminoglycoside antibiotics, antifungal antibiotics, cephalosporin antibiotics, macrolide antibiotics, miscellaneous beta-lactam antibiotics, penicillin antibiotics, quinolone antibiotics, sulfonamide antibiotics, tetracycline antibiotics, antimycobacterials, antituberculosis antimycobacterials, antiprotozoals, antimalarial antiprotozoals, antiviral agents, anti-retroviral agents, scabicides, and urinary anti-infectives; antineoplastic agents, including but not limited to alkylating agents, nitrogen mustard aklylating agents, nitrosourea alkylating agents, antimetabolites, purine analog antimetabolites, pyrimidine analog antimetabolites, hormonal antineoplastics, natural antineoplastics, antibiotic natural antineoplastics, and *vinca* alkaloid natural antineoplastics; autonomic agents, including but not limited to anticholinergics, antimuscarinic anticholinergics, ergot alkaloids, parasympathomimetics, cholinergic agonist parasympathomimetics, cholinesterase inhibitor para-sympathomimetics, sympatholytics, alpha-blocker sympatholytics, beta-blocker sympatholytics, sympathomimetics, and adrenergic agonist sympathomimetics; cardiovascular agents, including but not limited to antianginals, betablocker antianginals, calcium-channel blocker antianginals, nitrate antianginals, antiarrhythmics, cardiac glycoside antiarrhythmics, class I antiarrhythmics, class II antiarrhythmics, class III antiarrhythmics, class IV antiarrhythmics, antihypertensive agents, alpha-blocker antihypertensives, angiotensin-converting enzyme inhibitor (ACE inhibitor) antihypertensives, beta-blocker antihypertensives, calcium-channel blocker antihypertensives, central-acting adrenergic antihypertensives, diuretic antihypertensive agents, peripheral vasodilator antihypertensives, antilipemics, bile acid sequestrant antilipemics, HMG-CoA reductase inhibitor antilipemics, inotropes, cardiac glycoside inotropes, and thrombolytic agents; dermatological agents, including but not limited to antihistamines, anti-inflammatory agents, corticosteroid anti-inflammatory agents, antipruritics/local anesthetics, topical anti-infectives, antifungal topical anti-infectives, antiviral topical anti-infectives, and topical antineoplastics; electrolytic and renal agents, including but not limited to acidifying agents, alkalinizing agents, diuretics, carbonic anhydrase inhibitor diuretics, loop diuretics, osmotic diuretics, potassium-sparing diuretics, thiazide diuretics, electrolyte replacements, and uricosuric agents; enzymes, including but not limited to pancreatic enzymes and thrombolytic enzymes; gastrointestinal agents, including but not limited to antidiarrheals, antiemetics, gastrointestinal anti-inflammatory agents, salicylate gastrointestinal anti-inflammatory agents, antacid anti-ulcer agents, gastric acid-pump inhibitor anti-ulcer agents, gastric mucosal anti-ulcer agents, H2-blocker anti-ulcer agents, cholelitholytic agents, digestants, emetics, laxatives and stool softeners, and prokinetic agents; general anesthetics, including but not limited to inhalation anesthetics, halogenated inhalation anesthetics, intravenous anesthetics, barbiturate intravenous anesthetics, benzodiazepine intravenous anesthetics, and opiate agonist intravenous anesthetics; hematological agents, including but not limited to antianemia agents, hematopoietic antianemia agents, coagulation agents, anticoagulants, hemostatic coagulation agents, platelet inhibitor coagulation agents, thrombolytic enzyme coagulation agents, and plasma volume expanders; hormones and hormone modifiers, including but not limited to abortifacients, adrenal agents, corticosteroid adrenal agents, androgens, antiandrogens, antidiabetic agents, sulfonylurea antidiabetic agents, antihypoglycemic agents, oral contraceptives, progestin contraceptives, estrogens, fertility agents, oxytocics, parathyroid agents, pituitary hormones, progestins, antithyroid agents, thyroid hormones, and tocolytics; immunobiologic agents, including but not limited to immunoglobulins, immunosuppressives, toxoids, and vaccines; local anesthetics, including but not limited to amide local anesthetics and ester local anesthetics; musculoskeletal agents, including but not limited to anti-gout anti-inflammatory agents, corticosteroid anti-inflammatory agents, gold compound anti-inflammatory agents, immunosuppressive anti-inflammatory agents, nonsteroidal anti-inflammatory drugs (NSAIDs), salicylate anti-inflammatory agents, skeletal muscle relaxants, neuromuscular blocker skeletal muscle relaxants, and reverse neuromuscular blocker skeletal muscle relaxants; neurological agents, including but not limited to anticonvulsants, barbiturate anticonvulsants, benzodiazepine anticonvulsants, anti-migraine agents, anti-parkinsonian agents, anti-vertigo agents, opiate agonists, and opiate antagonists; ophthalmic agents, including but not limited to antiglaucoma agents, beta-blocker anti-glaucoma agents, miotic anti-glaucoma agents, mydriatics, adrenergic agonist mydriatics, antimuscarinic mydriatics, ophthalmic anesthetics, ophthalmic anti-infectives, ophthalmic aminoglycoside anti-infectives, ophthalmic macrolide anti-infectives, ophthalmic quinolone anti-infectives, ophthalmic sulfonamide anti-infectives, ophthalmic tetracycline anti-infectives, ophthalmic anti-inflammatory agents, ophthalmic corticosteroid anti-inflammatory agents, and ophthalmic nonsteroidal anti-inflammatory drugs (NSAIDs); psychotropic agents, including but not limited to antidepressants, heterocyclic antidepressants, monoamine oxidase inhibitors (MAOIs), sclerosants including but not limited to talc, alcohol or doxycyclin, selective serotonin re-uptake inhibitors (SSRIs), tricyclic antidepressants, antimanics, antipsychotics, phenothiazine antipsychotics, anxiolytics, sedatives, and hypnotics, barbiturate sedatives and hypnotics, benzodiazepine anxiolytics, sedatives, and hypnotics, and psychostimulants; respiratory agents, including but not limited to antitussives, bronchodilators, adrenergic agonist bronchodilators, antimuscarinic bronchodilators, expectorants, mucolytic agents, respiratory anti-inflammatory agents, leukotriene modifiers and respiratory corticosteroid anti-inflammatory agents; toxicology agents, including but not limited to antidotes, heavy metal antagonists/chelating agents, substance abuse agents, deterrent substance abuse agents, and withdrawal substance abuse agents; minerals; and vitamins, including but not limited to vitamin A, vitamin B, vitamin C, vitamin D, vitamin E, and vitamin K.

In some embodiments, the pharmaceutically active agents can include an antimicrobial agent. The term "antimicrobial agent" as used herein refers to any entity with antimicrobial activity, i.e. the ability to inhibit or reduce the growth and/or kill a microbe, for example, bacteria. In various embodiments, the antimicrobial agent can be a compound (e.g., antibiotics or antiseptic agent) indicated for treatment of a bacterial infection in a human or veterinary subject.

In some embodiments, an antimicrobial agent can be an antibiotic. As used herein, the term "antibiotic" is art recognized and includes antimicrobial agents naturally produced by microorganisms such as bacteria (including *Bacillus* species), actinomycetes (including *Streptomyces*) or fungi that inhibit growth of or destroy other microbes, or genetically-engineered thereof and isolated from such natural source. Substances of similar structure and mode of action can be synthesized chemically, or natural compounds can be modified to produce semi-synthetic antibiotics.

Additional examples of antimicrobial agents include, but are not limited to, silver nanoparticles, rods, crystals, or any other structures, and/or silver salts.

Pharmaceutical Compositions

As used herein, the term "pharmaceutical composition" refers to a chemical compound or composition capable of inducing a desired therapeutic effect in a subject. In some embodiments, a pharmaceutical composition comprises a pre-formed dissolvable hydrogel described herein. In some embodiments, a pharmaceutical composition comprises components of the linear, branched and/or dendritic cross-linkable polymers described herein to be applied to a target site (e.g., a wound) to form a dissolvable hydrogel described herein in situ at the target site (e.g., a wound). In certain embodiments, a pharmaceutical composition comprises a therapeutically effective amount of a bioactive agent described herein distributed in one or more embodiments of the dissolvable hydrogel described herein. In some embodiments, the pharmaceutical composition can comprise a prodrug of the compounds provided herein. In certain embodiments, a pharmaceutical composition can comprise inactive ingredients, such as, for example, carriers and excipients.

The phrase "therapeutically effective amount" refers to the amount of a pharmaceutical composition that elicits the biological or medicinal response in a tissue, system, animal, individual, patient, or human that is being sought by a researcher, veterinarian, medical doctor or other clinician.

As used herein, the term "pharmaceutically acceptable" refers to a formulation of a compound that does not significantly abrogate the biological activity, a pharmacological activity and/or other properties of the compound when the formulated compound is administered to a subject. In certain embodiments, a pharmaceutically acceptable formulation does not cause significant irritation to a subject.

As used herein, pharmaceutically acceptable derivatives of a compound include, but are not limited to, salts, esters, enol ethers, enol esters, acetals, ketals, orthoesters, hemiacetals, hemiketals, acids, bases, solvates, hydrates, PEGylation, or prodrugs thereof. Such derivatives can be readily prepared by those of skill in this art using known methods for such derivatization. The compounds produced can be administered to animals or humans without substantial toxic effects and are either pharmaceutically active or prodrugs. Pharmaceutically acceptable salts include, but are not limited to, amine salts, such as but not limited to chloroprocaine, choline, N,N-dibenzyl-ethylenediamine, ammonia, diethanolamine and other hydroxyalkylamines, ethylenediamine, N-methylglucamine, procaine, N-benzyl-phenethylamine, 1-para-chloro-benzyl-2-pyrrolidin-1'-ylmethyl-benzimidazole, diethylamine and other alkylamines, piperazine and tris(hydroxymethyl)-aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula $C=C(OR)$ where R is hydrogen, alkyl, alkenyl, alkynyl, aryl, heteroaryl, aralkyl, heteroaralkyl, cycloalkyl, or heterocyclyl. Pharmaceutically acceptable enol esters include, but are not limited to, derivatives of formula $C=C(OC(O)R)$ where R is hydrogen, alkyl, alkenyl, alkynyl, aryl, heteroaryl, aralkyl, heteroaralkyl, cycloalkyl, or heterocyclyl. Pharmaceutically acceptable solvates and hydrates are complexes of a compound with one or more solvent or water molecules, or one to about 100, or one to about 10, or one to about two, three, or four, solvent or water molecules.

In some embodiments, the pharmaceutical composition can further comprise a pharmaceutically-acceptable carrier. As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each earner must be "acceptable" in the sense of being compatible with the other ingredients of the formulation and not injurious to the patient. Some examples of materials which can serve as pharmaceutically-acceptable carriers include: (1) sugars, such as lactose, mannose, fructose, dextrose, trehalose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

As used herein, the term "administer" refers to the placement of a composition into a subject by a method or route which results in at least partial localization of the composition at a desired site such that desired effect is produced. Examples of administration routes can include, but are not limited to, transdermal, topical (including buccal and sublingual) administration and/or by surgery.

In some embodiments, the pharmaceutical composition comprising components of the crosslinkable polymers can be administered to a target site (e.g., a wound) by injection such that a dissolvable hydrogel can form in situ at the target site (e.g., a wound). In some embodiments, the pharmaceutical composition comprising a pre-formed dissolvable hydrogel can be administered to a target site (e.g., a wound) by direct implantation and surgery.

Embodiments of various aspects described herein can be defined in any of the following numbered paragraphs:

1. A method comprising:
    (a) contacting a wound with a hydrogel composition comprising a dissolvable hydrogel layer, wherein the dissolvable hydrogel layer comprises linear, branched, and/or dendritic crosslinkable polymers held together by covalent bonds formed between the first crosslinkable polymer and the second crosslinkable polymer, wherein the dissolvable hydrogel layer comprises thioester linkages; and
    (b) allowing the dissolvable hydrogel layer to adhere to tissue surrounding the wound.
2. The method of paragraph 1, further comprising dissolving the dissolvable hydrogel layer by adding a thiolate compound to result in a thiol-thioester exchange, thereby releasing the hydrogel composition from the wound.
3. A method comprising:
    (a) contacting a wound with a hydrogel composition comprising a dissolvable hydrogel layer, wherein the dissolvable hydrogel layer comprises linear, branched, and/or dendritic crosslinkable polymers held together by thioester linkages formed between the first crosslinkable polymer and the second crosslinkable polymer;
    (b) allowing the dissolvable hydrogel layer to adhere to tissue surrounding the wound; and
    (c) dissolving the dissolvable hydrogel layer by adding a thiolate compound to result in a thiol-thioester exchange, thereby releasing the hydrogel composition from the wound.
4. The method of any of paragraphs 1-3, wherein the dissolvable hydrogel layer is derived from a first water-soluble linear, branched, and/or dendritic crosslinkable polymer comprising at least two thiol moieties and a second water-soluble linear, branched, and/or dendritic crosslinkable polymer comprising at least two crosslinking moieties that are capable of reacting with said at least two thiol moieties of the first crosslinkable polymer to form the thioester linkages between the first and second crosslinkable polymers.
5. The method of paragraph 1 or 2, wherein the dissolvable hydrogel layer is derived from a first water-soluble linear, branched, and/or dendritic crosslinkable polymer comprising at least two thioester linkages and a second water-soluble linear, branched, and/or dendritic crosslinkable polymer comprising at least two crosslinking moieties that are capable of forming a linkage with the first water-soluble linear, branched, and/or dendritic polymer.
6. The method of paragraph 1 or 2, wherein the dissolvable hydrogel layer is derived from a first water-soluble linear, branched and/or dendritic crosslinkable polymer comprising at least two nucleophilic moieties that are capable of forming a linkage with at least two crosslinking moieties of the second-water soluble linear, branched and/or dendritic polymer; wherein at least one of the first and second water-soluble linear, branched and/or dendritic crosslinkable polymers comprises at least two thioester linkages.
7. The method of any of paragraphs 1-6, wherein the linear crosslinkable polymer comprises polyesters, poly ethers, polyether-esters, polyglycerols, polyamino acids, polyester-amines, polyurethanes, polycarbonates, polyamino alcohols, thiols, amines, N-hydroxysuccinimide (NHS) moieties, maleimide (MAL) moieties, or any combinations thereof.
8. The method of any of paragraphs 1-7, wherein the branched crosslinkable polymer comprises polyesters, polyethers, polyether-esters, polyglycerols, polyamino acids, polyester-amines, polyurethanes, polycarbonates, polyamino alcohols, thiols, amines, N-hydroxysuccinimide (NHS) moieties, Maleimide (MAL) moieties, or any combinations thereof.

9. The method of any of paragraphs 1-8, wherein the dendritic crosslinkable polymer comprises polyesters, polyethers, polyether-esters, polyamino acids, polyester-amines, polyurethanes, polycarbonates, polyamino alcohols, thiols, amines, N-hydroxysuccinimide (NHS) moieties, Maleimide (MAL) moieties, or any combinations thereof.

10. The method of any of paragraphs 1-9, wherein the first crosslinkable polymer has a chemical structure selected from the group consisting of structure (i)-structure (xii) shown as follows:

(i)

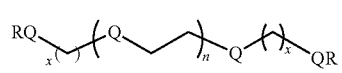

(ii)

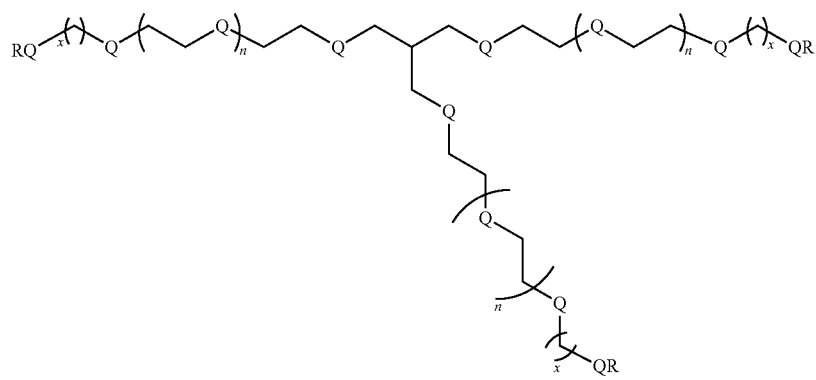

(iii)

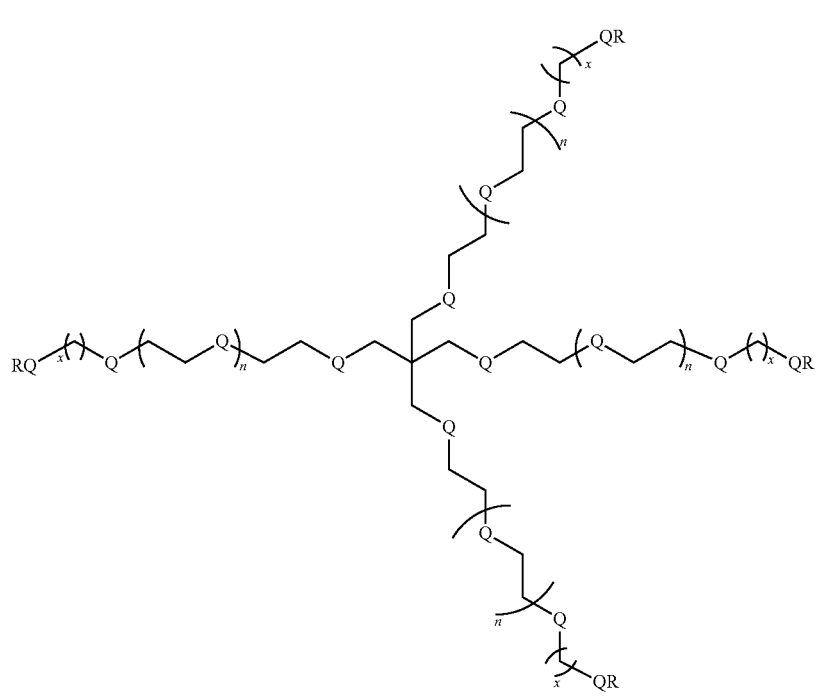

(iv)
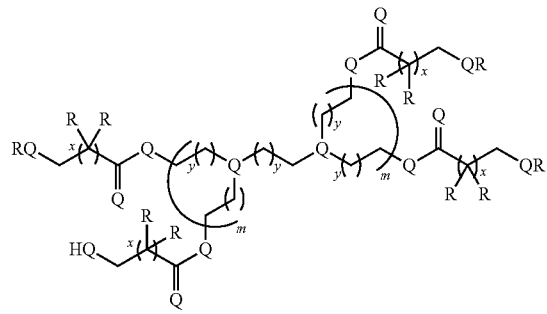
(v)
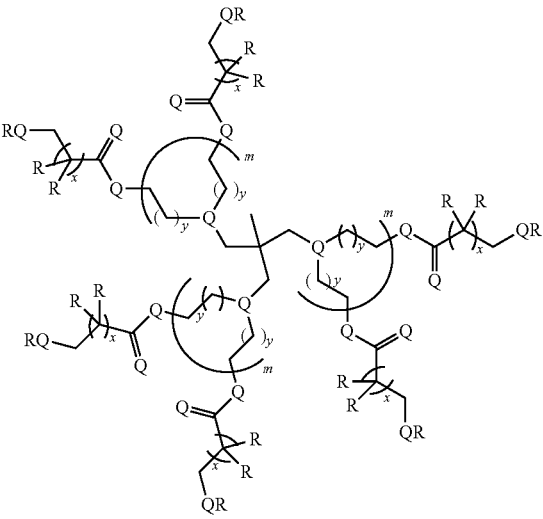
(vi)
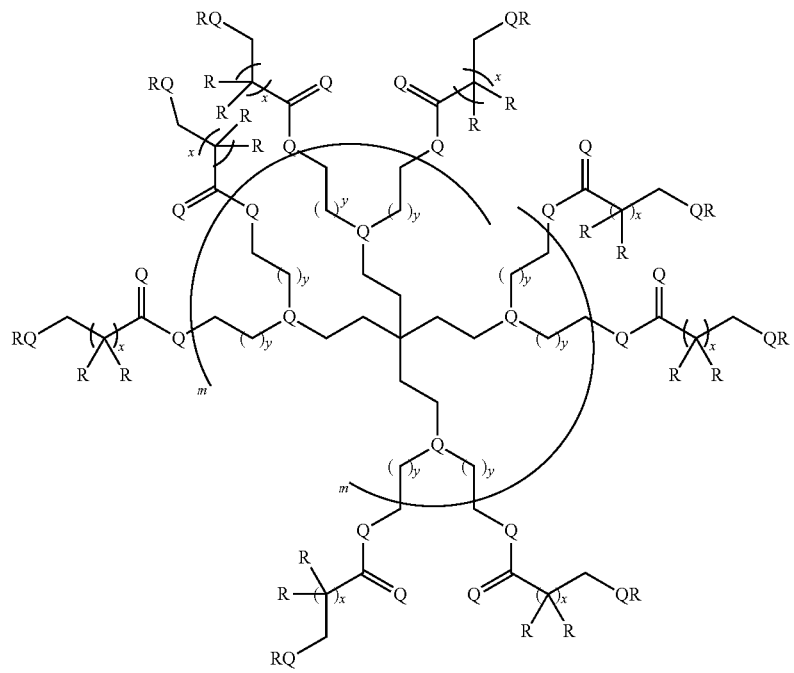
(vii)
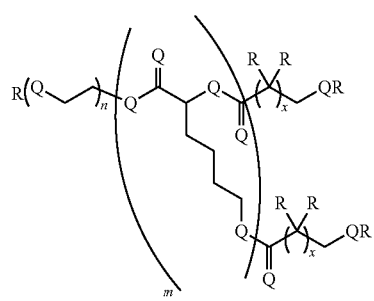
(viii)
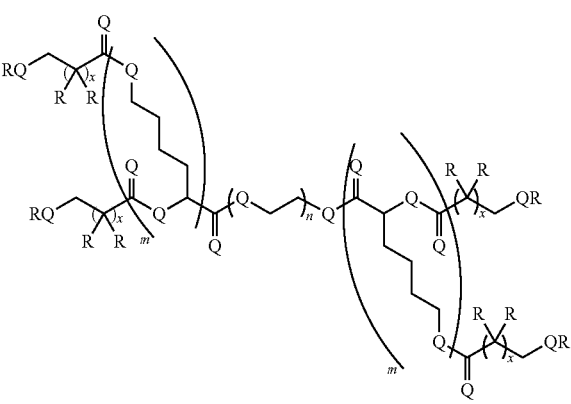

-continued

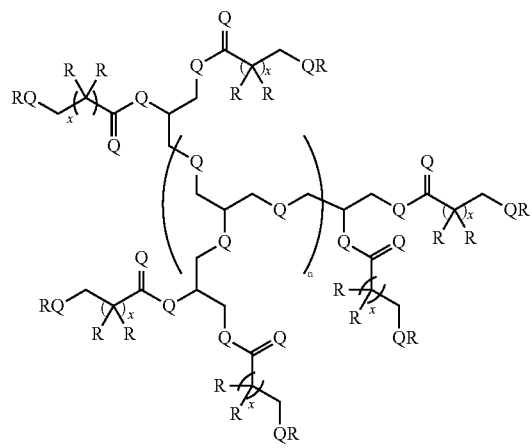
(ix)

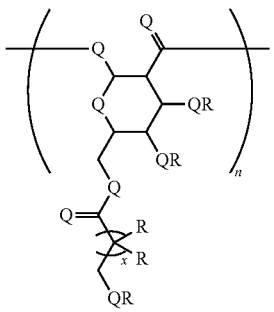
(x)

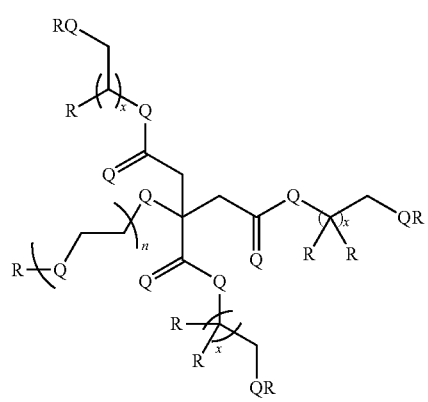
(xi)

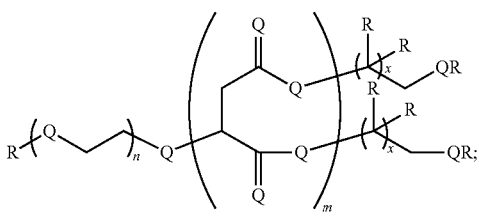
(xii)

and any combinations thereof; and wherein:
- Q is independently selected from the group consisting of O, S, Se, NH, $CH_2$ and any combination thereof;
- R is selected from the group consisting of a hydrogen, straight or branched alkyl, cycloalkyl, aryl, olefin or alkene, alkyne, silyl, alkylsilyl, arylsilyl, alkylaryl or arylalkyl chain of 1-50 carbons, fluorocarbon, and any combinations thereof, wherein each alkyl, cycloalkyl, aryl, olefin, alkyne, silyl, alkylsilyl, arylsilyl, alkylaryl, fluorocarbon, or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, halogen substituents; and any combinations thereof; and
- m, n, and x are each independently selected from an integer of 0-1000.

11. The method of any of paragraphs 4-10, wherein said at least two crosslinking moieties comprise at least one N-hydroxysuccinimide (NHS) or maleimide (MAL) moeity.

12. The method of any of paragraphs 4-10, wherein said at least two crosslinking moieties comprise at least two N-hydroxysuccinimide (NHS) or maleimide (MAL) moeities.

13. The method of any of paragraphs 1-12, wherein the second cross-linkable polymer has a chemical structure selected from the group consisting of structure (xiii)-structure (xI) shown as follows:

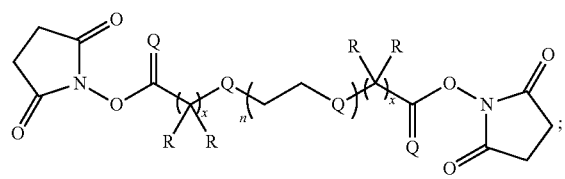
(xiii)

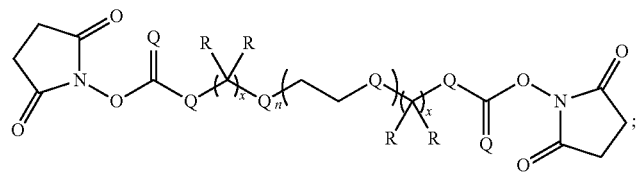
(xiv)
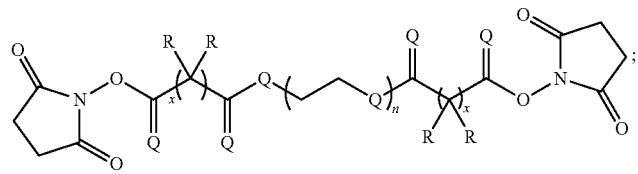
(xv)
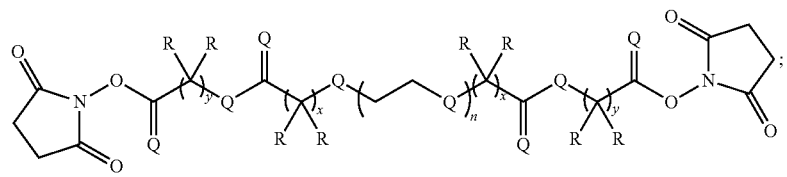
(xvi)
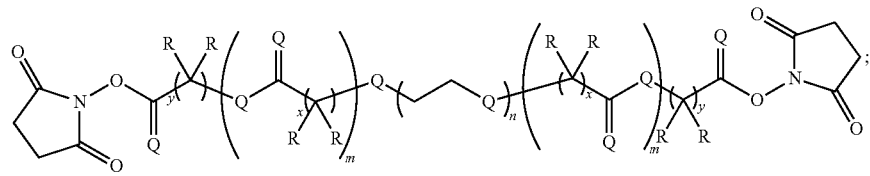
(xvii)
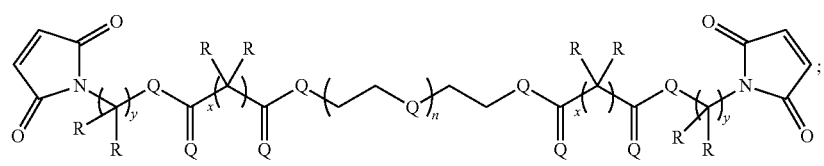
(xviii)
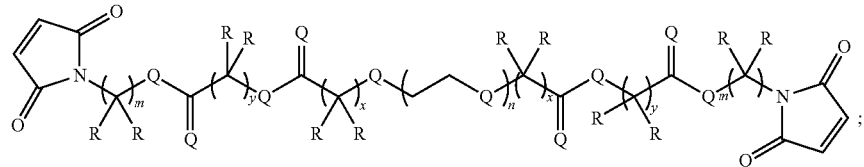
(xix)
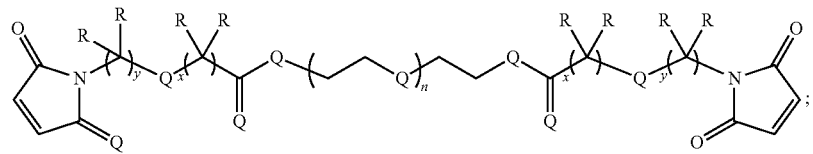
(xx)

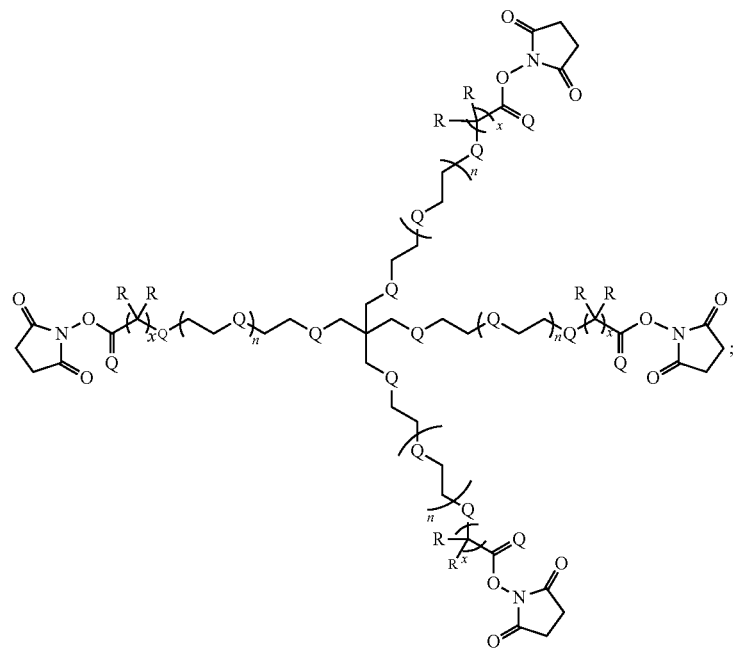
(xxi)
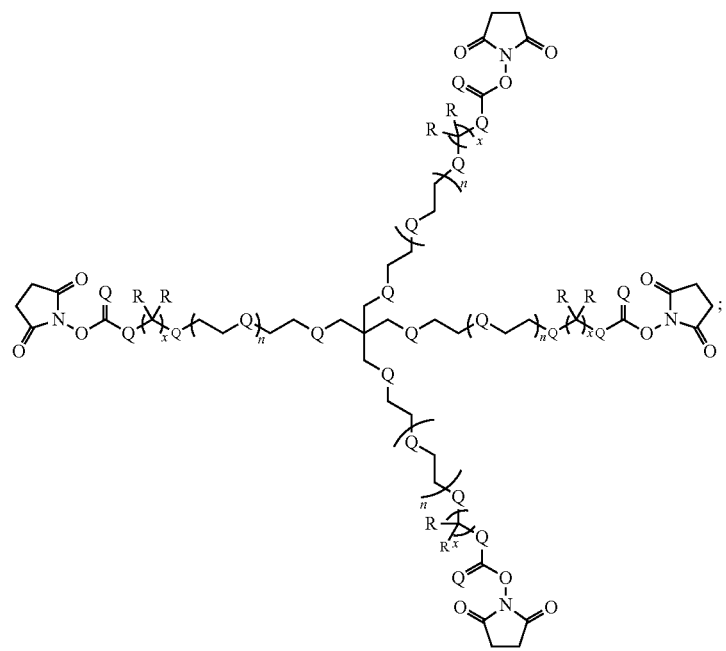
(xxii)

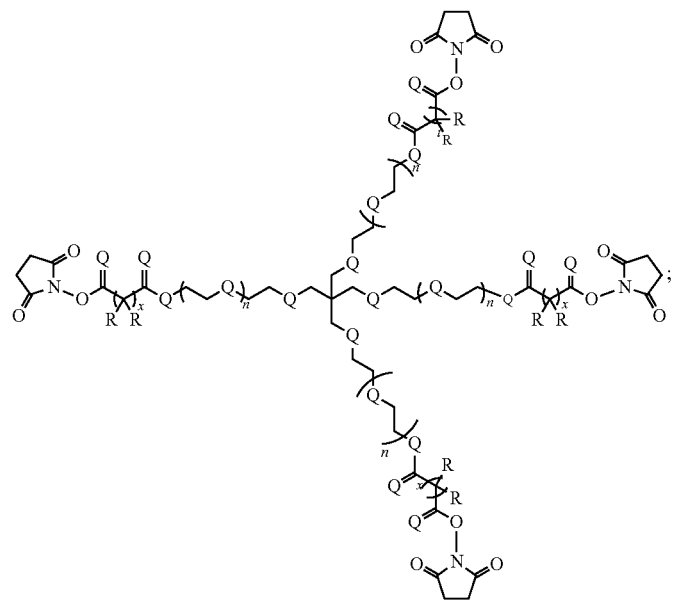
(xxiii)
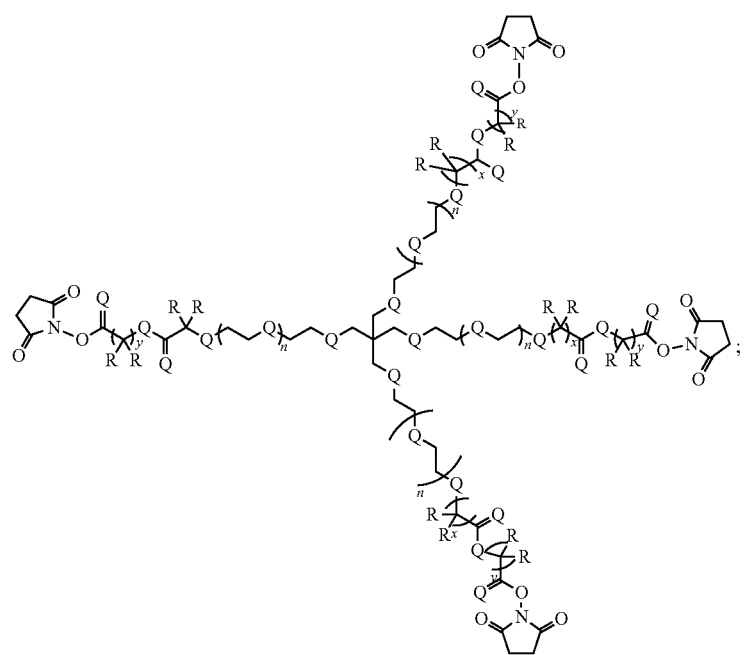
(xxiv)

-continued
(xxv)
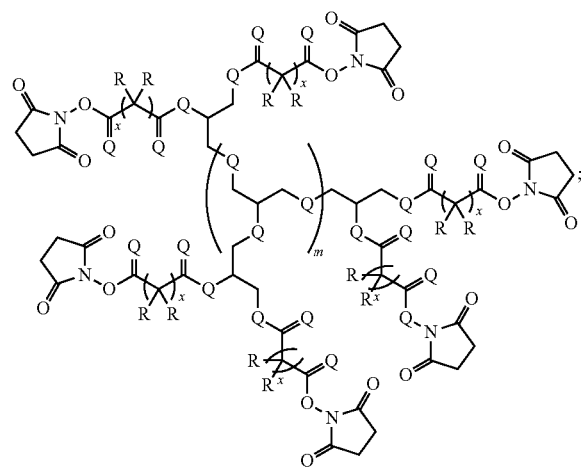
(xxvi)
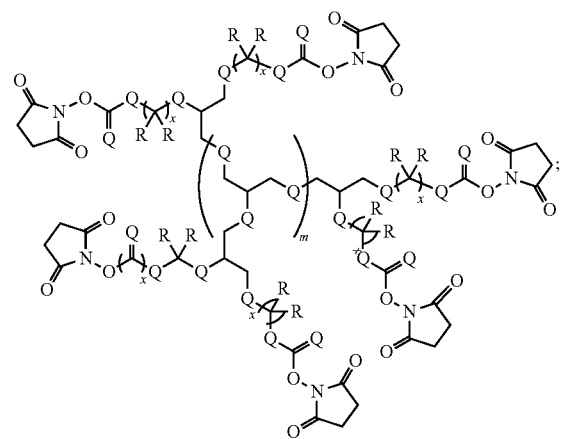
(xxvii)
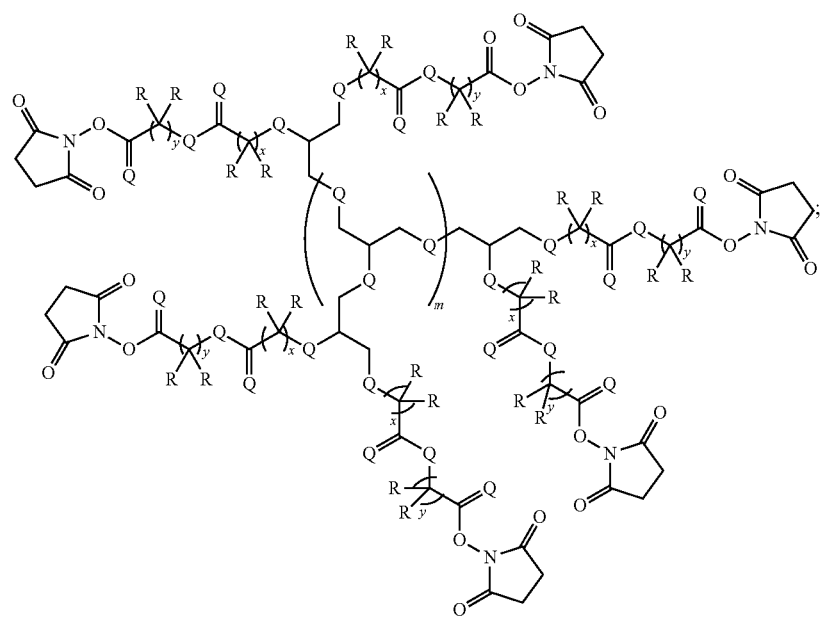

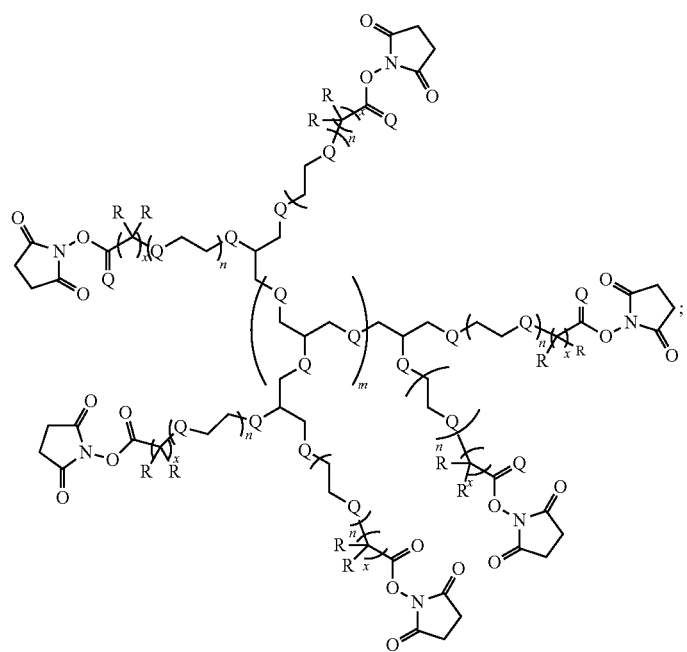
(xxviii)
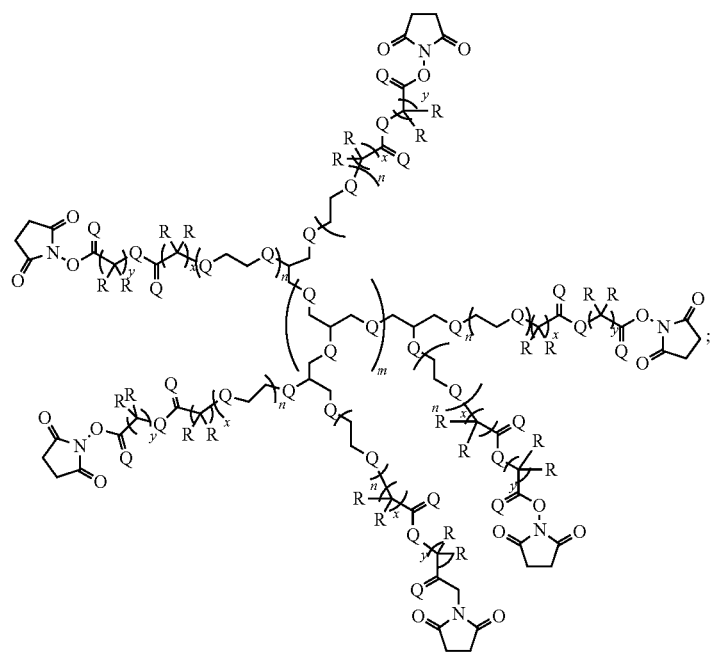
(xxix)

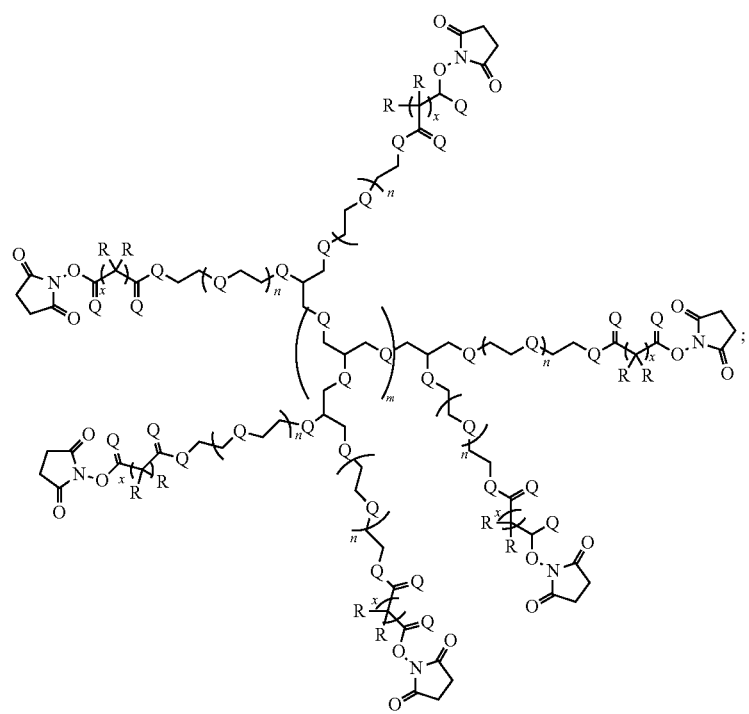
(xxx)
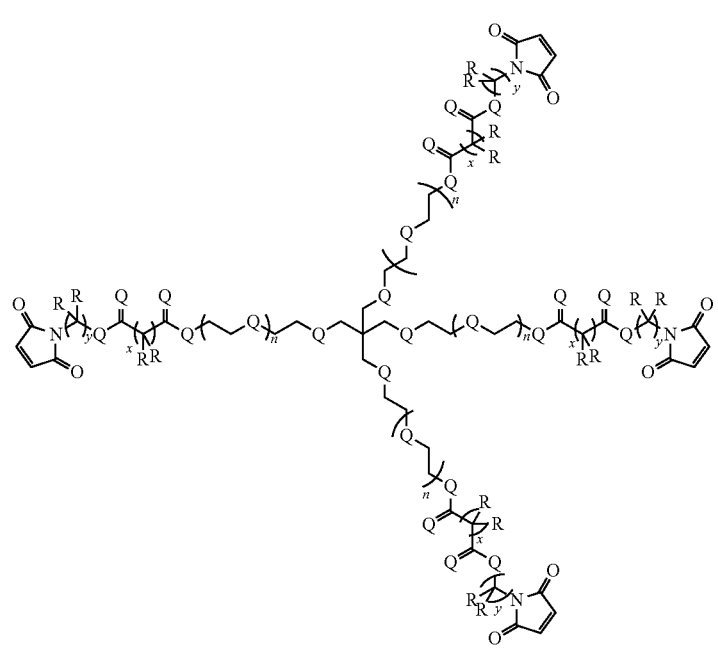
(xxxi)

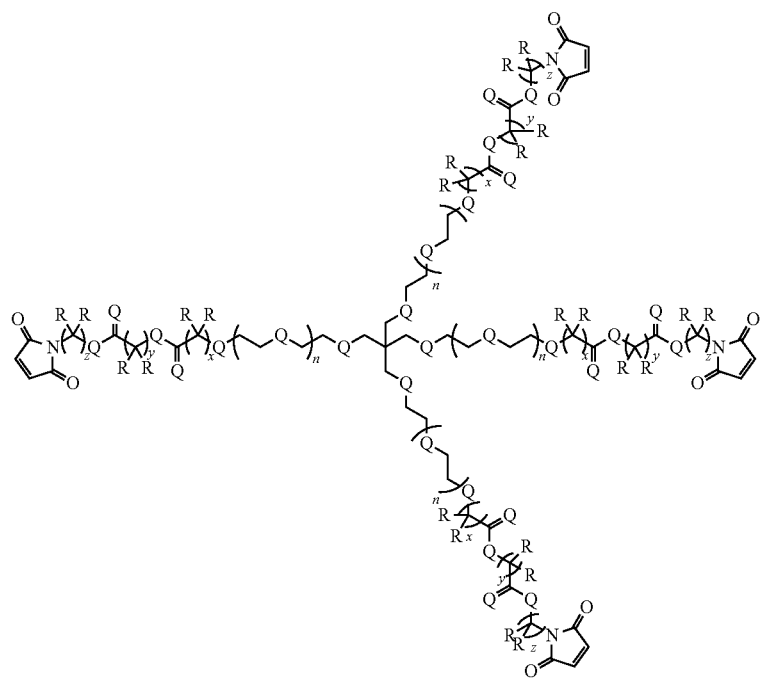
(xxxii)
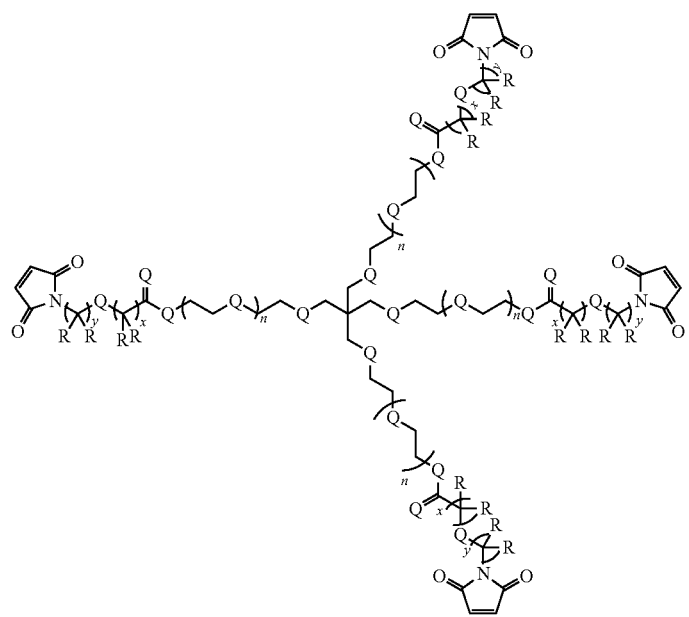
(xxxiii)

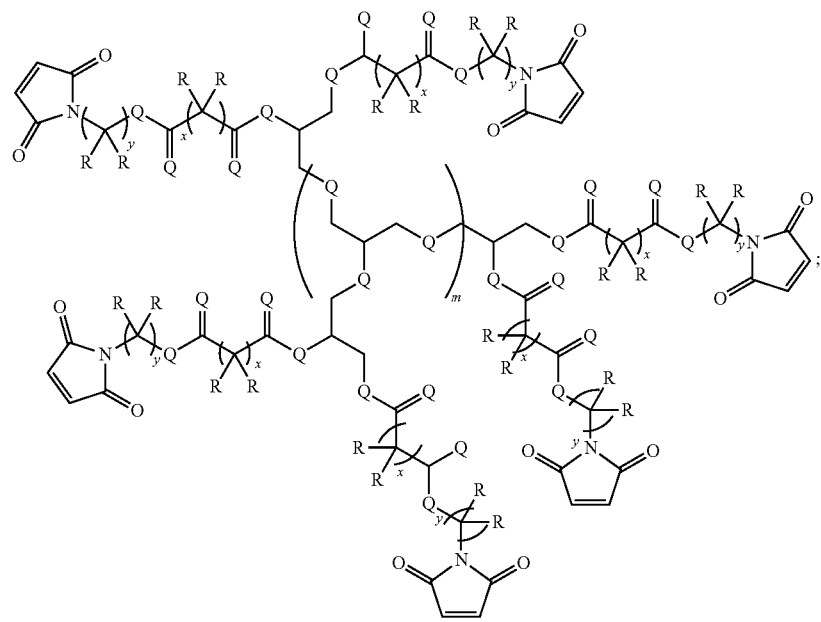
(xxxiv)
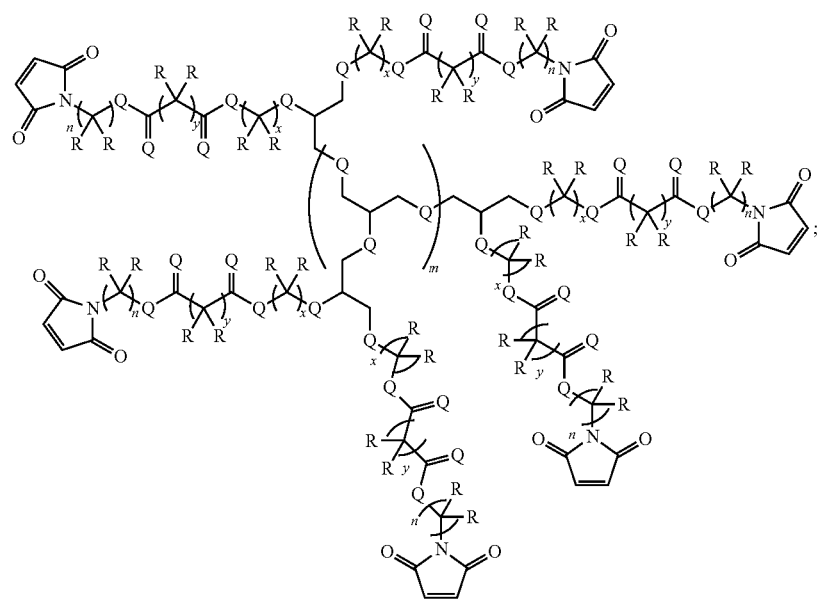
(xxxv)

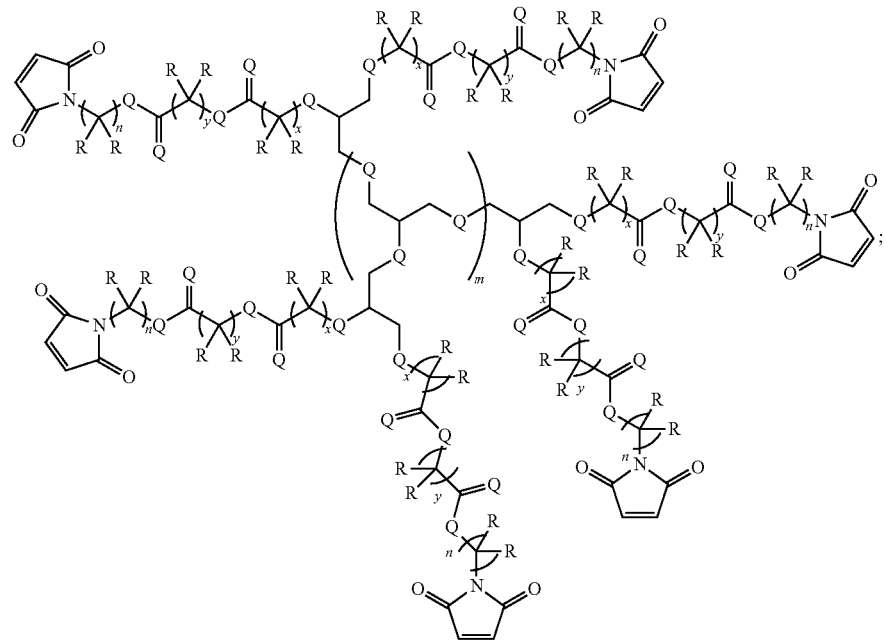
(xxxvi)
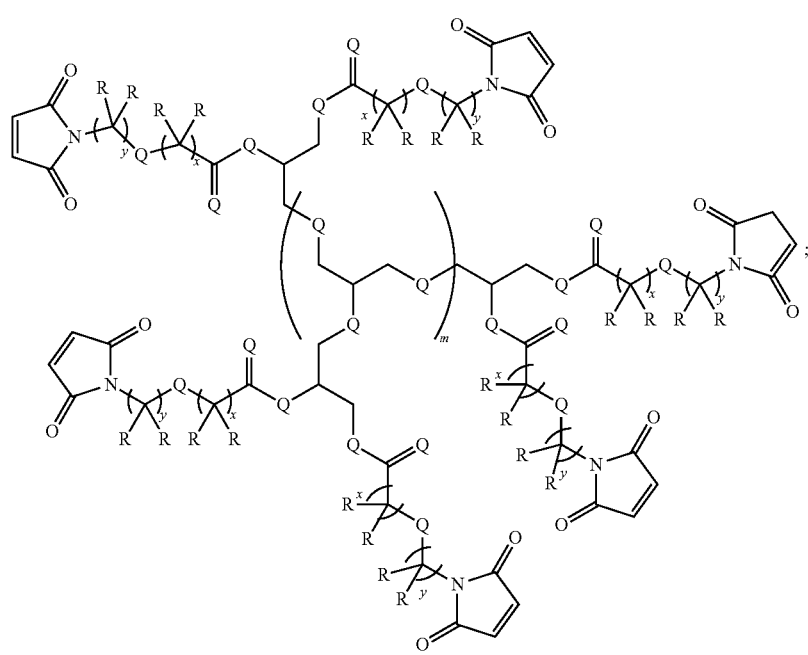
(xxxvii)

(xxxviii)
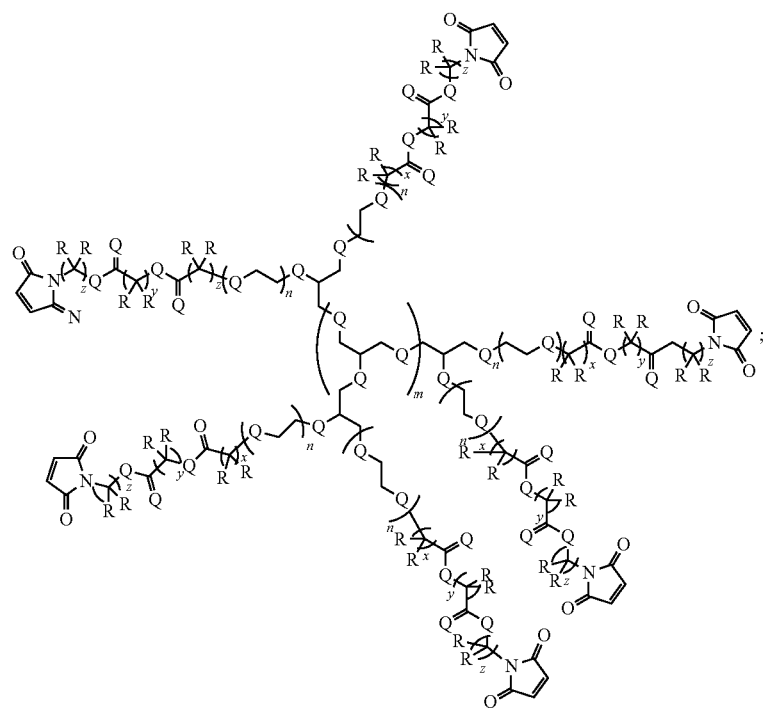
(xxxix)
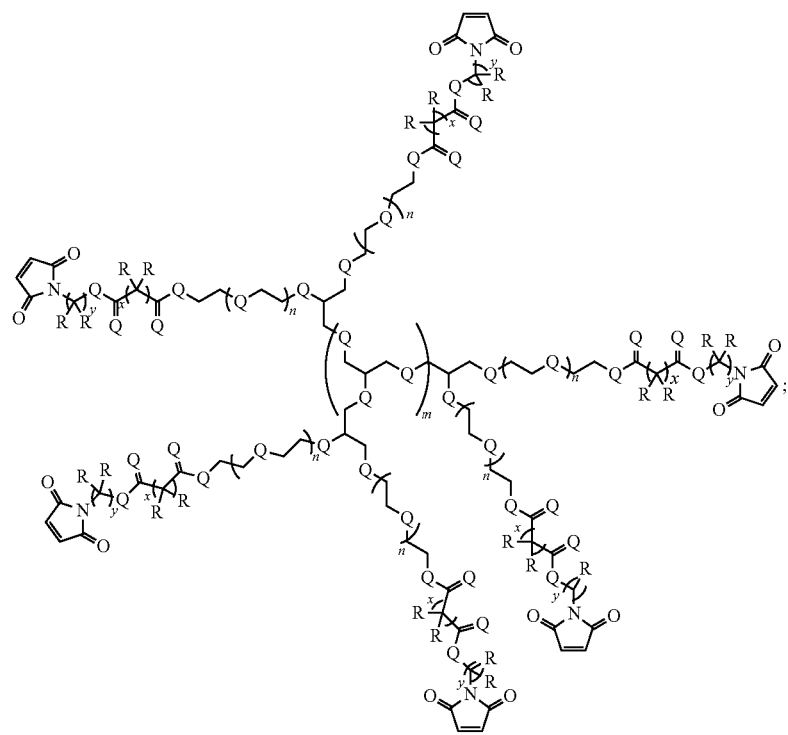

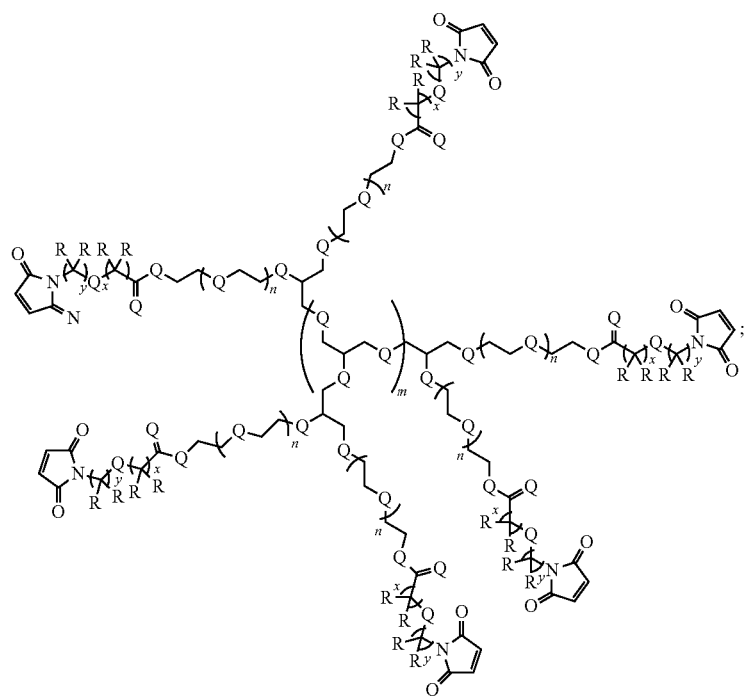

(xl)

and any combination thereof; and wherein
Q is independently selected from the group consisting of O, S, Se, NH, CH$_2$ and any combination thereof;
R is selected from the group consisting of a hydrogen, straight or branched alkyl, cycloalkyl, aryl, olefin or alkene, alkyne, silyl, alkylsilyl, arylsilyl, alkylaryl or arylalkyl chain of 1-50 carbons, fluorocarbon, and any combinations thereof, wherein each alkyl, cycloalkyl, aryl, olefin, alkyne, silyl, alkylsilyl, arylsilyl, alkylaryl, fluorocarbon, or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, halogen substituents; and any combinations thereof; and
m, n, x, y and z are each independently selected from an integer of 0-1000.

14. The method of any of paragraphs 10-13, wherein R is selected from the group consisting of poly(ethylene glycol), poly(ethylene oxide), poly(hydroxyacid), a carbohydrate, a protein, a polypeptide, an amino acid, a nucleic acid, a nucleotide, a polynucleotide, a DNA segment, a RNA segment, a lipid, a polysaccharide, an antibody, a pharmaceutical agent, an epitope for a biological receptor, and any combinations thereof.

15. The method of any of paragraphs 1-14, wherein the thiolate compound is selected from the group consisting of linear, branched and/or dendritic multi-thiol macromolecule, poly(ethylene glycol) thiol, thiol containing glycerol, thiol containing peptide, cysteine, cystine, alkyl ester of cysteine, alkyl ester of cystine, MeSCH2SH, (R)/(S)-3-methyl-3-sulfanylhexan-1-ol, Ethanethiol, 1-Propanethiol, 2-Propanethiol, Butanethiol, tert-Butyl mercaptan, Pentanethiols, Thiophenol, Dimercaptosuccinic acid, Thioacetic acid, 5-mercapto-4H-[1,2,4]triazol-3-ol, 2-mercaptoacetamide, 2-Mercaptoethanol, 1,2-Ethanedithiol, Ammonium thioglycolate, Cysteamine, Methyl thioglycolate, Thiolactic acid, 1-Mercapto-2-propanol, 2-methoxyethanethiol, 3-Mercapto-1-propanol, 2,3-Dimercapto-1-propanol, 1-Thioglycerol, Mercaptosuccinic acid, 4-ethyl-5-mercapto-4H-1,2,4-triazol-3-ol, N-Carbamoyl-L-cysteine, 2-Methyl-3-sulfanylpropanoic acid, 4-mercaptobutyric acid, N-Acetyl cysteamine, 3-Methyl-1-butanethiol, 1,5-Pentanedithiol, 4-Chlorothiophenol, 4-Aminothiophenol, Benzyl mercaptan, 2-Furanmethanethiol, 3-Mercaptohexanol, Furfuryl thiol, derivatives thereof, a disulfide complex of one or more thereof, and any combinations thereof.

16. The method of any of paragraphs 1-15, wherein the dissolvable hydrogel layer is at least partially flexible.

17. The method of any of paragraphs 1-16, wherein the dissolvable hydrogel layer is at least partially adhesive.

18. The method of any of paragraphs 1-17, wherein the dissolvable hydrogel layer is capable of withstanding a pressure of at least about 2 mmHg.

19. The method of any of paragraphs 1-18, wherein the dissolvable hydrogel layer is transparent.

20. The method of any of paragraphs 1-19, wherein the dissolvable hydrogel layer is hydrophilic.

21. The method of any of paragraphs 1-20, wherein the dissolvable hydrogel layer is elastic or viscoelastic.

22. The method of any of paragraphs 1-21, wherein the dissolvable hydrogel layer has about 5 wt % to about 70 wt % of the crosslinkable polymers.

23. The method of any of paragraphs 1-22, wherein the hydrogel composition further comprises a bioactive agent.

24. The method of paragraph 23, wherein the bioactive agent is selected from the group consisting of pharmaceutical agents, drugs, cells, gases and gaseous precursors, synthetic organic molecules, proteins, enzymes, growth factors, vitamins, steroid, polyanions, nucleosides, nucleotides, polynucleotides, nanoparticles, diagnostic agents, genetic materials, and any combinations thereof.

25. The method of any of paragraphs 1-24, wherein the hydrogel composition is formulated to form a bandage, glue, sealant, dressing, scaffold, coating, or covering.

26. The method of any of paragraphs 1-25, wherein the hydrogel composition is used with vacuum assisted closure.

27. The method of any of paragraphs 1-26, wherein the thiolate compound is formulated as a solution or a spray.

28. A dissolvable hydrogel composition comprising: an adhesive hydrogel layer comprising a first water-soluble linear, branched, and/or dendritic crosslinkable polymer and a second water-soluble linear, branched, and/or dendritic crosslinkable polymer held together by thioester linkages formed between the first crosslinkable polymer and the second crosslinkable polymer,
wherein the first crosslinkable polymer comprises at least two thiol moieties and the second crosslinkable polymer comprises at least two crosslinking moieties that are capable of reacting with said at least two thiol moieties of the first crosslinkable polymer to form the thioester linkages between the first crosslinkable polymer and the second crosslinkable polymer.

29. A dissolvable hydrogel composition comprising: an adhesive hydrogel layer comprising a first water-soluble linear, branched and/or dendritic crosslinkable polymer and a second water-soluble linear, branched and/or dendritic crosslinkable polymer held together by covalent bonds formed between the first crosslinkable polymer and the second crosslinkable polymer, wherein the adhesive hydrogel layer comprises thioester linkages.

30. The dissolvable hydrogel composition of paragraph 29, wherein the first crosslinkable polymer comprises at least two thiol moieties and the second crosslinkable polymer comprises at least two crosslinking moieties that are capable of reacting with said at least two thiol moieties of the first crosslinkable polymer to form the thioester linkages between the first crosslinkable polymer and the second crosslinkable polymer;

31. The dissolvable hydrogel composition of paragraph 29, wherein the first crosslinkable polymer comprises at least two thioester linkages and the second crosslinkable polymer comprises at least two crosslinking moieties that are capable of forming a linkage with the first crosslinkable polymer.

32. The dissolvable hydrogel composition of paragraph 29, wherein the first crosslinkable polymer comprises at least two nucleophilic moieties that are capable of forming a linkage with at least two crosslinking moieties of the second crosslinkable polymer that comprises at least two thioester linkages.

33. The dissolvable hydrogel composition of any of paragraphs 28-32, wherein the linear crosslinkable polymer comprises polyesters, polyethers, polyglycerols, polypeptides, polyether-esters, polyamino acids, polyester-amines, polyurethanes, polycarbonates, polyamino alcohols, thiols, amines, N-hydroxysuccinimide (NHS) moieties, maleimide (MAL) moieties, or any combinations thereof 34. The dissolvable hydrogel composition of any of paragraphs 28-33, wherein the branched crosslinkable polymer comprises polyesters, polyethers, polyglycerols, polypeptides, polyether-esters, polyamino acids, polyester-amines, polyurethanes, polycarbonates, polyamino alcohols, thiols, amines, N-hydroxysuccinimide (NHS) moieties, maleimide (MAL) moiety, or any combinations thereof.

35. The dissolvable hydrogel composition of any of paragraphs 28-34, wherein the dendritic crosslinkable polymer comprises polyesters, polyethers, polyglycerols, polypeptides, polyether-esters, polyamino acids, polyester-amines, polyurethanes, polycarbonates, polyamino alcohols, thiols, amines, N-hydroxysuccinimide (NHS) moieties, maleimide (MAL) moieties, or any combinations thereof.

36. The dissolvable hydrogel composition of any of paragraphs 28-35, wherein when both the first and second crosslinkable polymers are branched or dendritic crosslinkable polymers, at least one of the first and the second dendritic crosslinkable polymers does not comprise poly(ethylene glycol).

37. The dissolvable hydrogel composition of any of paragraphs 28-36, wherein the first crosslinkable polymer has a chemical structure selected from the group consisting of structure (i) to structure (xii) shown as follows:

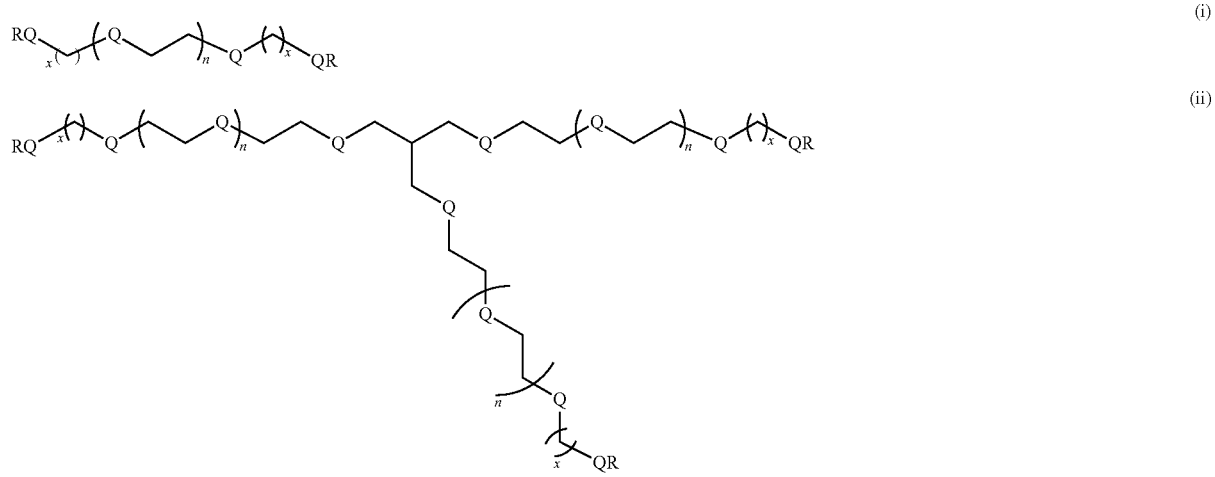

-continued
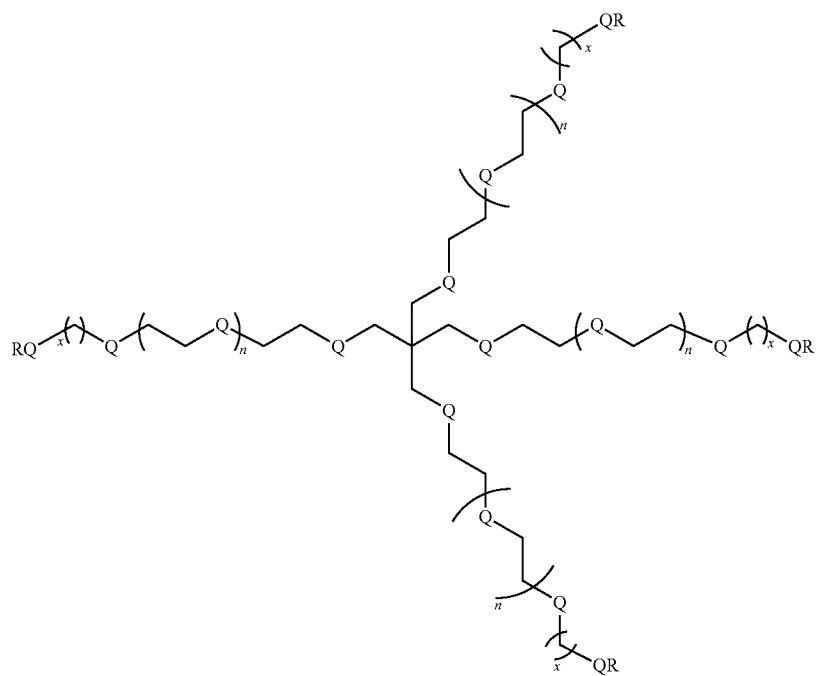
(iii)
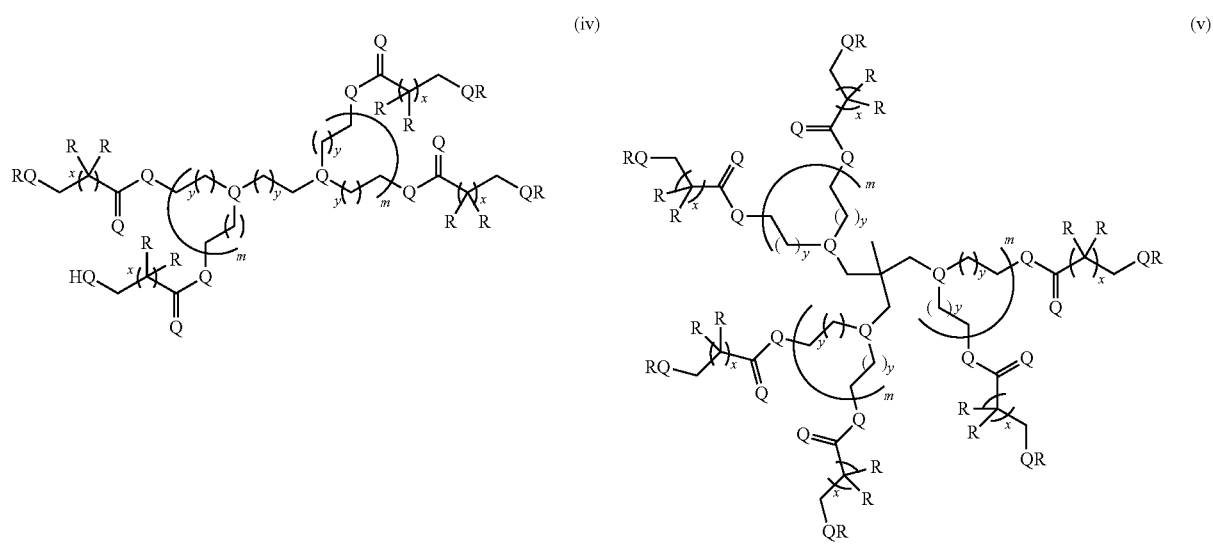
(iv)          (v)

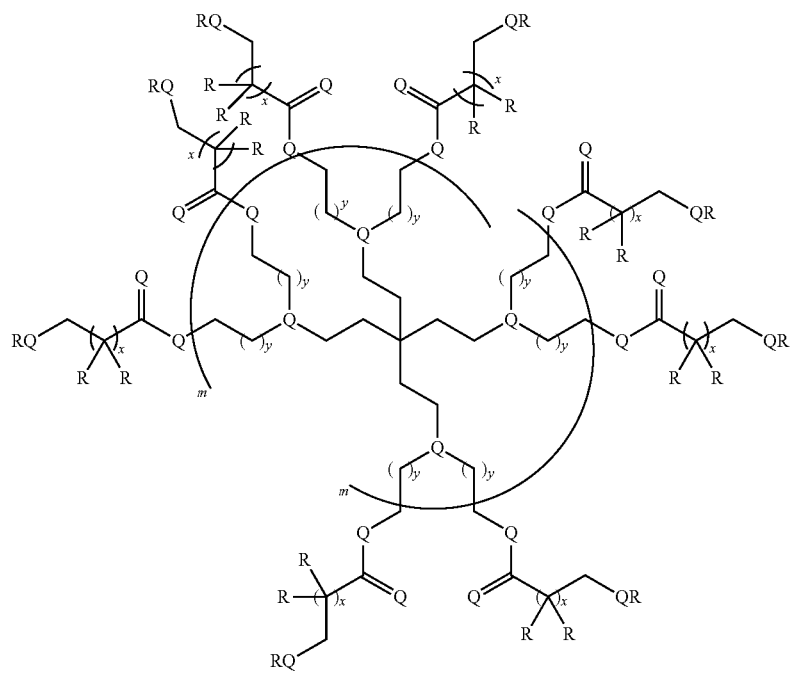
(vi)
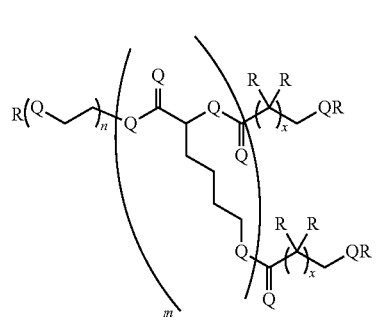
(vii)
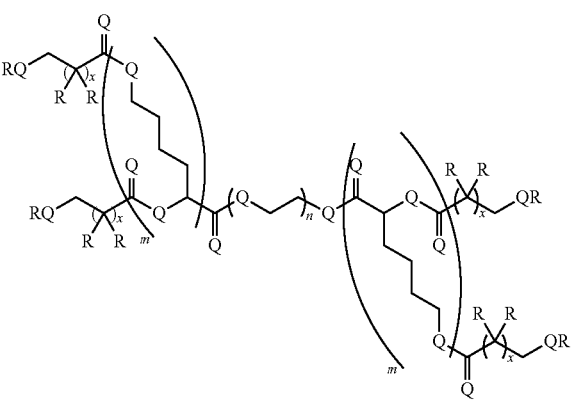
(viii)
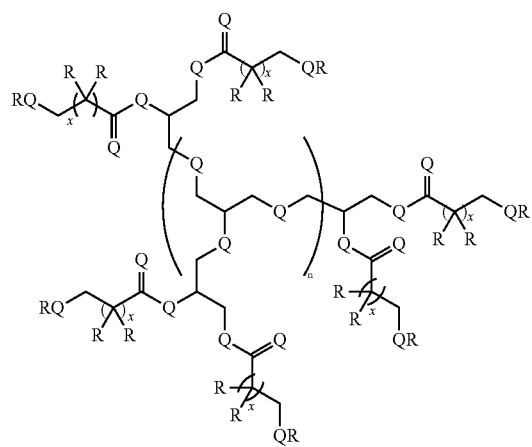
(ix)
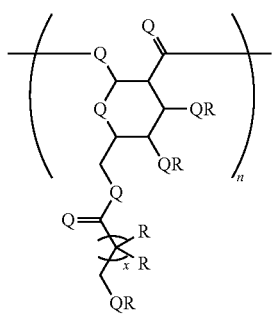
(x)

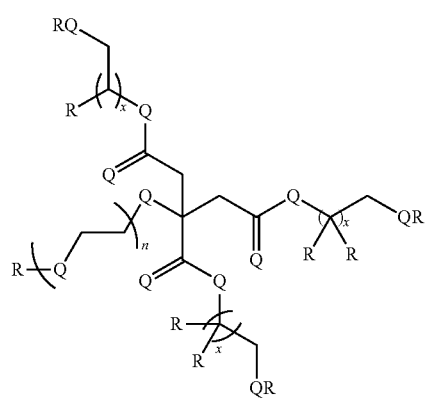

(xi)

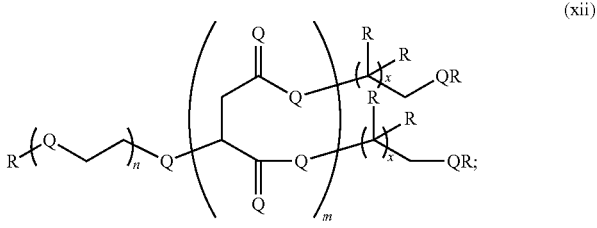

(xii)

and any combinations thereof; and wherein:
Q is independently selected from the group consisting of O, S, Se, NH, CH$_2$, and any combination thereof;
R is selected from the group consisting of a hydrogen, straight or branched alkyl, cycloalkyl, aryl, olefin or alkene, alkyne, silyl, alkylsilyl, arylsilyl, alkylaryl or arylalkyl chain of 1-50 carbons, fluorocarbon, and any combinations thereof, wherein each alkyl, cycloalkyl, aryl, olefin, alkyne, silyl, alkylsilyl, arylsilyl, alkylaryl, fluorocarbon, or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, halogen substituents; and any combinations thereof; when at least two R groups are in the same structure, R can be different from each other and m, n, x, and y are each independently selected from an integer of 0-1000.

38. The dissolvable hydrogel composition of any of paragraphs 28-37, wherein said at least two crosslinking moieties comprise at least one N-hydroxysuccinimide (NHS) moiety or maleimide (MAL) moiety.

39. The dissolvable hydrogel composition of any of paragraphs 28-38, wherein said at least two crosslinking moieties comprise at least two N-hydroxysuccinimide (NHS) moieties or maleimide (MAL) moieties.

40. The dissolvable hydrogel composition of any of paragraphs 28-39, wherein the second crosslinkable polymer has a chemical structure selected from the group consisting of structure (xiii) to structure (xI) shown as follows:

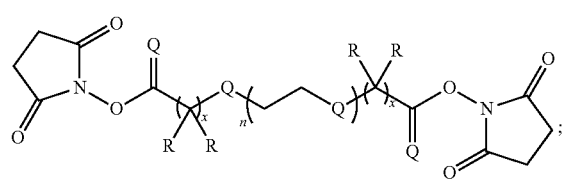

(xiii)

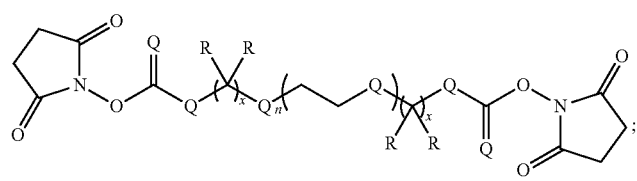

(xiv)

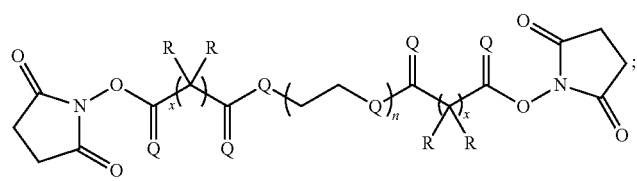

(xv)

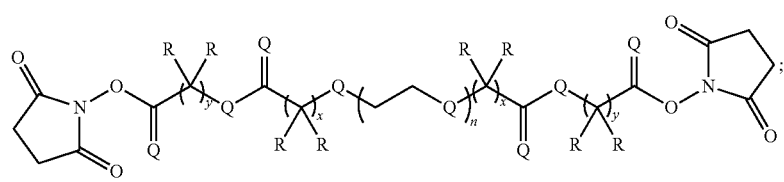

(xvi)

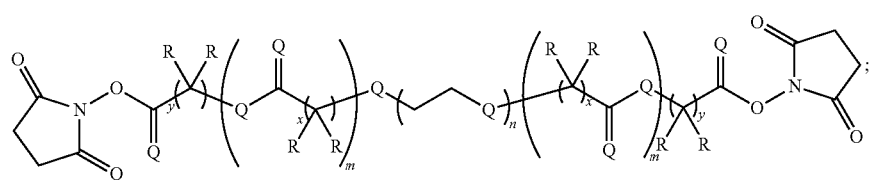
(xvii)
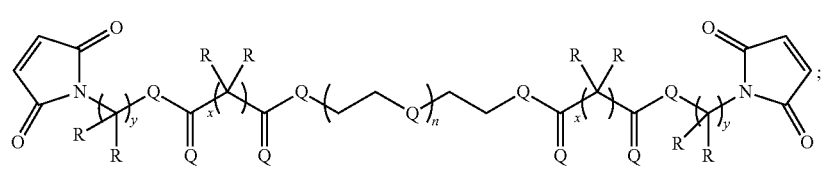
(xviii)
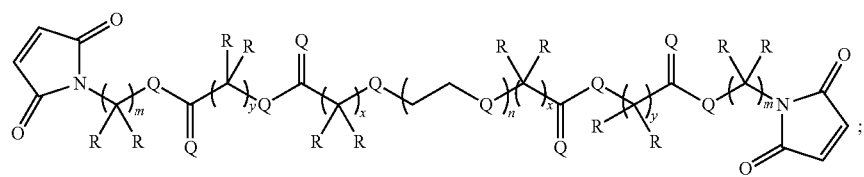
(xix)
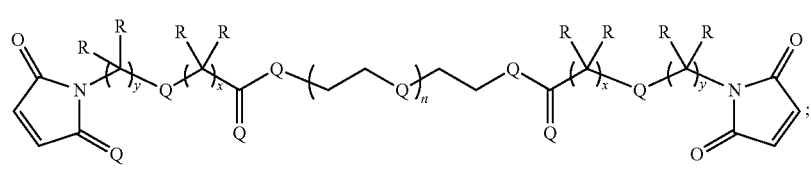
(xx)
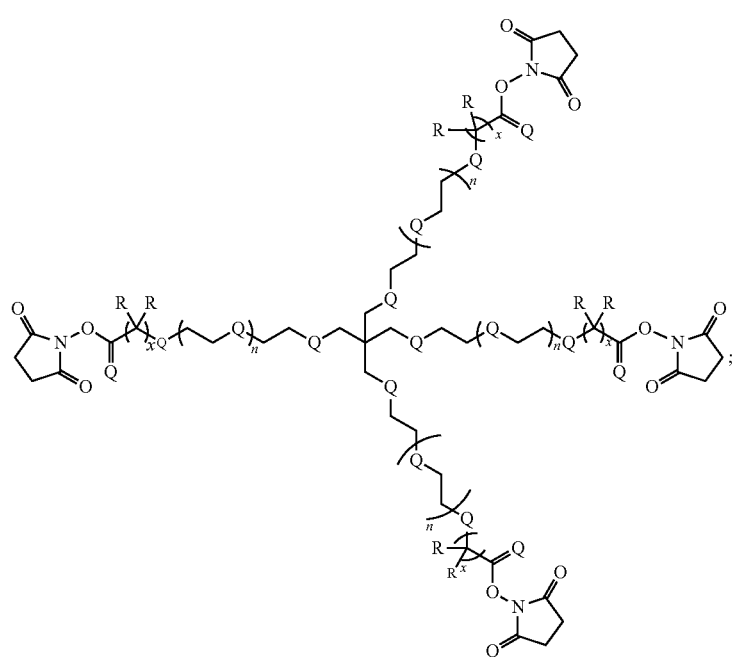
(xxi)

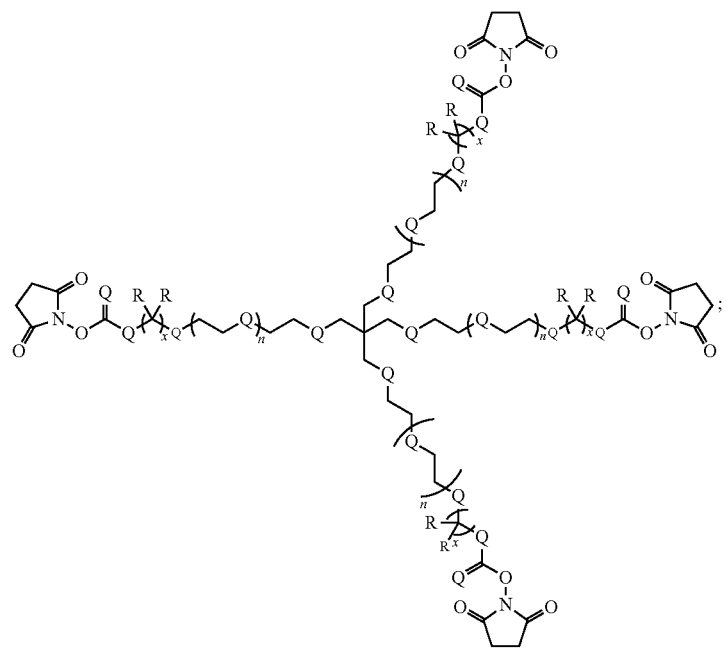
(xxii)
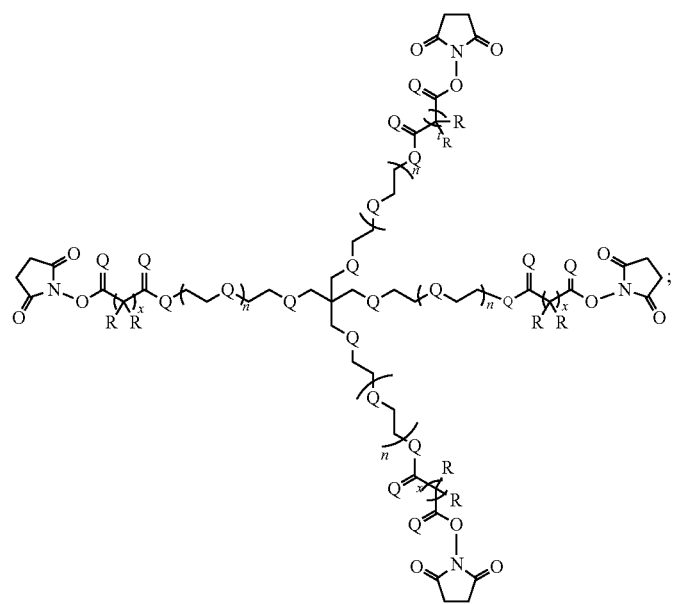
(xxiii)

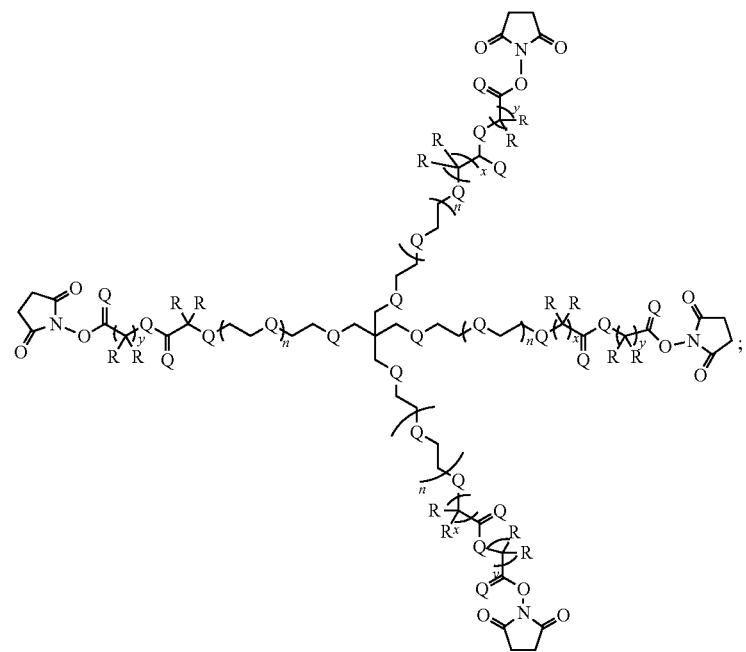
(xxiv)
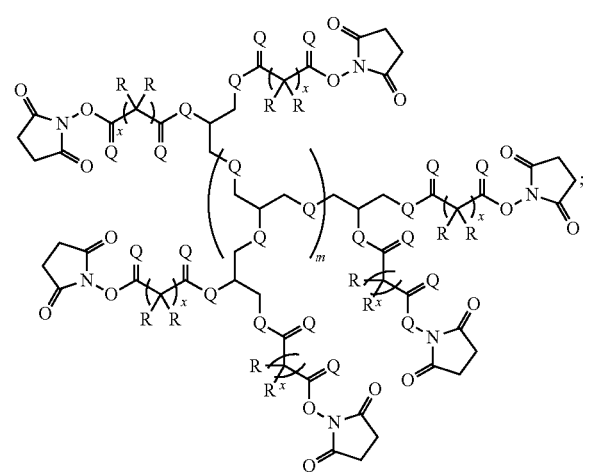
(xxv)
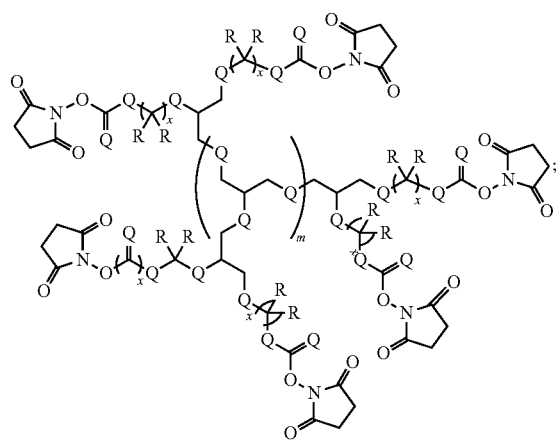
(xxvi)

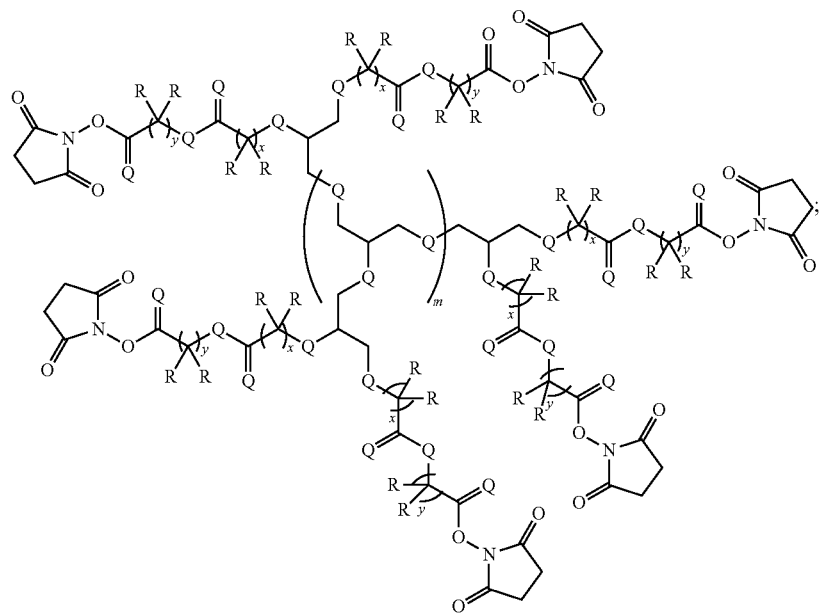
(xxvii)
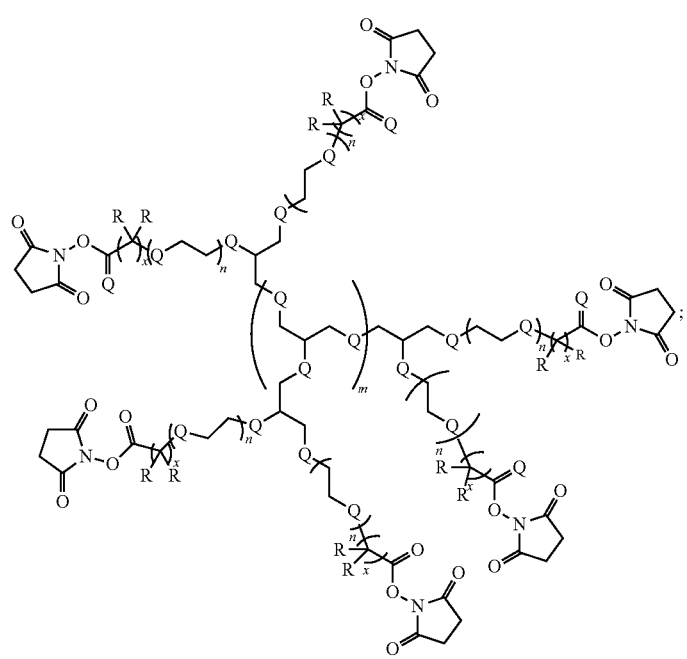
(xxviii)

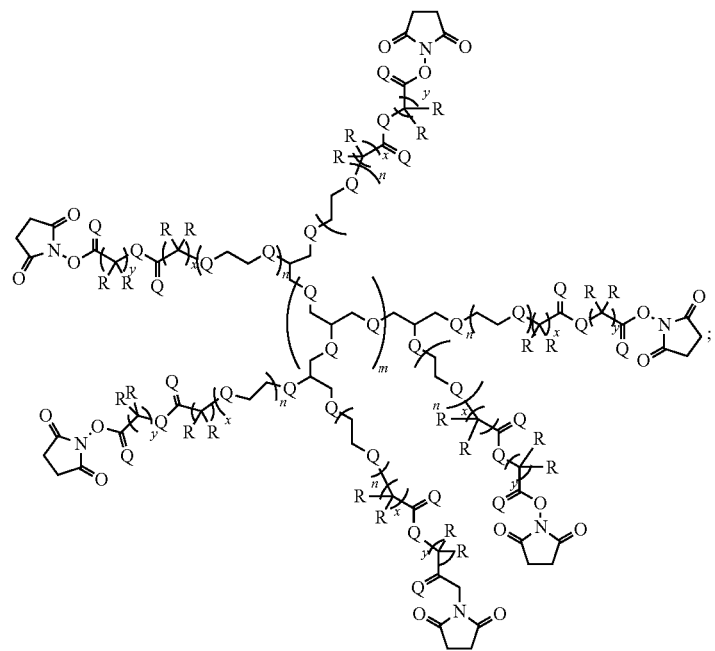
(xxix)
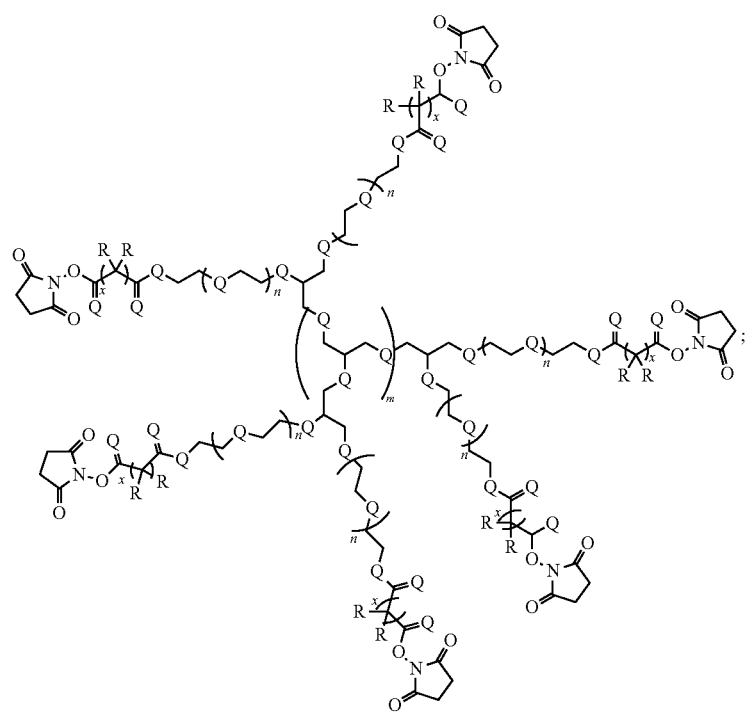
(xxx)

-continued
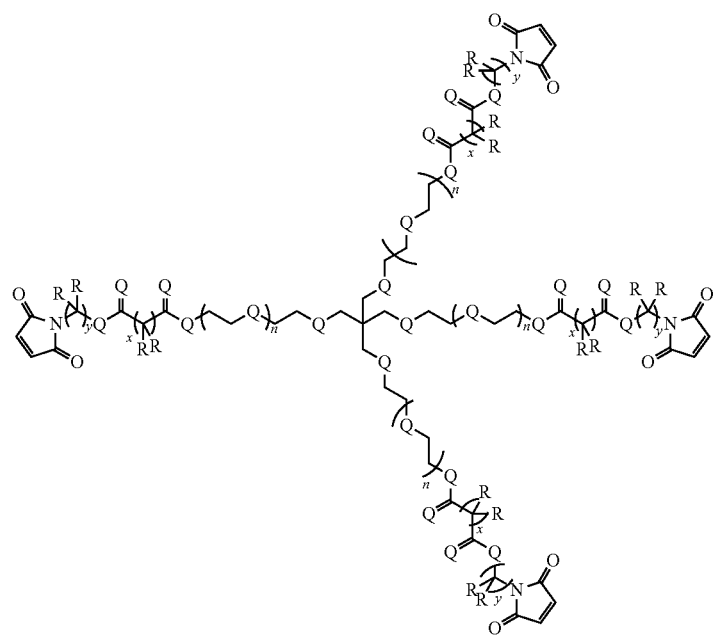
(xxxi)
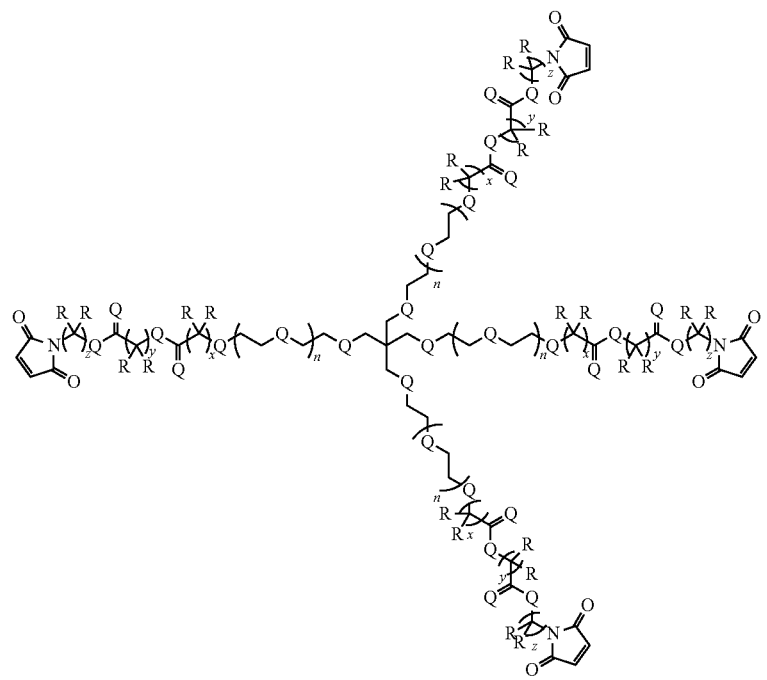
(xxxii)

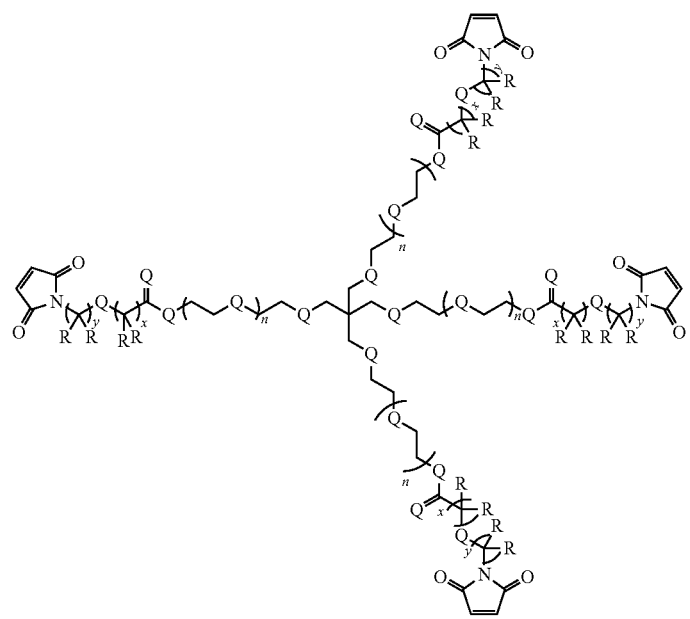
(xxxiii)
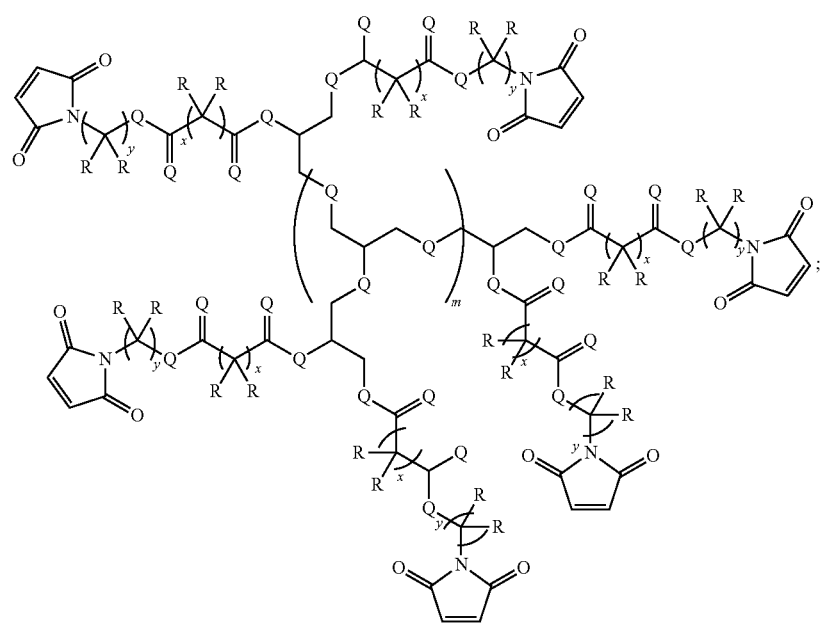
(xxxiv)

-continued
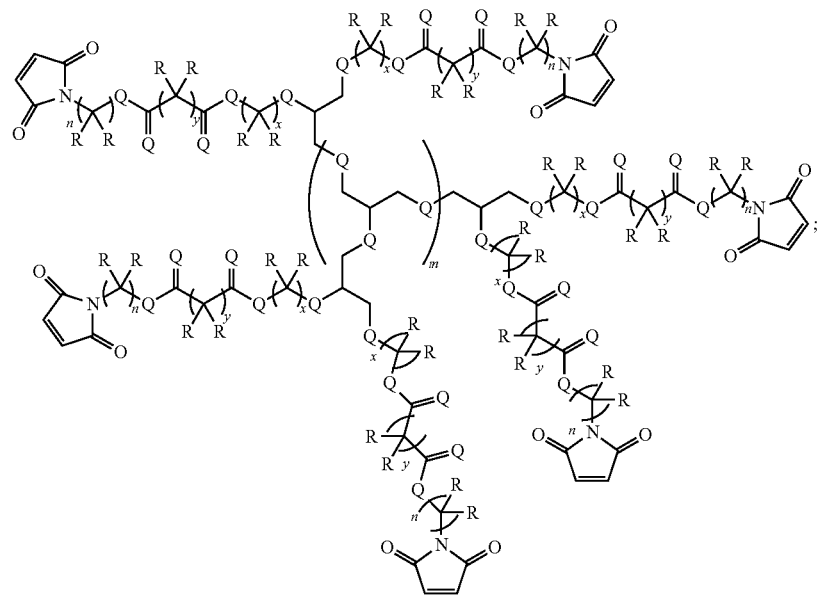
(xxxv)
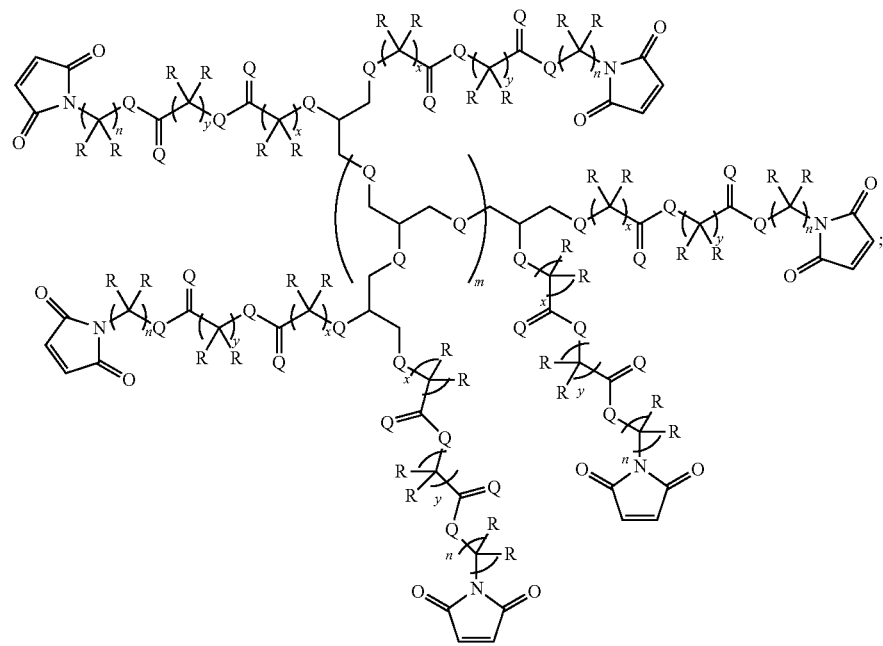
(xxxvi)

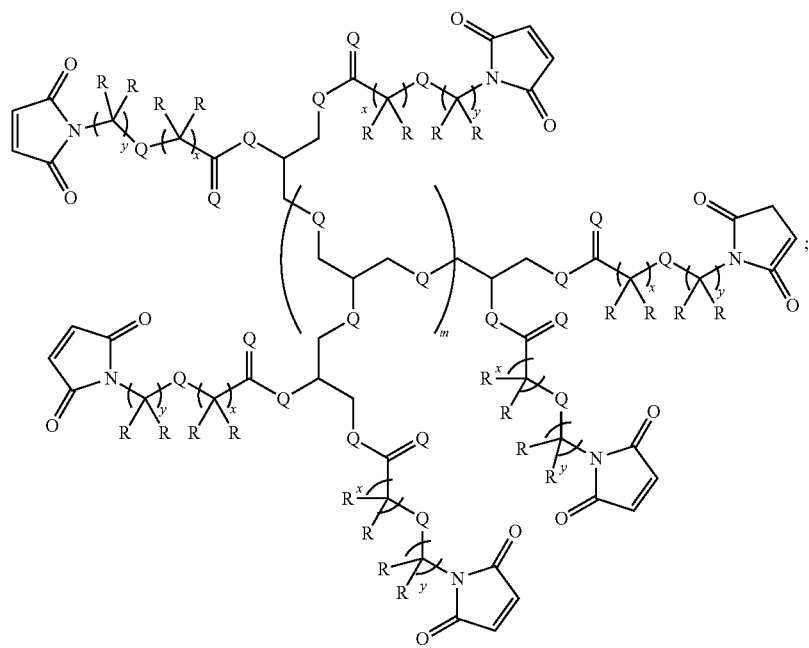
(xxxvii)
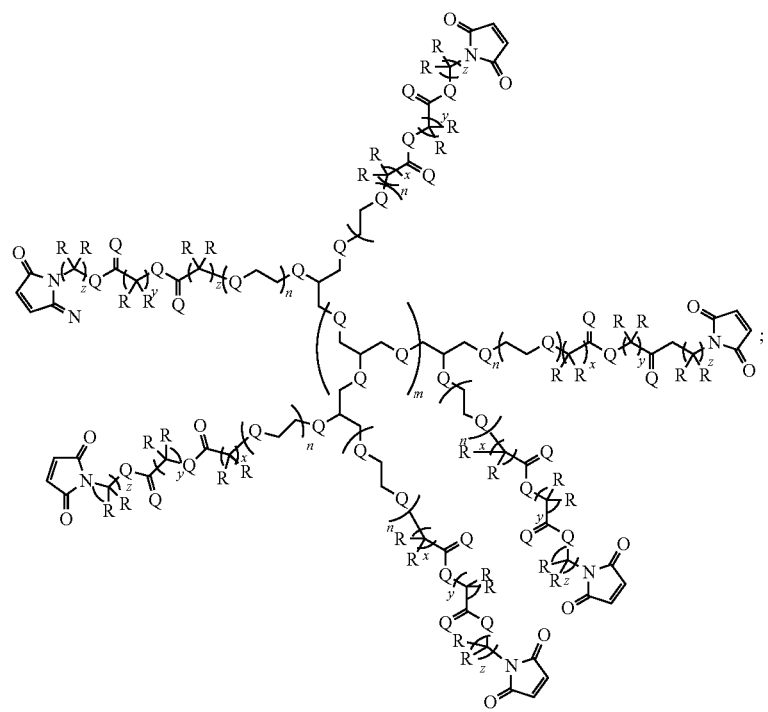
(xxxviii)

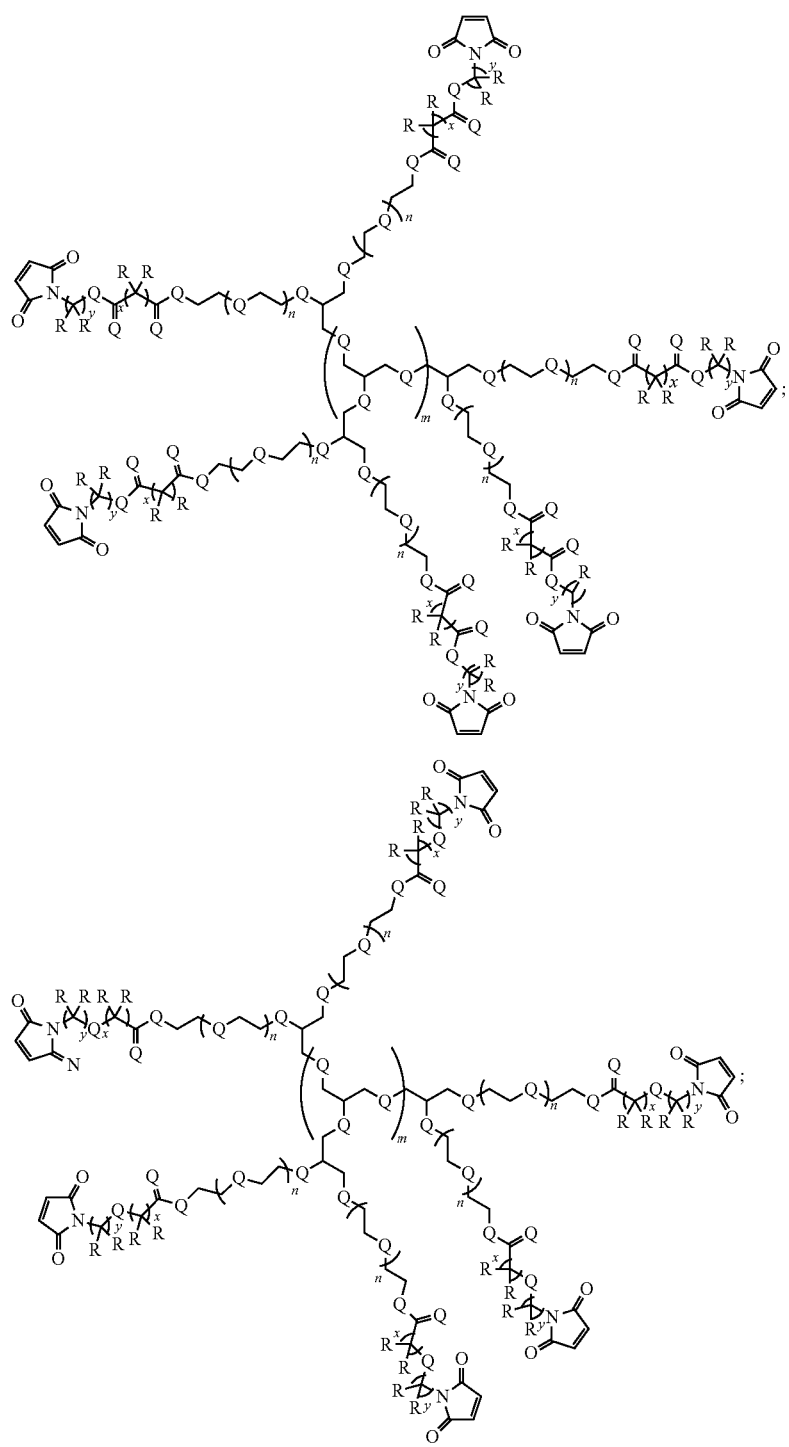

(xxxix)

(xl)

and any combination thereof; and wherein
Q is independently selected from the group consisting of O, S, Se, NH, CH$_2$, and any combination thereof;
R is selected from the group consisting of a hydrogen, straight or branched alkyl, cycloalkyl, aryl, olefin or alkene, alkyne, silyl, alkylsilyl, arylsilyl, alkylaryl or arylalkyl chain of 1-50 carbons, fluorocarbon, and any combinations thereof, wherein each alkyl, cycloalkyl, aryl, olefin, alkyne, silyl, alkylsilyl, arylsilyl, alkylaryl, fluorocarbon, or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, halogen substituents; and any combinations thereof; when at least two R groups are in the same structure, R can be different from each other and m, n, x, y and z are each independently selected from an integer of 0-1000.

41. The dissolvable hydrogel composition of any of paragraphs 37-40, wherein R is selected from the group consisting of poly(ethylene glycol), poly(ethylene oxide), poly(hydroxyacid), a carbohydrate, a protein, a polypeptide, an amino acid, a nucleic acid, a nucleotide, a polynucleotide, a DNA segment, a RNA segment, a lipid, a polysaccharide, an antibody, a pharmaceutical agent, an epitope for a biological receptor, and any combinations thereof.

42. The dissolvable hydrogel composition of any of paragraphs 28-41, wherein the first crosslinkable polymer has a chemical structure as follows:

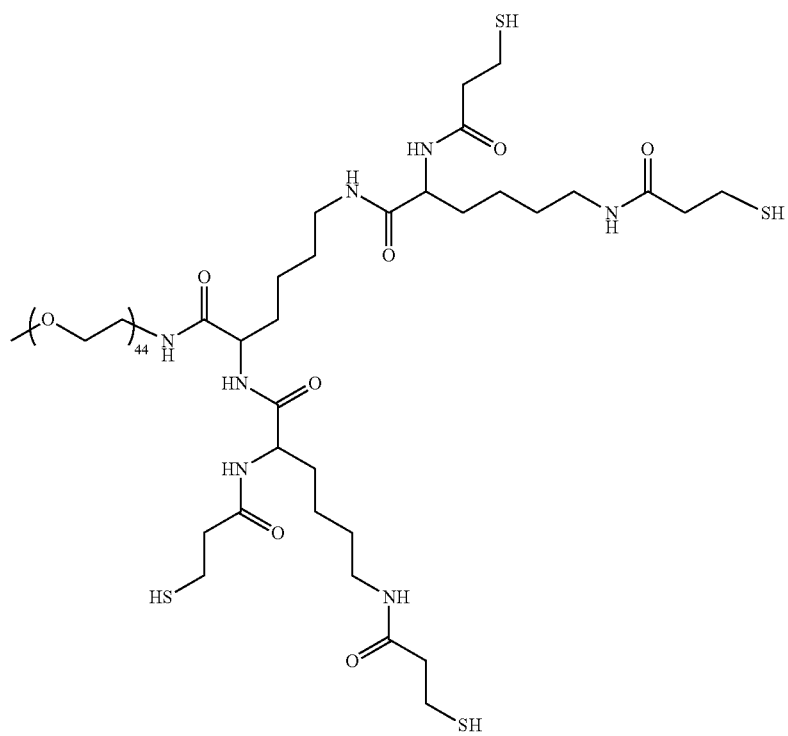

43. The dissolvable hydrogel composition of any of paragraphs 28-42, wherein the second crosslinkable polymer is poly(ethylene glycol) disuccinimidyl valerate.

44. The dissolvable hydrogel composition of any of paragraphs 28-43, wherein the adhesive hydrogel layer is at least partially flexible.

45. The dissolvable hydrogel composition of any of paragraphs 28-44, wherein the adhesive hydrogel layer is capable of withstanding a pressure of at least about 2 mmHg.

46. The dissolvable hydrogel composition of any of paragraphs 28-45, wherein the adhesive hydrogel layer is transparent.

47. The dissolvable hydrogel composition of any of paragraphs 28-46, wherein the adhesive hydrogel layer is hydrophilic.

48. The dissolvable hydrogel composition of any of paragraphs 28-47, wherein the adhesive hydrogel layer is elastic or viscoelastic.

49. The dissolvable hydrogel composition of any of paragraphs 28-48, wherein the adhesive hydrogel layer has about 5 wt % to about 70 wt % of the crosslinkable polymers.

50. The dissolvable hydrogel composition of any of paragraphs 28-49, further comprising a bioactive agent.

51. The dissolvable hydrogel composition of paragraph 50, wherein the bioactive agent is selected from the group consisting of pharmaceutical agents, drugs, cells, gases and gaseous precursors, synthetic organic molecules, proteins, enzymes, growth factors, vitamins, steroids, polyanions, nucleosides, nucleotides, polynucleotides, nanoparticles, diagnostic agents, genetic materials, and any combinations thereof.

52. The dissolvable hydrogel composition of any of paragraphs 28-51, wherein the adhesive layer is hydrolytically stable at pH in a range of about 0 to at least about 9.

53. The dissolvable hydrogel composition of any of paragraphs 28-52, wherein the dissolvable hydrogel composition is formulated to form a bandage, glue, sealant, dressing, scaffold, coating, or covering.

54. The dissolvable hydrogel composition of any of paragraphs 28-53, wherein the dissolvable hydrogel composition is adapted for use with vacuum assisted closure.

55. A kit comprising:
a dissolvable hydrogel composition comprising: an adhesive hydrogel layer comprising linear, branched, and/or dendritic crosslinkable polymers held together by thioester linkages formed between the linear, branched, and/or dendritic crosslinkable polymers; and
a thiolate compound.

56. A kit comprising:
- a dissolvable hydrogel composition comprising: an adhesive hydrogel layer comprising linear, branched and/or dendritic crosslinkable polymers held together by covalent bonds formed between the first crosslinkable polymer and the second crosslinkable polymer, wherein the adhesive hydrogel layer comprises thioester linkages; and
- a thiolate compound.

57. The kit of paragraph 56, wherein the adhesive hydrogel layer is derived from a first water-soluble linear, branched, and/or dendritic crosslinkable polymer comprising at least two thiol moieties and a second water-soluble linear, branched, and/or dendritic crosslinkable comprising at least two crosslinking moieties that are capable of reacting with said at least two thiol moieties of the first crosslinkable polymer to form the thioester linkages between the first and the second crosslinkable polymers.

58. The kit of paragraph 56, wherein the adhesive hydrogel layer is derived from a first water-soluble linear, branched, and/or dendritic crosslinkable polymer comprising at least two thioester linkages and a second water-soluble linear, branched, and/or dendritic crosslinkable polymer comprising at least two crosslinking moieties that are capable of forming a linkage with the first water-soluble linear, branched, and/or dendritic polymer.

59. The kit of paragraph 56, wherein the adhesive hydrogel layer is derived from a first water-soluble linear, branched and/or dendritic crosslinkable polymer comprising at least two nucleophilic moieties that are capable of forming a linkage with the second water-soluble linear, branched and/or dendritic polymer, wherein at least one of the first and second water-soluble linear, branched and/or dendritic crosslinkable polymers comprises at least two thioester linkages.

60. The kit of any of paragraphs 55-59, wherein the adhesive hydrogel layer is hydrolytically stable at pH in a range of about 0 to at least about 9.

61. The kit of any of paragraphs 55-60, wherein the adhesive hydrogel layer has a larger molecular weight than the crosslinkable polymers.

62. The kit of any of paragraphs 55-61, wherein the adhesive hydrogel layer has a molecular weight of at least about 100 kDa.

63. The kit of any of paragraphs 55-62, wherein the dissolvable hydrogel composition is formulated to form a bandage, sealant, coating or covering.

64. The kit of any of paragraphs 55-63, further comprising at least one component for performing vacuum assisted closure.

65. The kit of any of paragraphs 55-64, wherein the dissolvable hydrogel composition further comprises a bioactive agent.

66. A kit comprising:
- a first water-soluble linear, branched, and/or dendritic crosslinkable polymer comprising at least two thiol moieties, wherein the first crosslinkable polymer is at least about 200 Da;
- a second water-soluble linear, branched, and/or dendritic crosslinkable polymer that can react with the first crosslinkable polymer to form a dissolvable and adhesive hydrogel, wherein the second crosslinkable polymer comprises at least two crosslinking moieties that are capable of reacting with the thiol moieties of the first crosslinkable polymer to form thioester linkages between the first and the second crosslinkable polymers; and wherein the second crosslinkable polymer is at least about 200 Da; and a thiolate compound.

67. A kit comprising:
- a first water-soluble linear, branched, and/or dendritic crosslinkable polymer comprising at least two thioester linkages, wherein the first crosslinkable polymer is at least about 200 Da;
- a second water-soluble linear, branched, and/or dendritic crosslinkable polymer that can react with the first crosslinkable polymer to form a dissolvable and adhesive hydrogel, wherein the second crosslinkable polymer comprises at least two crosslinking moieties that are capable of forming a linkage with the first crosslinkable polymer; and wherein the second crosslinkable polymer is at least about 200 Da; and
- a thiolate compound.

68. A kit comprising:
- a first water-soluble linear, branched and/or dendritic crosslinkable polymer that can react with the second crosslinkable polymer to form a dissolvable and adhesive thioester hydrogel, wherein the first crosslinkable polymer comprises at least two nucleophilic moieties that are capable of forming a linkage with the second crosslinkable polymer; and wherein the first crosslinkable polymer is at least about 200 Da;
- a second water-soluble linear, branched and/or dendritic crosslinkable polymer comprising at least two thioester linkages, wherein the second crosslinkable polymer is at least about 200 Da; and
- a thiolate compound.

69. The kit of any of paragraphs 55-68, wherein the first crosslinkable polymer, the second crosslinkable polymer, and the thiolate compound are each independently formulated in a form selected from the group consisting of a spray, a foam, a solution, a powder, and any combinations thereof.

70. The kit of any of paragraphs 55-69, further comprising a bioactive agent.

71. The kit of paragraph 70, wherein the bioactive agent is selected from the group consisting of pharmaceutical agents, drugs, cells, gases and gaseous precursors, synthetic organic molecules, proteins, enzymes, growth factors, vitamins, steroids, polyanions, nucleosides, nucleotides, polynucleotides, nanoparticles, diagnostic agents, genetic materials, and any combinations thereof.

72. The kit of any of paragraphs 55-71, wherein the thiolate compound is provided in an amount such that the stoichiometric ratio of the number of thiols in the thiolate compound to the number of thioester linkages in the dissolvable hydrogel is greater than 1:1.

73. The kit of any of paragraphs 55-72, wherein the first crosslinkable polymer has a chemical structure selected from the group consisting of structure (i) to structure (xii) shown as follows:

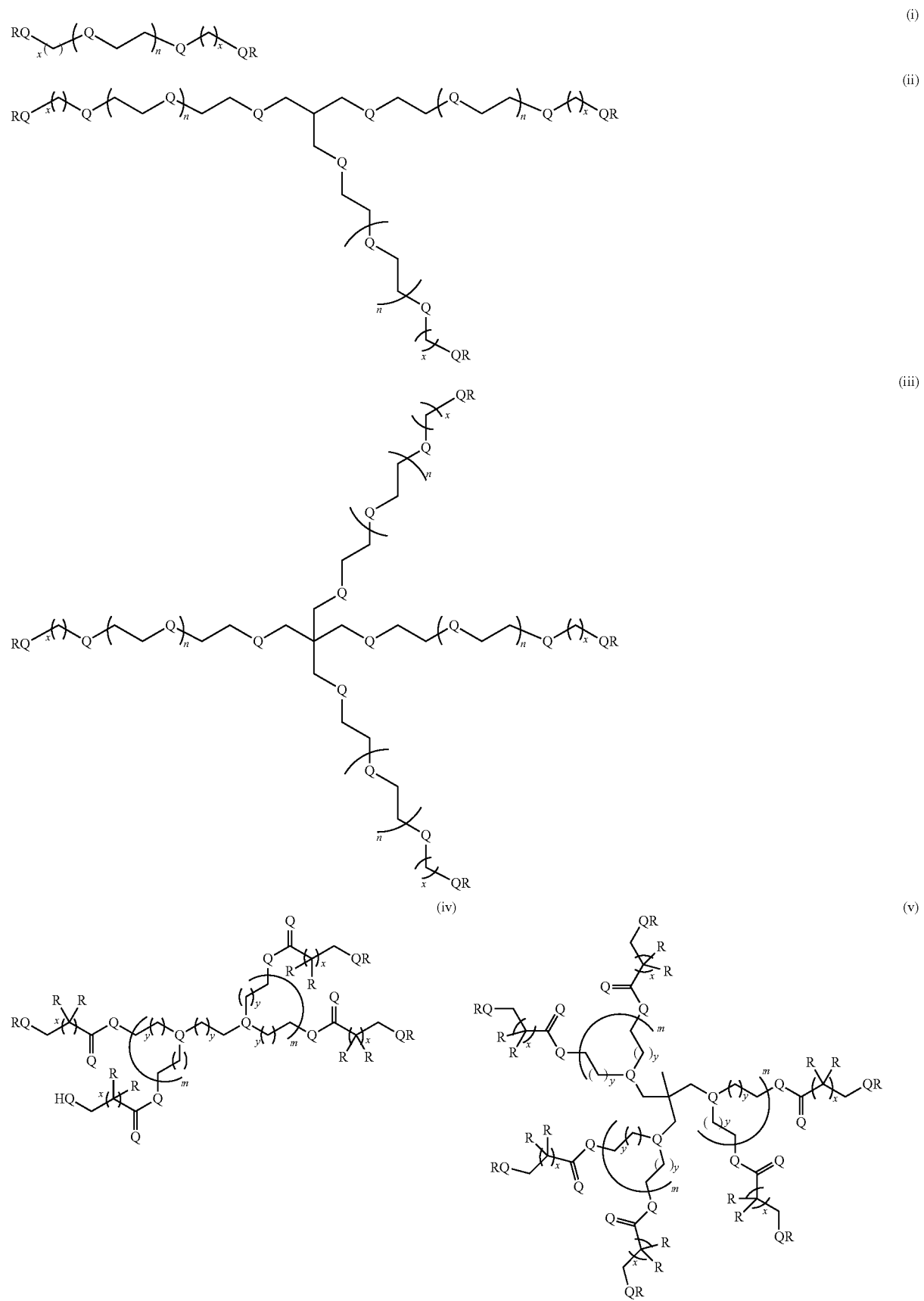

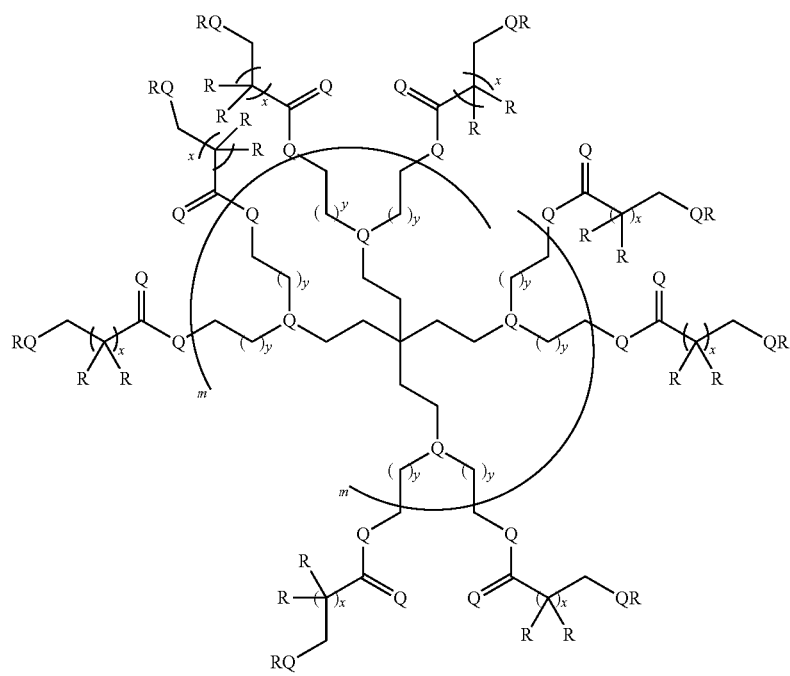
(vi)
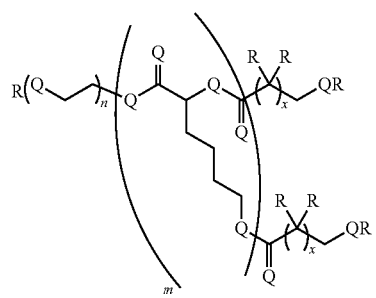
(vii)
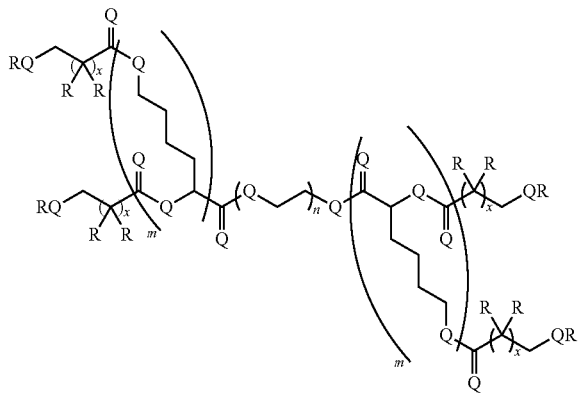
(viii)
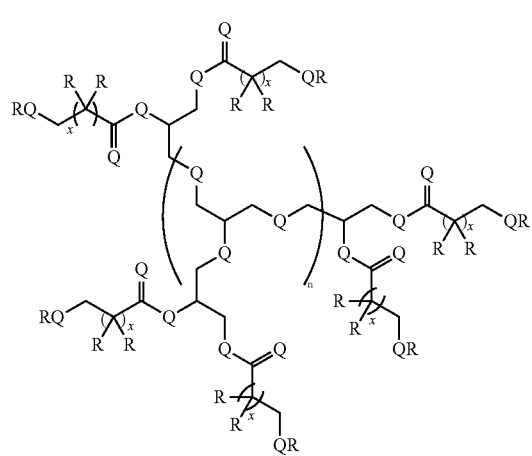
(ix)
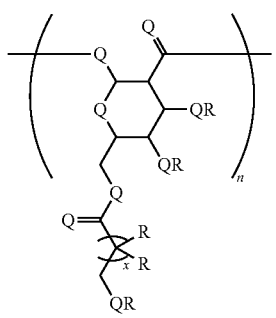
(x)

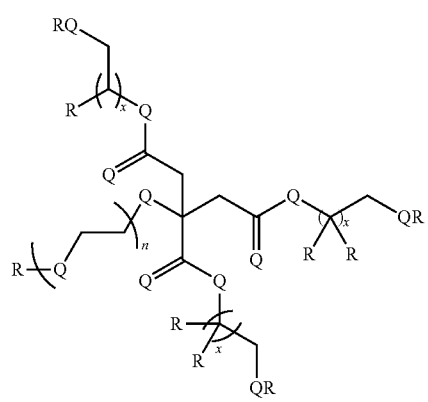
(xi)

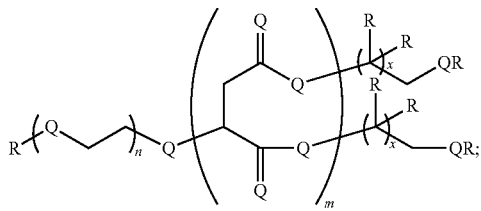
(xii)

and any combinations thereof; and wherein:
Q is independently selected from the group consisting of O, S, Se, NH, $CH_2$ and any combination thereof;
R is selected from the group consisting of a hydrogen, straight or branched alkyl, cycloalkyl, aryl, olefin or alkene, alkyne, silyl, alkylsilyl, arylsilyl, alkylaryl or arylalkyl chain of 1-50 carbons, fluorocarbon, and any combinations thereof, wherein each alkyl, cycloalkyl, aryl, olefin, alkyne, silyl, alkylsilyl, arylsilyl, alkylaryl, fluorocarbon, or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, halogen substituents; and any combinations thereof; and m, n, x, and y are each independently selected from an integer of 0-1000.

74. The kit of any of paragraphs 55-73, wherein said at least two crosslinking moieties of the second crosslinkable polymer comprises at least one N-hydroxysuccinimide (NHS) moiety or maleimide (MAL) moiety.

75. The kit of any of paragraphs 55-74, wherein said at least two crosslinking moieties of the second crosslinkable polymer comprises at least two N-hydroxysuccinimide (NHS) moieties or maleimide (MAL) moieties.

76. The kit of any of paragraphs 55-75, wherein the second crosslinkable polymer has a chemical structure selected from the group consisting of structure (xiii) to structure (xI) shown as follows:

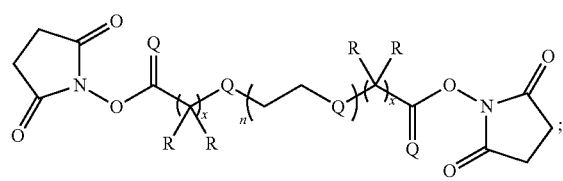
(xiii)

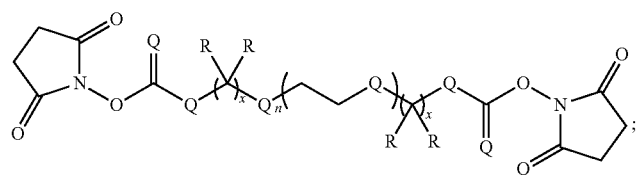
(xiv)

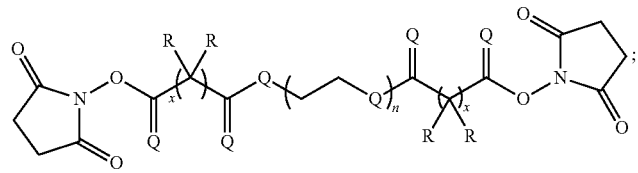
(xv)

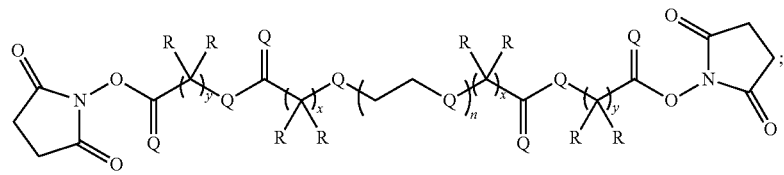
(xvi)

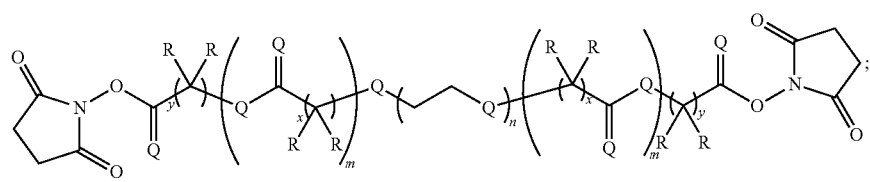
(xvii)
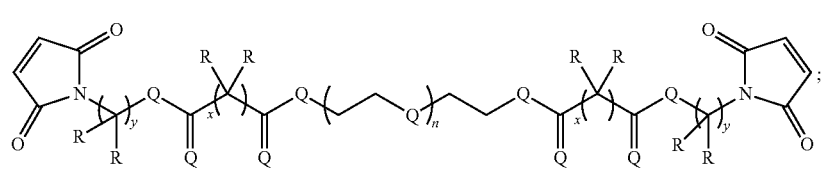
(xviii)
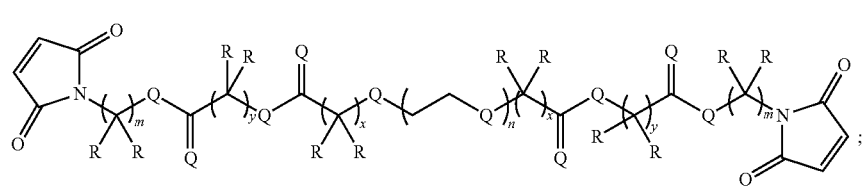
(xix)
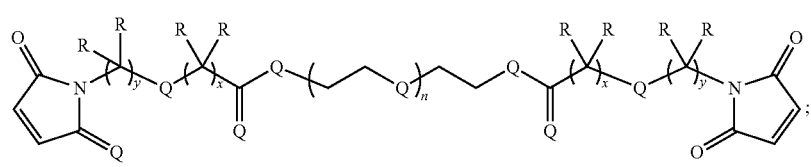
(xx)
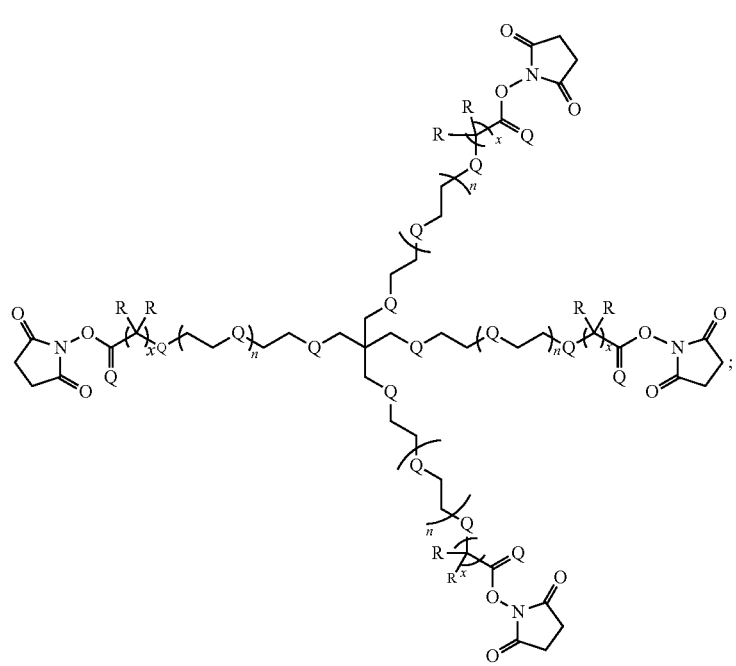
(xxi)

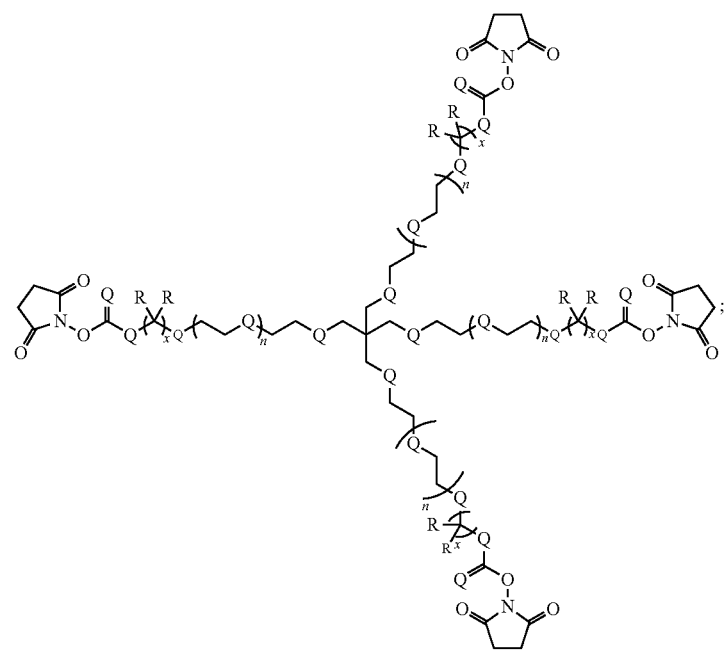
(xxii)
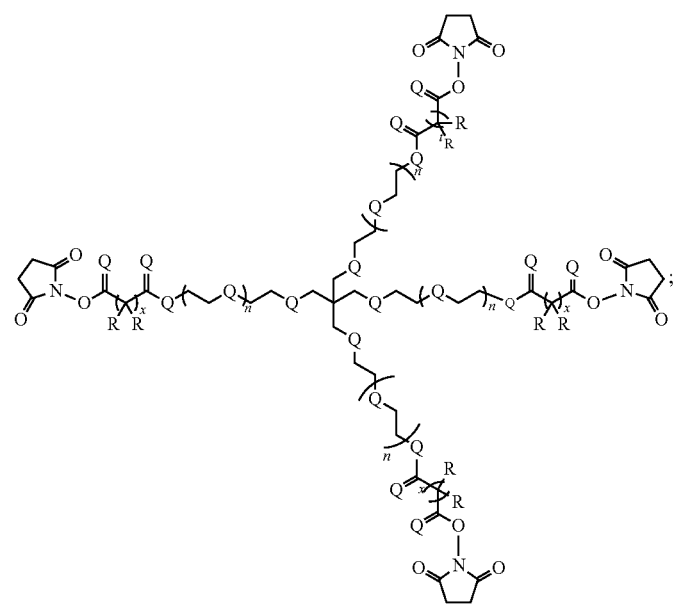
(xxiii)

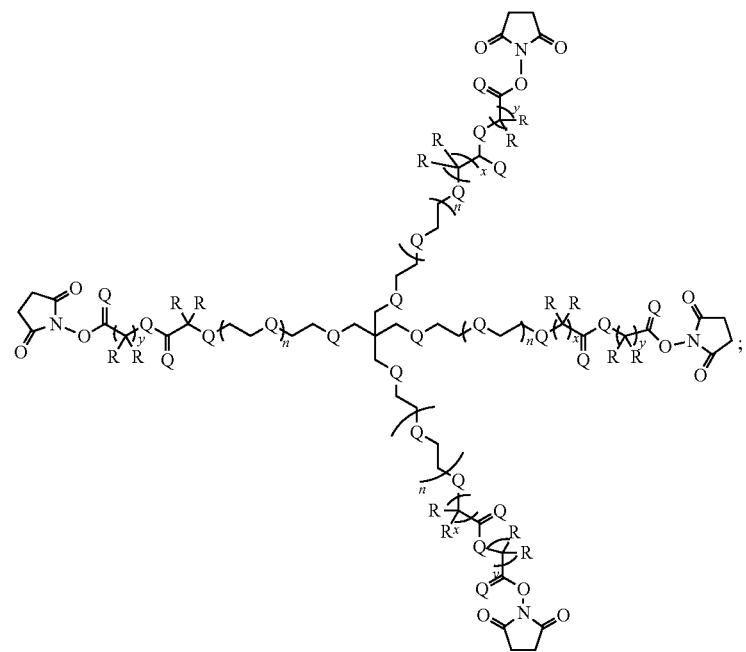
(xxiv)
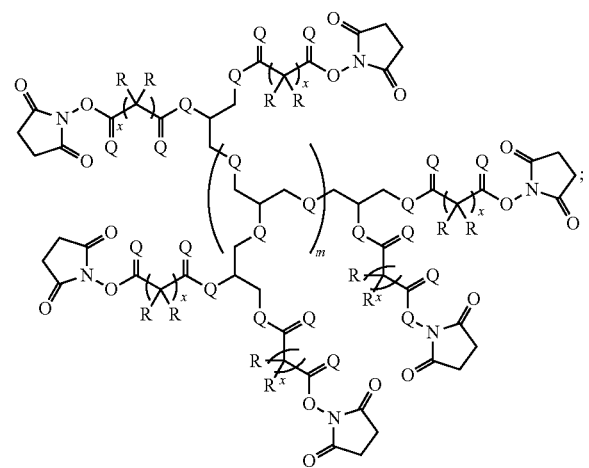
(xxv)
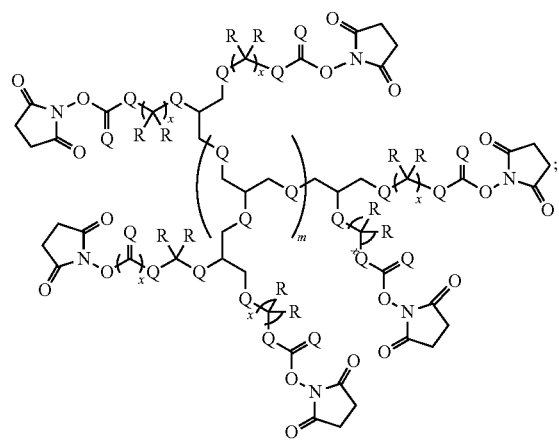
(xxvi)

-continued
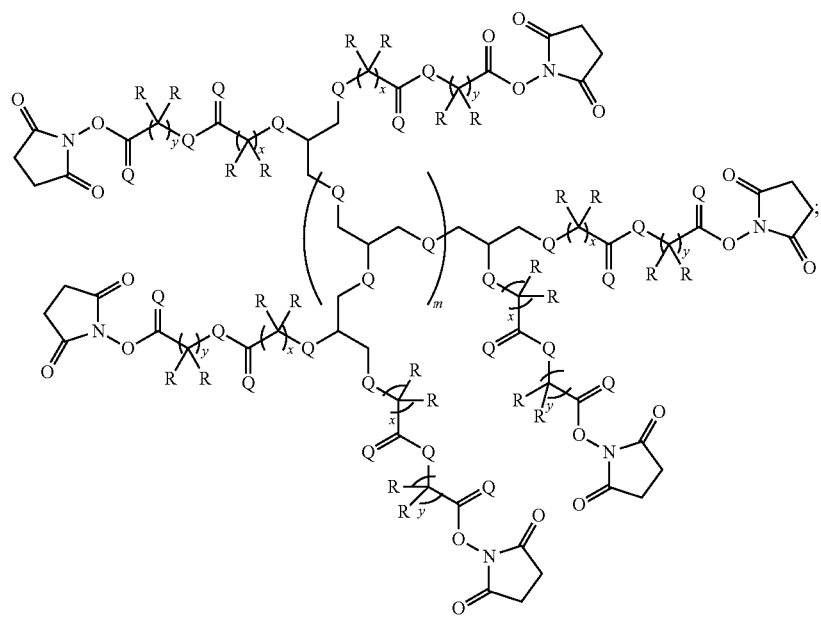
(xxvii)
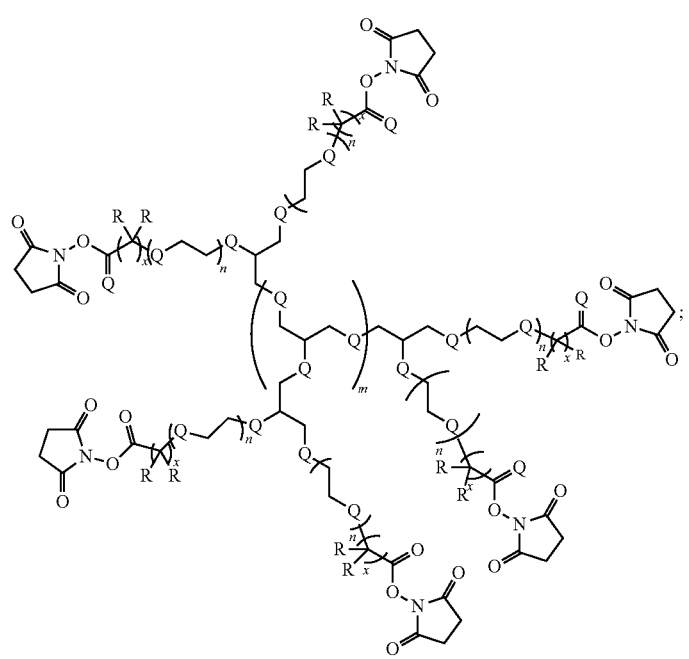
(xxviii)

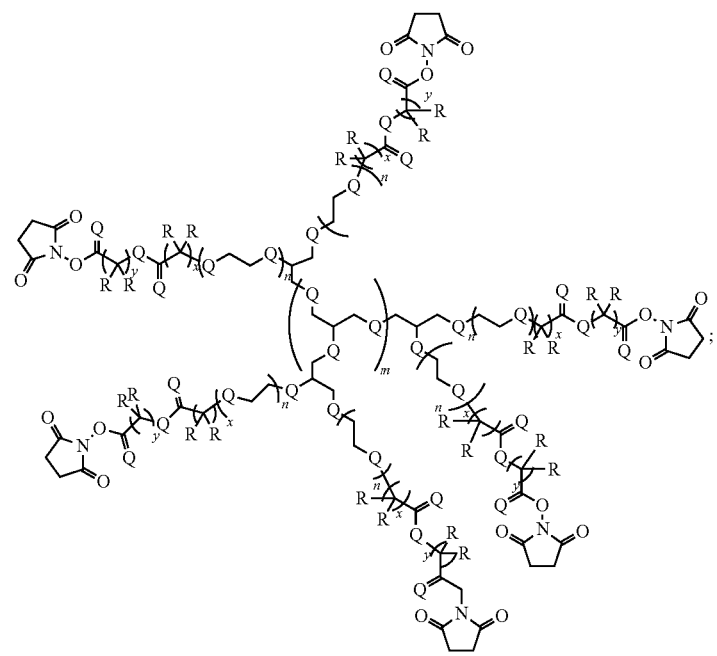
(xxix)
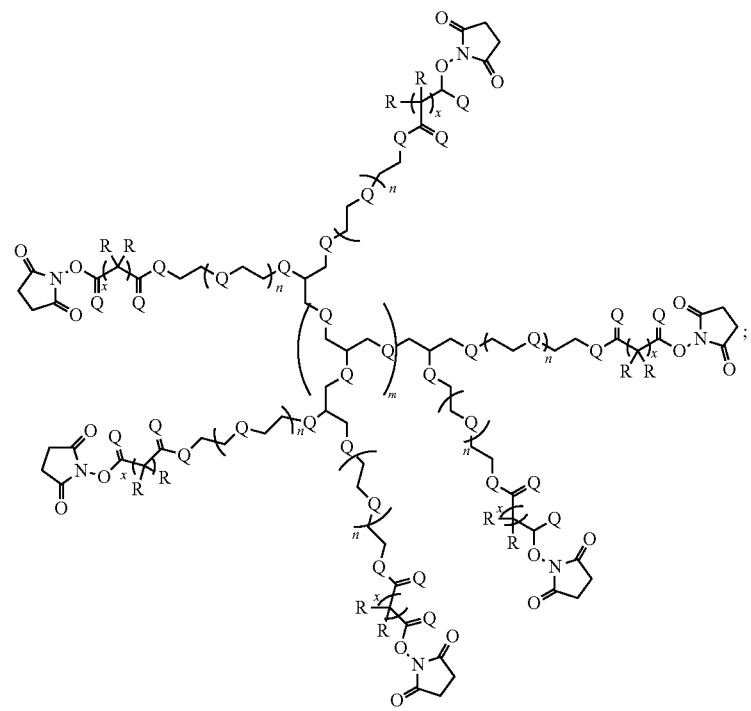
(xxx)

-continued
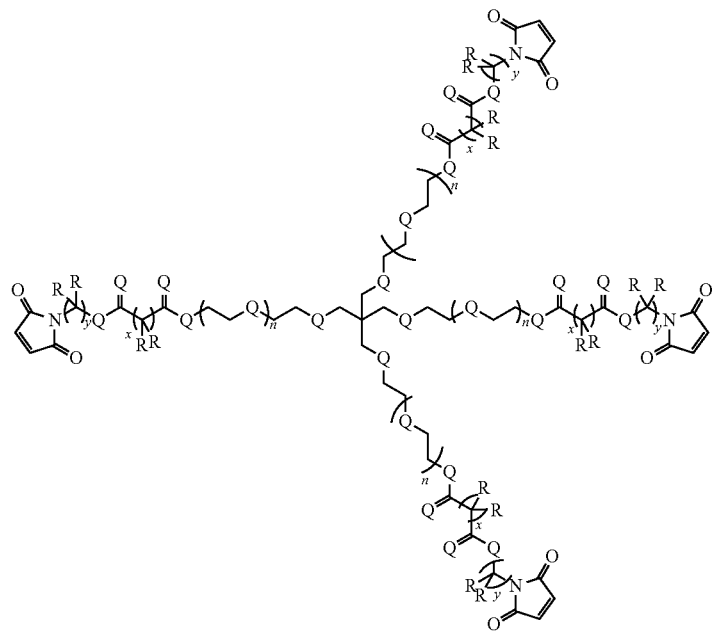
(xxxi)
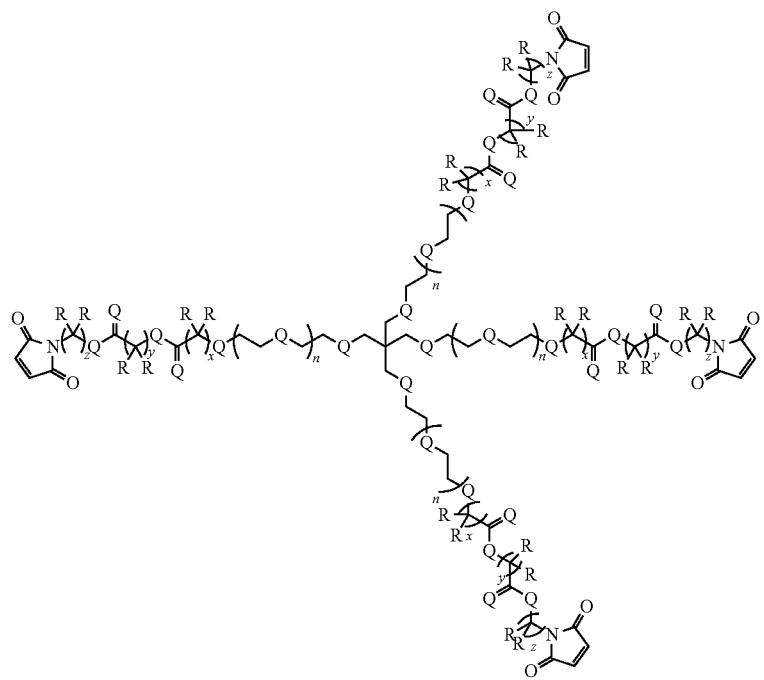
(xxxii)

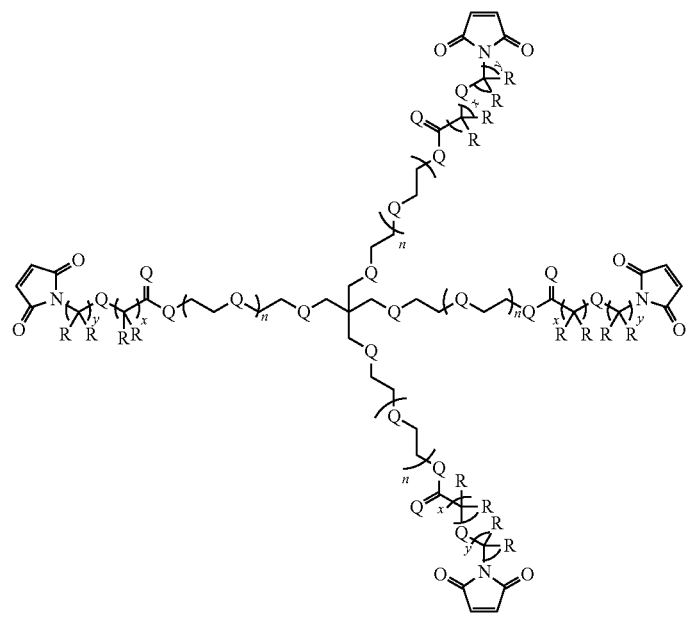
(xxxiii)
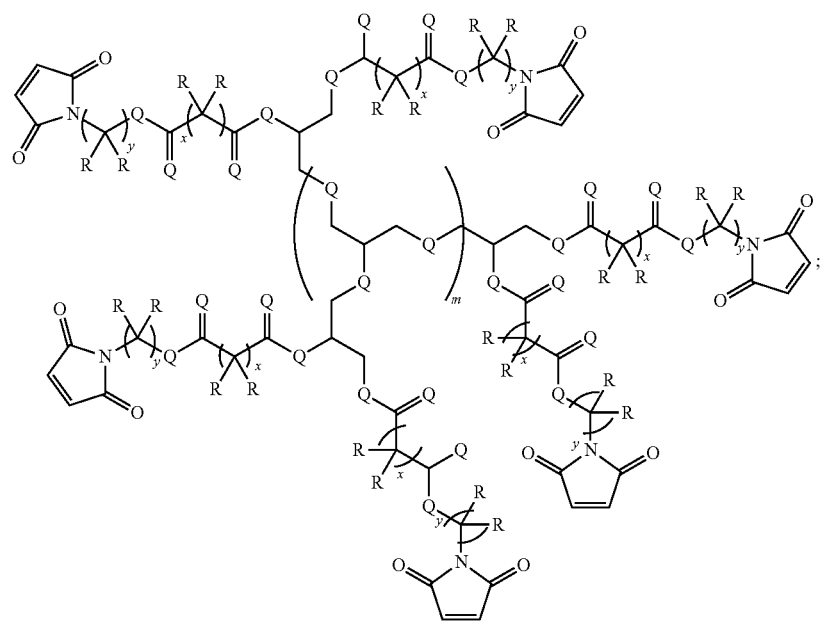
(xxxiv)

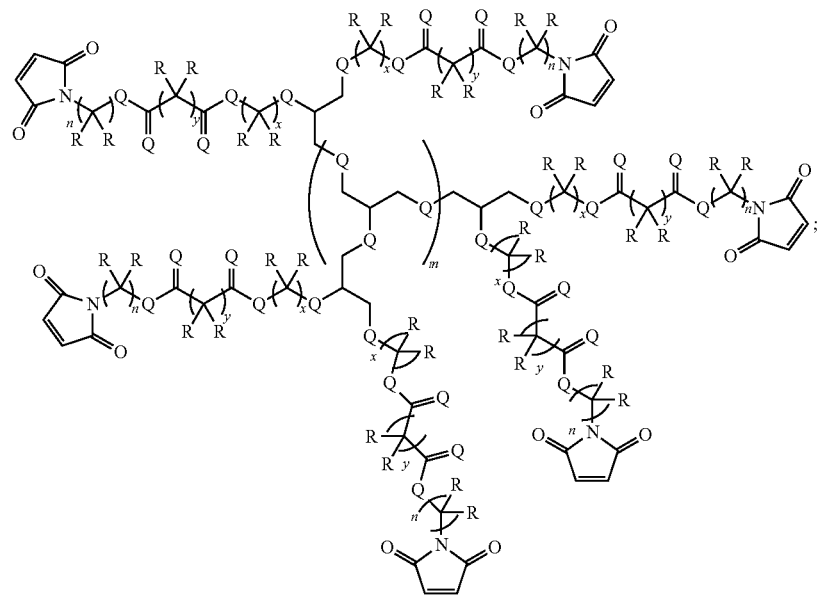
(xxxv)
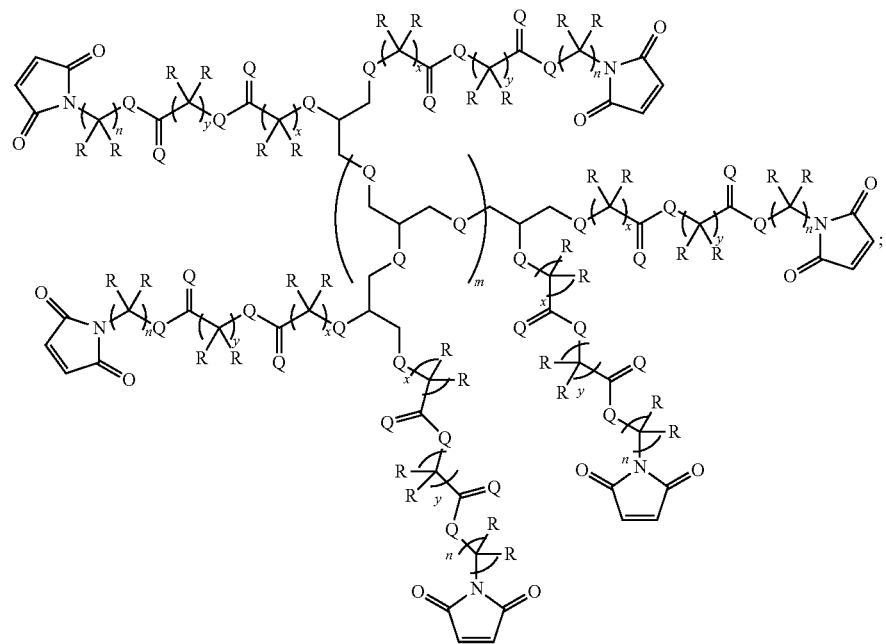
(xxxvi)

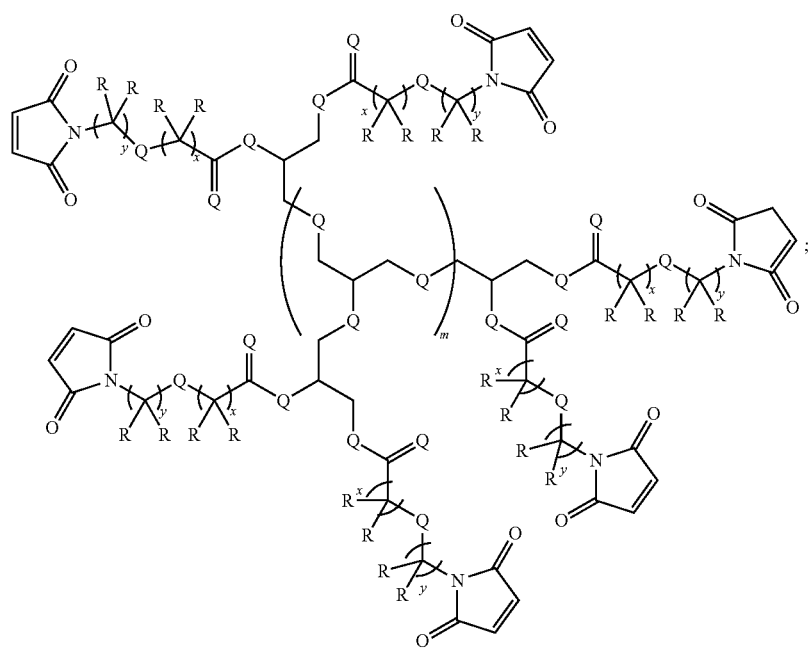
(xxxvii)
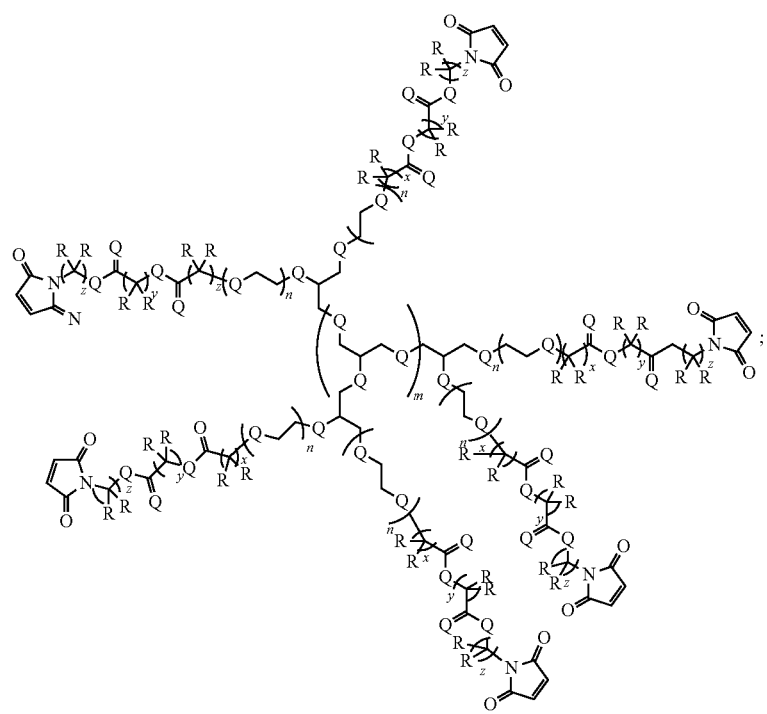
(xxxviii)

-continued

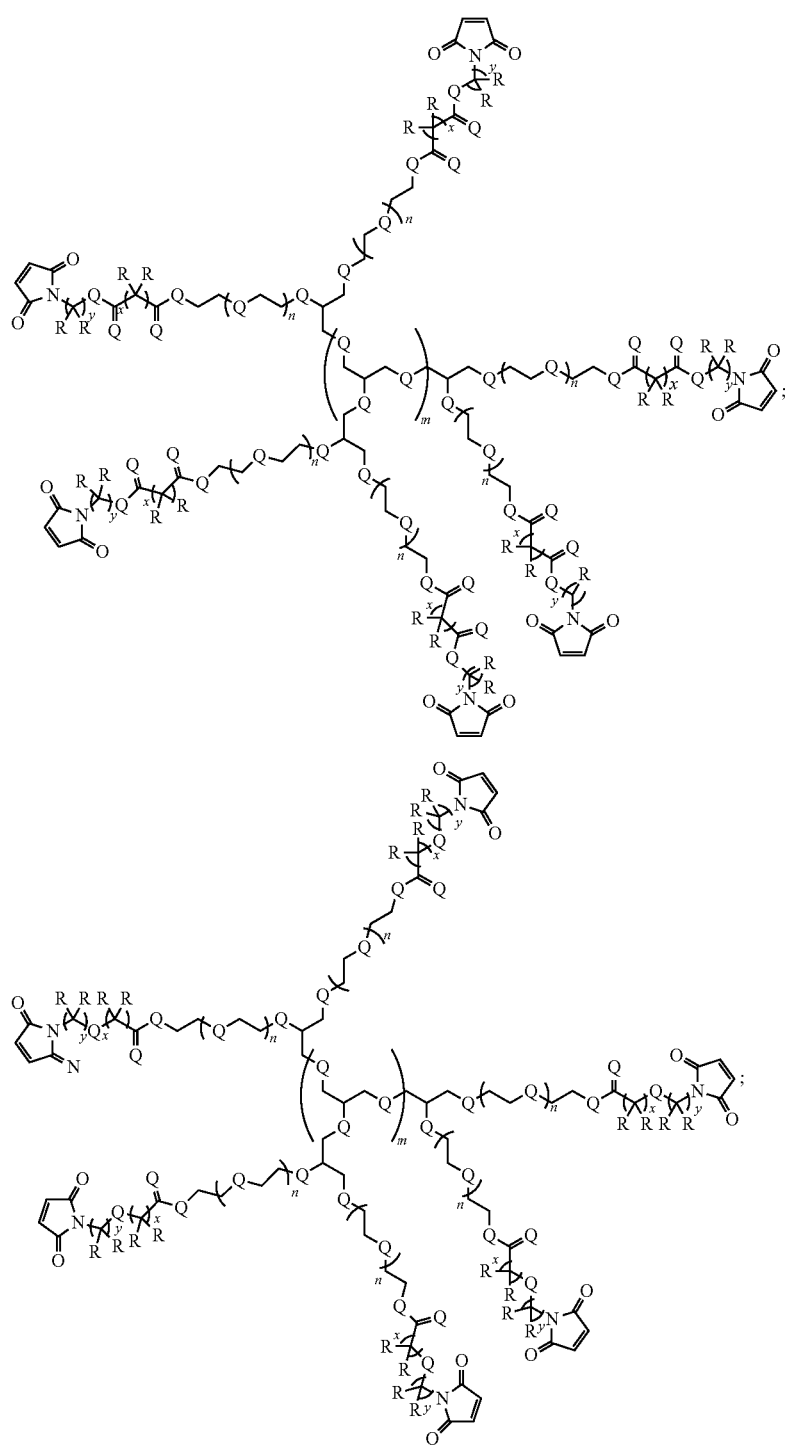

(xxxix)

(xl)

and any combination thereof; and wherein

Q is independently selected from the group consisting of O, S, Se, NH, CH$_2$ and any combination thereof;

R is selected from the group consisting of a hydrogen, straight or branched alkyl, cycloalkyl, aryl, olefin or alkene, alkyne, silyl, alkylsilyl, arylsilyl, alkylaryl or arylalkyl chain of 1-50 carbons, fluorocarbon, and any combinations thereof, wherein each alkyl, cycloalkyl, aryl, olefin, alkyne, alkyne, silyl, alkylsilyl, arylsilyl, alkylaryl, fluorocarbon, or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, halogen substituents; and any combinations thereof; and m, n, x, y, and z are each independently selected from an integer of 0-1000.

77. The kit of any of paragraphs 73-76, wherein R is selected from the group consisting of poly(ethylene glycol), poly(ethylene oxide), poly(hydroxyacid), a carbohydrate, a protein, a polypeptide, an amino acid, a nucleic acid, a nucleotide, a polynucleotide, a DNA segment, a RNA segment, a lipid, a polysaccharide, an antibody, a pharmaceutical agent, an epitope for a biological receptor, and any combinations thereof.

78. The kit of any of paragraphs 55-77, wherein the first crosslinkable polymer has a chemical structure as follows:

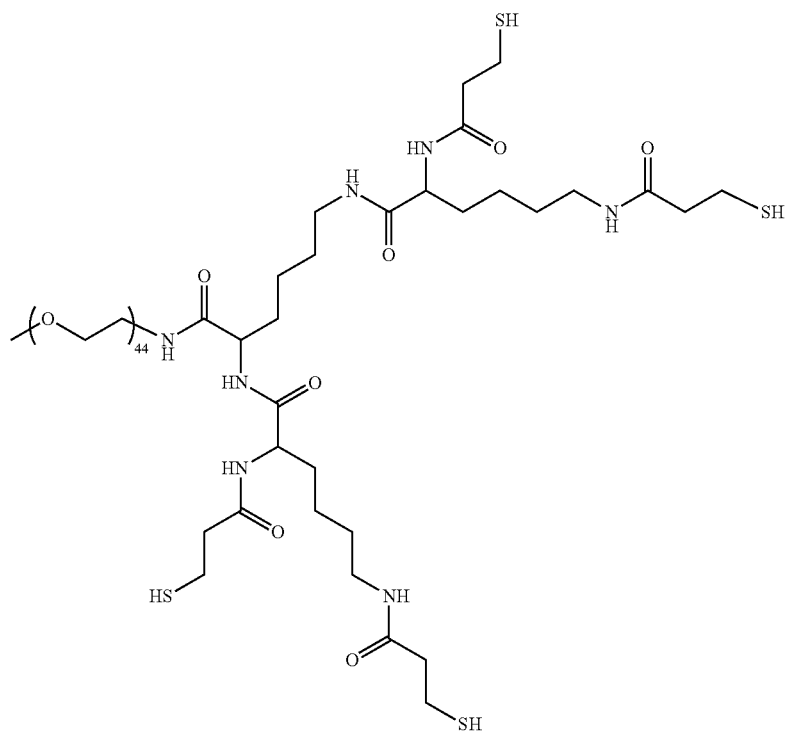

79. The kit of any of paragraphs 55-78, wherein the first crosslinkable polymer has a chemical structure as follows:

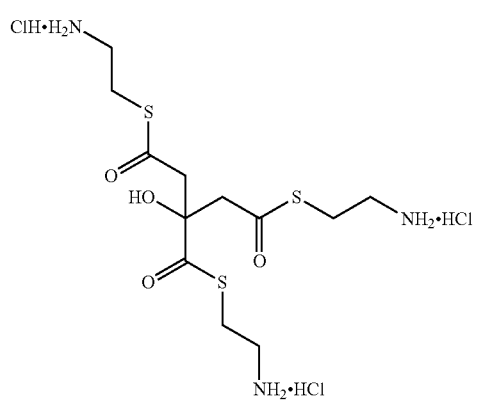

80. The kit of any of paragraphs 55-79, wherein the second crosslinkable polymer is poly(ethylene glycol) disuccinimidyl valerate.

81. The kit of any of paragraphs 55-80, wherein the thiolate compound is selected from the group consisting of linear, branched and/or dendritic multi-thiol macromolecules, poly(ethylene glycol) thiol, thiol-containing glycerol, thiol-containing peptides, cysteine, cystine, alkyl ester of cysteine, alkyl ester of cystine, MeSCH2SH, (R)/(S)-3-methyl-3-sulfanylhexan-1-ol, Ethanethiol, 1-Propanethiol, 2-Propanethiol, Butanethiol, tert-Butyl mercaptan, Pentanethiols, Thiophenol, Dimercaptosuccinic acid, Thioacetic acid, 5-mercapto-4H-[1,2,4]triazol-3-ol, 2-mercaptoacetamide, 2-Mercaptoethanol, 1,2-Ethanedithiol, Ammonium thioglycolate, Cysteamine, Methyl thioglycolate, Thiolactic acid, 1-Mercapto-2-propanol, 2-methoxyethanethiol, 3-Mercapto-1-propanol, 2,3-Dimercapto-1-propanol, 1-Thioglycerol, Mercaptosuccinic acid, 4-ethyl-5-mercapto-4H-1,2,4-triazol-3-ol, N-Carbamoyl-L-cysteine, 2-Methyl-3-sulfanylpropanoic acid, 4-mercaptobutyric acid, N-Acetylcysteamine, 3-Methyl-1-butanethiol, 1,5-Pentanedithiol, 4-Chlorothiophenol, 4-Aminothiophenol, Benzyl mercaptan, 2-Furanmethanethiol, 3-Mercaptohexanol, Furfuryl thiol, derivatives thereof, a disulfide complex of one or more thereof.

82. The kit of any of paragraphs 55-81, wherein the adhesive hydrogel layer is at least partially flexible.

83. The kit of any of paragraphs 55-82, wherein the adhesive hydrogel layer is capable of withstanding a pressure of at least about 2 mmHg.

84. The kit of any of paragraphs 55-83, wherein the adhesive hydrogel layer is transparent.

85. The kit of any of paragraphs 55-84, wherein the adhesive hydrogel layer is hydrophilic.

86. The kit of any of paragraphs 55-85, wherein the adhesive hydrogel layer is elastic or viscoelastic.

87. The kit of any of paragraphs 55-86, wherein the adhesive hydrogel layer has about 5 wt % to about 70 wt % of the crosslinkable polymers.
88. A kit of any of paragraphs 55-87 for treatment of a wound in a tissue of a subject.
89. The kit of paragraph 88, wherein the tissue is selected from the group consisting of skin, heart, blood vessel, liver, urinary tract, lung, gastrointestinal tract, stomach, joint, bone, brain, ear, alveolar bone, lymphatic tissue, buccal tissue, and any combinations thereof.

Some Selected Definitions of Terms

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In certain embodiments of the aspects described herein, the subject is a mammal, e.g., a primate, e.g., a human. A subject can be male or female. Preferably, the subject is a mammal. The mammal can be a human, non-human primate, mouse, rat, dog, cat, horse, or cow, but are not limited to these examples. Mammals other than humans can be advantageously used as subjects that represent animal models of tissue repair, regeneration and/or reconstruction. In addition, the methods and compositions described herein can be used to treat domesticated animals and/or pets.

As used herein, the terms "treating" or "treatment" encompass either or both responsive and prophylaxis measures, e.g., designed to inhibit, slow, or delay the onset of a symptom of a disease or disorder, achieve a full or partial reduction of a symptom or disease state, and/or to alleviate, ameliorate, lessen, or cure a disease or disorder and/or its symptoms. As used herein, amelioration of the symptoms of a particular disorder by administration of a particular compound or pharmaceutical composition refers to any lessening of severity, delay in onset, slowing of progression, or shortening of duration, whether permanent or temporary, lasting or transient that can be attributed to or associated with administration of the compound or composition.

The term "statistically significant" or "significantly" refers to statistical significance and generally means a two standard deviation (2SD) below or above a reference level. The term refers to statistical evidence that there is a difference. It is defined as the probability of making a decision to reject the null hypothesis when the null hypothesis is actually true. The decision is often made using the p-value.

As used herein, the term "substantially" means a proportion of at least about 60%, or preferably at least about 70% or at least about 80%, or at least about 90%, at least about 95%, at least about 97% or at least about 99% or more, or any integer between 70% and 100%. In some embodiments, the term "substantially" means a proportion of at least about 90%, at least about 95%, at least about 98%, at least about 99% or more, or any integer between 90% and 100%. In some embodiments, the term "substantially" can include 100%.

As used herein, the term "comprising" means that other elements can also be present in addition to the defined elements presented. The use of "comprising" indicates inclusion rather than limitation.

The term "consisting of" refers to the components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment of the invention Other than in the operating examples, or where otherwise indicated, all numbers expressing quantities of ingredients or reaction conditions used herein should be understood as modified in all instances by the term "about." The term "about" when used in connection with percentages may mean±5%.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example." Furthermore, use of the term "including" as well as other forms, such as "includes," and "included," is not limiting.

Unless otherwise explained, all technical and scientific terms used herein have the same meaning as commonly understood by one of ordinary skill in the art to which this disclosure belongs. Definitions of common terms in diseases and disorders, separation and detection techniques can be found in The Merck Manual of Diagnosis and Therapy, 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

As used herein, the abbreviations for any protective groups, amino acids, and other compounds are, unless indicated otherwise, in accord with their common usage, recognized abbreviations, or the IUPAC-IUB Commission on Biochemical Nomenclature, Biochem., 11:942-944 (1972).

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

All patents and other publications identified throughout the specification are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

Some embodiments described herein are further illustrated by the following example which should not be construed as limiting.

The contents of all references cited throughout this application, examples, as well as the figures and tables are incorporated herein by reference in their entirety.

EXAMPLES

Example 1. An Exemplary Dissolvable Dendritic Thioester Hydrogel Based on Thiol-Thioester Exchange and Characterizations Thereof Reactions readily occurring in water are appealing for their potential use in biological and biomedical applications. For example, thiol-thioester exchange, the reaction between a thioester-containing small molecule and a thiolate anion to produce a new thioester and thiolate as products, proceeds in high yield in water, in solutions of pH relevant to biological processes, and at room temperature. See, e.g., Bracher, P. J., et al. Orig Life Evol Biosph 2011, 41, 399-4121. While common in biological processes and in native chemical ligation, thiol-thioester exchange has not been reported for use in organic synthesis or in the construction of reversible molecular assemblies or macromolecules such as hydrogel compositions. U. Yasuyuki, et al., Science 2009, 325, 73-77; and U. Yasuyuki, et al., Org. Biomol. Chem. 2009, 7, 2878-2884.

To this end, a strategy based on thiol-thioester exchange (a reversible covalent reaction) in a dendritic thioester hydrogel was evaluated. The use of the dendritic thioester hydrogel to close an ex vivo jugular vein puncture and its controlled dissolution for gradual wound re-exposure based on thiol-thioester exchanged were also presented herein. While hydrogels based on a thiol-disulfide interchange or native chemical ligation (NCL) are known (e.g., Hu, B.-H. et al, Biomacromolecules 2009, 10, 2194-2200; Anumolu, S. S. et al., Biomaterials 2011, 32, 1204-1217), presented herein is the first example of hydrogel disassembly based on thiol-thioester exchange (FIG. 1B). A dendritic macromomer, for example, as described in Ghobril, C. et al. Angewendte Chemie International Edition, 2013, 52, 14070-14074, was selected to synthesize a covalently crosslinked dendritic thioester hydrogel since the composition, structure and molecular weight can be precisely controlled to provide a macromer with multiple reactive sites to ensure rapid formation of a hydrogel.

As the hydrogel dissolution relies on thiol-thioester exchange, a thioester-linked hydrogel as well as a control amide-linked hydrogel were prepared. Specifically, a lysine-based peptide dendron 1 or 2 possessing four terminal thiols or amines, respectively, was synthesized in high yield (FIG. 2). First, the Cbz-protected G1 lysine (peptide dendron 4 indicated in FIG. 2) was synthesized following a previously reported procedure as described herein Wathier, M. et al., ChemMedChem 2006, 1, 821-825. A poly(ethylene glycol) amine of 2000 Mw was then introduced on the peptide dendron by a classic peptide coupling reaction to enhance aqueous solubility, followed by the catalytic hydrogenolysis of the Cbz groups to generate dendron 2. Dendron 1 was prepared by coupling the activated PFP-3-(tritylthio)propionic acid to dendron 2, followed by removal of the trityl groups using TFA and triethylsilane in DCM. The dendrons were characterized, e.g., by nuclear magnetic resonance (NMR), matrix-assisted laser desorption/ionization (MALDI) and/or infra-red (IR) spectroscopy. Syntheses of dendrons 1 and 2 are further described in detail as follows:

Synthesis of Dendron 2.

HOBt (4.4 mmol) and EDCI (4.4 mmol) were added to a solution of 4 shown in FIG. 2 (4 mmol) in DMF (40 mL) at room temperature and under nitrogen. Next, a solution of MPEG2000-NH$_2$ (4 mmol) and DIPEA (4.8 mmol) in DMF (20 mL) was added dropwise. The reaction mixture was stirred at room temperature overnight. The solvent was removed under vacuum, and the crude product mixture was redissolved in CH$_2$Cl$_2$. The organic phase was extracted with an aqueous sodium bicarbonate solution, water, and brine to yield the Cbz-protected dendron. This compound was then dissolved in methanol (200 mL), and Pd/C (10%) was added. Next, the reaction was stirred under hydrogen for 48 hrs. The solution was then filtered through celite, washed several times with methanol, and concentrated under vacuum. The transparent oil was triturated with ether until a precipitate formed. The solid was filtered and dried under vacuum to afford dendron 2 as a white solid (90%), which was used in the next step without further purification. $^1$H NMR (500 MHz, D$_2$O): δ=1.36-1.99 (m, 18H), 2.92 (m, 4H), 3.20 (m, 2H), 3.36-3.85 (m, ca. 180H), 3.38 (s, 3H), 4.15 (m, 1H), 4.24 (m, 1H) ppm; MALDI-TOF-MS (positive ion) [M+Na$^+$]: 2334; IR (neat): 3280, 2883, 1634, 1466, 1343, 1105, 963, 842 cm$^{-1}$.

Synthesis of Dendron 1.

Et$_3$SiH (3.75 mmol) and TFA (2 mL) were added to a solution of 5 shown in FIG. 2 (0.25 mmol) in CH$_2$Cl$_2$ (5 mL). The solution was stirred at room temperature for 3 hrs. The solvent and TFA were removed under vacuum, and the product was triturated in ether until a precipitate formed. The solid was filtered, washed several times with ether, and dried under vacuum. A solution of HCl (1 N) was added, and the aqueous phase was filtered and lyophilized. Water was then added, and the pH adjusted to 7. The aqueous phase was lyophilized again to afford dendron 1 as a white solid (95%). The last step was conducted quickly to avoid oxidation of the thiols in water. $^1$H NMR (500 MHz, D$_2$O): δ=1.37-1.77 (m, 12H), 1.82 (m, 6H), 2.57-2.70 (m, 8H), 2.80 (m, 8H), 3.24 (m, 6H), 3.42 (s, 3H), 3.50-3.74 (m, ca. 180H), 4.28-4.33 (m, 3H) ppm; $^{13}$C NMR (100 MHz, D$_2$O): δ=174.2, 173.8, 173.7, 71.1-66.6 (OCH$_2$CH$_2$), 58.5, 58.2, 54.4, 54.1, 40.2, 39.8, 39.5, 39.1, 30.8, 28.2, 22.8, 20.9, 20.4, 19.9 ppm; MALDI-TOF (positive ion) [M+Na$^+$]: 2687; IR (neat): 3300, 3056, 2869, 2553, 1653, 1558, 1457, 1348, 1096, 949, 843 cm$^{-1}$.

To prepare the hydrogels, a solution of dendron 1 or 2 in borate buffer (e.g., at pH ~9) was reacted with a solution of poly(ethylene glycol) disuccinimidyl valerate) of 3400 Mw (macromolecule 3 indicated in FIG. 1B: SVA-PEG-SVA) in PBS buffer at pH~6.5. The ratio of amine or thiol to SVA was about 1:1, and the total concentration of polymer in solution was either 10 wt % or 30 wt %. A hydrophilic gel formed spontaneously within seconds upon mixing the two aqueous solutions at either concentration. The gels exhibited viscoelastic properties and were transparent. Cylindrical hydrogel samples of 9-mm diameter and 3-mm thickness were prepared and analyzed after keeping at ~25° C. for about 2 hrs. The mechanical strength and viscoelastic properties of the hydrogels were investigated using rheological measurements. First, the strain sweep test was performed on both hydrogels, at a frequency of about 1 Hz, in order to establish the range of linear viscoelasticity (LVE). Then, the frequency sweep at a constant oscillatory stress of ~50 Pa was determined for all hydrogels before and after swelling (FIG. 3). PEG-LysSH and PEG-LysNH$_2$ hydrogels at either concentration showed strong elastic properties with low tan δ (<5° and exhibited a storage modulus G' greater than a loss modulus G" at frequencies between 0.1 and 10 Hz. Before swelling, G' values for 30 wt % PEG-LysSH (reversible) and PEG-LysNH$_2$ (non-reversible) hydrogels were about 37×10' and 14×10$^3$ Pa, respectively, at 1 Hz frequency (FIG. 3). The increase in modulus is also consistent with the increase in the wt % of the polymer, about 37×10$^3$ Pa (30 wt %) vs. 6×10$^3$ Pa (10 wt %) of PEG-LysSH hydrogel, at 1 Hz frequency.

After exposure to 5 ml PBS buffer at pH ~7.4, ~30 wt % PEG-LysSH and PEG-LysNH$_2$ hydrogels swelled up to 400 and 600%, respectively, and reached equilibrium after 48 hrs (data not shown). The G' values, at swelling equilibrium, decreased by approximately half, for both hydrogels (FIG. 3). Hydrogels at a concentration of 10 wt %, G' also decreased in a similar manner after 48 hours of exposure to PBS buffer, with the PEG-LysSH hydrogel possessing the lowest G' value (ca. 200 Pa) at a frequency of 1 Hz.

Without wishing to be bound by theory, in a competing process, thioesters can spontaneously hydrolyze in water to form carboxylic acids, which could prevent the formation of the gel. In the conditions described in this Example, PEG-LysSH hydrogels were formed within seconds and were stable to hydrolysis for several days. The rheological data show that both hydrogels exhibited suitable mechanical properties as evident by higher G' values, even after swelling for 48 hrs (except for 10 wt % PEG-LysSH). These results indicate that these hydrogels can be used as hemostats for treatment of wounds, as even after absorbing of water, they still maintain their integrity, which should prolong their contact time on skin and prevent structural breakage.

Next, the reversibility or dissolution capability of the 30 wt % PEG-LysSH and PEG-LysNH$_2$ based hydrogels were evaluated to determine if a thiol-thioester exchange between the thioester bonds in the hydrogel and a thiolate in aqueous solution (e.g., but not limited to cysteine) would dissolve the hydrogel and form an amide linkage to prevent hydrogel re-formation (FIG. 4). Three solutions that contained different nucleophiles were evaluated; these contained (1) 1-cysteine methyl ester (CME; reacts by an NCL-based mechanism); (2) the water-soluble thiolate 2-mercaptoethanesulfonate (MES); and (3) 1-lysine methyl ester (LME; the amine acts as the nucleophile). Under all three conditions, the dissolution of the hydrogel was evaluated at equilibrium after swelling in PBS buffer at pH 7.4. The PEG-LysNH$_2$ hydrogel that contains the amide bonds was used as a control system. It was observed that the pH of the buffer solution and the concentration of the thiolate solution had a significant impact on the rate of exchange, and thus on the dissolution time of the thioester hydrogel. Increasing the concentration of the CME solution to 0.5 M at a constant pH of 7.4 led to a decrease in the dissolution time of the hydrogel from $t_{1/2}$=30 min to $t_{1/2}$=18 min (FIG. 4 (5)). Similarly, when the pH was increased to 8.5 at a constant concentration of the CME solution (0.3 M), the thioester bridges in the gel were rapidly cleaved, and the hydrogel completely dissolved with $t_{1/2}$=12 min ($t_{1/2}$=25 min at pH 7.4; FIG. 4 (6)). Upon exposure of the PEG-LysSH hydrogel to an excess of MES solution (0.3 M) in PBS at pH 8.5, the dissolution time of the gel ($t_{1/2}$=10 min) was comparable to that in CME solution. Interestingly, an LME solution (0.3 M) in PBS at pH 8.5 did not cleave the thioester bridges of the PEG-LysSH hydrogel even after 60 min, which demonstrates that a thiol-thioester exchange is responsible for the dissolution of the hydrogel in the presence of CME. As expected, when the PEG-LysNH$_2$ hydrogel was exposed to CME solution (0.3 M) at pH 8.5, the gel did not dissolve, even after one hour of exposure (FIG. 4, (2)).

Example 2. Assessment of an Exemplary Dissolvable Dendritic Thioester Hydrogel for Use in Hemostasis of a Wound In order to evaluate the PEG-LysSH hydrogel for hemostasis of wound, its adherence to ex vivo human skin tissues was first assessed. A solution of ~30 wt % PEG-LysSH hydrogel solution (or 30 wt % of PEG-LysNH$_2$ hydrogel as a control) in borate buffer was mixed with a solution of SVA-PEG-SVA (indicated as macromolecule 3 in FIG. 1B) in PBS and applied to the ex vivo human skin. The gel formed within seconds and reached equilibrium after 1 hr. As shown in FIGS. 5A-5B, torsional stress was applied on both PEG-LysSH (FIG. 5A) and PEG-LysNH$_2$ (FIG. 5B) hydrogels to assess their adherence strength and flexibility on the skin. Upon the application of the torsional stress, both gels remained intact. Next, the dissolution of the thioester-crosslinked hydrogel upon exposure to ~0.3 M CME in PBS buffer, at pH ~8.5 was evaluated. As shown in FIG. 5C, after ~30 mins, the PEG-LysSH hydrogel was completely dissolved and washed off while PEG-LysNH$_2$ only swelled and was still adhered on the skin even after several hrs.

An in vitro cytotoxicity study with the PEG-LysSH hydrogel (30 wt %) was performed with NIH3T3 murine fibroblast cells. The viability of the cells was 97±3% after exposure to the hydrogel for 24 hours and similar to that of the untreated control (p>0.05). The cytotoxicity of CME buffer solutions (0.1 M and 0.3 M) at pH 7.4 and 8.5 in the presence of the thioester hydrogel was also assessed. The cells were completely viable after exposure to the cysteine buffer solutions for one hour at either pH or concentration.

An in vitro macrophage activation study was performed with PEG-LysSH to determine whether the hydrogel induces an immune response. Macrophages were exposed to the PEG-LysSH hydrogel (30 wt %) for 24 hours (n=3), or lipopolysaccharide (LPS; 1 mgmL$^{-1}$), a component of Gram-negative bacteria that elicits an immune response as the positive control. Media samples were then tested for IL-6, a marker of macrophage activation. LPS exposure afforded a statistically higher IL6 response than the hydrogel (p<0.01); the response to the hydrogel was statistically indistinguishable (p>0.05) to that of a media only control. The PEG-LysSH hydrogel (30 wt %) does not activate macrophages with concomitant production of IL-6.

Figures 6A, 6B, 6C, 6D:
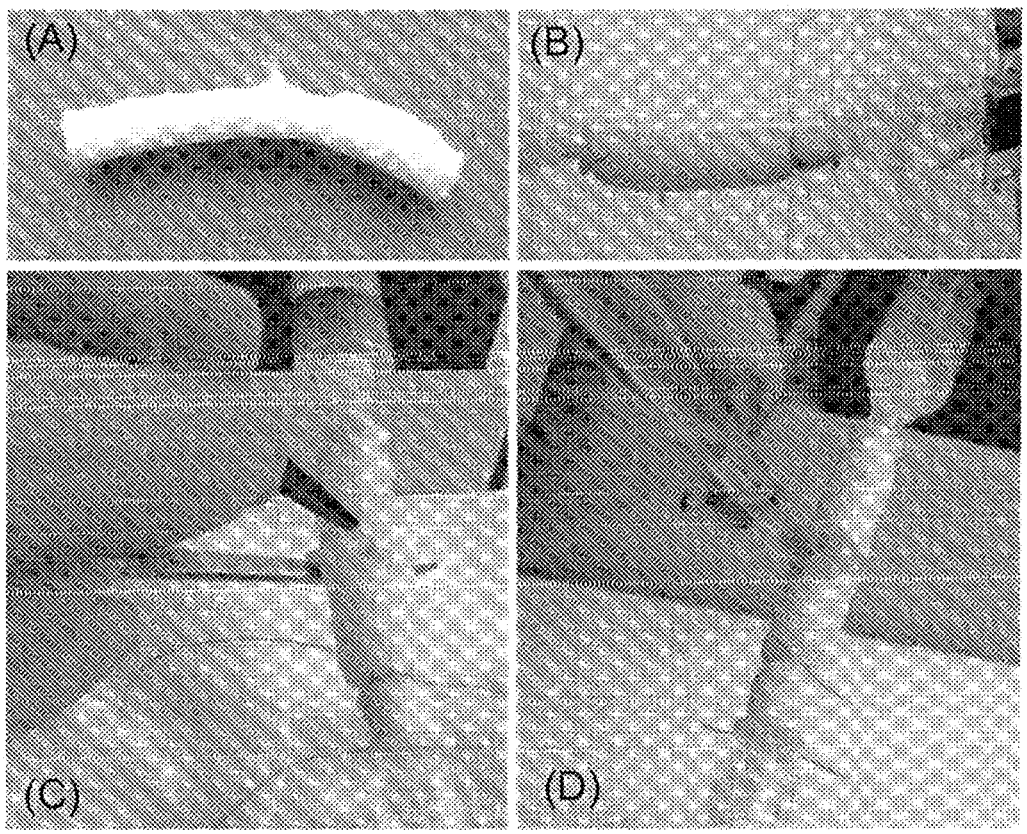
FIGS. 6A-6F are photographs showing an example use of one embodiment of a dissolvable hydrogel as a tissue sealant.

The PEG-LysSH hydrogel was also evaluated as a sealant on an ex vivo jugular vein, in order to simulate a trauma caused by bleeding. As shown in FIGS. 6A-6B, the jugular vein was first linked to a syringe pump and filled with PBS solution. Prior to the application of the gel, the pressure was increased in the vein to ensure that the system is leak-proof and that it could withstand pressures of ca. 250 mmHg (the upper limit of detection; n=3), which is significantly greater than normal arterial blood pressure (120 mmHg). Next, a 2.5 mm hole was made on the vein surface, and the pressure dropped to zero (FIG. 6C). Dendron 1 and SVA-PEG-SVA 3 (as shown in FIG. 1B) were quickly mixed at room temperature, and a solution of 100 µL (30 wt %) was applied to the puncture site (FIG. 6D). Within 5 min of closing the incision, the hydrogel sealant secured the wound without leakage as the syringe pump continuously increased the pressure to approximately 250 mmHg (n=3) (As a comparison, normal arterial blood pressure is typically around 120/80 mmHg). Application of CME afforded dissolution of the sealant, and the wound leaked again. The procedure with the hydrogel sealant was facile to carry out and did not inflict additional tissue trauma.

Presented herein relates to synthesis of one or more embodiments of a dendritic thioester hydrogel, which can gel within seconds from multiple thioester linkages formed between the thiol residues of dendron 1 and the poly (ethylene glycol) macromer, e.g., SVA-PEG-SVA (macromolecule 3). In some embodiments, the thioester gel can exhibit strong mechanical properties even after swelling in PBS buffer, as shown by the high storage modulus G' value and can adhere to human skin tissue even when torsional stress was applied. The thioester hydrogel can be completely dissolved and/or washed off upon exposure to a thiolate solution based on the thiol-thioester exchange mechanism. While thiol-thioester exchange process occurs between small molecules and/or protein fragments in biological processes, it has not been yet explored in macromolecular assemblies such as hydrogels. The use of a reversible thioester hydrogel based on the thiol-thioester exchange mechanism can be versatile, e.g., for hemostasis of wounds as opposed to commercially available wound dressings that typically require mechanical debridement and/or surgical excision of removal of the dressings or clotting agent. For example, the novel capability of controlled dissolution of a thioester hydrogel described herein can allow for gradual wound re-exposure in a surgical theatre setting for definitive surgical care, e.g., without inflicting any unnecessary tissue trauma or damage.

Example 3. Stability of an Exemplary Dissolvable Dendritic Thioester Hydrogel

The hydrolysis of alkyl thioesters is thermodynamically favorable to form a thiol and carboxylic acid, and it is generally believed that thioesters are not stable in aqueous solution. Specifically, in small molecules this hydrolysis rate is pH dependent. Thioester hydrolysis has been previously reported in the context of the origins of life that small molecule thioesters such as $CH_3C(O)SCH_3$ (with a molecule weight of about 90 Da or 90 g/mol) hydrolyze 10,000 times faster at high pH (e.g., above pH~7) and low pH (e.g., below pH~3) and are relatively stable at pH ~3 to ~7.

However, the hydrolysis of alkyl thioesters present in crosslinked polymer systems such as crosslinked hydrogels which have high water content has not yet been studied. Surprisingly, in accordance with various embodiments described herein, a thioester crosslinked hydrogel formed between thiol and an activated ester is stable at pH from 0 to about 9 (FIG. 7). Without wishing to be bound by theory, this increase in stability can be, at least in part, a result of the polymer chain backbone stabilizing the thioester bond since hydrolysis would require the polymer chain to change conformation or rearrange in space. As the chains are generally confined to an area via the crosslinked hydrogel, a conformational change or rearrangement of polymer chains can become less favorable.

Thiol-thioester exchange in water, where a thiol replaces a thiol in a thioester, is known to occur readily in solution with small molecules. For example, adding an equivalent number of free thiols to a solution of thioester small molecules (e.g., thiol: thioester stoichiometric ratio is about 1:1) is sufficient to lead to thiol-thioester exchange. In contrast, thioester crosslinked hydrogels are unexpectedly stable. As shown in FIG. 7, when the equivalent number of thiols added to a thioester hydrogel was four (based on the number thioester linkages), there was almost no change in mechanical properties over a period of at least about 60 minutes. Thiol-thioester exchange reactions appeared to occur very slowly or insignificantly. Thus, adding an equivalent number of free thiols to a thioester crosslinked hydrogel is not sufficient to allow significant thiol-thioester exchange to occur. Instead, the thioester crosslinked hydrogel can be dissolved upon addition of an excess of free thiols (e.g., as shown in FIG. 4). These combined data indicate that the thioester exchange reaction in a thioester crosslinked hydrogel is generally slow and unfavorable unless an excess of free thiols is used. Without wishing to be bound by theory, as the polymer chains are generally confined to an area via the crosslinked hydrogel, a conformational change or rearrangement of polymer chains can become less favorable.

Example 4. Comparison of an Exemplary Thioester Crosslinked Hydrogel to a S—S Crosslinked Hydrogel The stability and reactivity of thioester-crosslinked hydrogels is in stark contrast to S—S crosslinked hydrogels. The S—S bond is previously known to cleave under reducing conditions and when the S—S bond is incorporated into a hydrogel, the same reducing conditions can cleave the bond and degrade the hydrogel. However, as discussed above, the thioester bonds incorporated into a crosslinked hydrogel appear to be more stable during a thioester exchange reaction unless an excess of free thiols is used.

Further, on a weight basis of polymer added, the S—S crosslinked hydrogels (8-arm-PEG-SH (20 kDa), Sinko, P. J. et al. Biomaterials 2011, 32, 1204-1217) are generally weak relative to the thioester-crosslinked dendritic hydrogels. For example, a ~10 wt % S—S hydrogel has a storage modulus G' of about 3000 Pa (as compared to ~6000 Pa for a ~10 wt % thioester dendritic hydrogel as shown in FIG. 3) and is thus limited in its ability to seal a wound. In addition, the preparation of S—S crosslinked pegylated hydrogels of greater wt % or with small macromers forming more S—S linkages per volume requires a significant amount of $H_2O_2$ solution in water—more than what is available in the market—45% $H_2O_2$ or the use of large volumes of added $H_2O_2$ further reducing the overall wt % of the final hydrogel solution. Thus, there is a practical limitation in making S—S pegylated hydrogels of higher weight percents (e.g., ~50% or higher) or smaller volumes. However, the thioester crosslinked hydrogels have no such limitation and can be made at high weight percents as well as at small volumes.

Figures 6E, 6F:
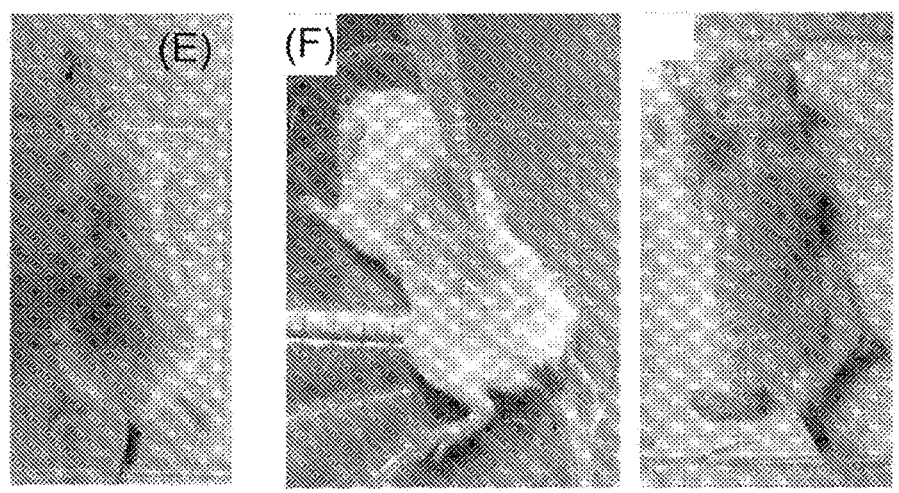

Example 5. Use of an Exemplary Thioester-Linked Hydrogel as a Sealant in an In Vivo Burn Model A deep second-degree burn mice model (9 weeks old female Balb/c) was employed to assess the wound-healing efficacy of the thioester hydrogel sealant (FIG. 6E). The mice were anesthetized with ketamine (90 mg/kg)/xylazine (10 mg/kg) intra-peritoneally and then transferred to a warm environment that maintains a constant body temperature. Burns were caused through contact with an aluminum bar (r=10 mm) preheated for ~100° C. for ~15 s, prior to inflicting the burn areas on the skin of the mice. The thioester hydrogel was applied to the site of the burn wound and it adhered to the skin for at least several hours. The reversibility of the thioester hydrogel was also assessed in mice that had the hydrogel on top of the burn wound (FIG. 6F). Cysteine methyl ester solution was applied via a syringe on top of the hydrogel and was kept for 30-45 minutes. After this time, the hydrogel was completely dissolved (n=3).

Example 6. Another Example of a Thioester Hydrogel and Characterization Thereof

Figure 8A:
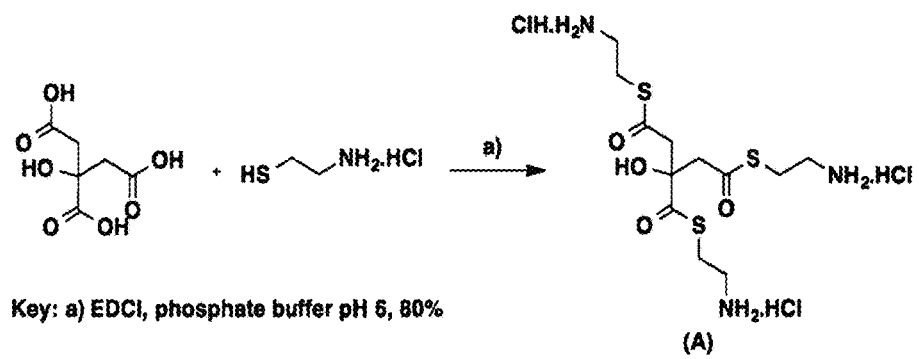
FIGS. 8A-8C show another embodiment of a thioester hydrogel (using citric acid and NHS-PEG-NHS) and its rheological properties.

In this example, citric acid and NHS-PEG-NHS (e.g., Mw ~2400 Da) were used to form a dissolvable hydrogel. The rheological properties were performed on a RA 1000 controlled strain rheometer from TA Instrument equipped with a peltier temperature control. Each sample was allowed to reach the equilibrium at 20° C. for 10 min. 20 mm steel plate diameter geometry was used to measure the rheological properties. All rheological measurements were performed with a cover and at 20° C. to avoid evaporation. After equilibrium an oscillatory frequency sweep (from 0.1 to 10 Hz) was performed at 20° C. This measures the storage modulus G' and the lost modulus G". All data as shown in FIG. 8C are reported at a frequency of 1 Hz.

In order to form a dissolvable hydrogel using citric acid and PEG-NHS, citric acid was first reacted with a thiol-containing molecule to create a thioester bond in the molecule. For example, as shown in FIG. 8A, N-(3-Dimethylaminopropyl)-N'-ethylcarbodiimide hydrochloride (EDCI.HCl) (41.66 mmol) was added to a solution of citric acid (10.4 mmol) and cysteamine hydrochloride (31.2 mmol) in water (40 mL). The reaction mixture was stirred at room temperature overnight. Then, about 30 mL of NaOH (0.1 M) were added and the product was extracted with dichloromethane (3×100 mL). After evaporation of the solvent the crude product was dissolved in water using HCl 0.1M until pH 6 then freeze-dried to obtain the product A (S,S,S-tris(2-aminoethyl) 2-hydroxypropane-1,2,3-tris(carboxylothioate) hydrochloride salt) as a white powder without further purification. $^1$H NMR (CDCl$_3$): δ=2.4 (s, 4H, CH$_2$—CO); 3.4 (m, 6H, CH$_2$—CH$_2$); 4.0 (m, 6H, CH$_2$—CH$_2$) ppm. FAB MS: 391 m/z (M+Na$^+$) (theory: 369 m/z (M$^+$)).

Then about 50 mg of the product A was dissolved in 1000 μl of phosphate buffer pH 8 (solution 1) where G'=0 Pa, G"=0 Pa. About 375 mg of PEG-NHS was dissolved in 1000 μl of phosphate buffer pH 7 (solution 2) where G'=0 Pa, G"=0 Pa.

Figure 8B:
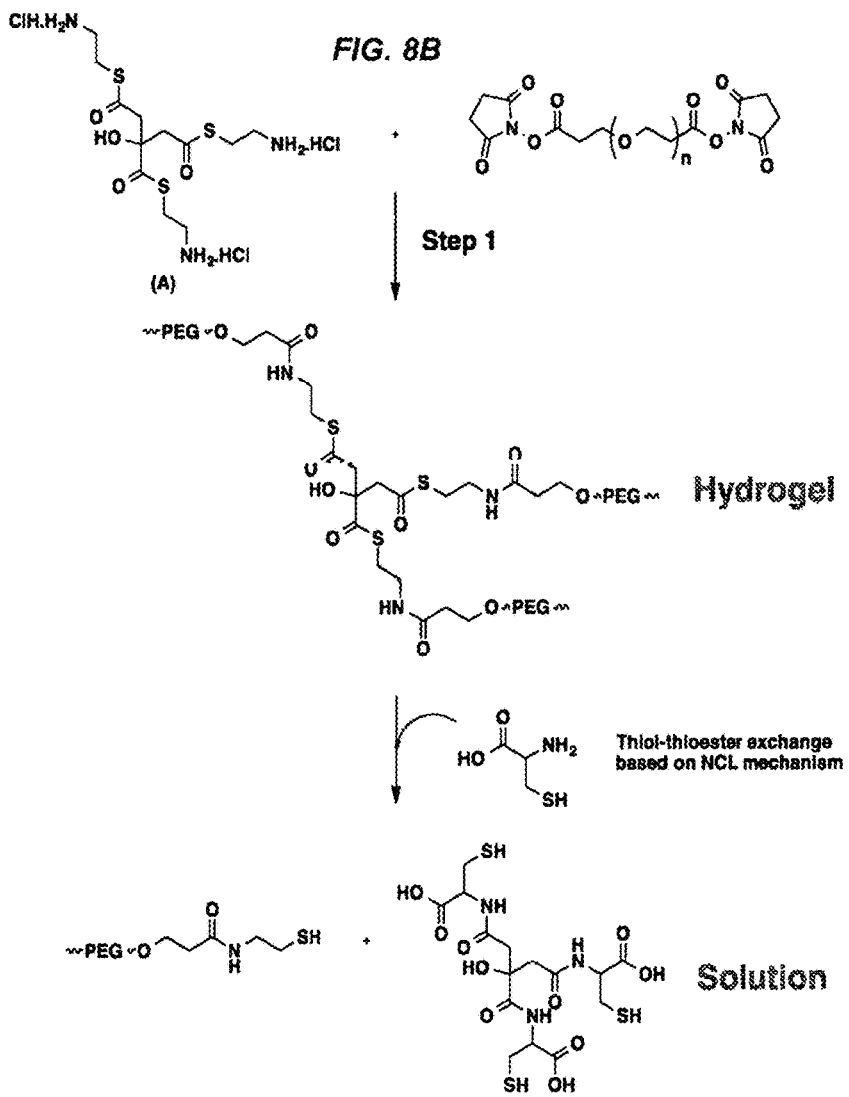
Figure 8C:
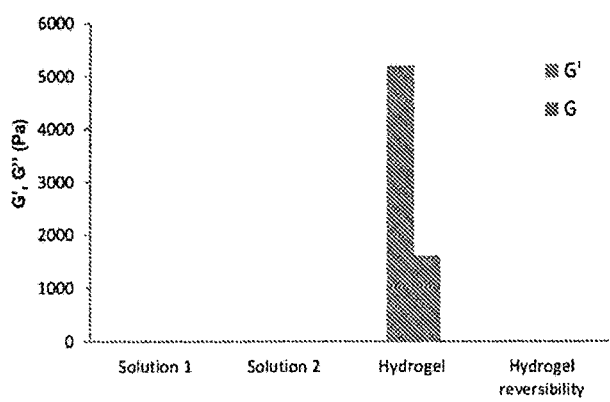

As shown in FIG. 8B, a thioester hydrogel was formed within 1 minute when solutions 1 and 2 were mixed (Step 1). The thioester hydrogel was strong and elastic enough to be handled by hand. The thioester hydrogel has a shear storage modulus G' of about 5,200 Pa and a shear loss modulus G" of about 1,600 Pa. To dissolve the thioester hydrogel (Step 2), the thioester hydrogel was then soaked in a saturated solution of cysteine (10 mL in water, G'=0 Pa, G"=0 Pa) and all the hydrogel was resorbed after about 2 hours, as evidenced by the values of G'=0 Pa, G"=0 Pa.

Example 7. Another Example of a Thioester Hydrogel and Characterization Thereof

Figure 9A:
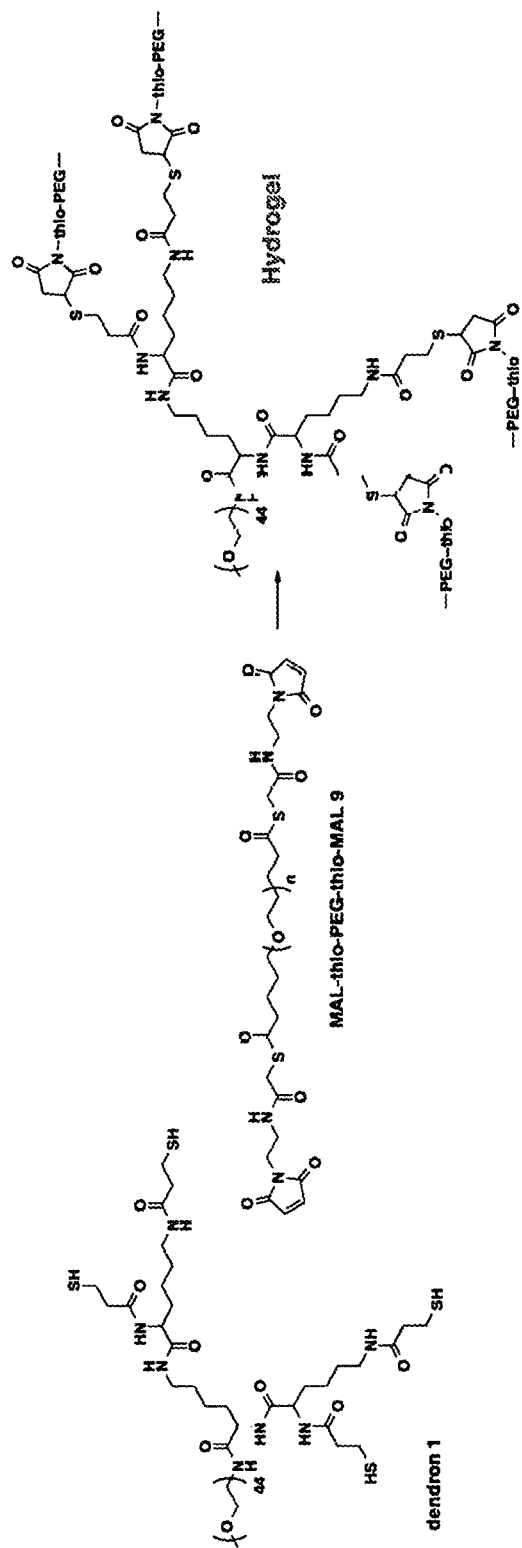
FIGS. 9A-9E show another embodiment of a thioester hydrogel (using dendron 1 described in FIG. 2 and MAL-thio-PEG-thio-MAL 9 containing thioester linkages within its structure) and its rheological properties.

In this example, dendron 1 as shown in FIG. 2 and MAL-thio-PEG-thio-MAL 9 (e.g., Mw ~3400 Da) were used to form a dissolvable hydrogel (FIG. 9A). The rheological properties were performed on a RA 1000 controlled strain rheometer from TA Instrument equipped with a peltier temperature control. Each sample was allowed to reach the equilibrium at 20° C. for 2 min. 8 mm steel plate diameter geometry was used to measure the rheological properties. All rheological measurements were performed at 20° C. to avoid evaporation. After equilibrium an oscillatory frequency sweep (from 0.1 to 10 Hz) was performed at 20° C. This measures the storage modulus G' and the lost modulus G". The data as shown in FIG. 9C are reported at a frequency of 1 Hz, 50 Pa oscillatory stress and 20° C.

Figure 9B:
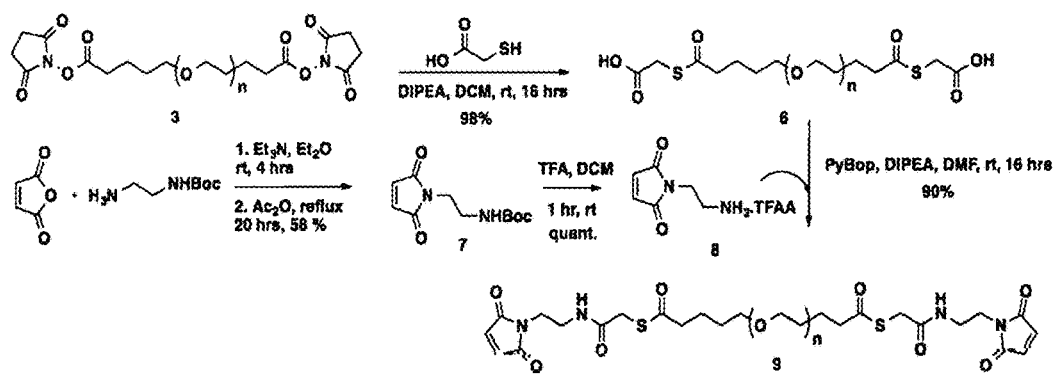
Figure 9C:
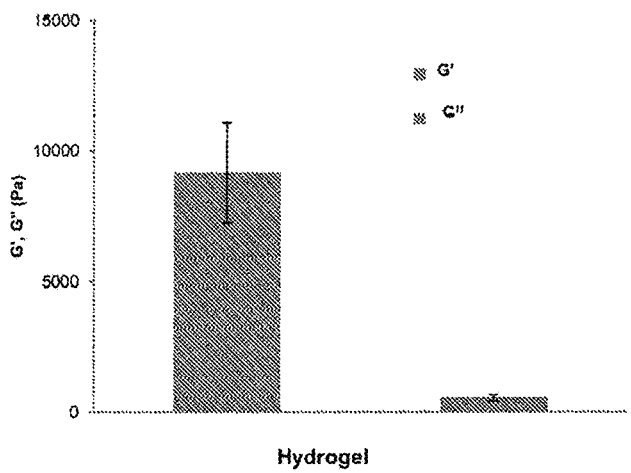

In order to form a dissolvable hydrogel using dendron 1 and MAL-thio-PEG-thio-MAL 9, the second-water soluble macromolecule was synthesized as detailed in FIG. 9B. For example, to a solution of SVA-PEG-SVA 3 (3 mmol) in dichloromethane (20 mL), DIPEA (18.7 mmol) and thioglycolic acid (9.37 mmol) were added under nitrogen. The reaction mixture was stirred at room temperature for 16 hours. Then, about 20 mL of citric acid (10 wt %) were added and the product was extracted with dichloromethane (20 mL). The organic phase was then washed with water (25 mL) and brine (25 mL), dried over sodium sulfate, filtered and concentrated. After evaporation of the solvent, the crude product was triturated in diethyl ether and after filtration, a white powder 6 (98%) was obtained and used in the next step without further purification. $^1$H NMR (500 MHz, CDCl$_3$): δ=3.77-3.47 (m, ca. 300H), 3.45 (t, J=6.5 Hz, 4H), 2.63 (t, J=7.4 Hz, 4H), 1.78-1.72 (m, 4H), 1.63-1.57 (m, 4H) ppm; $^{13}$C NMR (100 MHz, CDCl$_3$) δ=197.2, 169.8, 70.4, 70.0, 43.1, 30.9, 28.6, 22.1 ppm; MALDI-TOF (pos) (M$^+$) 3606; IR (neat) 3485, 2879, 2697, 1714, 1649, 1466, 1344, 1110, 949, 842 cm$^{+1}$.

Compound 6 (3 mmol) was then dissolved in DMF (60 mL) under nitrogen. DIPEA (12 mmol) and PyBOP (7.5 mmol) were added to the solution followed by compound 8 (7.5 mmol). The reaction mixture was stirred at room temperature for 16 hours. The reaction mixture was added dropwise to cold diethyl ether and a precipitate is formed. The solid was filtered, washed several times with diethyl ether then dissolved in dichloromethane (50 mL). Then, about 50 mL of a saturated solution of ammonium chloride were added and the product was extracted with dichloromethane (50 mL). The organic phase was washed with water, brine, dried over sodium sulfate, filtered and concentrated. After evaporation of the solvent, the crude product was triturated in diethyl ether, filtered and dried. The white powder was then dissolved in water and filtered. The filtrate was lyophilized to obtain a white powder 9 (90%). $^1$H NMR (500 MHz, D$_2$O): δ=6.84 (s, 4H), 3.84-3.6 (m, ca. 304H), 3.55 (m, 4H), 3.42 (m, 4H), 2.71 (m, 4H), 1.72-1.67 (m, 4H), 1.64-1.59 (m, 4H) ppm; $^{13}$C NMR (100 MHz, CDCl$_3$) δ=198.8, 170.6, 168.4, 134.1, 70.55, 70.5, 70.3, 70.1, 43.18, 38.6, 37.0, 32.3, 28.6, 21.9 ppm; MALDI-TOF (pos) (M$^+$) 3852; IR (neat) 3345, 2882, 1710, 1536, 1466, 1343, 1105, 963, 842 cm$^{-1}$.

Synthesis of Compound 8.

To a solution of N-tert-Butoxycarbonyl-1,2-diaminoethane (31.6 mmol) and triethylamine (47.4 mmol) in diethyl ether (60 mL), was added dropwise and at 0° C. a solution of maleic anhydride (31.6 mmol) in diethyl ether (60 mL). The reaction mixture was stirred for 4 hours during which the reaction was allowed to reach room temperature. After concentrating the solution, the residue was dissolved in acetone (150 mL). Triethylamine (47.4 mmol) was added and the mixture heated to reflux. Acetic anhydride (47.8 mmol) was added and the solution heated to reflux for 20 hours. The solvent was then evaporated under vacuum and the crude purified by silica gel chromatography (cyclohexane/ethyl acetate 1/1). After the column, the product was crystallized in EtOAc/hexane to yield a white solid 7 (58%). The NMR spectra are similar to those reported in the literature (Richter, M. et al. Chem. Eur. J. 2012, 18, 16708-16715).

Compound 7 (17 mmol) was dissolved in dichloromethane (30 mL) and TFA (25 mL) was added at 0° C. The reaction mixture was stirred at room temperature for 1 hour then concentrated under vacuum. The crude was triturated in cold diethyl ether and filtered to yield quantitatively compound 8 as a white solid. $^1$H NMR (500 MHz, DMSO$_d$): δ=8.02 (m, 3H), 7.04 (s, 2H), 3.66 (t, J=5.8 Hz, 2H), 2.99 (t, J=5.8 Hz, 2H) ppm.

To form the dissolvable hydrogel, 100 μL solution of dendron 1 (16 mg) in borate buffer pH 9 was mixed to 100 μL solution of MAL-thio-PEG-thio-MAL 9 (44 mg) in PBS buffer pH 6.5. The hydrogel (30 wt %) was formed instantly (1 second).

Figure 9D:
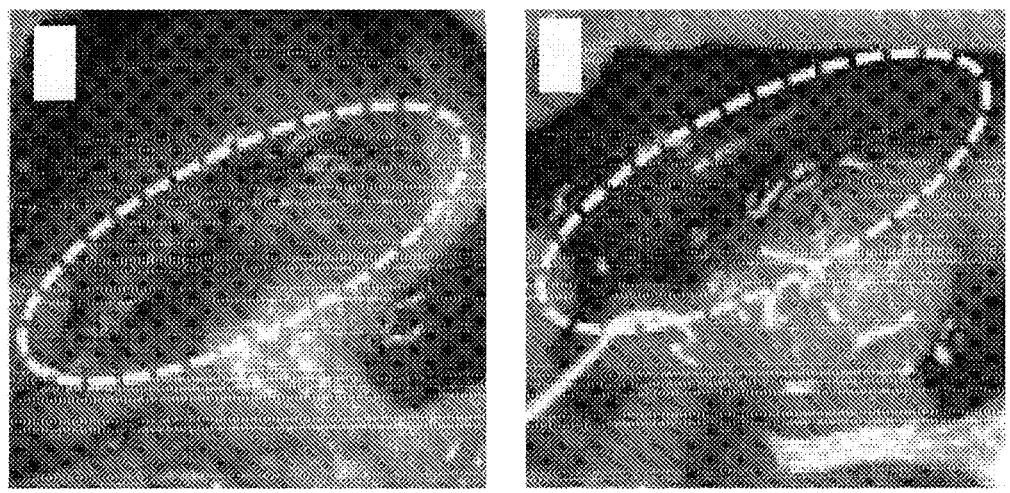
Figure 9E:
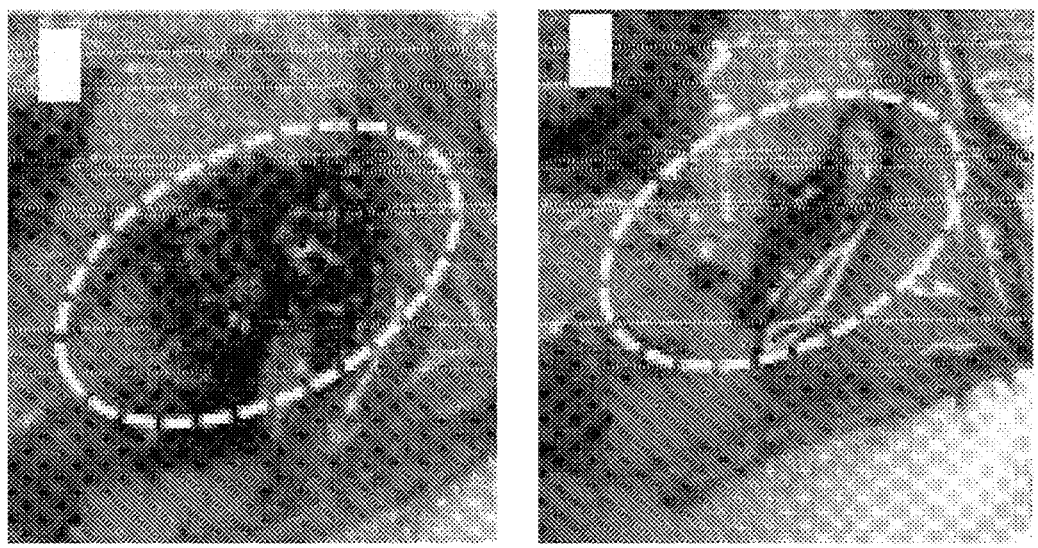

The efficacy of the dissolvable hemostatic hydrogel was assessed in an in vivo hepatic and aortic injury rat model as shown in FIGS. 9D-9E. Female Sprague Dawley rats were anesthetized with 5% isoflurane in an induction chamber, then maintained with 2% isoflurane through a nose cone, during the experiments. All animals were anticoagulated with heparin 5 minutes prior to the start of the operation. For hepatic injury model, the capsule of the median lobe was scored in three spots (lateral, medial, and in the midline), 1 cm from the hepatic border, with a handheld cautery. The portion of the median lobe distal to the marks was sharply excised with scissors. The wound was left to bleed for 20 seconds, after which the hydrogel was applied on the wound surface. In the control group, no treatment was administered. After 20 minutes, the blood loss was collected with pre-weighted gauzes and quantified (FIG. 9D, left panel). Similarly, for aortic injury model, a 25-gauge needle puncture was made on the abdominal aorta causing severe arterial bleeding. The hydrogel was immediately applied on the wound surface, whereas in the control group no treatment was administered. After 20 minutes, the blood loss was quantified and compared to the control (FIG. 9E, left panel). The application of the thioester hydrogel on the wound surface reduced the post-injury blood loss by 35% in severe hepatic hemorrhage and by 20% in aortic hemorrhage when compared to untreated controls (p=0.02 and p=0.03, respectively).

The reversibility of the thioester hydrogel was also assessed in the in vivo hepatic and aortic injury model. After applying the hydrogel on the incisions, a solution of cysteine methyl ester (e.g., 0.3M) was added and the hydrogel was completely dissolved (FIGS. 9D-9E, right panel).

Figure 10A:
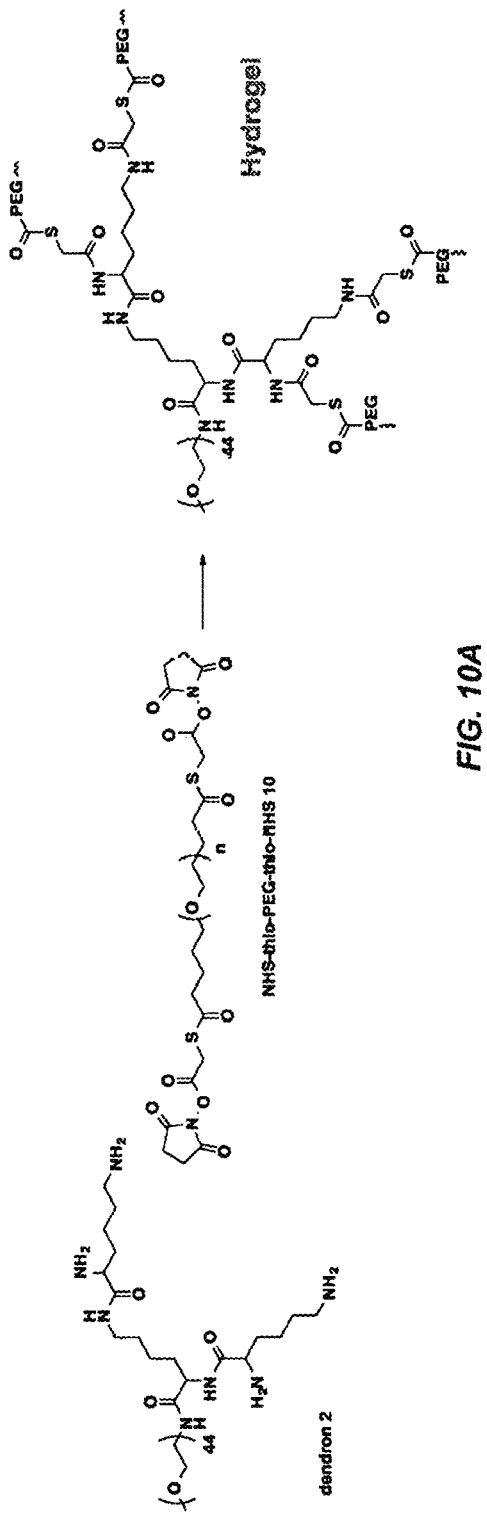
FIGS. 10A-10B show another embodiment of a thioester hydrogel (using dendron 2 described in FIG. 2 and NHS-thio-PEG-thio-NHS 10 containing thioester linkages within its structure).
Figure 10B:
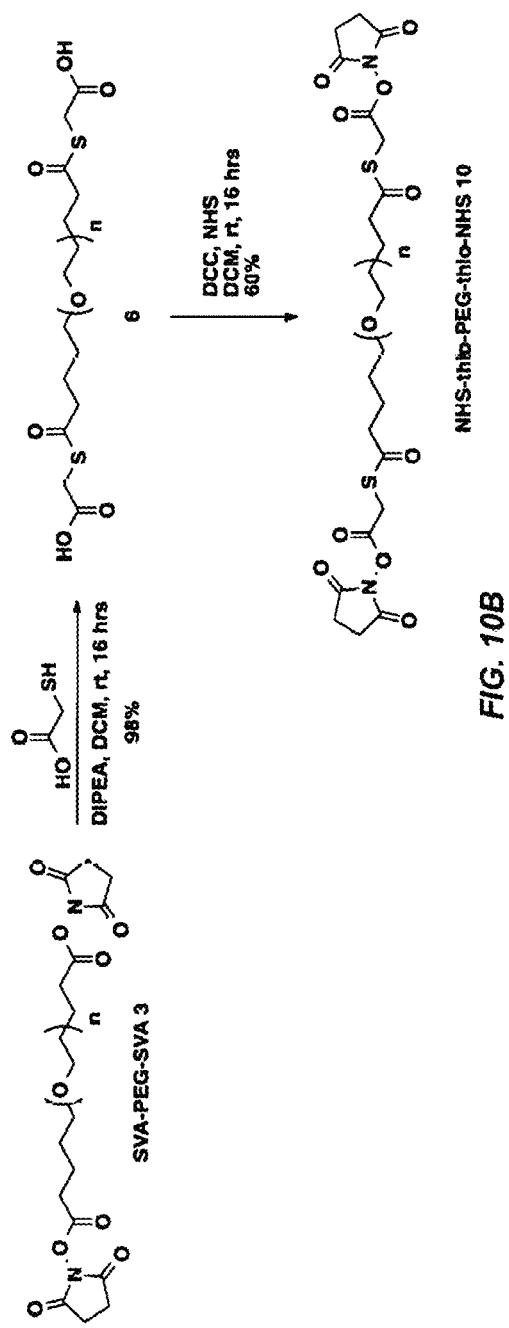

Example 8. Another Example of a Thioester Hydrogel and Characterization Thereof In this example, dendron 2 and NHS-thio-PEG-thio-NHS 10 (e.g., Mw ~3400 Da) were used to form a dissolvable hydrogel as shown in FIG. 10A. In this example, the thio-ester linkage is present within the NHS-PEG-NHS crosslinker. The second-water soluble macromolecule 10 was synthesized as detailed in FIG. 10B. For example, to a solution of macromer 6 (0.26 mmol) in dichloromethane (3 mL), N-hydroxysuccinimide (0.57 mmol) and N,N'-dicyclohexyl carbodiimide (0.57 mmol) were added under nitrogen. The reaction mixture was stirred at room temperature for 16 hours, and the urea was then removed by filtration. The solvent was evaporated under vacuum and the crude triturated in diethyl ether. After filtration, a white solid 10 (60%) was formed. $^1$H NMR (500 MHz, CDCl$_3$): δ=3.61 (m, ca. 300H), 2.81 (s, 8H), 2.66 (m, 4H), 1.77-1.73 (m, 4H), 1.62-1.58 (m, 4H) ppm.

In order to form the dissolvable hydrogel, 123 μl solution of dendron 2 (16 mg) in borate buffer pH 9 was mixed with 67 μl solution of NHS-thio-PEG-thio-NHS 10 (42 mg) in PBS buffer pH 6.5. The hydrogel (30 wt %) was formed in 10-20 seconds. Application of a solution of cysteine methyl ester (e.g., about 0.3 M) resulted in the hydrogel being dissolved.

REFERENCES

[1] Bracher, P. J., Snyder, P. W., Bohall, B. R., Whitesides, G. W. Orig Life Evol Biosph 2011, 41, 399-412

[2] (a) Yasuyuki, U., Beierle, J. M., Leman, L. J., Orgel, L. E., Ghadiri, M. R. Science 2009, 325, 73-77; (b) Yasuyuki, U., Al-Sayah, M., Montenegro, J., Beierle, J. M., Leman, L. J Ghadiri, M. R. Org. Biomol. Chem. 2009, 7, 2878-2884

[3] (a) Ruan, L., Zhang, H., Luo, H., Liu, J., Tang, F., Shi, Y.-K., Zhao, X. PNAS 2009, 106, 5105-5110; (b) Aboushwareb, T., Eberli, D., Ward, C., Broda, C., Holcomb, J., Atala, A., Dyke, M. V., J. Biomed. Mater. Res. Part B: Appl. Biomater. 2009, 90B, 45-54; (c) Hattori, H., Amano, Y., Nogami, Y., Takase, B., Ishihara, M. Annals of Biomedical Engineering, 2010, 38, 3724-3732; (d) Luo, Z., Wang, S., Zhang, S. Biomaterials, 2011, 32, 2013-2020.

[4] Alam, H. B., Burris, D., DaCorta, J. A., Rhee, P. Military Medicine 2005, 170, 63-69

[5] (a) Hu, B.-H., Su, J., Messersmith, P. B. Biomacromolecules 2009, 10, 2194-2200; (b) Anumolu, S. S., Menjoge, A. R., Deshmukh, M., Gerecke, D., Stein, S., Laskin, J., Sinko, P. J. Biomaterials 2011, 32, 1204-1217

[6] (a) Wathier, M., Jung, P. J., Carnahan, M. A., Kim, T., Grinstaff, M. W. JACS 2004, 126, 12744-12745; (b) Oelker, A. M., Berlin, J. A., Wathier, M., Grinstaff, M. W. Biomacromolecules 2011, 12, 1658-1665

[7] Wathier, M., Johnson, M. S., Carnahan, M A., Baer, C., McCuen, B W., Kim, T., Grainstaff, M. W. ChemMedChem 2006, 1, 821-825

[8] Ghobril, C., Charoen, K., Rodriguez, E. K., Nazarian, A., Grinstaff, M. W. Angew. Chem. Int. Ed. 2013, 52, 14070-14074

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A dissolvable hydrogel composition comprising: an adhesive hydrogel layer comprising
   (a) a first water-soluble crosslinkable polymer and
   (b) a second water-soluble linear, branched, and/or dendritic crosslinkable polymer;
   wherein the first and second cross-linkable polymers are linked by thioester linkages, wherein the first crosslinkable polymer comprises at least two thiol moieties and the second crosslinkable polymer comprises at least two cross-linking moieties that are capable of reacting with said at least two thiol moieties of the first crosslinkable polymer to form the thioester linkages between the first crosslinkable polymer and the second crosslinkable polymer, and wherein the first crosslinkable polymer has a chemical structure selected from the group consisting of structure (i) to structure (xii) shown as follows:

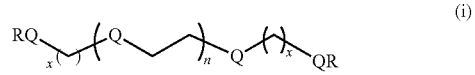

(i)

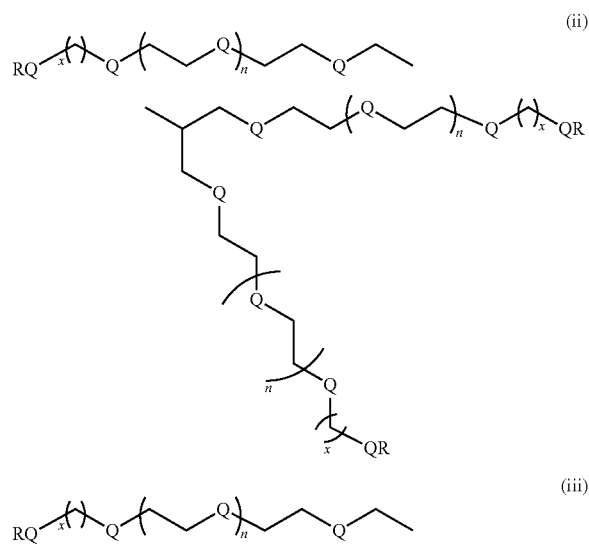
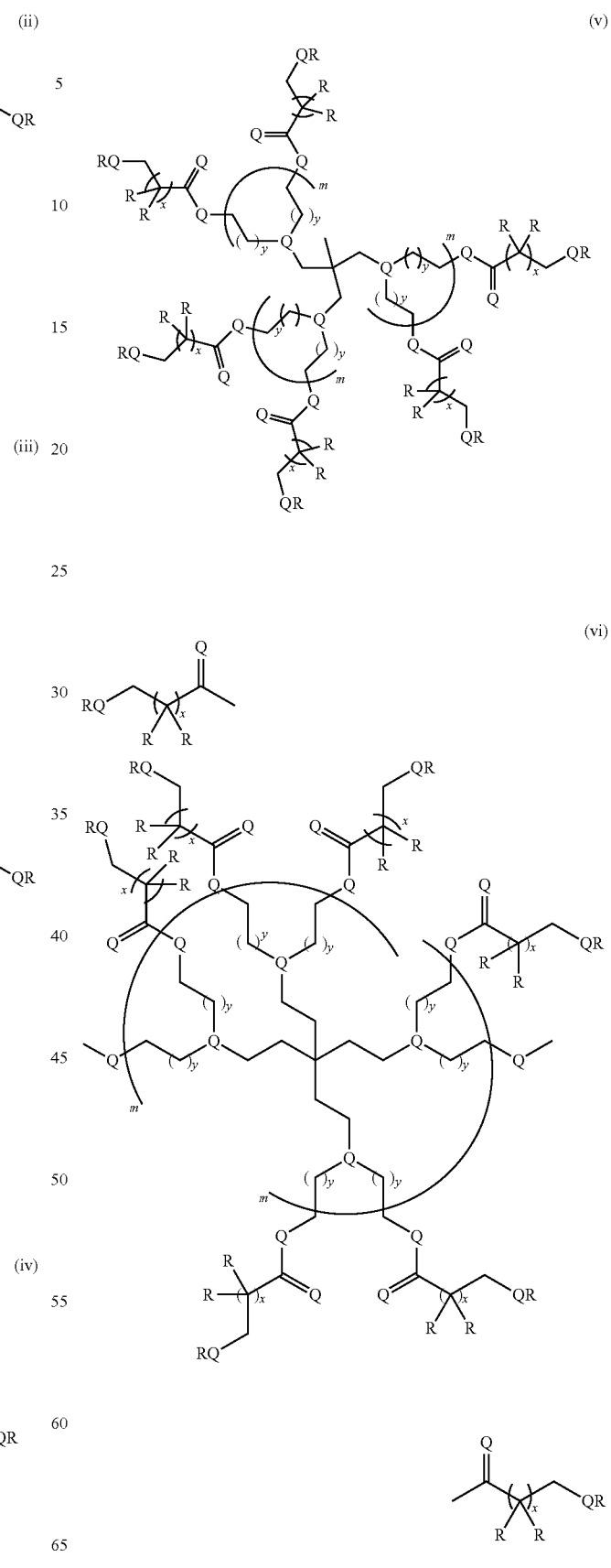

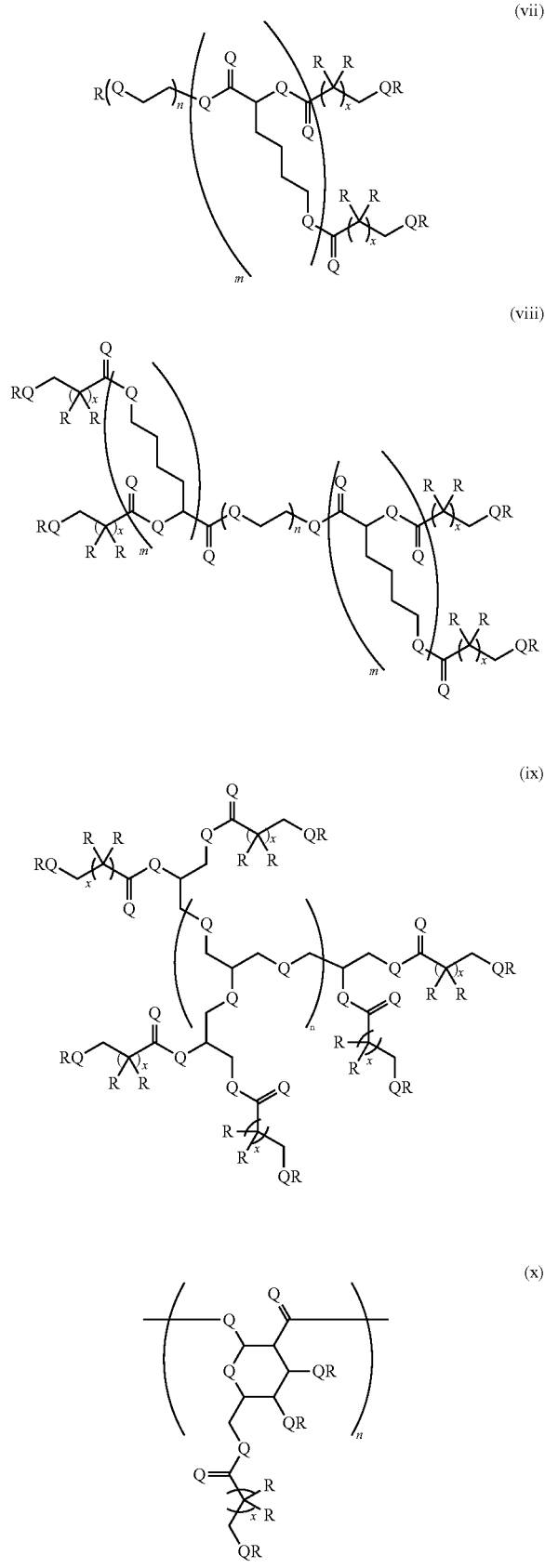

and any combination thereof, and wherein:

each Q is independently selected from the group consisting of O, S, Se, NH, CH$_2$, and any combination thereof;

each R is independently selected from the group consisting of hydrogen, straight or branched chain alkyl, cycloalkyl, aryl, olefin or alkene, alkyne, silyl, alkylsilyl, arylsilyl, alkylaryl or arylalkyl chain of 1-50 carbons, fluorocarbon, and any combinations thereof, wherein each alkyl, cycloalkyl, aryl, olefin, alkyne, silyl, alkylsilyl, arylsilyl, alkylaryl, fluorocarbon, or arylalkyl chain is optionally substituted internally or terminally by one or more hydroxyl, hydroxyether, carboxyl, carboxyester, carboxyamide, amino, mono- or di-substituted amino, thiol thioester, sulfate, phosphate, phosphonate, halogen, poly(ethylene glycol), poly(ethylene oxide), poly(hydroxyacid), a carbohydrate, a protein, a polypeptide, an amino acid, a nucleic acid, a nucleotide, a polynucleotide, a DNA segment, a RNA segment, a lipid, a polysaccharide, an antibody, a pharmaceutical agent, an epitope for a biological receptor; and any combinations thereof; and m, n, x, and y are each independently selected from an integer of 0-1000, provided that at least two of -QR for each of structures (i) to (xii) are —SH.

2. The dissolvable hydrogel composition of claim 1, wherein the linear crosslinkable polymer comprises polyesters, polyethers, polyglycerols, polypeptides, polyether-esters, polyamino acids, polyester-amines, polyurethane, polycarbonates, polyamino alcohols, thiols, N-hydroxysuccinimide (NHS) moiety, Maleimide (MAL) moiety, or any combinations thereof.

3. The dissolvable hydrogel composition of claim 1, wherein the branched crosslinkable polymer comprises polyesters, polyethers, polyglycerols, polypeptides, polyether-esters, polyamino acids, polyester-amines, polyurethane, polycarbonates, polyamino alcohols, thiols, N-hydroxysuccinimide (NHS) moiety, Maleimide (MAL) moiety, or any combinations thereof.

4. The dissolvable hydrogel composition of claim 1, wherein the dendritic crosslinkable polymer comprises polyesters, polyethers, polyglycerols, polypeptides, polyetheresters, polyamino acids, polyester-amines, polyurethane, polycarbonates, polyamino alcohols, thiols, N-hydroxysuccinimide (NHS) moiety, Maleimide (MAL) moiety, or any combinations thereof.

5. The dissolvable hydrogel composition of claim 1, wherein when both the first and second crosslinkable polymers are branched or dendritic crosslinkable polymers, at least one of the first and the second dendritic crosslinkable polymers does not comprise poly(ethylene glycol).

6. The dissolvable hydrogel composition of claim 1, wherein said at least two cross-linking moieties comprise at least one N-hydroxysuccinimide (NHS) moiety or Maleimide (MAL) moiety.

7. The dissolvable hydrogel composition of claim 1, wherein the second crosslinkable polymer has a chemical structure selected from the group consisting of structure (xiii) to structure (xI), shown as follows:

(xiii)
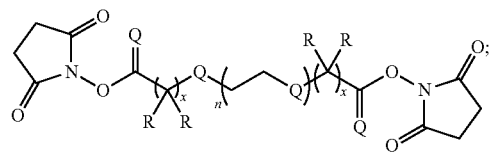

(xiv)
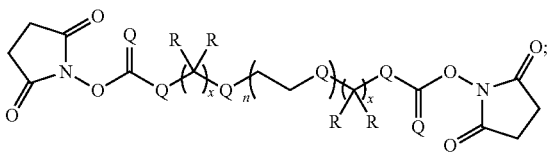

(xv)
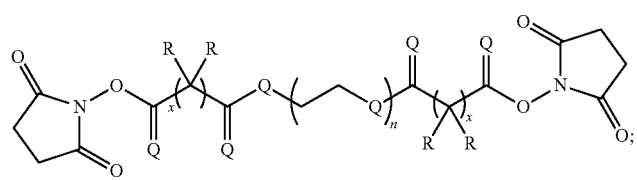

(xvi)
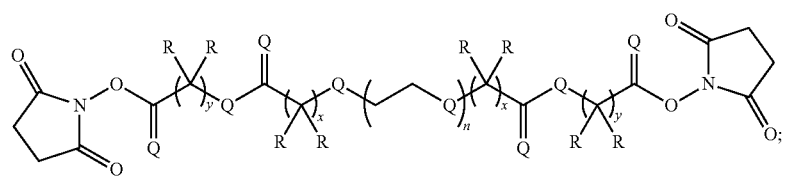

(xvii)
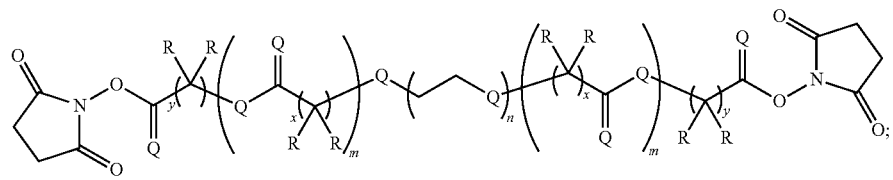

(xviii)
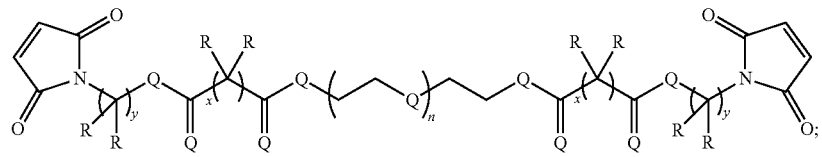

(xix)
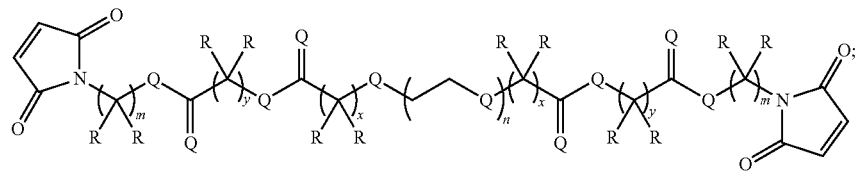

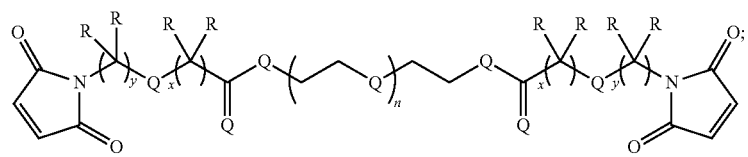
(xx)
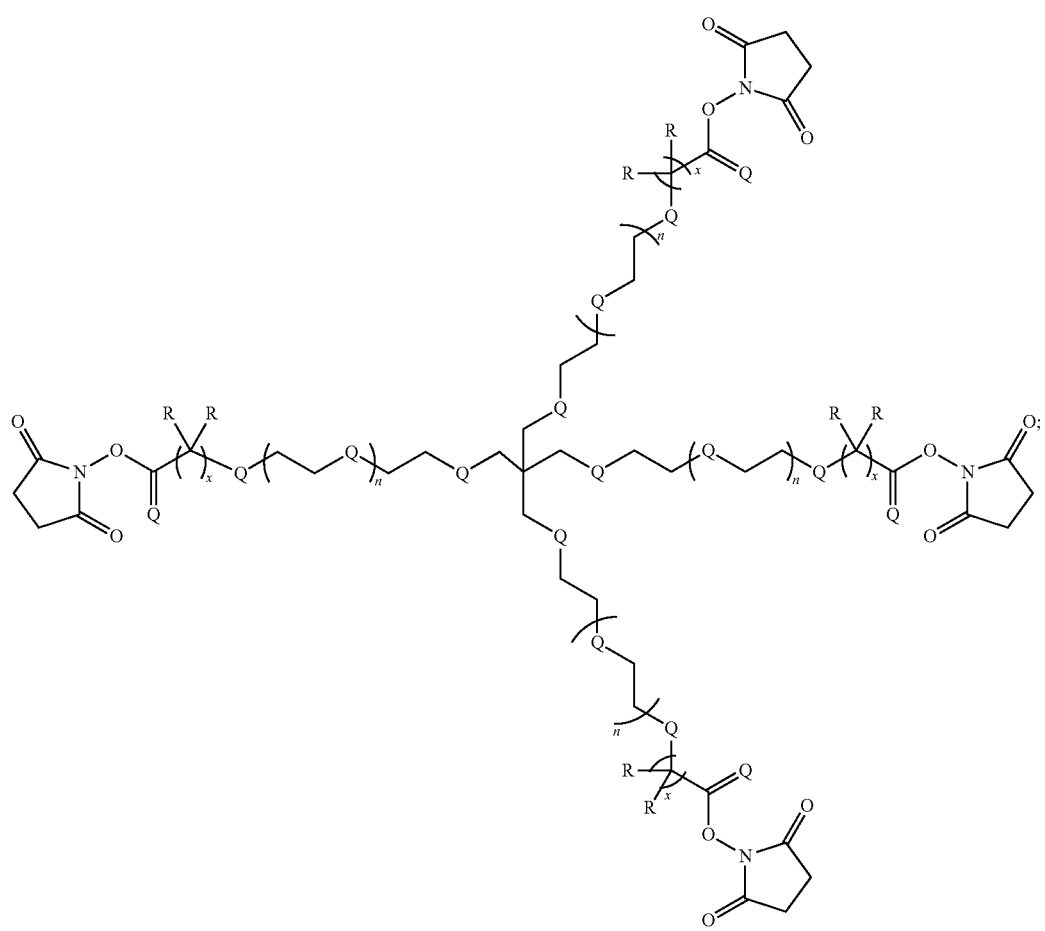
(xxi)

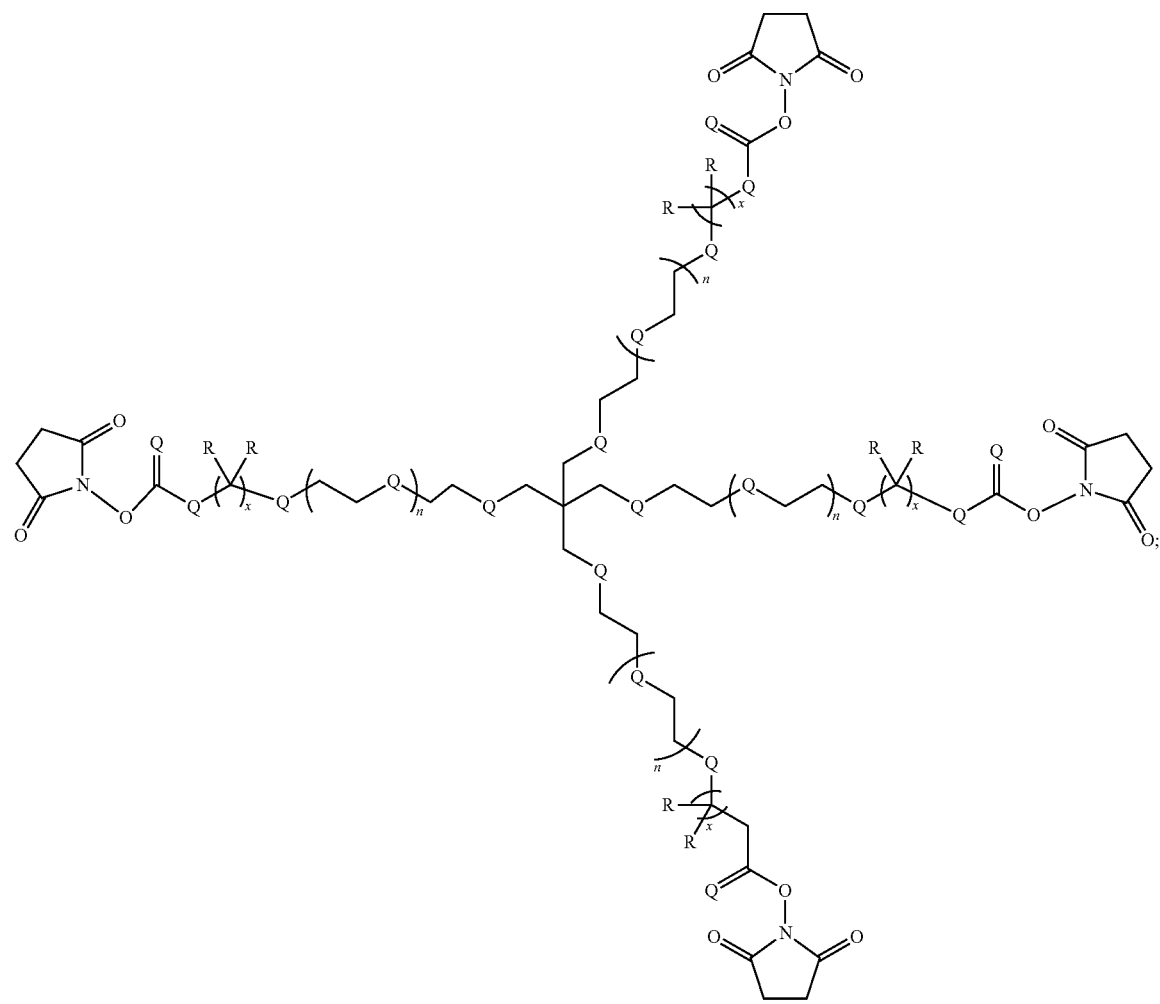

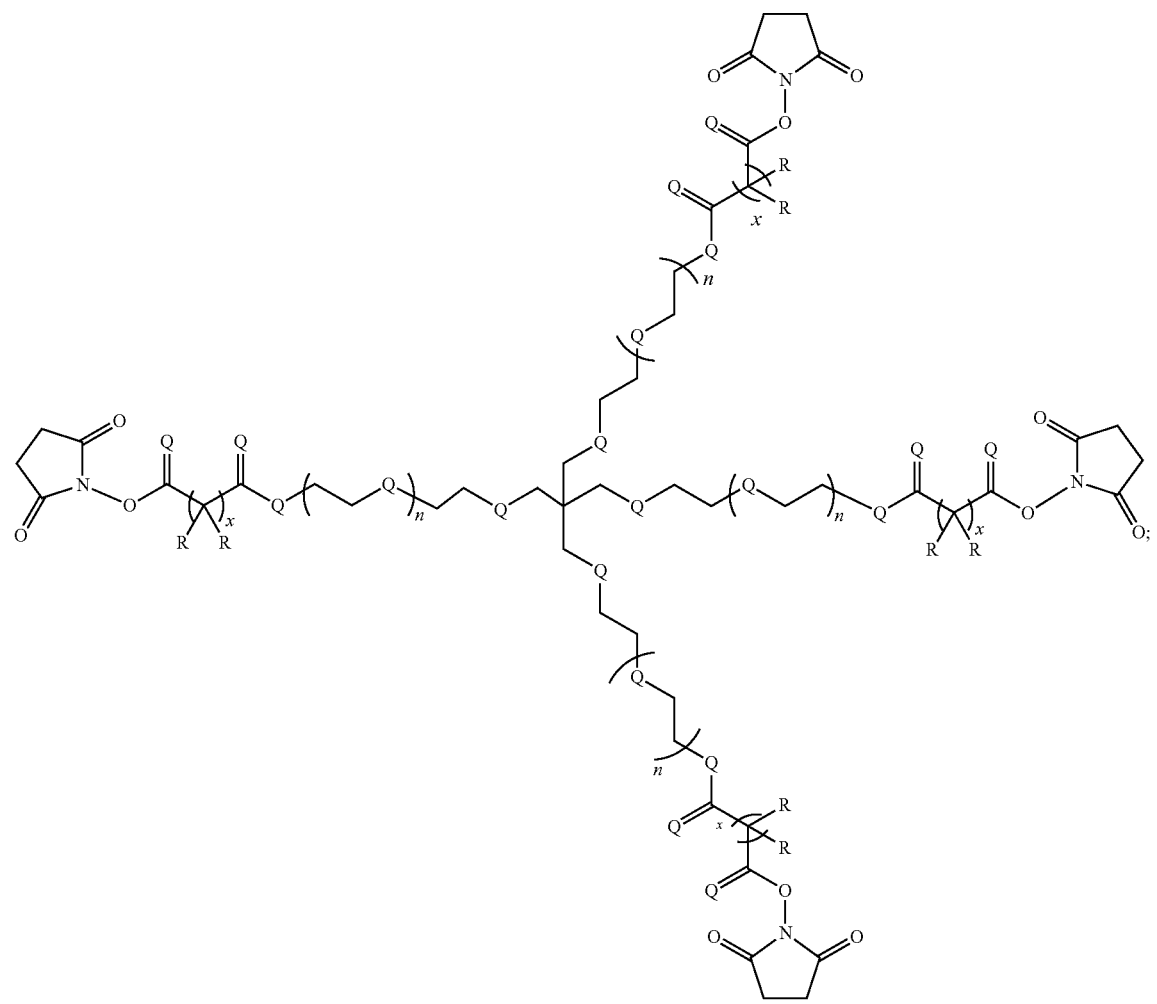
(xxiii)

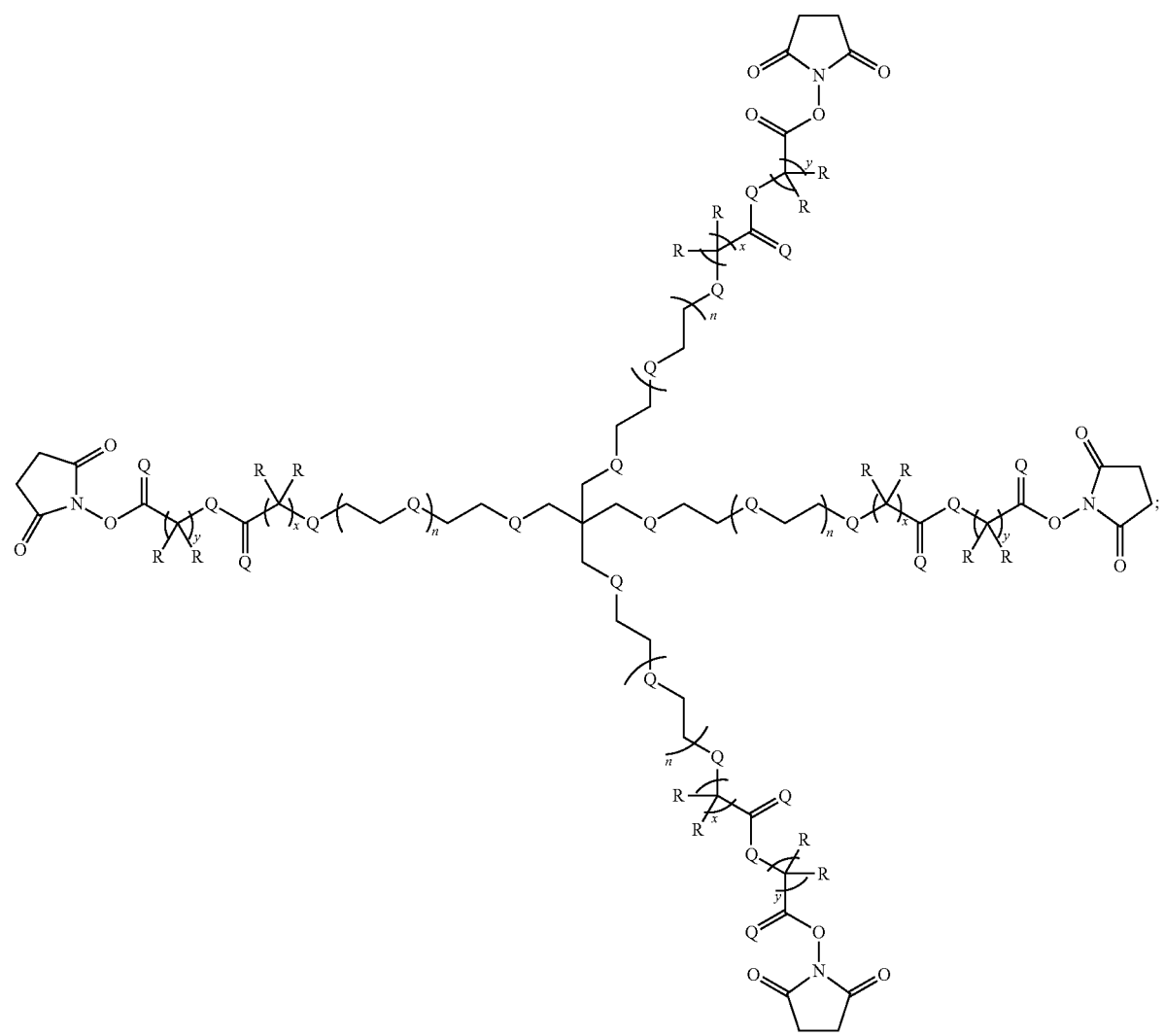
(xxiv)

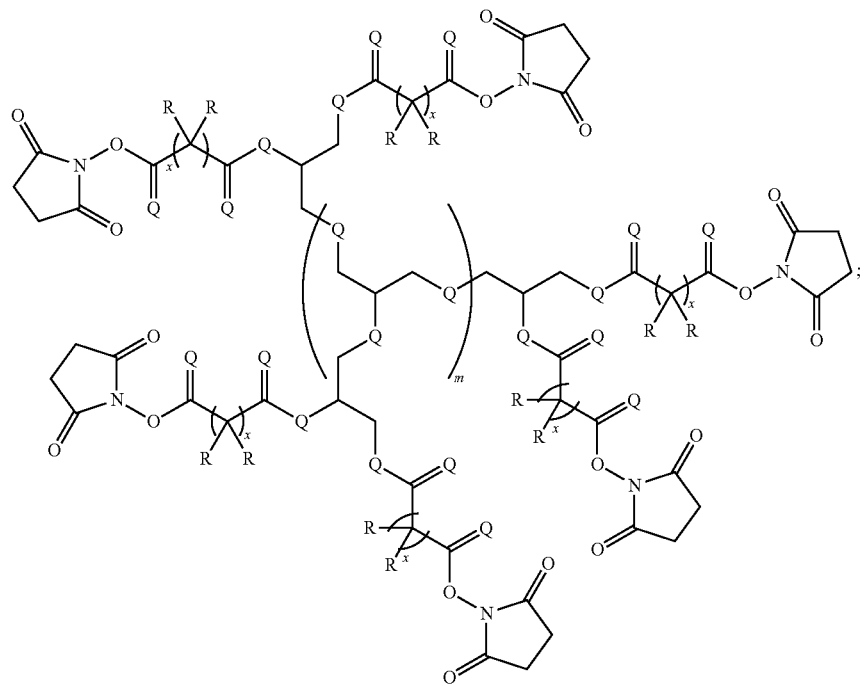
(xxv)
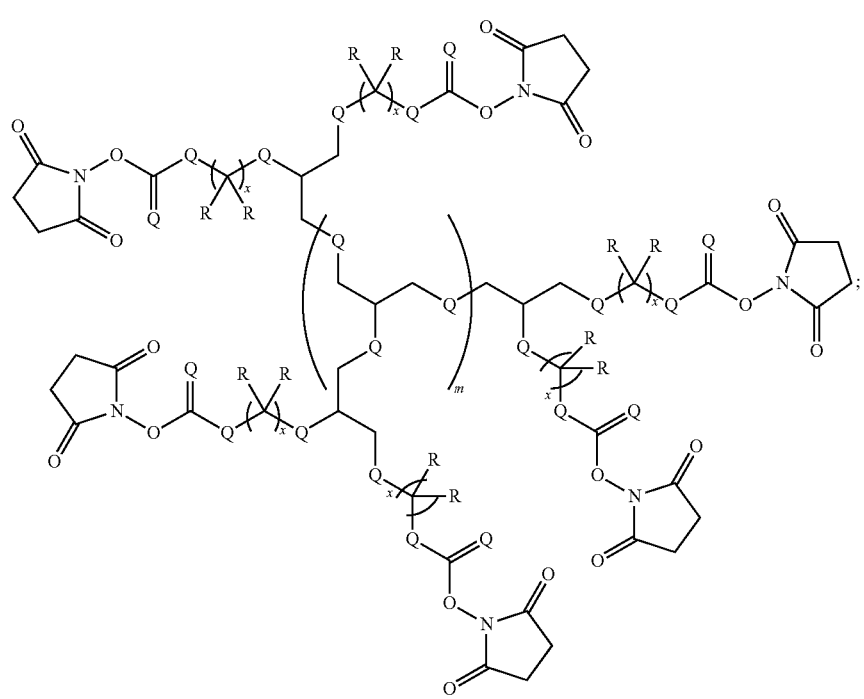
(xxvi)

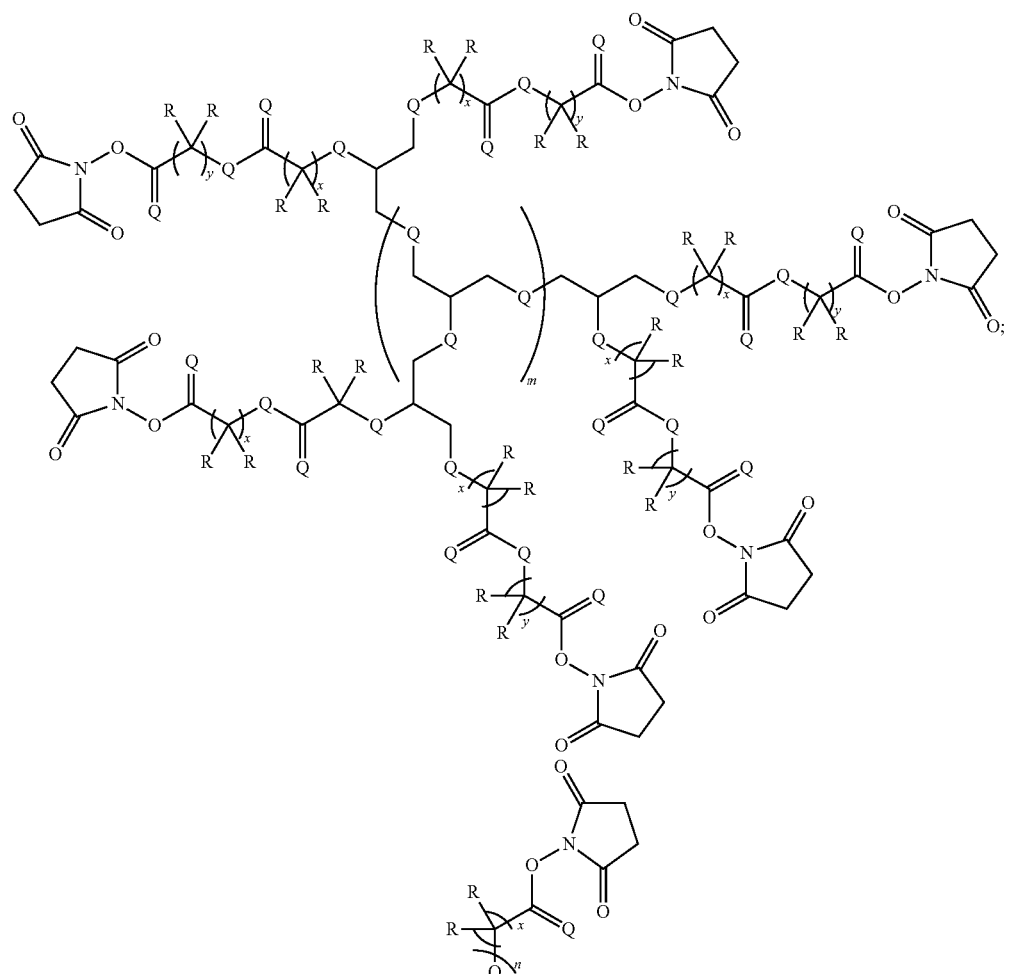
(xxvii)
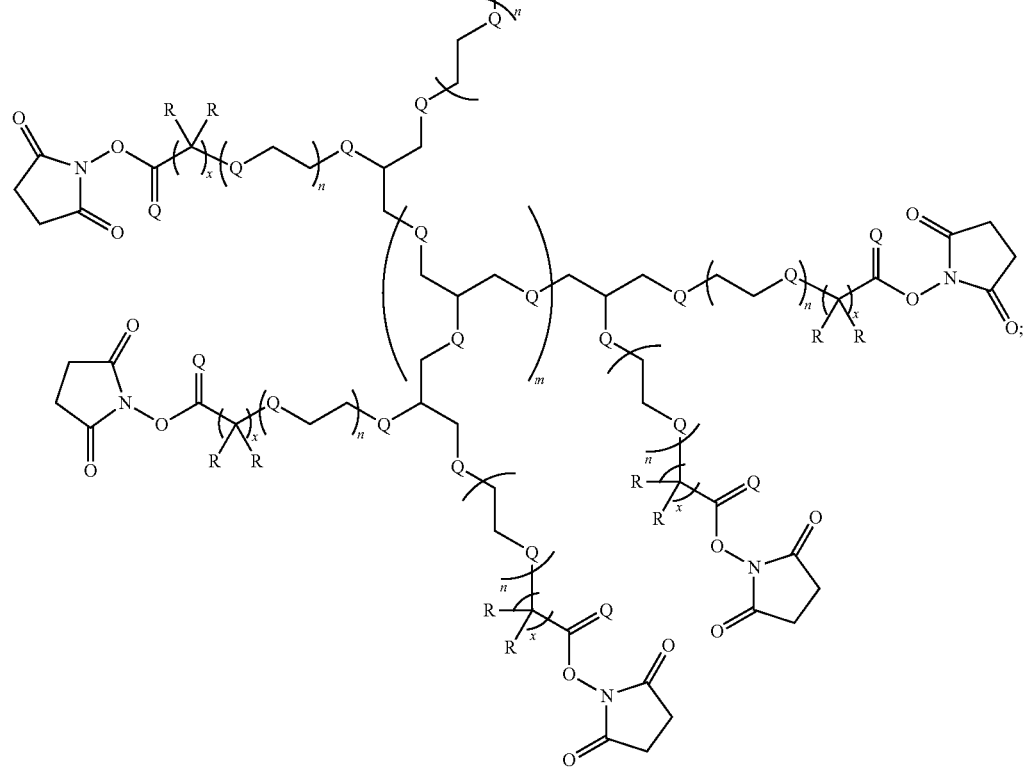
(xxviii)

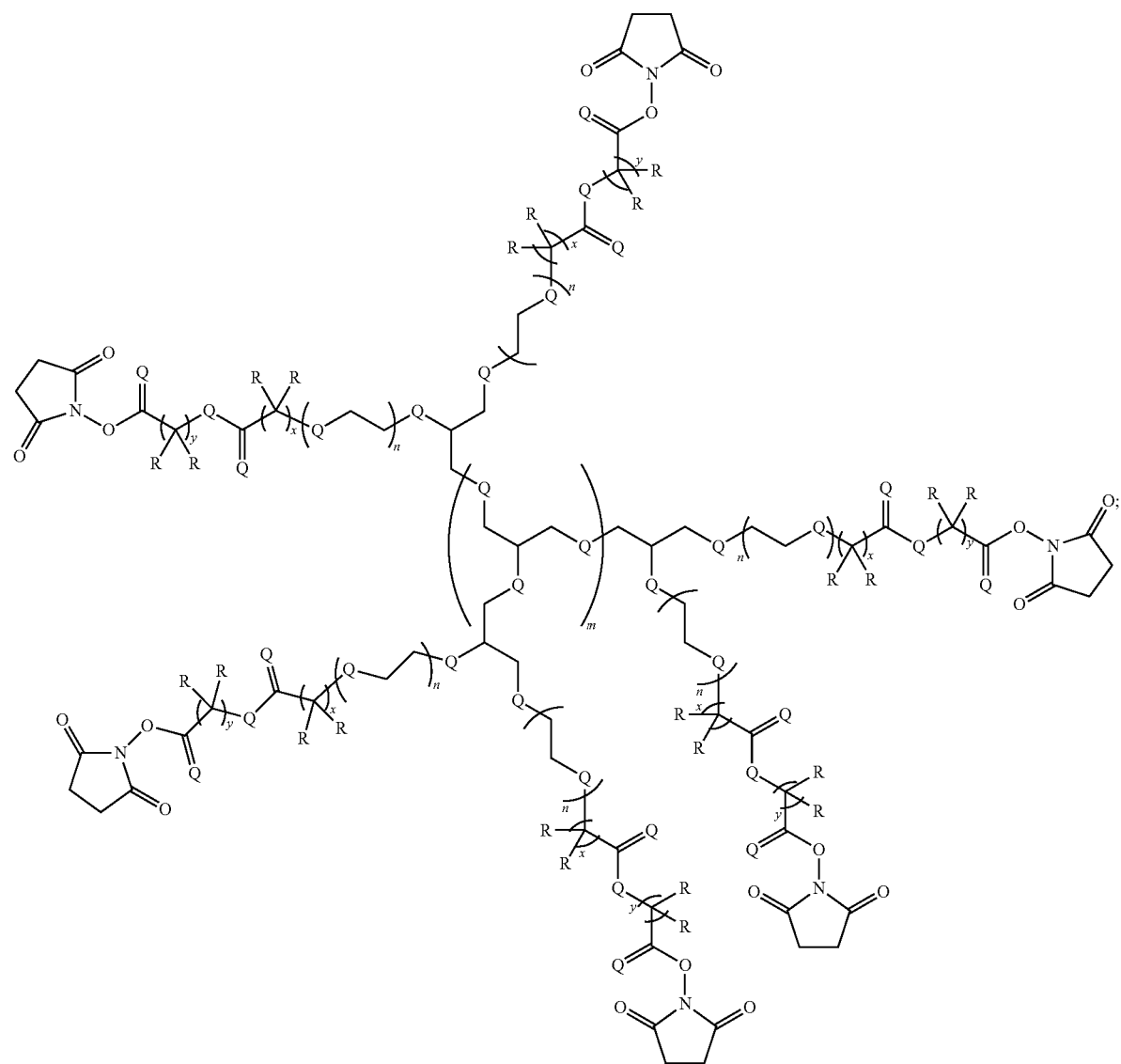
(xxix)

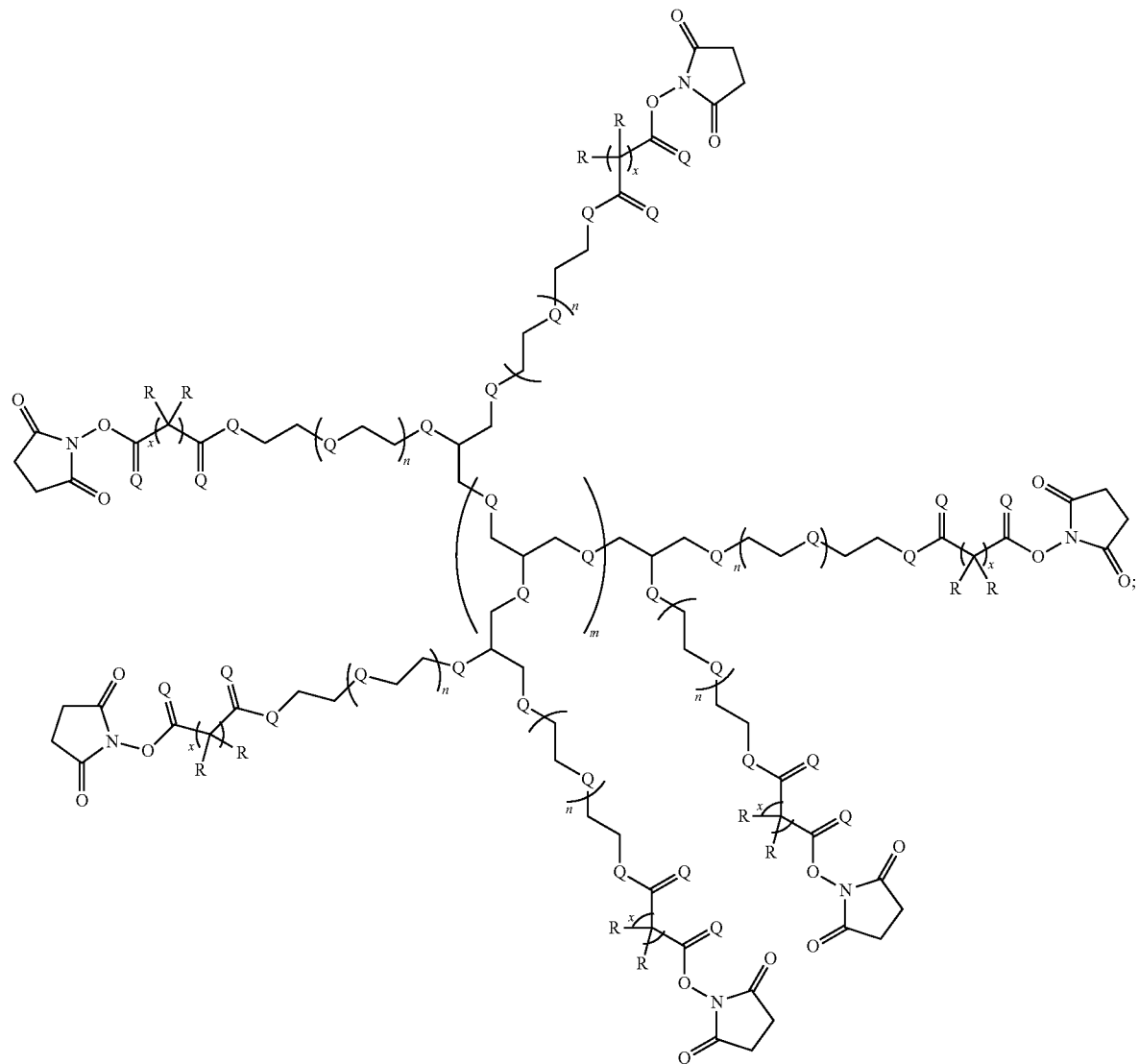
(xxx)

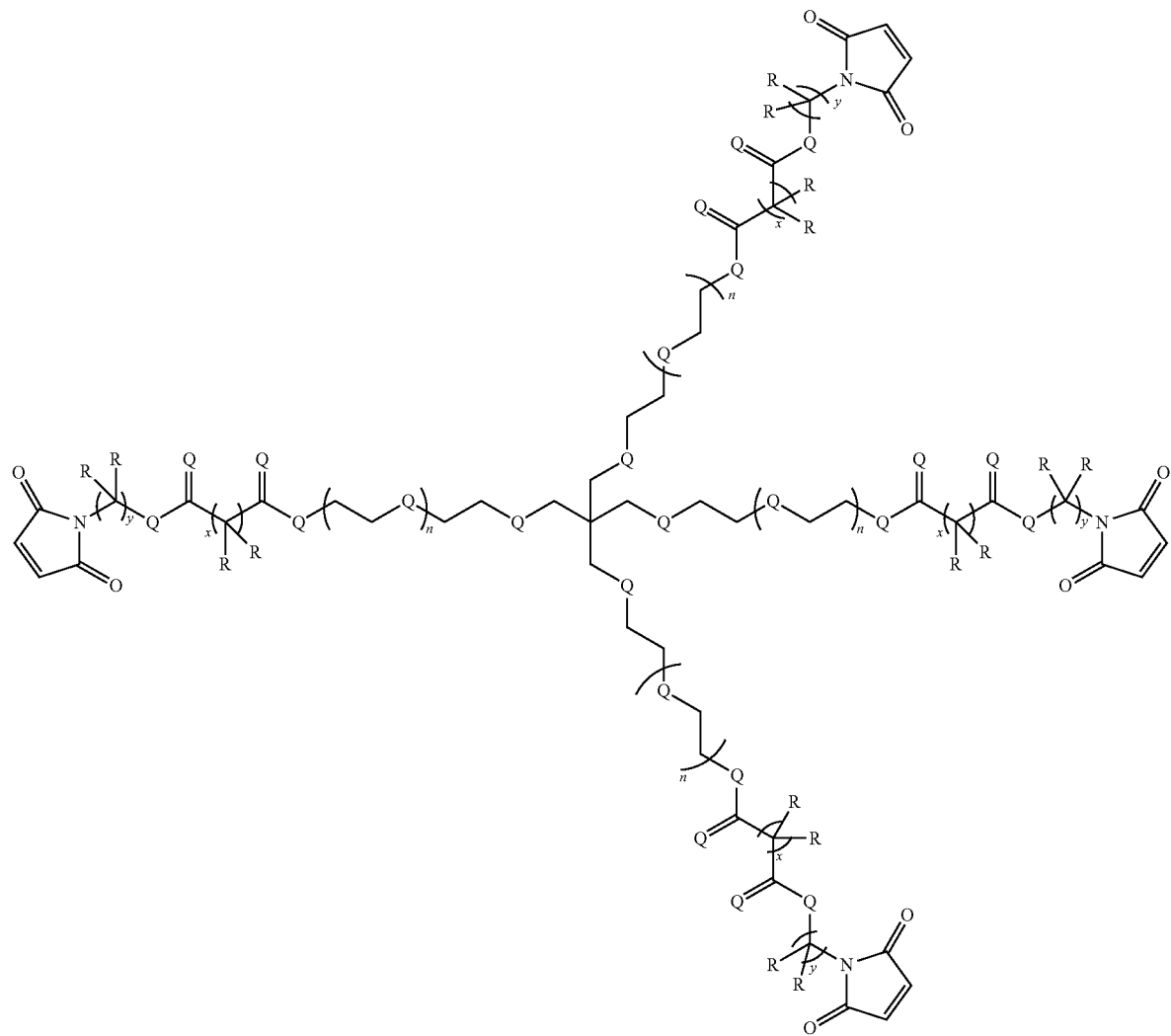
(xxxi)

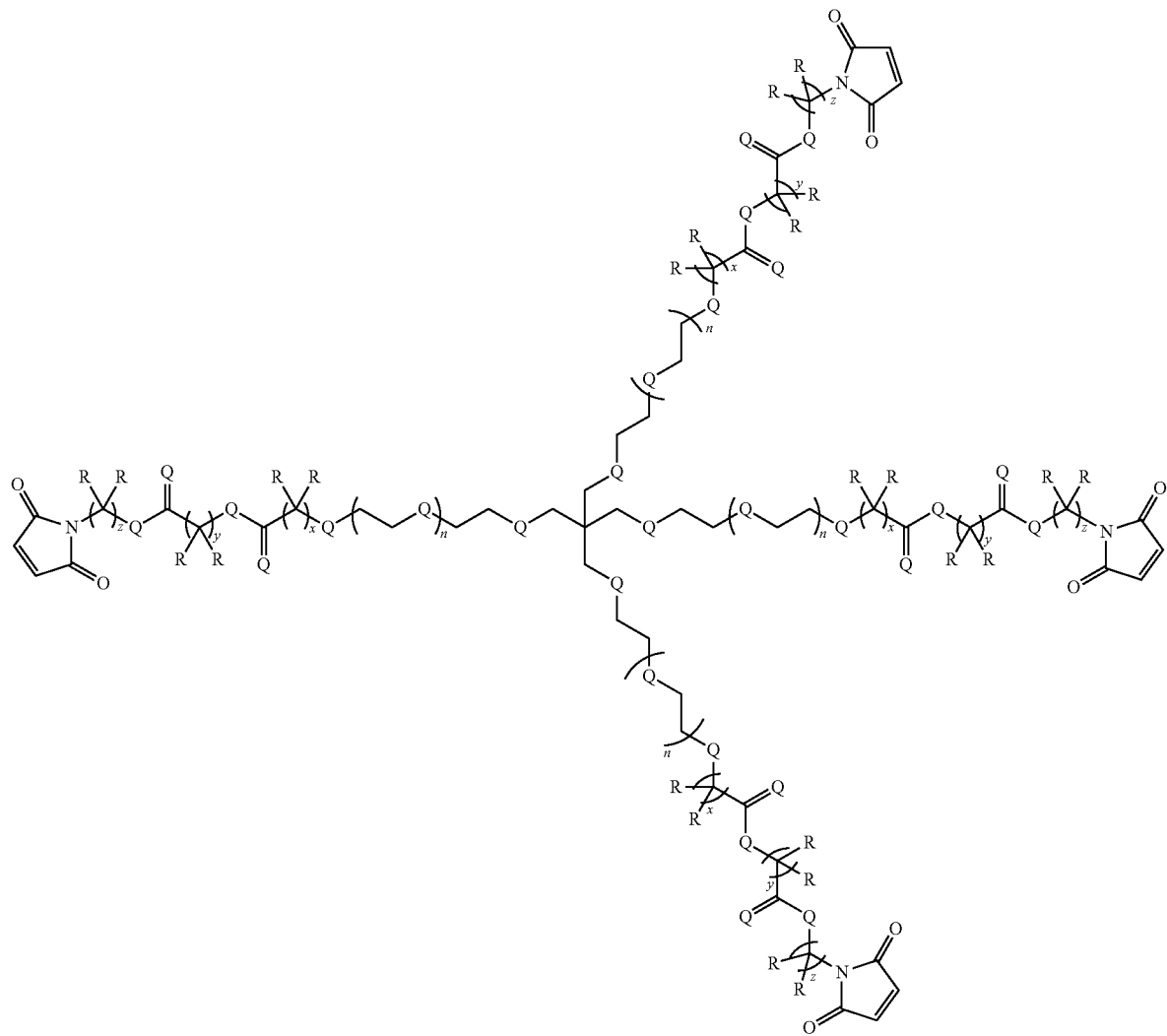
(xxxii)

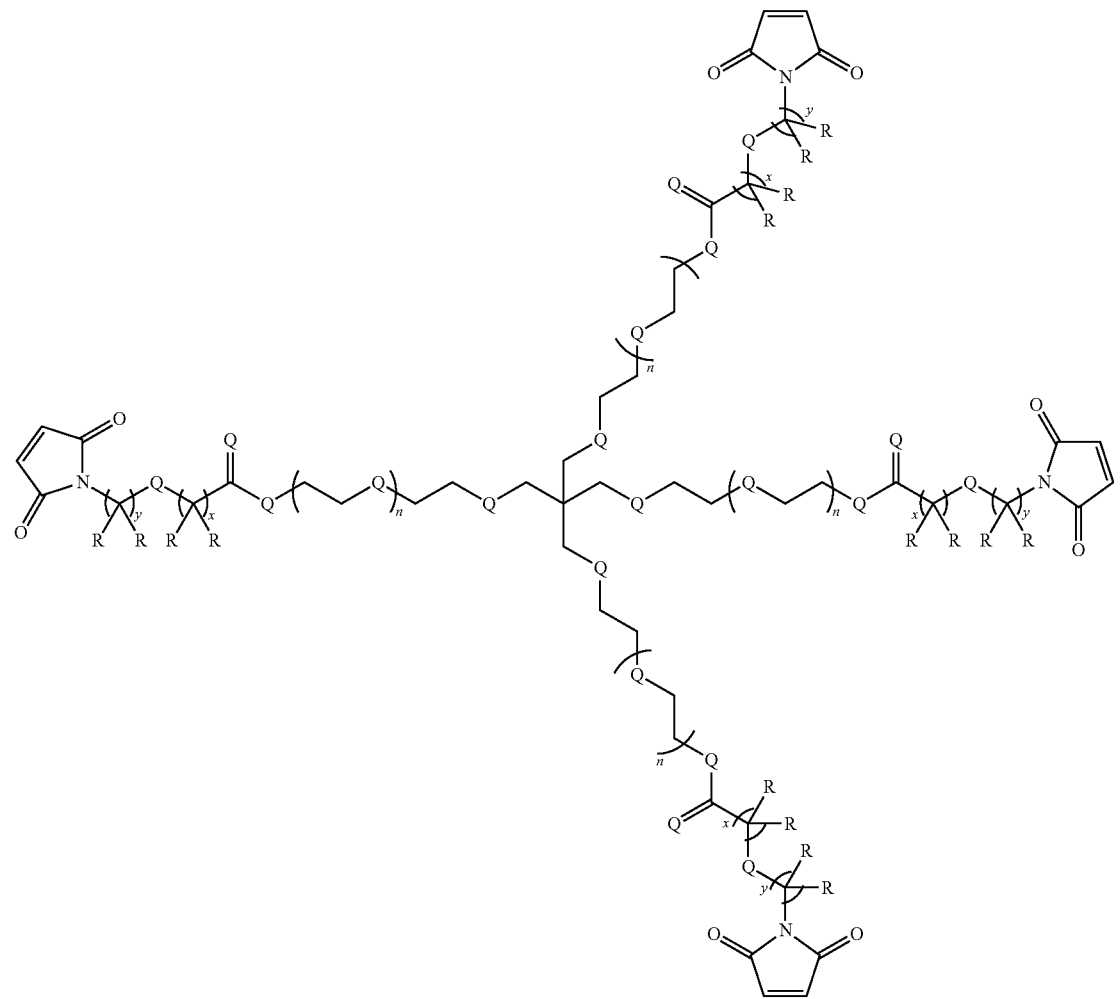
(xxxiii)

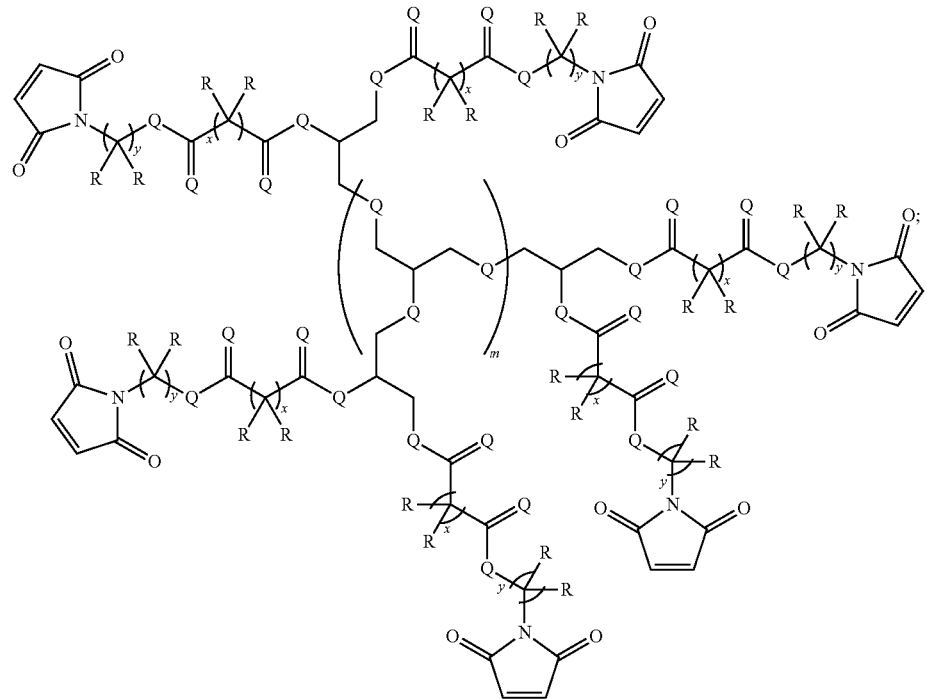
(xxxiv)
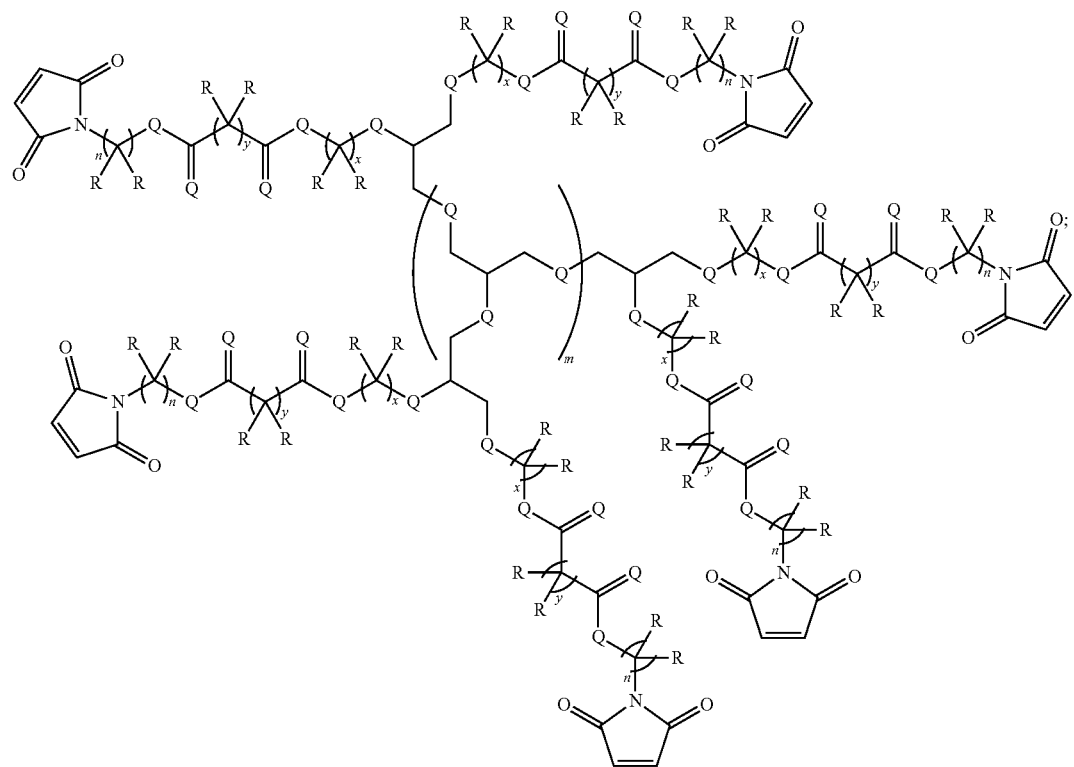
(xxxv)

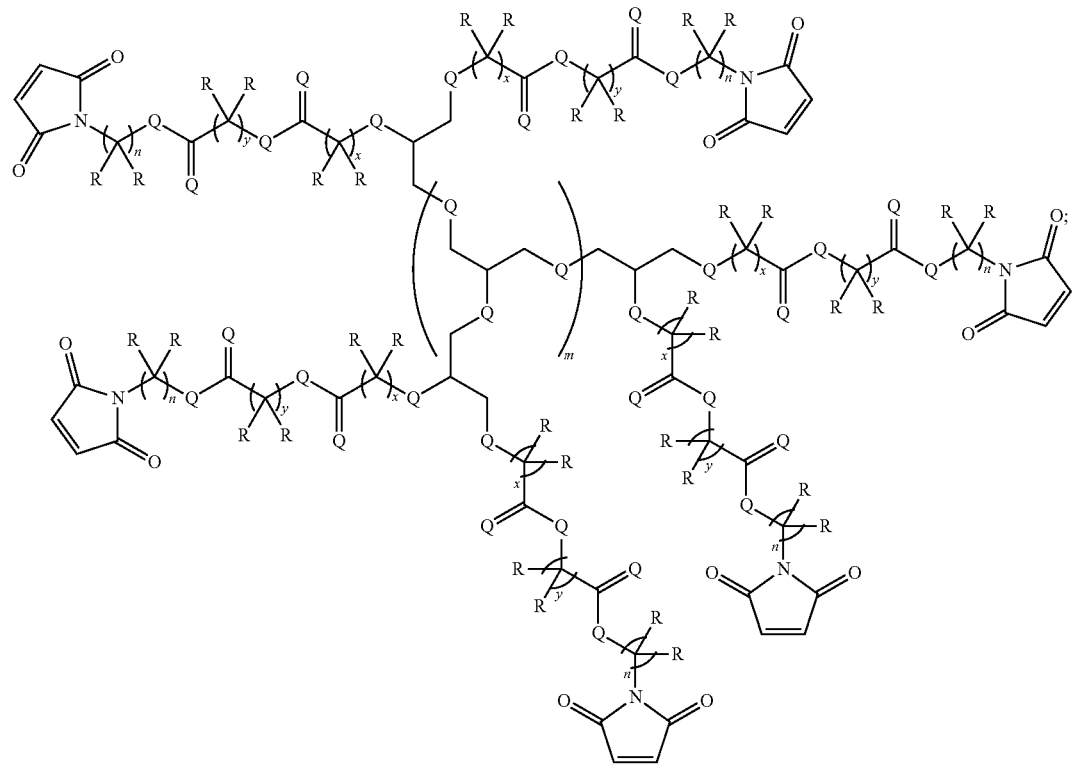
(xxxvi)
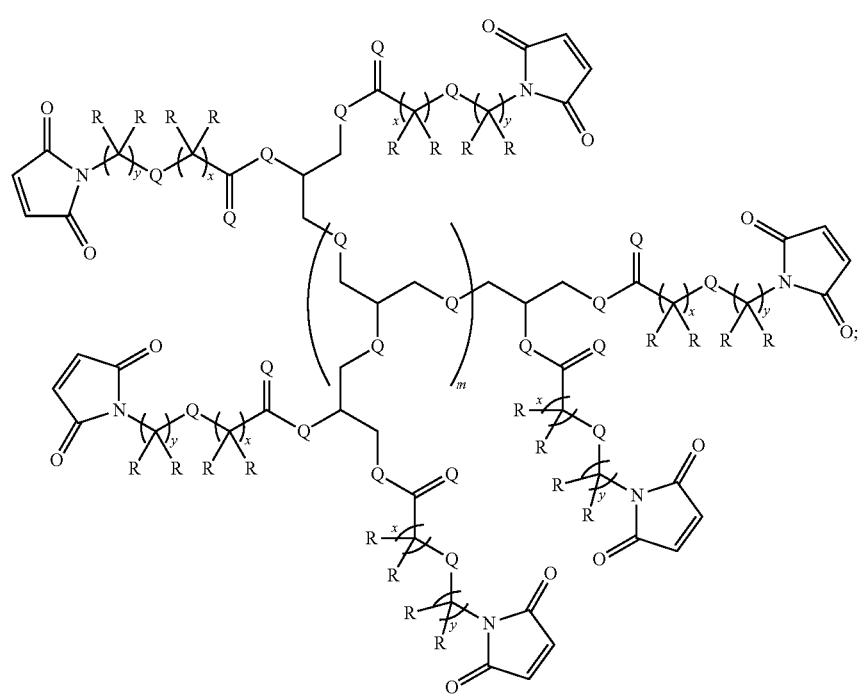
(xxxvii)

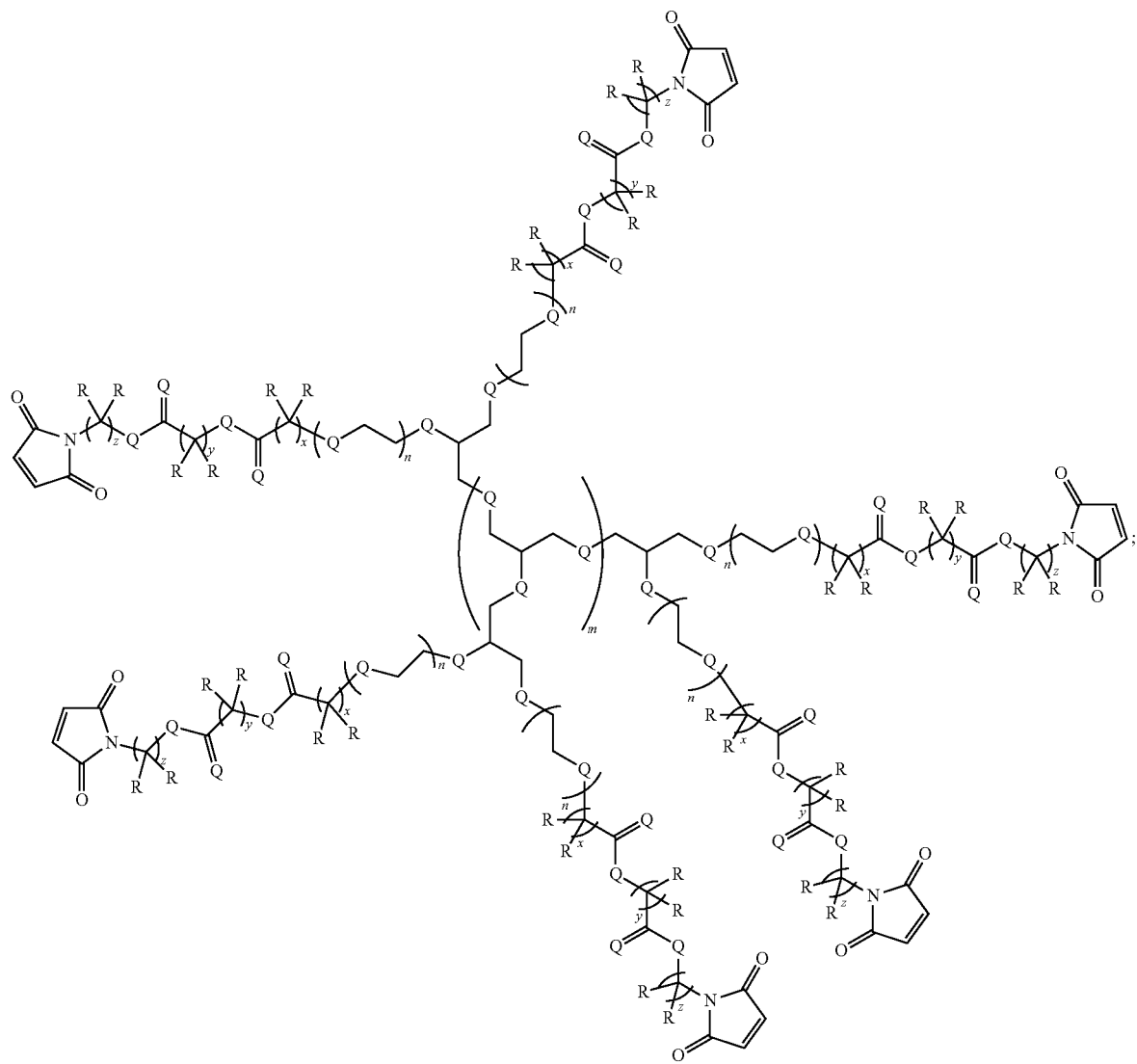
(xxxviii)

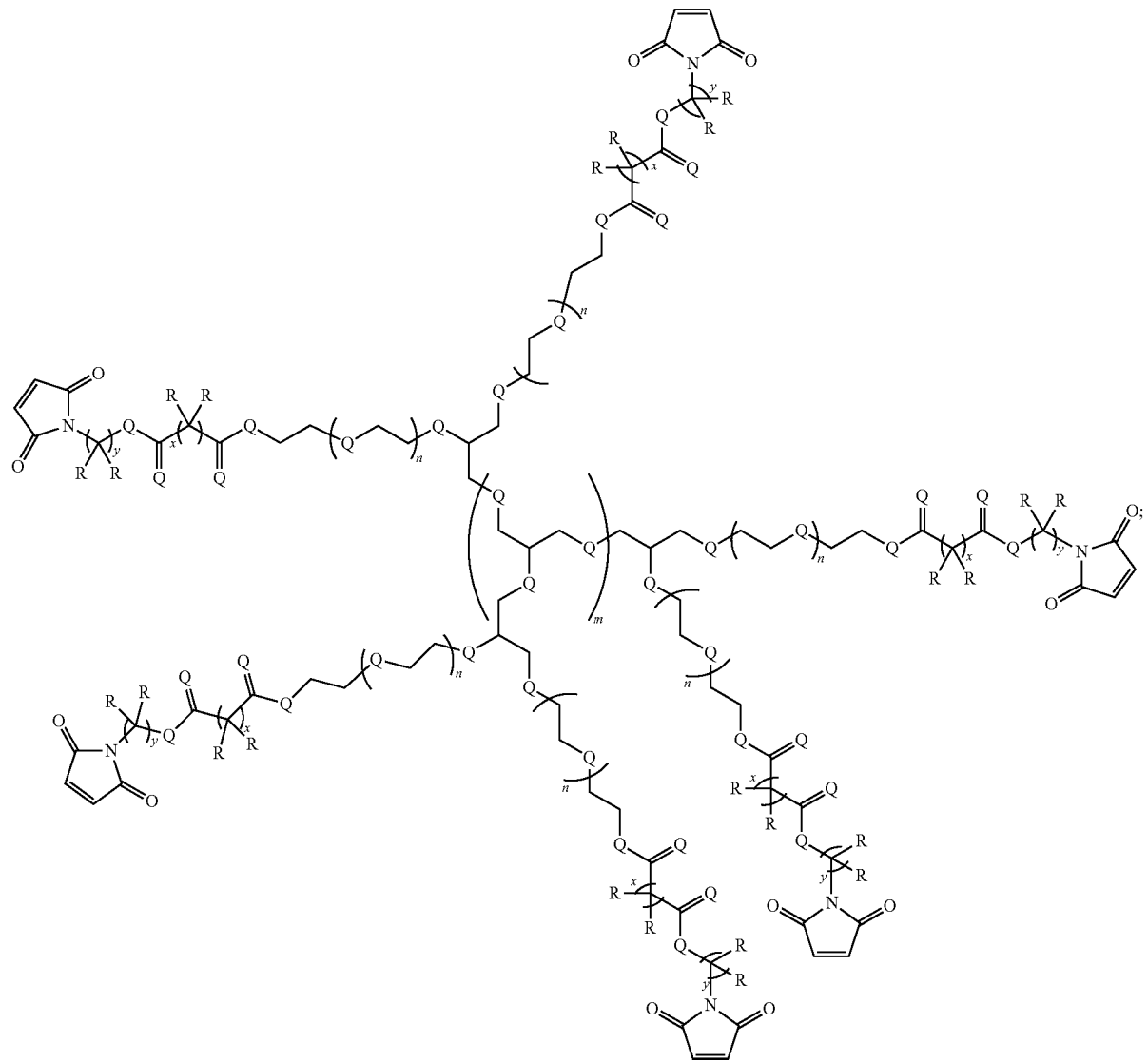
(xxxix)

-continued (xl)

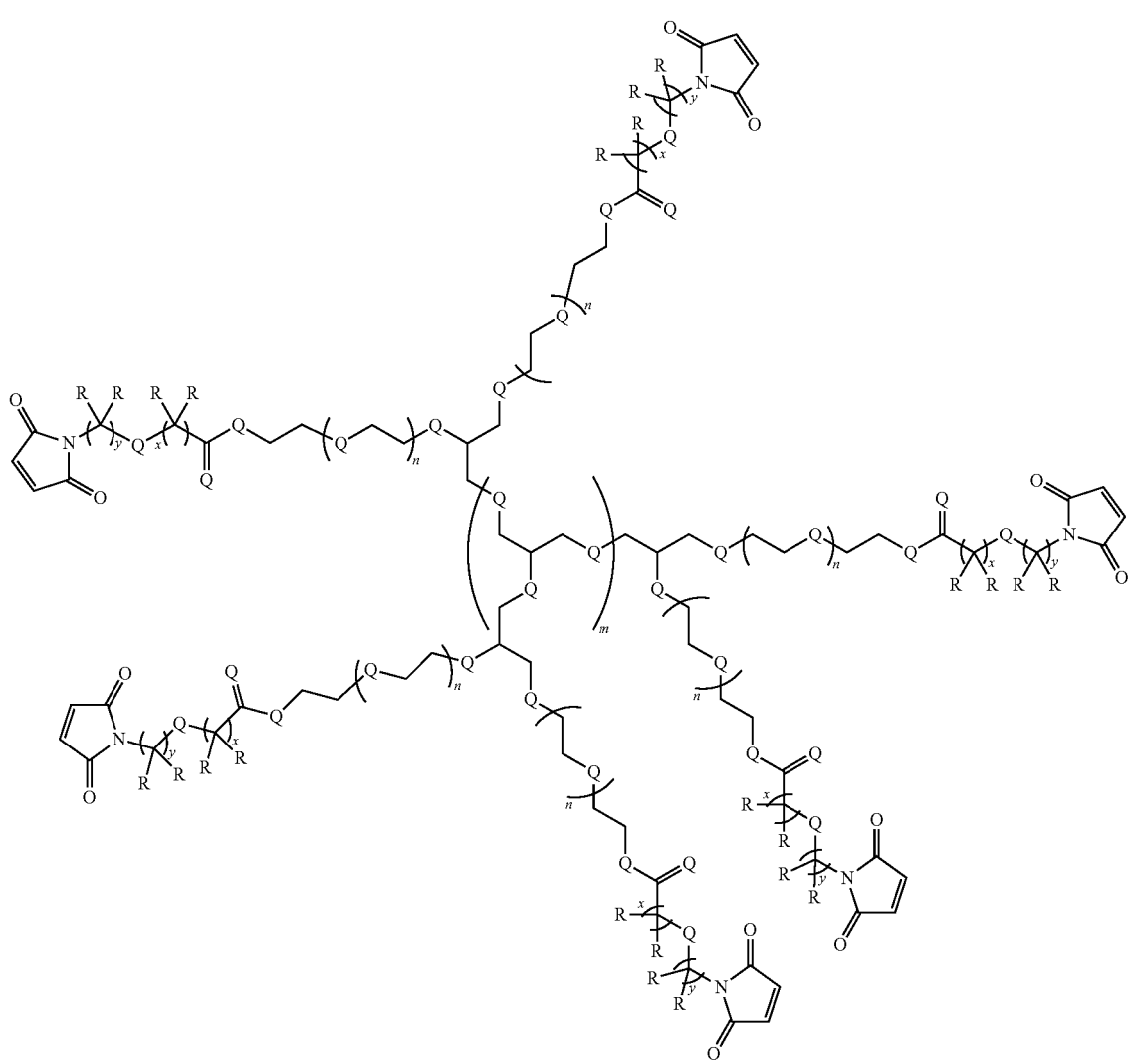

and any combination thereof; and wherein
each Q is independently selected from the group consisting of O, S, Se, NH, $CH_2$, and any combination thereof;
each R is independently selected from the group consisting of a hydrogen, straight or branched alkyl, cycloalkyl, aryl, olefin or alkene, alkyne, silyl, alkylsilyl, arylsilyl, alkylaryl or arylalkyl chain of 1-50 carbons, fluorocarbon, and any combinations thereof, wherein each alkyl, cycloalkyl, aryl, olefin, alkyne, silyl, alkylsilyl, arylsilyl, alkylaryl, fluorocarbon, or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, halogen substituents; and any combinations thereof; and m, n, x, y and z are each independently selected from an integer of 0-1000.

8. The dissolvable hydrogel composition of claim 1, wherein the first crosslinkable polymer has a chemical structure as follows:

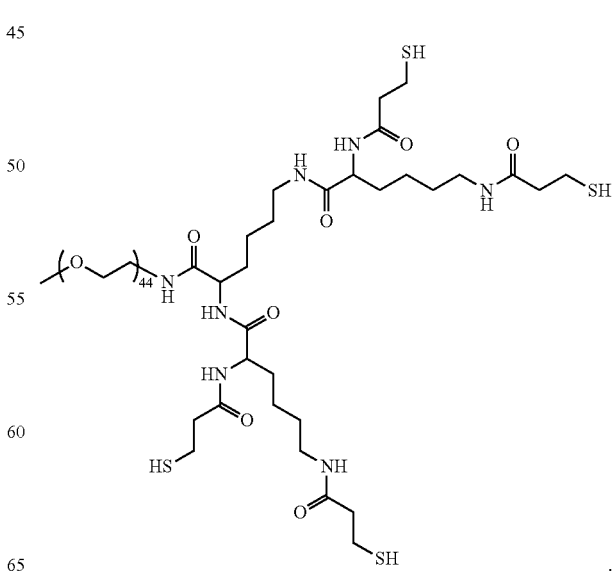

9. The dissolvable hydrogel composition of claim 1, wherein the second crosslinkable polymer is poly(ethylene glycol) disuccinimidyl valerate.

10. The dissolvable hydrogel composition of claim 1, wherein the adhesive hydrogel layer is at least partially flexible.

11. The dissolvable hydrogel composition of claim 1, wherein the adhesive hydrogel layer is capable of withstanding a pressure of at least about 2 mmHg.

12. The dissolvable hydrogel composition of claim 1, wherein the adhesive hydrogel layer is transparent.

13. The dissolvable hydrogel composition of claim 1, wherein the adhesive hydrogel layer is hydrophilic.

14. The dissolvable hydrogel composition of claim 1, wherein the adhesive hydrogel layer is elastic or viscoelastic.

15. The dissolvable hydrogel composition of claim 1, wherein the adhesive hydrogel layer has about 5 wt % to about 70 wt % of the crosslinkable polymers.

16. The dissolvable hydrogel composition of claim 1, further comprising a bioactive agent.

17. The dissolvable hydrogel composition of claim 16, wherein the bioactive agent is selected from the group consisting of pharmaceutical agents, drugs, cells, gases and gaseous precursors, synthetic organic molecules, proteins, enzymes, growth factors, vitamins, steroid, polyanions, nucleosides, nucleotides, polynucleotides, nanoparticles, diagnostic agents, genetic materials, and any combinations thereof.

18. The dissolvable hydrogel composition of claim 1, wherein the adhesive layer is hydrolytically stable at pH in a range of about 0 to at least about 9.

19. The dissolvable hydrogel composition of claim 1, wherein the dissolvable hydrogel composition is formulated to form a bandage, glue, sealant, coating, or covering.

20. A kit comprising a dissolvable hydrogel composition of claim 1.

21. The kit of claim 20,
wherein the first crosslinkable polymer is at least about 200 Da;
and wherein the second crosslinkable polymer is at least about 200 Da.

22. A method of wound management comprising:
(a) contacting a wound with a dissolvable hydrogel composition of claim 1;
(b) allowing the dissolvable hydrogel layer to adhere to tissue surrounding the wound; and
(c) dissolving the dissolvable hydrogel layer by adding a thiolate compound to result in a thiol-thioester exchange, thereby releasing the hydrogel composition from the wound.

23. The method of claim 22, wherein the thiolate compound is formulated as a solution or a spray.

* * * * *